(12) United States Patent
Lum et al.

(10) Patent No.: US 11,679,203 B2
(45) Date of Patent: Jun. 20, 2023

(54) MEDICAL DEVICE INCLUDING AN AIR EVACUATION SYSTEM

(71) Applicant: Becton, Dickinson and Company, Franklin Lakes, NJ (US)

(72) Inventors: Chee Leong Lum, Pequannock, NJ (US); Peter Douglas, Hillsdale, NJ (US); Waheed Abid, Valley Stream, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 258 days.

(21) Appl. No.: 17/119,237

(22) Filed: Dec. 11, 2020

(65) Prior Publication Data

US 2021/0146056 A1 May 20, 2021

Related U.S. Application Data

(62) Division of application No. 16/130,406, filed on Sep. 13, 2018, now Pat. No. 10,898,650, which is a
(Continued)

(51) Int. Cl.
*A61M 5/315* (2006.01)
*A61M 5/36* (2006.01)
(Continued)

(52) U.S. Cl.
CPC ..... *A61M 5/31513* (2013.01); *A61B 5/15048* (2013.01); *A61B 5/150213* (2013.01);
(Continued)

(58) Field of Classification Search
CPC .......................... A61M 5/2466; A61M 5/2459
See application file for complete search history.

(56) References Cited

U.S. PATENT DOCUMENTS 1,643,531 A 9/1927 Wolf
3,291,128 A 12/1966 O'Neil
(Continued)

FOREIGN PATENT DOCUMENTS

GB 2176711 A 1/1987

OTHER PUBLICATIONS

European Search Report in EP11158108 dated Sep. 4, 2012, 8 pages.
(Continued)

*Primary Examiner* — Jenna Zhang
(74) *Attorney, Agent, or Firm* — Servilla Whitney LLC

(57) ABSTRACT

Medical device assemblies capable of aspirating liquid into a syringe barrel or other medical devices while evacuating any air from the syringe are described. An exemplary medical device includes a syringe barrel, plunger rod and stopper assembly having an air permeable and liquid impermeable porous portion and structure for forming a vacuum within either the stopper or the plunger rod. Described is a medical device including a syringe barrel, plunger rod and stopper assembly having an air permeable and liquid impermeable porous portion and structure for forming a vacuum within chamber between the stopper and plunger rod wherein the plunger rod includes a sealing edge and is moveable relative to the stopper. Exemplary medical devices may include a vent for allowing air that permeates through the porous portion to escape to atmosphere. Methods for aspirating a syringe barrel with a liquid are also provided.

5 Claims, 85 Drawing Sheets

Related U.S. Application Data division of application No. 14/870,474, filed on Sep. 30, 2015, now Pat. No. 10,173,011, which is a division of application No. 12/762,672, filed on Apr. 19, 2010, now Pat. No. 9,174,007.

(60) Provisional application No. 61/313,917, filed on Mar. 15, 2010.

(51) Int. Cl.

| | | |
|---|---|---|
| *A61M 5/24* | (2006.01) | |
| *A61M 5/38* | (2006.01) | |
| *A61B 5/15* | (2006.01) | |
| *A61M 5/31* | (2006.01) | |
| *B65B 3/00* | (2006.01) | |
| *B65B 3/12* | (2006.01) | |
| *A61B 5/153* | (2006.01) | |
| *A61M 5/178* | (2006.01) | |

(52) U.S. Cl.
CPC .. *A61B 5/150221* (2013.01); *A61B 5/150236* (2013.01); *A61B 5/150244* (2013.01); *A61B 5/150251* (2013.01); *A61B 5/150519* (2013.01); *A61M 5/2466* (2013.01); *A61M 5/3145* (2013.01); *A61M 5/31511* (2013.01); *A61M 5/36* (2013.01); *A61M 5/38* (2013.01); *B65B 3/003* (2013.01); *B65B 3/12* (2013.01); *A61B 5/15003* (2013.01); *A61B 5/153* (2013.01); *A61B 5/150259* (2013.01); *A61B 5/150404* (2013.01); *A61B 5/150755* (2013.01); *A61M 5/1782* (2013.01); *A61M 2005/3101* (2013.01); *A61M 2005/3112* (2013.01); *A61M 2005/3114* (2013.01); *A61M 2005/3123* (2013.01); *A61M 2005/31516* (2013.01)

(56) References Cited

U.S. PATENT DOCUMENTS

| | | | | |
|---|---|---|---|---|
| 3,405,712 | A | * | 10/1968 | Pierick .................. A61M 5/284 604/88 |
| 3,656,480 | A | | 4/1972 | Rubricius |
| 3,669,111 | A | | 6/1972 | Dubner |
| 3,736,932 | A | * | 6/1973 | Satchell .............. A61M 5/3145 604/190 |
| 3,809,298 | A | | 5/1974 | Harris, Sr. et al. |
| 3,864,979 | A | | 2/1975 | Ayres |
| 3,886,930 | A | | 6/1975 | Ryan |
| 3,938,513 | A | | 2/1976 | Hargest |
| 3,946,732 | A | * | 3/1976 | Hurscham ............. A61J 1/2093 604/88 |
| 3,960,139 | A | | 6/1976 | Bailey |
| 3,978,846 | A | | 9/1976 | Bailey |
| 4,008,718 | A | | 2/1977 | Pitesky |
| 4,016,879 | A | | 4/1977 | Mellor |
| 4,057,052 | A | | 11/1977 | Kaufman et al. |
| 4,206,768 | A | | 6/1980 | Bailey |
| 4,207,870 | A | | 6/1980 | Eldridge |
| 4,266,558 | A | | 5/1981 | Akhavi |
| 4,266,559 | A | | 5/1981 | Akhavi |
| 4,327,745 | A | * | 5/1982 | Ford, Jr. .......... A61B 5/150236 600/578 |
| 4,340,067 | A | | 7/1982 | Rattenborg |
| 4,373,535 | A | * | 2/1983 | Martell .................. A61B 5/153 600/578 |
| 4,572,210 | A | | 2/1986 | McKinnon |
| 4,657,028 | A | | 4/1987 | Rich et al. |
| 4,660,569 | A | | 4/1987 | Etherington |
| 4,774,963 | A | | 10/1988 | Ichikawa et al. |
| 5,086,783 | A | | 2/1992 | Macors et al. |
| 5,238,003 | A | | 8/1993 | Baidwan et al. |
| 5,314,416 | A | | 5/1994 | Lewis et al. |
| 5,531,683 | A | * | 7/1996 | Kriesel ............... A61M 5/2448 604/82 |
| 5,993,657 | A | | 11/1999 | Williams et al. |
| 6,102,699 | A | | 8/2000 | Galehr et al. |
| 6,155,991 | A | | 12/2000 | Beat et al. |
| 6,626,874 | B1 | | 9/2003 | Duchamp |
| 7,351,228 | B2 | | 4/2008 | Keane et al. |
| 8,172,794 | B2 | | 5/2012 | Lum et al. |
| 8,172,795 | B2 | | 5/2012 | Lum et al. |
| 2003/0199816 | A1 | * | 10/2003 | Ramming ............. A61M 5/284 604/191 |
| 2006/0111671 | A1 | | 5/2006 | Klippenstein |
| 2007/0179452 | A1 | | 8/2007 | Kosinski |
| 2008/0114304 | A1 | * | 5/2008 | Nalesso ............. A61M 39/221 604/207 |
| 2008/0264261 | A1 | | 10/2008 | Kavazov et al. |
| 2008/0269687 | A1 | | 10/2008 | Chong et al. |
| 2010/0179488 | A1 | | 7/2010 | Spiegel et al. |
| 2011/0127294 | A1 | | 6/2011 | Pearcy et al. |

OTHER PUBLICATIONS

Final Office Action in U.S. Appl. No. 12/762,672 dated Feb. 13, 2015, 13 pages.
Final Office Action in U.S. Appl. No. 12/762,672 dated Jan. 7, 2013, 9 pages.
Non-Final Office Action in U.S. Appl. No. 12/762,672 dated Aug. 1, 2014, 11 pages.
Non-Final Office Action in U.S. Appl. No. 12/762,672 dated Jun. 12, 2012, 7 pages.

\* cited by examiner

MEDICAL DEVICE INCLUDING AN AIR EVACUATION SYSTEM

CROSS-REFERENCE TO RELATED APPLICATIONS

This application is a divisional of U.S. patent application Ser. No. 16/130,406, filed Sep. 13, 2018, now allowed, which is a divisional of U.S. patent application Ser. No. 14/870,474, filed Sep. 30, 2015, now issued as U.S. Pat. No. 10,173,011, which is a divisional of U.S. patent application Ser. No. 12/762,672, filed Apr. 19, 2010, now issued as U.S. Pat. No. 9,174,007, which claims priority under 35 U.S.C. § 119(e) to U.S. Provisional Application No. 61/313,917, filed Mar. 15, 2010, the disclosures of which are hereby incorporated in its entirety by reference thereto.

TECHNICAL FIELD

Aspects of the present invention relate to medical devices for use with containers capable of evacuating air trapped within the container while filling the container with liquid.

BACKGROUND

Syringe barrels contain, store, transfer and measure liquids, typically containing medicaments or other fluids for delivery to a patient. Medical devices, including plunger rods and stoppers, are used to aspirate and expel liquid from syringe barrels. During aspiration, air can become trapped within the syringe barrel. The presence of air within the syringe barrel can result in inaccurate dosage measurements and other issues.

Typically, air is removed from syringe barrels, by inverting the syringe barrel to force the air trapped within the barrel to the opening through which the fluid is aspirated. The air is then expelled through the opening by applying a force on the plunger rod in the distal direction. This expulsion process, however, can result in the expulsion of a portion of the liquid aspirated into the syringe barrel. In addition, this method of removing air from the syringe barrel may require the user to agitate the barrel of the syringe to force the air bubbles to move toward the opening.

Attempts to remove air from syringe barrels have included the use of a venting system to allow air to flow out of syringe barrels and other containers. Filters have been utilized to allow air to escape but prevent the desired liquid from also flowing out of the chamber of the barrel. Such attempts, however, rely on natural forces to passively cause a pressure differential across the filter to force air to permeate through the filter. In some instances, the filtering devices are part of a separate component that must be attached to the tip of syringes by the user prior to use of the syringe. There is a need to alleviate the need for users to actively remove air from syringe barrels and other containers before use.

SUMMARY

In this disclosure, a convention is followed wherein the distal end of the device is the end closest to a patient and the proximal end of the device is the end away from the patient and closest to a practitioner.

Several aspects of a medical device including structure to evacuate air from a syringe barrel or other container when aspirating liquid into the syringe barrel or container are provided. Exemplary syringe barrels described herein include a side wall having an inside surface defining a chamber for retaining fluid, an open proximal end and a distal end including a distal wall with a tip extending distally therefrom having an open passageway in fluid communication with said chamber. The medical devices include a plunger rod and stopper assembly disposed within the chamber of the syringe barrels or other containers.

In accordance with one or more embodiments, a medical device for use with a syringe barrel is provided and includes a plunger rod disposed within the chamber of the syringe barrel and moveable in the proximal and distal direction within the chamber, a stopper assembly disposed within the chamber of the syringe barrel and moveable in the proximal and distal direction within the chamber, the stopper assembly forming a fluid-tight seal with the inside surface of the syringe barrel, the stopper having a distal face, a proximal end and a body extending from the distal face to the proximal end defining a stopper cavity, means for creating a vacuum within the stopper cavity; and means for permitting air to enter the stopper cavity and preventing liquid from entering the stopper cavity. In one or more embodiments, the medical device may include means for venting the air within the stopper cavity that was evacuated from the chamber. The vent may be associated with the stopper and/or plunger rod to release the evacuated air from the stopper cavity. The porous portion may include a selective barrier that defines a liquid penetration pressure and an air penetration pressure that is less than the liquid penetration pressure. In one or more specific embodiments, the means for permitting air into the cavity and preventing liquid from entering the cavity comprises a porous portion including one of a hydrophilic filter, a hydrophobic filter, a swellable polymer or a combination thereof.

In one or more embodiments, the plunger rod and stopper of one or more embodiments are configured to create a pressure differential between the stopper cavity and a portion of the chamber extending from the distal wall and the distal face of the stopper assembly. The porous portion may be associated with the stopper to permit air to flow into the stopper cavity and to prevent liquid from entering the stopper cavity. The structures and configurations of the plunger rod, stopper assembly and porous portion are described below with reference to various aspects.

In one or more embodiments of the present invention according to a first aspect of the invention, the stopper is attached to the distal end of the plunger rod and includes an expandable portion that expands the stopper cavity to create a vacuum within the stopper cavity. The expandable portion may include a bendable wall, which may comprise an elastomeric material and has a spring constant that permits rapid expansion of the bendable wall.

The stopper may also include a proximal end having an opening in fluid communication with the stopper cavity. The stopper also includes a sealing portion disposed between the distal face of the stopper and the expandable portion that forms a fluid-tight seal with the inside surface of the syringe barrel. In one or more embodiments, the sealing portion remains stationary despite an initial movement of the plunger rod in a proximal direction that causes the expandable portion to expand to draw air into the stopper cavity through the porous portion associated with the stopper. The distal face of the stopper according to one or more embodiments may be flexible and may flex concavely during movement of the plunger rod in a proximal direction and may flex convexly during movement of the plunger rod in the distal direction. In one or more embodiments, the distal face may be convexly shaped to conform to the distal wall of the barrel.

The distal end of embodiments of the plunger rod according to a first aspect is disposed within the stopper cavity and forms a releasable seal with the opening at the proximal end of the stopper and is proximally and distally moveable within the stopper cavity. In one or more embodiments, the distal end of the plunger rod includes a tapered neck shaped to form a releasable seal with the opening at the proximal end of the stopper, which may include an undercut that is shaped to receive the tapered neck of the plunger rod.

When the medical device according to a first aspect is assembled for use, an initial movement of the plunger rod in a proximal direction relative to the stopper forms the releasable seal between the distal end of the plunger rod and the opening, and the expandable portion expands and draws air from the chamber into the stopper cavity through the porous portion disposed between the distal face and the stopper cavity. In one or more embodiments, movement of the plunger rod in a distal direction relative to the stopper subsequent to the initial movement in the proximal direction releases the releasable seal between the distal end of the plunger rod and the opening at the proximal end of the stopper. The release of the releasable seal allows the air within the stopper cavity to escape through the opening at the proximal end of the stopper.

In one or more embodiments according to a first aspect, the expandable portion of the stopper is configured to permit movement of the plunger rod relative to the stopper in a distal and a proximal direction. In a specific embodiment, the expandable portion of the stopper is configured so that upon a continuous movement of the plunger rod relative to the stopper in a distal direction, the distal end of the plunger rod blocks the porous portion and prevents air from exiting the stopper cavity through the porous portion.

One or more embodiments according to a second aspect of the present invention also utilize a stopper that is attached to the distal end of the plunger rod and includes an expandable portion that expands the stopper cavity to create a vacuum within the stopper cavity and the proximal end of the stopper includes an opening in fluid communication with the stopper cavity. According to the second aspect, the expandable portion includes a pump body having a distal end attached to the proximal end of the stopper and includes a proximal end defining a plunger-engaging portion attached to the proximal end of the plunger rod. The pump body according to one or more embodiments includes a wall that defines a pump cavity in fluid communication with the stopper cavity. In one or more embodiments, the wall may include a corrugated wall formed from an elastomeric material and has a spring constant that permits expansion of the corrugated wall. The pump body is configured so that upon application of an initial force on the plunger rod in the distal direction relative to the stopper causes the pump body to compress and a release of the initial force on the plunger rod in the distal direction allows the pump body to expand and draw air from the chamber into the stopper cavity through the porous portion disposed between the distal face and the stopper cavity. In one or more embodiments, the stopper may include a sealing portion disposed between the distal face and the expandable portion that forms a fluid-tight seal with the inside surface of the syringe barrel. During expansion of the pump body, the sealing portion remains stationary.

In one or more embodiments according to a second aspect of the present invention, the pump body may include a valve and a valve opening disposed at the proximal end of the pump body in fluid communication with the pump cavity. The valve may be configured to open upon application of a force in the distal direction on the plunger rod and close upon release of the force in the distal direction on the plunger rod.

In one or more embodiments according to a third aspect of the present invention, the distal end of the plunger rod includes an opening covered by a pierceable wall and a plunger rod cavity including a vacuum and the stopper includes a stopper hub with a hollow spike extending from the proximal end in fluid communication with the stopper cavity for piercing the pierceable wall of the plunger rod. The stopper hub may include an open distal end and an open proximal end in fluid communication with the stopper cavity, the proximal end including a plunger-engaging portion to engage the distal end of the plunger rod. When assembled and in use, the proximal end of the stopper hub and the distal end of the plunger rod are configured to be positioned in a first position so that the hollow spike is disposed at a distance from the pierceable wall. In addition, the proximal end of the stopper hub and the distal end of the plunger rod are configured to engage in a second position so that the hollow spike pierces the pierceable wall and the vacuum draws air from the chamber into the stopper cavity through the porous portion disposed between the distal face and the stopper cavity.

In one or more embodiments of the medical device according to a fourth aspect, the stopper assembly includes an opening in the distal face in fluid communication with the stopper cavity and a plug extending partially through the opening and capable of forming a fluid-tight seal with the opening. The plug includes a distal end, a proximal end, a head disposed at the proximal end and an elongate core extending from the head to the distal end, the elongate core including a channel extending from the head to a distance from the distal end and extending partially through the opening such that a portion of the channel is disposed distally adjacent the opening to permit fluid communication between the opening and the stopper cavity and the head is disposed proximally adjacent the opening.

In one or more embodiments according to a fourth aspect, the porous portion is formed from a swellable polymer and is disposed adjacent to the plug. The porous portion forms an expandable barrier between the head of the plug and the opening. Upon contact with a liquid, the porous portion expands and applies a force on the head in a proximal direction that causes the channel to be positioned proximally adjacent the opening and allows the elongate core to form a fluid-tight seal with the opening, preventing fluid communication between the opening and the stopper cavity.

The plunger rod according to one or more embodiments of a fourth aspect of the present invention may include a sealing portion for forming a fluid-tight seal with the interior surface of the barrel and is moveable within the chamber in the proximal and distal directions independently from the stopper assembly. In such embodiments, upon application of a force on the plunger rod in the proximal direction, the plunger rod moves in the proximal direction and creates a vacuum within the stopper cavity that draws air from the chamber through the channel of the plug into the stopper cavity. In one or more embodiments, contact between the liquid and the porous portion causes the porous portion to expand and apply a force on the head in a proximal direction that causes the channel to be positioned proximally adjacent the opening and prevents fluid communication between the opening and the stopper cavity. The application of a force on the plunger rod in a distal direction causes the plunger rod to engage the stopper and causes the plunger rod and stopper to move in the distal direction to expel the liquid drawn into the chamber through the tip and opening.

In one or more specific embodiments according to a fourth aspect, the stopper and the plunger rod may be disposed at a pre-determined distance from the distal wall of the syringe barrel to permit use of the medical device to administer a fixed-dose of liquid. In such embodiments, upon application of a force on the plunger rod in a proximal direction, the stopper remains stationary at a distance from the distal wall of the syringe barrel, and a liquid and air are drawn into the chamber by the vacuum created within the chamber by sealing portion of the plunger rod and movement of the plunger rod in the proximal direction relative to the stopper. The air drawn into the chamber by the vacuum is evacuated through the channel of the plug into the stopper cavity and, upon contact with the liquid, the porous portion expands and applies a force on the head in a proximal direction that causes the channel to be positioned proximally adjacent the opening and prevents fluid communication between the opening and the stopper cavity. Thereafter, application of a force on the plunger rod in a distal direction causes the plunger rod to engage the stopper and causes the plunger rod and stopper to move in the distal direction to expel the liquid drawn into the chamber through the tip and opening.

In one or more embodiments according to a fifth aspect, the distal face of the stopper comprises an opening in fluid communication with the stopper cavity and the stopper comprises a duct assembly extending partially through the opening and capable of sealing the opening. In such embodiments, the porous portion is formed from a swellable polymer and is disposed adjacent to the duct assembly, which comprises distal end, a proximal end, a base disposed at the proximal end and a duct member extending from the base to the distal end. The porous portion is positioned to form expandable barrier between the base and the opening of the stopper. The duct member may include a tubular wall having an open distal end and a lateral opening permitting fluid communication between the open distal end and the stopper cavity. In one or more embodiments, the lateral opening of the duct member extends from the base to a distance between the open distal end and the base. In one or more embodiments, the duct member extends partially through the opening of the stopper such that the open distal end is disposed distally adjacent the opening to permit fluid communication between the opening and the stopper cavity and the base is disposed proximally adjacent the opening. When assembled and in use, upon contact with a liquid, the porous portion expands and applies a force on the base in a proximal direction that causes the open distal end of the duct member to be positioned proximally adjacent the opening and prevents fluid communication between the opening and the stopper cavity.

In one or more specific embodiments according to a fifth aspect, the plunger rod includes a sealing portion for forming a fluid-tight seal with the interior surface of the barrel and is moveable within the chamber in the proximal and distal directions independently from the stopper assembly. In such embodiments, upon application of a force on a plunger rod in a proximal direction, the plunger rod moves in the proximal direction and creates a vacuum within the stopper cavity that draws air from the chamber into the stopper cavity through the open distal end and lateral opening of the duct member. Upon contact with the liquid, the porous portion expands and applies a force on the base in a proximal direction that causes the channel to be positioned proximally adjacent to the opening of the stopper and prevents fluid communication between the opening of the stopper and the stopper cavity. The plunger rod may be attached to the stopper via a plunger engaging means disposed on the stopper and the application of a force on the plunger rod in the distal direction that causes the plunger rod to engage the stopper. After engagement of the plunger rod and the stopper, the application of a force on a plunger rod in the proximal direction causes the plunger rod and stopper to move in the proximal direction and draws liquid into the chamber and application of a force on the plunger rod in the distal direction causes the plunger rod and stopper to move in the distal direction to expel the liquid drawn into the chamber.

One or more embodiments according to a sixth aspect of the present invention includes a stopper having a distal face with an opening in fluid communication with the stopper cavity, an opening at the proximal end of the stopper assembly in fluid communication with the stopper cavity and a stopper hub defining a hub cavity attached to the proximal end of the stopper. In one or more embodiments, the stopper hub includes an open distal end and an open proximal end in fluid communication with the stopper cavity. The distal end of the plunger rod forms a fluid tight seal with the stopper hub and is slidably engaged with the stopper hub to move in a proximal direction relative within the hub cavity to form a vacuum within the hub cavity. The open proximal end of the stopper hub may include a peripheral wall and the distal end of plunger rod comprises a disc member forming a fluid-tight seal with the peripheral wall. The peripheral wall of one or more embodiments includes means for preventing distal movement of the plunger rod relative to the stopper hub, after an initial proximal movement of the plunger rod relative to the stopper hub. In one or more specific embodiments, the peripheral wall of the stopper hub may include a vent in fluid communication with the chamber and the exterior of the medical device. The vent allows the air evacuated from the chamber of the syringe barrel into the stopper cavity to escape.

When one or more embodiments according to a sixth aspect are assembled and in use, application of an initial force on the plunger rod in a proximal direction expands the hub cavity and creates a vacuum within the hub cavity that draws air from the chamber into the stopper cavity through the porous portion disposed between the distal face and stopper cavity. The application of a continuous force on the plunger rod in a proximal direction causes the plunger rod and stopper to move in a proximal direction and draws liquid into the chamber. In one or more embodiments, the application of a force on the plunger rod in the distal direction causes the plunger rod and stopper to move in the distal direction and the stopper hub to remain expanded.

In one or more embodiments of the present invention according to a seventh aspect, the stopper assembly includes an opening in fluid communication with the stopper cavity and the proximal end of the stopper assembly is attached to the plunger rod. The plunger rod according to one or more embodiments has a nested configuration and includes a body including a distal end, an open proximal end and an inside surface extending the stopper cavity from the distal face to the open proximal end of the plunger rod, and a second plunger rod piece is disposed within the stopper cavity and moveable in the proximal and distal direction within the stopper cavity. The second plunger rod piece includes a sealing edge forming a fluid-tight seal with the inside surface of the body of the plunger rod.

In one or more embodiments, the body comprises a retainer for restricting movement of the second plunger rod piece within the stopper cavity after an initial movement of the second plunger rod piece in a proximal direction relative to the body. When assembled and in use, upon the initial movement of the second plunger rod piece in a proximal direction, a vacuum is created within the stopper cavity drawing air from the chamber into the stopper cavity through the porous portion disposed between the distal face and the stopper cavity. Upon application of a force on the body in a proximal direction draws liquid into the chamber and application of a force on the body in the distal direction expels the liquid drawn into the chamber.

The seventh aspect of the present invention also includes a two-piece plunger rod assembly. In one or more embodiments, the medical device includes a syringe barrel as otherwise described herein, and a plunger rod assembly disposed within the chamber moveable in the proximal and distal direction within the chamber. The plunger rod assembly include s a proximal end, a distal end including a sealing edge for forming a fluid-tight seal with the inside surface of the syringe barrel and a body extending from the proximal end to the distal end, the body including an inside surface defining a plunger rod cavity. The distal end of the plunger rod may include an opening in fluid communication with the plunger rod cavity. The plunger rod assembly also includes a slidable portion disposed within the plunger rod cavity and moveable in the proximal and distal direction within the plunger rod cavity. The slidable portion is configured or shaped to form a fluid-tight seal with the inside surface of the plunger rod cavity. The plunger rod and slidable portion configured to create a pressure differential between the plunger rod cavity and a portion of the chamber extending from the distal wall and the sealing edge of the plunger rod. The medical device also includes a porous portion associated with the plunger rod to permit air to flow into the plunger cavity and to prevent liquid from entering the plunger rod cavity. The slidable portion may include a retainer for restricting movement of the slidable portion within the plunger rod cavity after an initial movement of the slidable portion in a proximal direction relative to the plunger rod.

In use, the initial movement of the slidable portion of the plunger rod assembly in a proximal direction creates a vacuum within the plunger rod cavity that draws air from the chamber into the plunger rod cavity through the porous portion. Upon application of a force on the plunger rod in a proximal direction, a vacuum is created in the chamber of the syringe barrel that draws liquid into the chamber and the application of a force on the plunger rod in the distal direction expels the liquid drawn into the chamber.

In one or more embodiments according to an eighth aspect of the present invention, utilizes a plunger rod having vacuum therein and includes an open distal end that is attached to the proximal end of the stopper assembly. In one or more embodiments, the distal end of the plunger rod includes a sidewall support defining a hollow interior within which the porous portion is disposed. The plunger rod may optionally include a second porous portion disposed within the hollow interior of the plunger rod. The distal face of the stopper assembly forms a pierceable seal with the stopper cavity and is pierceable to release the vacuum within the plunger rod. A needle disposed within the open passageway of the syringe barrel and extends distally from the open passageway and proximally into the chamber of the syringe barrel. The needle includes an open distal end, an open proximal end including a piercing point for piercing the distal face of the stopper assembly, a vent disposed adjacent to the proximal end in fluid communication with the open distal end and the open proximal end of the needle.

When assembled and in use, the plunger rod and stopper are disposed within the chamber such that the piercing point does not penetrate the distal face and the vacuum within the plunger rod remains intact. Upon an application of an initial force on the plunger rod in the distal direction, the piercing point pierces the distal face and releases the vacuum that draws air from the chamber into the stopper cavity. Upon application of a force on the plunger rod in a proximal direction, the distal face forms a fluid tight seal with the stopper cavity and prevents liquid from entering the stopper cavity as the liquid is drawn into the chamber.

One or more embodiments according to a ninth aspect pertain to a method for filling a syringe barrel with liquid. In one or more embodiments, the method includes providing a syringe barrel having a chamber having an air source, a needle cannula having an opening, a plunger rod assembly including a sealing means for forming a fluid tight seal with the syringe barrel, and means for evacuating an air from the chamber into the plunger rod assembly, submerging the opening of the needle cannula in a liquid, providing a vacuum within the plunger rod assembly, drawing the air source and the liquid into the chamber and evacuating the air source from the chamber into the plunger rod assembly. The method may optionally include venting the air from the plunger rod assembly. In one or more specific embodiments, the step of providing a vacuum within the plunger rod assembly comprises expanding a cavity within the plunger rod assembly. The step of submerging the opening of the needle cannula in one or more embodiments occurs after providing a vacuum within the plunger rod assembly.

DETAILED DESCRIPTION

Figure 1:
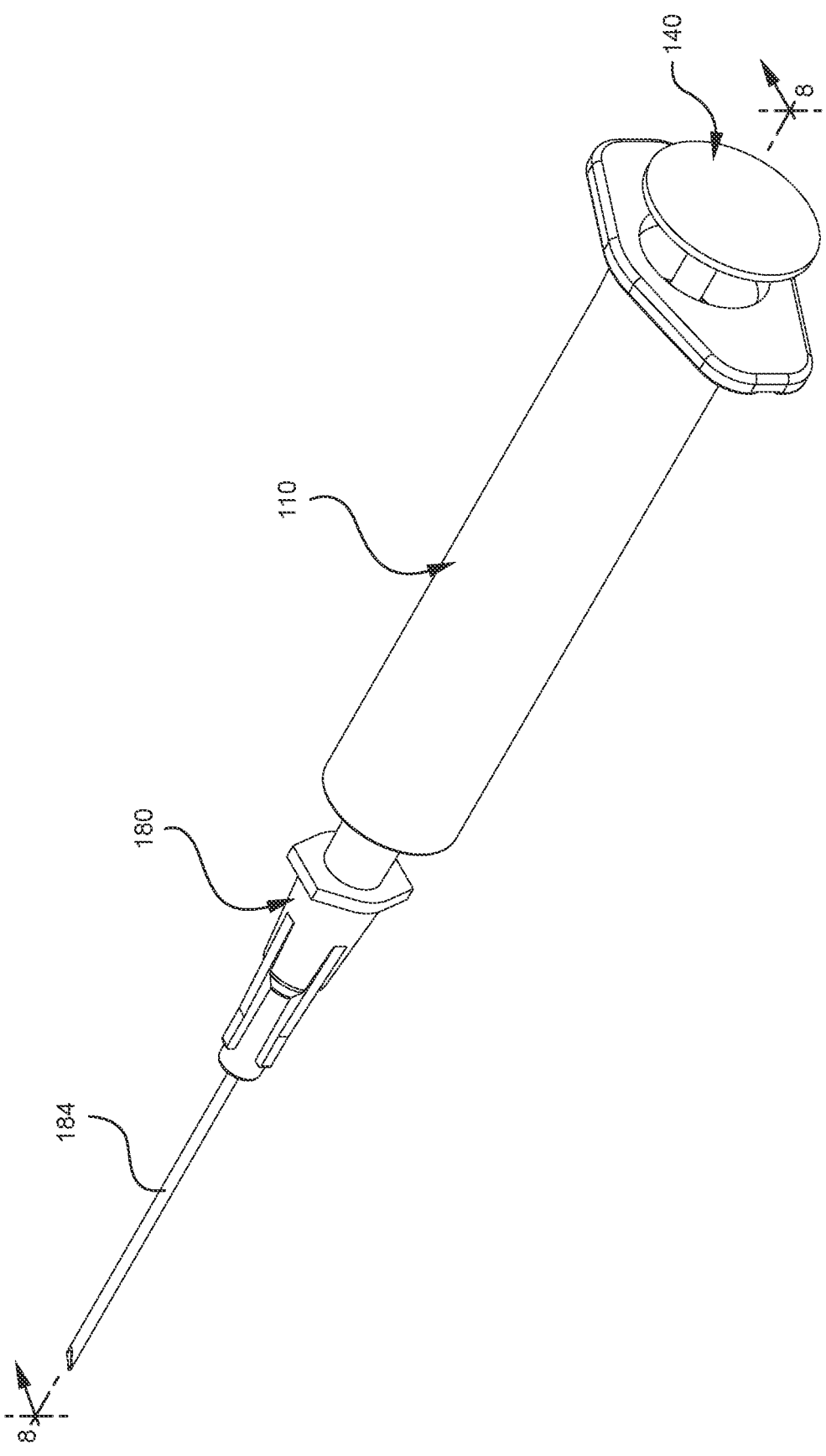
FIG. 1 illustrates a perspective view of a medical device including an assembled syringe and plunger rod.
Figure 2:
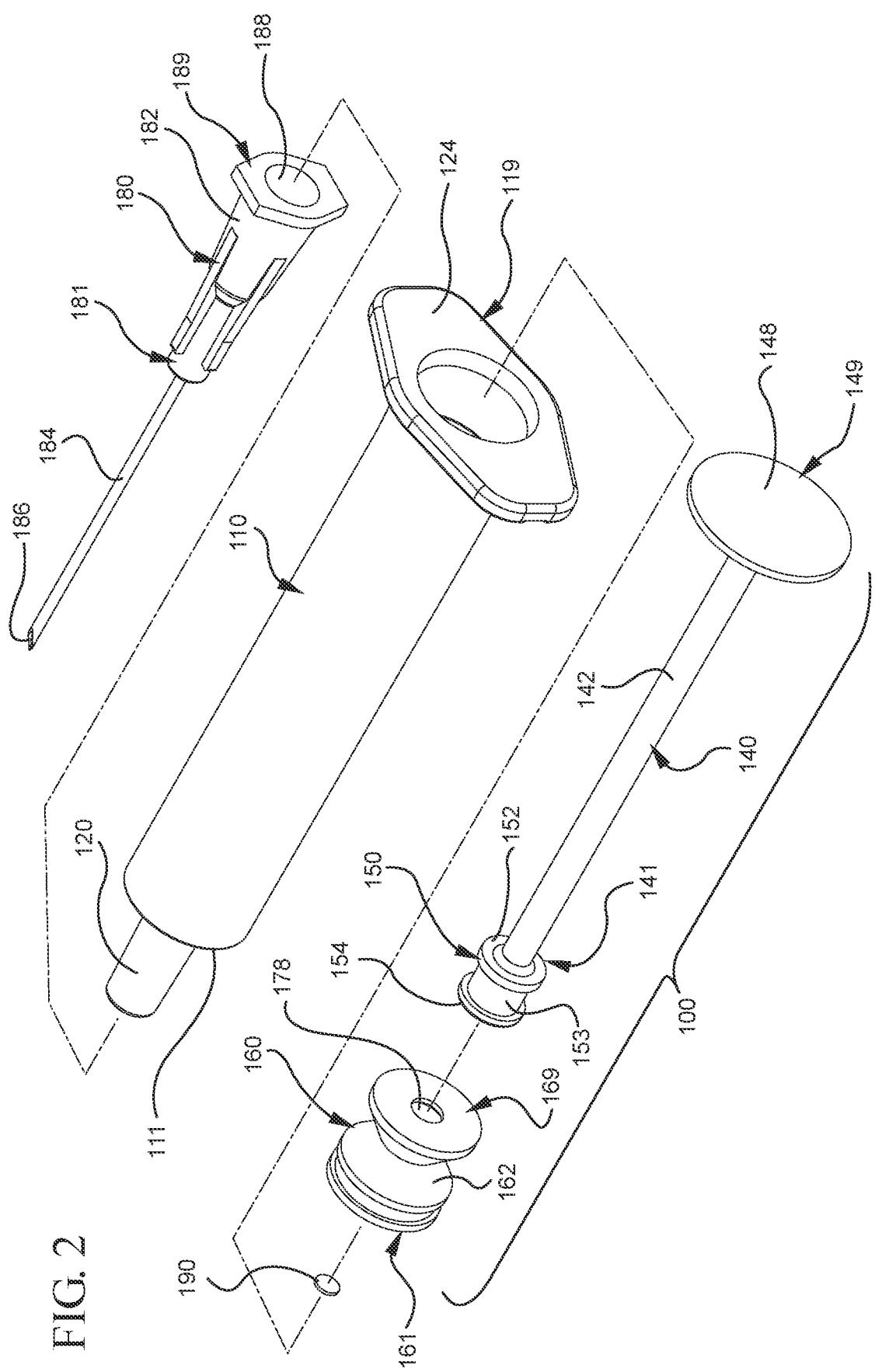
FIG. 2 illustrates a disassembled view of the medical device of FIG. 1.
Figure 84:
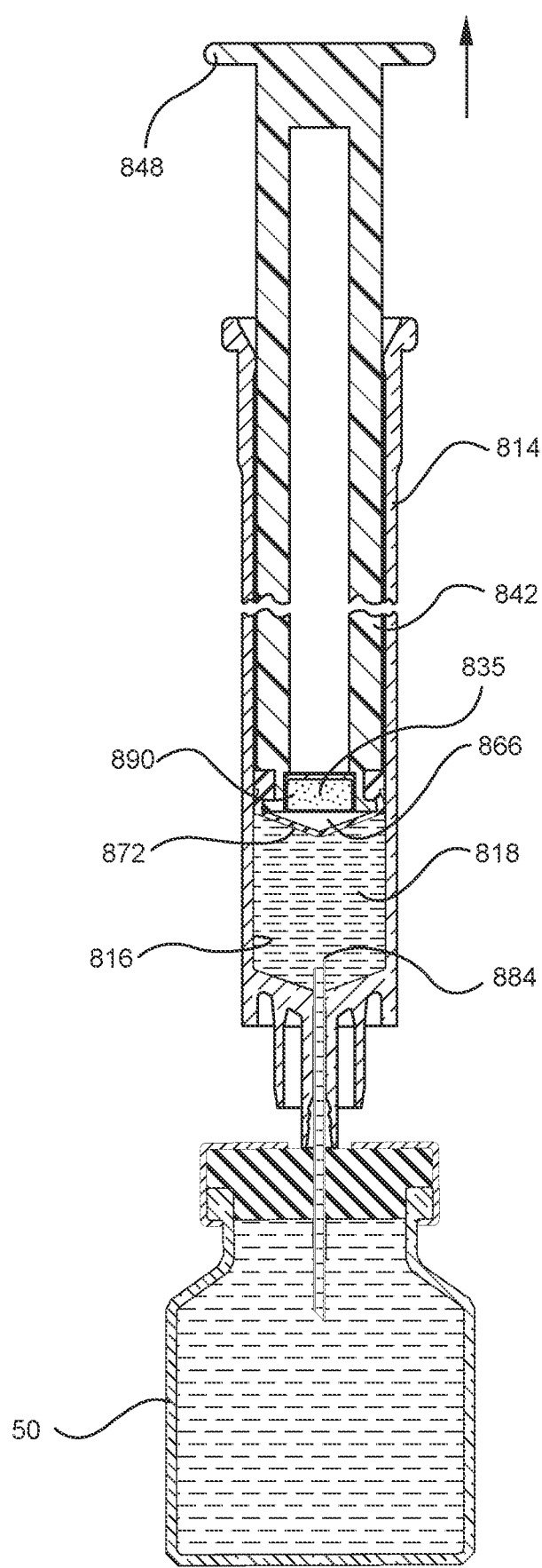
FIG. 84 shows the medical device shown in FIG. 82 filled with liquid from the vial.

Before describing several exemplary embodiments of the invention, it is to be understood that the invention is not limited to the details of construction or process steps set forth in the following description. The invention is capable of other embodiments and of being practiced or being carried out in various ways. It is to be understood that the configurations shown in FIGS. 1-84 are merely exemplary, and the components can be different in shape and size than shown.

The embodiments of the present invention described herein, with specific reference to various aspects, provides for a medical device including syringe barrel or other containers to draw liquid from a source into the syringe barrel. The medical devices described herein generally include a plunger rod and stopper assembly and means to actively remove or evacuate air from the liquid drawn into the syringe barrel or other container. The embodiments of the medical device may be used with other types of containers, in addition to syringe barrels, for example, needleless IV sets or other devices having a chamber that can be used to store and/or transfer liquid medication and/and/or other liquids. Syringe barrels described herein may include optional needle hubs, integrated needle cannulas and/or needle shields.

Aspects of the present invention described herein incorporate a mechanism that creates greater pressure differentials across a porous portion disposed or formed with one or more of the stopper, plunger rod and/or stopper-plunger rod assemblies described herein. Previous attempts to evacuate air from syringes have been largely limited to blood draw syringes and have relied on the pressure differential across hydrophobic filters, which is often referred to as a "bubble point" of the filter, i.e., the pressure to force air through the filter. In such devices, the pressure differential is largely created by the patient's arterial and/or venous pressure. Varying the pore size and materials used to form the hydrophobic filters have been attempted to solve the problems posed by situations or applications that provide a low pressure differential across the porous portion.

In embodiments of the present invention, means for evacuating air from syringes have been incorporated which provide a greater pressure differential. For example, as shown in FIGS. 1-13, the medical device 100 the stopper includes an expandable portion 162 that increases the pressure differential between the stopper cavity 166 of the stopper and the chamber 118 of the syringe barrel and is not reliant on external forces to create a pressure differential causing the air to permeate through the hydrophobic filter or porous portion 190. As will be described in further detail below, the second aspect of the present invention, shown in FIGS. 14-22, the medical device 200 utilizes a stopper hub 250 including a pump body 253 to create the increased pressure differential across the porous portion. In the embodiments according to the second aspect, a vacuum is created within the pump body 253 as the user applies an initial force in the distal direction to compress the pump body 253 and the pump body 253 springs back to an expanded state as the initial force on an attached plunger rod 240 is released to create a vacuum within the pump body 253, which creates an increased pressure differential across the porous portion. Embodiments according to a third aspect of the present invention shown in FIGS. 26-34, illustrate a medical device 300 including a plunger rod 340 having a pre-formed vacuum within the plunger rod 340 and a stopper 360 attached to the plunger rod and having a structure to release the vacuum within the plunger rod 340 into a cavity within the stopper 360, which provides a greater pressure differential across the porous portion. The embodiments shown according to the fourth aspect in FIGS. 35-44 utilize a plunger rod 440 having a first stopper 447 and a separate second stopper assembly 460 to form a vacuum between the plunger rod 440 and the stopper assembly 460. Embodiments according to the fifth aspect of the present invention shown in FIGS. 45-54 also utilize a plunger rod 540 having a sealing edge 547 and a separate stopper assembly 560 to form a vacuum within the chamber 518 of the syringe between the stopper assembly 560 and the plunger rod 540. Embodiments according to a sixth aspect of the invention shown in FIGS. 55-66 illustrate a plunger rod 640 slidably engaged to a stopper 660 to create a vacuum within a cavity 666 formed within the stopper 660. The embodiments according to a seventh aspect of the present invention utilize a two-piece plunger rod system that allows a user to move one plunger rod piece 750 relative to the other plunger rod piece 730 to form a vacuum in a space or stopper cavity 734 formed between the plunger rod pieces. The embodiments according to an eight aspect of the present invention utilize a stopper 860 and plunger rod 840 having a pre-formed vacuum disposed therein that may be released by a needle 880 that permits air to escape into stopper 860 and plunger rod 840 assembly. Accordingly, the medical devices described herein can be used in more applications, for example, the administration of medication to a patient, measurement of liquids in laboratory testing and the like regardless of the viscosity or other properties of the liquid.

The porous portion of the embodiments of the medical devices described herein may include a selective barrier that defines a liquid penetration pressure and an air penetration pressure that is less than the liquid penetration pressure. In one or more embodiments, the porous portion may include a hydrophilic filter, a hydrophobic filter, a swellable polymer and/or other suitable materials that are air permeable and liquid impermeable and/or combinations thereof. Examples of suitable hydrophilic filters include hydrophilic polytetrafluoroethylene membrane filters. Such filters are available from the W. L. Gore & Associates of Elkton, Md. Examples of suitable hydrophobic filters include a material known under the trademark "Tyvek" produced by E. I. duPont de Nemours and Company, Inc. of Wilmington, Del. which is a spunbonded olefin or a material known under the trademark "Acropor" that is made of acrylonitrile polyvinyl chloride reinforced with nylon and may be obtained from Gelman Instrument Company or Ann Arbor, Mich. Other suitable hydrophobic filters include filters made of polytetrafluoroethylene, nylon, cellulose nitrate, cellulose acetate, and polethersulfone.

Suitable hydrophobic filters resist liquid from wicking through the filter at a reasonable pressure gradient. In one or more embodiments, the hydrophobic filter has a water penetration pressure, or the pressure at which water permeates or penetrates the hydrophobic filter that is greater than the air penetration pressure, or the pressure at which air permeates or penetrates the hydrophobic filter. In a specific embodiment, the water penetration pressure of the hydrophobic filter is greater than the vacuum pressure generated within the chamber of the syringe barrel or other containers and/or within the stopper and plunger rod assemblies described herein. This difference in pressure creates a pressure differential across the porous portion that drives air and liquid toward the porous portion, with the liquid impermeable property of the porous portion preventing liquid from permeating through the porous portion and allowing air to permeate through the porous portion.

In accordance with one or more embodiments, the porous portion described herein may include a swellable polymer comprising a plurality of openings or holes that allow fluid communication of air through the openings. In one or more embodiments, the swellable polymer swells or expands upon contact with a liquid, thereby closing the openings or holes of the swellable polymer. In one or more embodiments, the swellable polymers are activated or swell upon contact with liquids that contain water. In accordance with one or more alternative embodiments, the swellable polymers are activated or swell upon contact with liquids, regardless of the water content of the liquids. Accordingly, in such embodiments, air contained within the syringe barrel is permitted to escape through the holes prior to contact between the swellable polymer and liquid. Upon contact with a liquid, the holes of the swellable polymer close and no fluid is permitted to enter the holes or escape from the syringe barrel. Examples of swellable polymers include hydrogel-forming polymers. As used herein, hydrogels include materials that may be characterized as having chemical structures with an affinity for aqueous solutions in which they swell rather than dissolve. Hydrogels may also be referred to as gelling material (AGM) or super-absorbent polymers (SAP). Exemplary swellable polymers may be produced by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylenebisacrylamide, trimethylolpropane triacrylate, ethylene glycol di(meth)acrylate, or triallylamine. Other known swellable polymers may also be utilized.

Alternatively, the porous portion may be formed from a combination of a hydrophobic filter and a swellable polymer. For example, the center of the porous portion may be formed from a swellable polymer and the remaining portion of the porous portion which surrounds the swellable polymer is formed from a hydrophobic filter, and/or vice versa. In one or more embodiments, the porous portion may be provided the form of a laminate including a first layer formed from a hydrophobic filter and a second layer formed from a swellable polymer. In one or more specific embodiments, the laminate porous portion may be positioned so the layered hydrophobic filter is the distal most layer and, thus, is in contact with the liquid before the swellable polymer or vice versa.

Previous attempts to evacuate air from syringe barrels and other containers have utilized filters that could interfere with the sealing mechanism of the stopper and plunger assembly. The size of such filters is often large enough to cover the distal face of the stopper and also the sealing portion that forms a seal with the syringe barrel. The presence of a filter between the sealing portion of the stopper and the syringe barrel can interfere with the fluid-tight engagement between the stopper and syringe barrel and prevent the proper formation of the vacuum within the syringe barrel to aspirate fluid or liquid. The use of a porous portion may be shaped and positioned to occupy a portion of the distal face to provide an evacuation system for the air within the syringe barrel to escape without interfering with the ability of the stopper or plunger rod to form a seal with the syringe barrel.

FIGS. 1-13 illustrate one of more embodiments of a medical device 100 according to a first aspect of the invention. The medical device 100 includes a plunger rod 140 attached to a stopper 160. For illustration, the medical device 100 is shown in use with a container in the form of a syringe barrel 110 with needle hub 180 in FIGS. 1-13. As shown more clearly in FIGS. 2 and 8, the syringe barrel 110 includes an open proximal end 119 and a distal end 111 and a distal wall 112. A sidewall 114 extends from the distal end 111 to the open proximal end 119 and includes an interior surface 116 that defines a chamber 118 for retaining or holding fluids, which may include liquid medication and/or other liquids. The distal end 111 may also include a tip 120 having an open passageway 122 therethrough in fluid communication with the chamber 118. The barrel 110 may include an optional finger flange 124 at the open proximal end 119 extending radially outwardly from the sidewall 114. As shown in FIGS. 1-13, a needle hub 180 is utilized to attach the needle cannula 184 to the tip 120. The needle hub 180 includes a needle cannula 184 with a lumen 186 or opening therethrough and may be attached to the tip 120 so that the lumen 186 is in fluid communication with the open passageway 122 and the chamber 118. As shown, the needle hub 180 includes a distal end 181 and a proximal end 189 and a body 182 defining a hollow space 188. When assembled, the tip 120 is inserted into the hollow space 188 through the open proximal end 189 of the needle hub 180 until the body 182 frictionally engages the tip 120. Alternatively, the needle cannula 184 may be attached to the tip 120, without the use of a needle hub, using other methods known in the art. The interior surface 116 of the syringe barrel 110 may have a smooth surface that is free of any protrusions or depressions. In addition, the body 182 of the needle hub 180 may also incorporate a smooth interior surface that is free of any protrusions or depressions. In use, the plunger rod 140 and stopper 160 are inserted into the open proximal end 119 of the syringe barrel 110.

Figure 4:
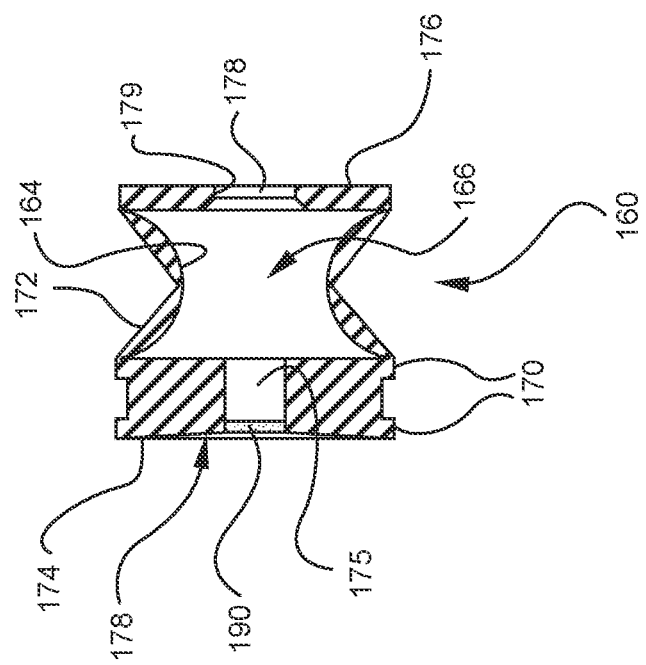
FIG. 4 illustrates a cross-sectional view of the stopper shown in FIG. 3 taken along line 4-4.
Figure 3A:
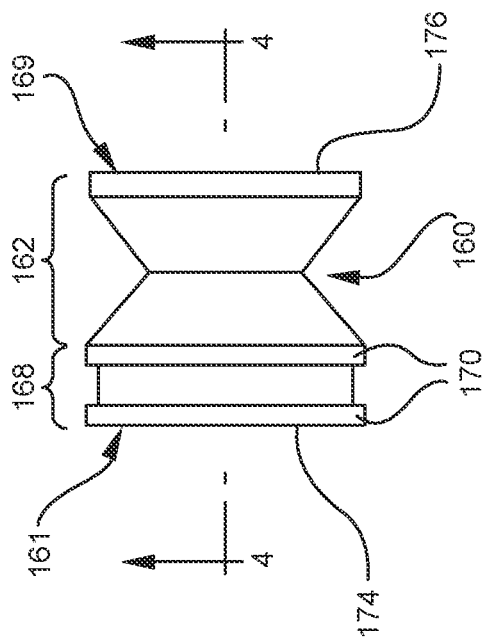
FIG. 3A shows a side elevational view of the stopper illustrated in FIGS. 1 and 2 in a compressed state.
Figure 3B:
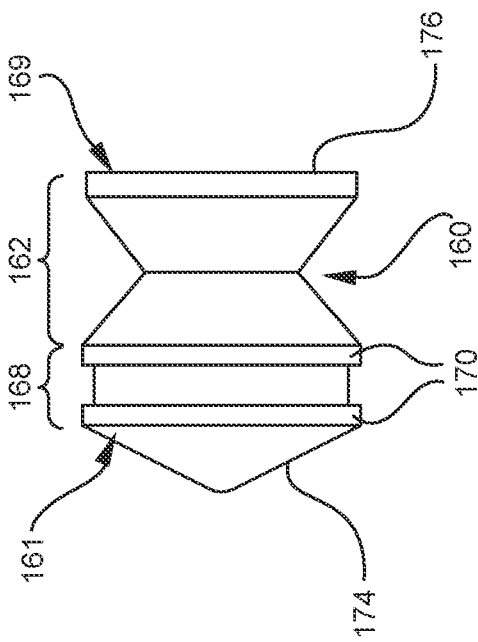
FIG. 3B shows a side elevational view of the a according to an alternative embodiment in a compressed state.
Figure 5:
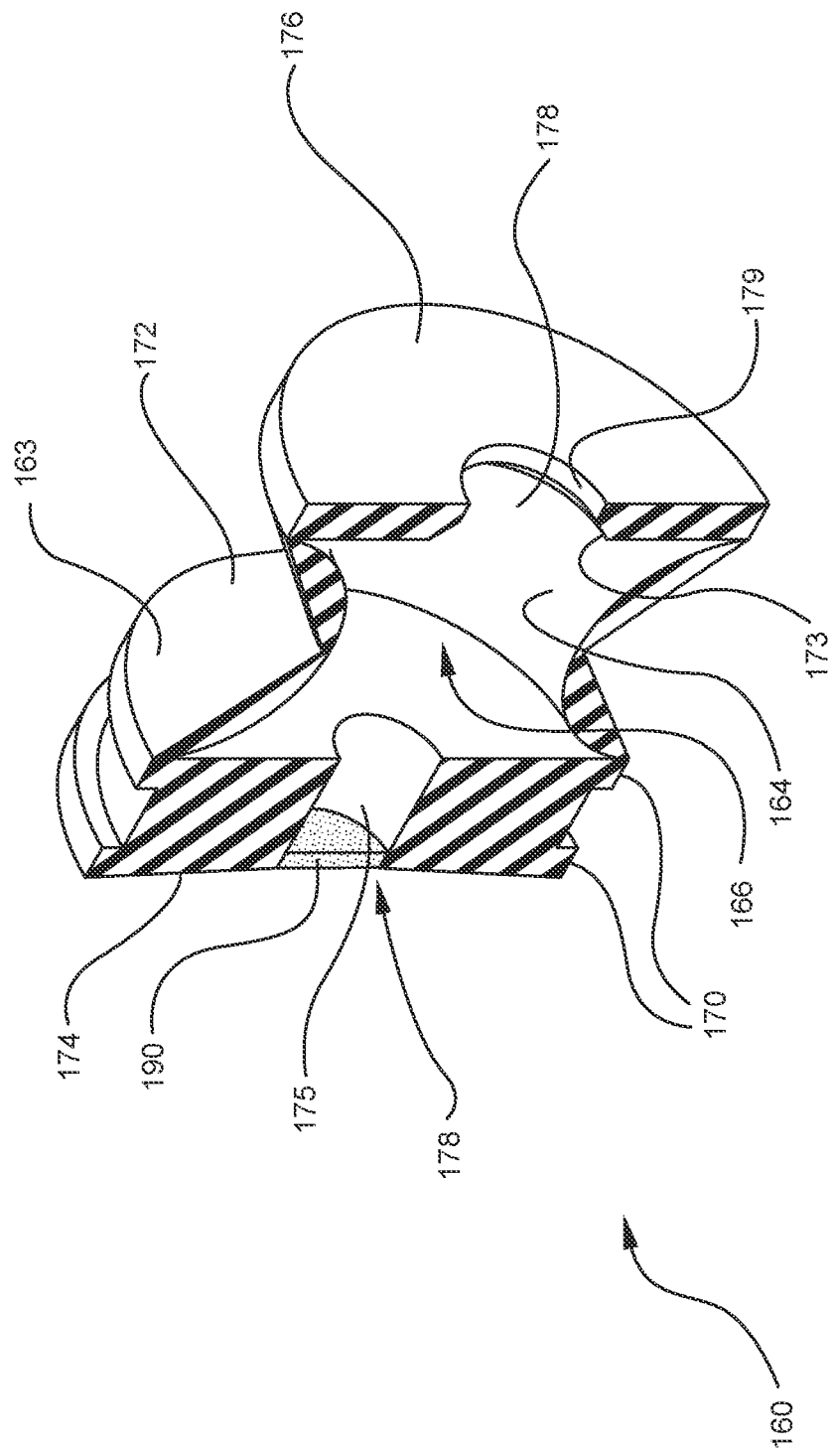
FIG. 5 illustrates a perspective cross-sectional view of the stopper shown in FIG. 4.

As more clearly shown in FIGS. 3-5, the stopper 160 includes a distal end 161 and a proximal end 169. The stopper 160 includes an expandable portion 162 adjacent to the proximal end 169, an outside surface 163 and an inside surface 164 defining a stopper cavity 166. The stopper 160 further includes a sealing portion 168 formed adjacent to the distal end 161. The stopper 160 may be formed from an elastomeric material, polymeric material or other material known in the art. The sealing portion 168 may be formed from an elastomeric material having greater rigidity than the elastomeric material forming the expandable portion 162. The expandable portion 162 may be formed from a compressible elastomeric material, for example, a rubber material. The sealing portion 168 includes at least one peripheral seal 170 shaped to form a fluid-tight seal with the interior surface 116 of a syringe barrel. The embodiments shown in FIGS. 4-6 include two peripheral edges. In one or more embodiments, the peripheral seal 170 may have a circular cross-section for forming a fluid-tight seal with a syringe barrel having an interior surface 116 with a circular cross-section. The sealing portion 168 and/or peripheral seal 170 may be formed from a material suitable for forming a fluid-tight seal with the interior surface 116 of the syringe barrel and may include the same or different material utilized to form the stopper 160.

Figure 7:
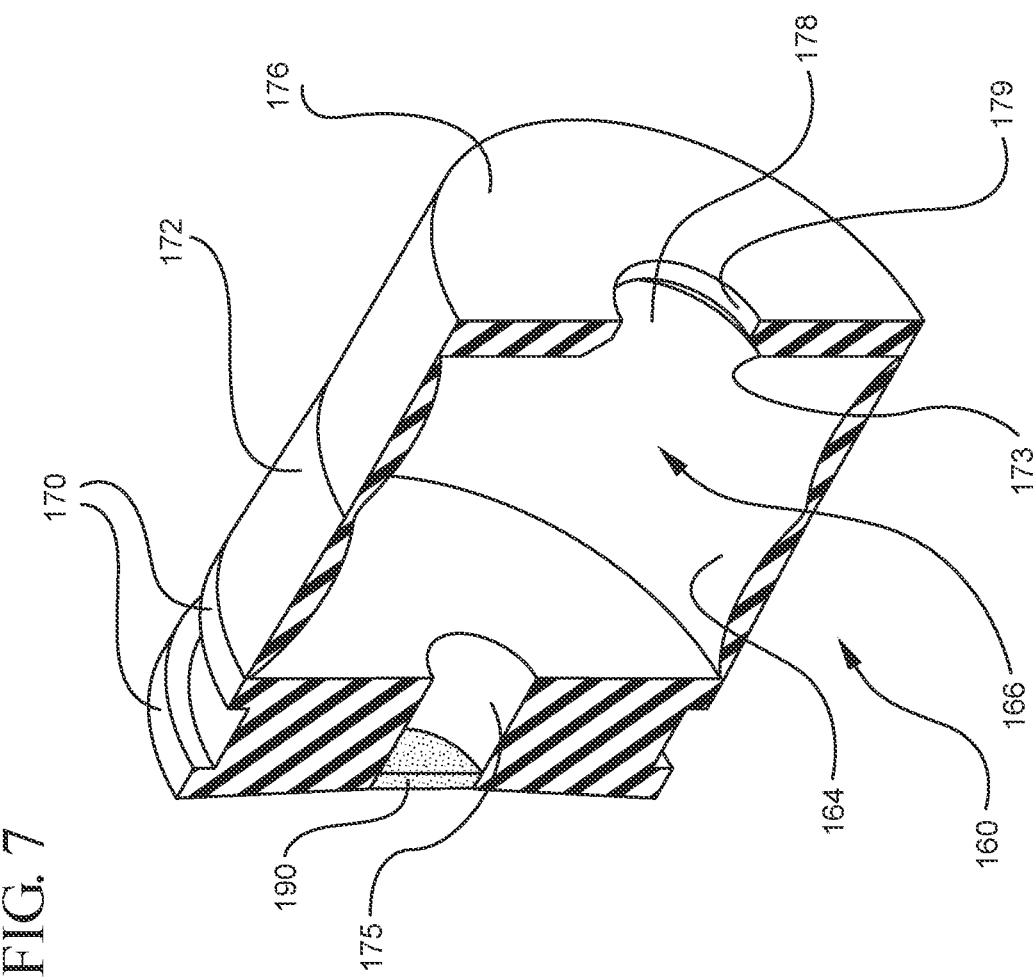
FIG. 7 illustrates a perspective cross-sectional view of the stopper shown in FIG. 6 taken along line 7-7.
Figure 6:
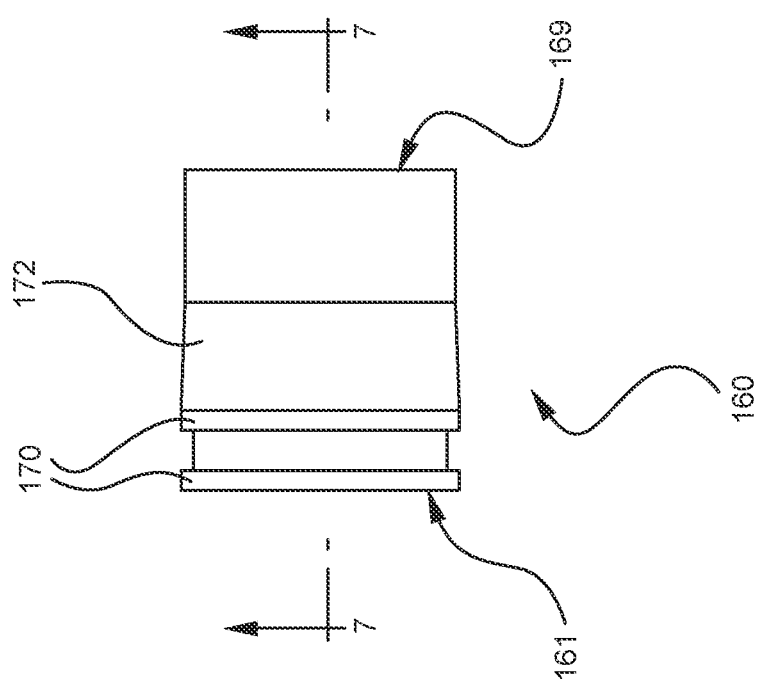
FIG. 6 illustrates a side elevational view of the stopper shown in FIG. 3A in an expanded state.
Figure 8:
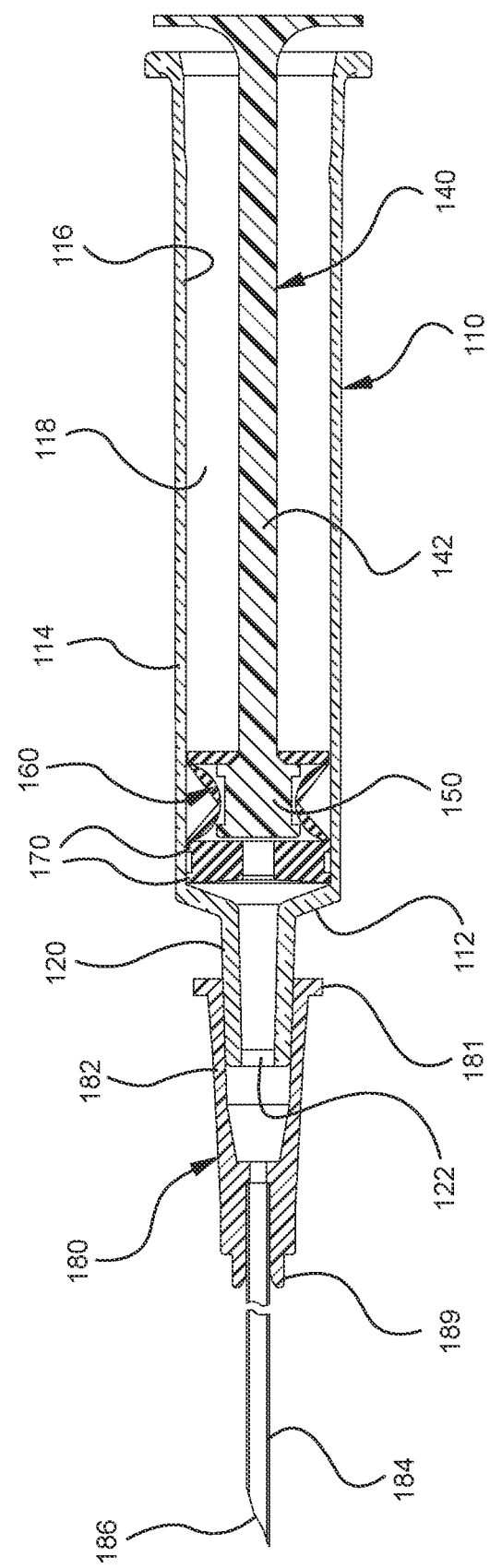
FIG. 8 illustrates a cross-sectional view of the medical device of FIG. 1 taken along line 8-8.
Figure 9:
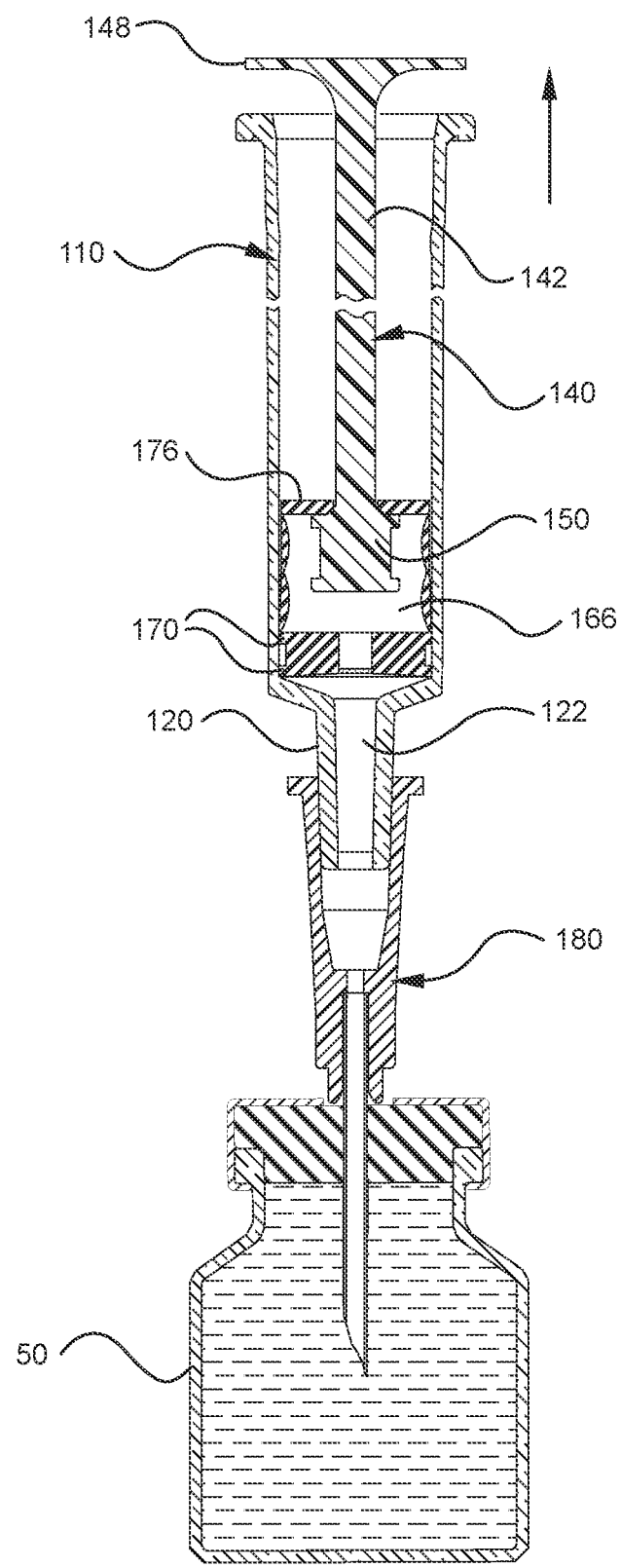
FIG. 9 illustrates a cross-sectional view of the medical device shown in FIG. 8 positioned to draw liquid from a vial after application of an initial force to the plunger rod in the proximal direction.
Figure 12:
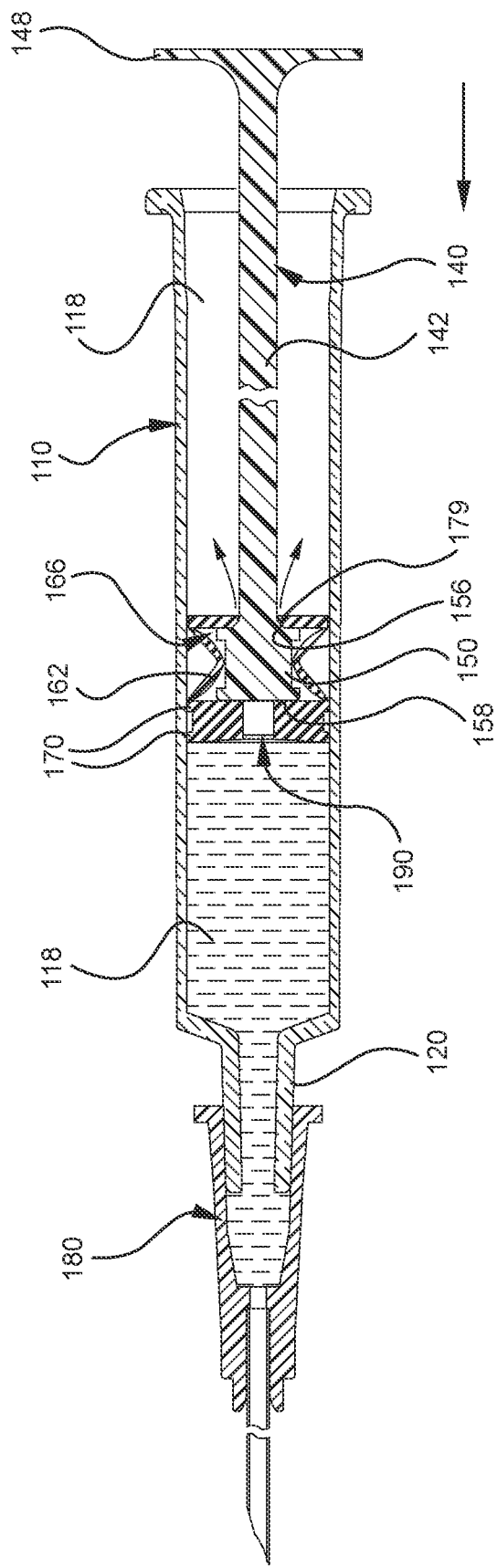
FIG. 12 illustrates air being evacuated from the cavity of the stopper shown in FIG. 11 upon application of an initial force to the plunger rod in the distal direction.
Figure 13:
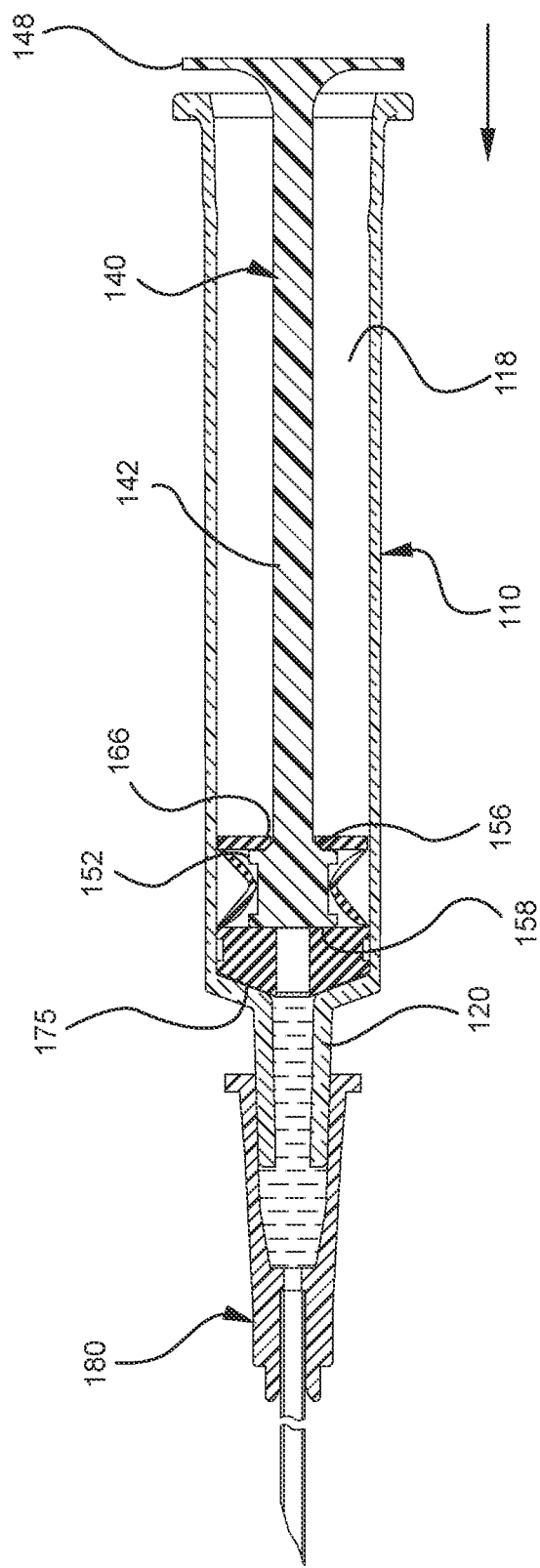
FIG. 13 illustrates the expulsion of the liquid from the syringe barrel upon application of a continuous force to the plunger rod in the distal direction.

In use, the expandable portion 162 is utilized to create a vacuum within the stopper cavity 166 by operating as a positive displacement pump by expanding the stopper cavity 166, which is sealed when the medical device are positioned with the open lumen 186 of the needle cannula 184 is submerged in the liquid to be aspirated into the syringe barrel 110. The pressure differential between the stopper cavity 166 and the chamber 118 draws the air within the chamber 118 into the stopper cavity 166, as will be discussed in greater detail below. To expand the stopper cavity 166, the expandable portion 162 of the stopper 160 includes a bendable wall 172. In the embodiments shown in FIGS. 1-13, the bendable wall 172 includes a single bend or corrugation. In a specific embodiment, the bendable wall 172 may include two or more bends or corrugations. The volume of the stopper cavity 166 expands and contracts as the length of the bendable wall 172 increases and decreases, respectively. Changes in the length and/or cross-sectional width of the bendable wall 172 cause the expandable portion 162 to compress to a compressed state, as shown in FIGS. 3-5, and expand to an expanded state, as shown in FIGS. 6 and 7. As shown in FIGS. 12 and 13, the length and/or cross-sectional width of the bendable wall 172 may decrease as an initial force is applied to the stopper 160 in the distal direction. This occurs, for example, when the plunger rod 140 and stopper 160 are assembled within the chamber 118 of a syringe barrel 110 and an initial force is applied to the plunger rod 140 in the distal direction. The length and/or cross-sectional width of the bendable wall 172 of one or more embodiments may increase as the plunger rod 140 exerts an initial force is applied to the stopper 160 in the proximal direction, for example, during aspiration of a syringe barrel. Alternatively, the length and/or cross-sectional width of the bendable wall 172 may increase as the plunger rod 140 exerts an initial force to the stopper 160 in the distal direction, for example, during expulsion of the liquid from the syringe barrel. The expansion of the length of the bendable wall 172 is shown in FIGS. 8 and 9 and will be discussed in greater detail below.

Alternatively, the bendable wall 172 resists compression after expansion. In one or more embodiments, the bendable wall 172 is molded or formed to have a geometry that creates a spring-like effect or reaction to the application of forces in the distal and/or proximal direction. The expandable portion 162 may be formed from an elastomeric material or other material that has a spring constant to expand and compress during normal operation of the medical device 100 and syringe barrel 110. Specifically, in one or more embodiments, the expandable portion 162 has permits expansion so the user does not experience any significant tactile response to the expansion and/or is not required to take active steps to expand the stopper 160. In one or more embodiments, the spring constant of the expandable portion 162 may be modified depending on the application and the viscosity of the liquid to be aspirated into the syringe barrel 110. The stopper 160 may be provided and assembled with the plunger rod in a compressed state, as shown in FIG. 8. In one or more embodiments, the user may compress the stopper prior to assembly with the plunger rod 140 and the syringe barrel 110 or other container.

In the embodiments shown in FIGS. 3-5, the bendable wall 172 has a single inward bend or single pinched area. The bendable wall 172 is compacted inwardly to reduced length and/or cross-sectional width of the expandable portion 162, reducing the size and/or volume of the stopper cavity 166. Expansion of the bendable wall 172 shown in FIGS. 3-5 is shown in FIGS. 6 and 7, where the single inward bend or single pinched area is expanded or released and the length and/or cross-sectional width of the bendable wall 172 expands to expand the size and/or volume of the stopper cavity 166 from a compressed state to an expanded state. It will be understood the bendable wall 172 may curve inwardly to reduce the length and/or cross-sectional width of the expandable portion 162. Alternatively, the expandable portion 162 may include a collapsible wall (now shown) having more than one telescoping segment that reduce and expand the length and/or cross-sectional width of the expandable portion 162.

According to one or more embodiments, the length and/or cross-sectional width of the expandable portion 162 of the stopper may be pre-defined for specific applications. In one or more embodiments, the length and/or cross-sectional width of the expandable portion 162 may be sized to draw in a pre-defined amount of air trapped within a syringe barrel 110. In a specific embodiment, the length and/or cross-sectional width of the expandable portion 162 may be sized to draw in a pre-defined amount of air trapped within the tip of a syringe. In a more specific embodiment, the volume of the stopper cavity 166 may be sized to hold a pre-defined amount of air trapped within a syringe barrel. In a specific embodiment, the volume of the stopper cavity 166 may be sized to hold a pre-defined amount of air trapped within the tip of a syringe.

The distal end 161 of the stopper 160 includes a distal face 174 including an opening 171 and a porous portion 190 and the proximal end 169 of the stopper 160 includes a proximal wall 176 having an aperture 178 defined by a rim 179. The distal face 174 also includes a conduit 175 in fluid communication with the stopper cavity 166 and the opening 171. In one or more embodiments, the distal face 174 is flexible and flexes concavely and convexly, as will be described in greater detail with reference to FIGS. 8-13. The distal face 174 may also be shaped convexly so that it conforms more closely to the shape of the distal wall 112 of the syringe barrel 110 to expel as much liquid from the chamber 118 as possible. A porous portion 190 is disposed in the conduit 175 and/or opening 171 and in fluid communication with the conduit 175, stopper cavity 166 and the opening 171. In one or more embodiments, the porous portion 190 is air permeable and liquid impermeable. In other words, the porous portion 190 forms a selective barrier that a liquid penetration pressure and an air penetration pressure that is less than the liquid penetration pressure.

The porous portion 190 may have a circular shape. Alternatively, the porous portion 190 may have a square and/or rectangular shape. In one embodiment, the porous portion 190 may be integrally formed or disposed on the distal face 174, adjacent to the opening 171. In a specific embodiment, the porous portion has a cross-sectional width that is smaller than the cross-sectional width of the distal face 174. The porous portion may also be integrally formed and/or disposed adjacent to the conduit 175 on the inside surface 164 of the stopper. In a specific embodiment, the porous portion 190 may have a cross-sectional with that is smaller than the cross-sectional width of the inside surface 164 of the stopper.

The porous portion 190 can be integrally formed on the distal face 174 and covers the opening 171, with the peripheral edges of the distal face 174 and the sealing portion 168 remaining non-porous. In a specific embodiment, the porous portion 190 is separated from the sealing portion 168 by the distal face 174. In a more specific embodiment, the porous portion 190 is separated from the sealing portion 168 by the peripheral seal 170.

The porous portion may also be shaped to fit within the opening 171 and form a fluid-tight engagement with the opening. For example, the porous portion may extend from the distal face 174 into the conduit 175. In one or more embodiments, the porous portion 190 may have a periphery that is molded to a portion of the distal face 174. In one or more embodiments, the porous portion 190 may be attached to the distal face 174 of the stopper by mechanical means, for example, adhesives and/or molding. In a specific embodiment, the distal face 174 may include a pocket (not shown) for securing the porous portion 190 adjacent to the distal face 174 and the opening 171.

The porous portion 190 may include a hydrophobic filter, swellable polymer, other materials that are air permeable and liquid impermeable and/or combinations thereof, as described above.

Referring to FIGS. 1-13, the medical device 100 includes a structure for venting the air evacuated through the porous portion 190 from the medical device 100 and/or syringe barrel 110. The proximal wall 176 of the stopper 160 may include an undercut 173 adjacent the rim 179 that defines the aperture 178. In one or more embodiments, the aperture 178 is sized and/or shaped to permit attachment of the plunger rod 140 to the stopper 160. As shown, the undercut 173 is sized and shaped to form a releasable seal between the plunger rod 140 and stopper 160 and prevent fluid communication between the stopper cavity 166 and the aperture 178. When released, the releasable seal also forms a vent for the evacuated air.

As shown more clearly in FIG. 8, the plunger rod 140 includes a distal end 141, a proximal end 149, and an elongate body 142 extending from the distal end 141 and the proximal end 149. The plunger rod 140 may be made of a rigid plastic or other material that has a greater rigidity than the stopper 160. Examples of such materials include polypropylene, polyethylene, polycarbonate and combinations thereof. As illustrated in FIG. 8, the elongate body 142 may be cylindrical. The shape of the elongate body 142 may be rectangular, or may be formed by two perpendicularly intersecting beams.

The proximal end 149 of the plunger rod 140 includes an optional thumbpress 148. The distal end 141 of the plunger rod 140 includes a stopper-engaging portion 150. In accordance with one or more embodiments of the present invention, the stopper-engaging portion 150 is shaped to fit within the stopper cavity 166 of the stopper 160 and to retain the stopper 160 at the distal end 141 of the plunger rod. In a specific embodiment, the plunger rod 140 and stopper 160 may be integrally formed or permanently attached, while allowing the stopper 160 to expand and compress.

The stopper-engaging portion 150 has a size and shape to allow a slidable engagement between the plunger rod 140 and the stopper 160. Specifically, the stopper-engaging portion 150 of the plunger rod may be able to slide distally and proximally within the stopper cavity 166 of the stopper 160, while maintaining the attachment or engagement between the plunger rod 140 to the stopper 160.

Figure 9A:
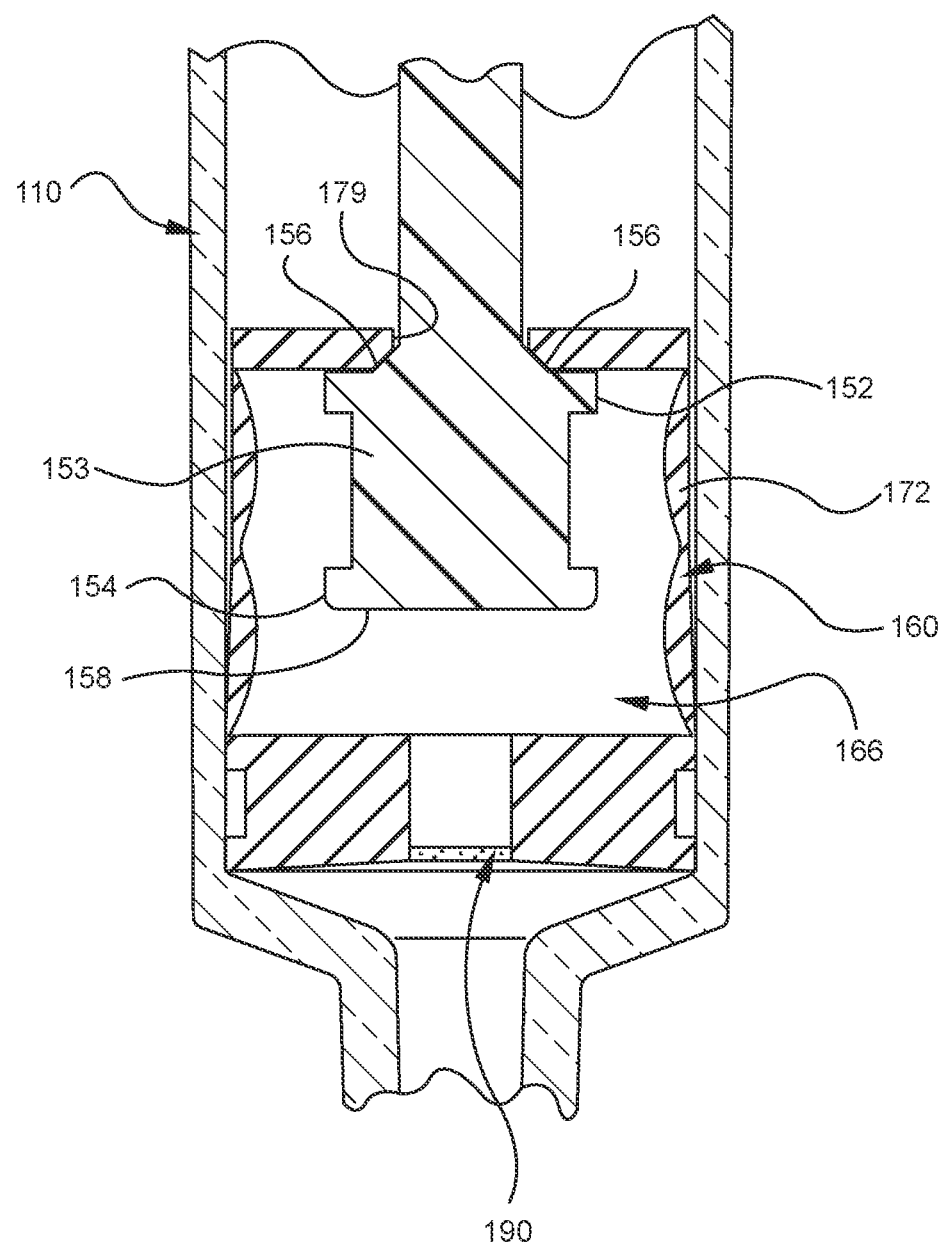
FIG. 9A is an enlarged partial view of the stopper and stopper-engaging portion shown in FIG. 9.

In the embodiment more clearly shown in FIGS. 9 and 9A, the stopper-engaging portion 150 includes a tapered neck portion 156 distally adjacent the elongate body 142 of the plunger rod 140. A first protrusion 152 is positioned distally adjacent the tapered neck portion 156, a boss member 153 distally adjacent the first protrusion 152 and a second protrusion 154 distally adjacent the boss member 153. The first protrusion 152 has a cross-sectional width to prevent separation of the plunger rod 140 from the stopper 160 and, more specifically, the separation between the plunger rod 140 from the rim 179 of the stopper 160. The second protrusion 154 includes a perpendicular face 158, which have a cross-sectional width equal to or greater than the cross-sectional width of opening 171 and/or the porous portion 190 to block the air evacuated into the stopper cavity 166 from entering the chamber 118 of the syringe barrel 110 or other container during expulsion of the aspirated liquid from the syringe barrel 110. In such embodiments, the second protrusion 154 blocks or covers the opening 171 and/or porous portion 190 and forces the air within the stopper cavity 166 of the stopper to escape through the aperture 178 when the releasable seal between the tapered neck portion 156 of the plunger rod and rim 179 and/or undercut 173 of the stopper 160 is released.

The first and/or second protrusions 152, 154 may be disc shaped. The first and/or second protrusions 152, 154 may have a rectangular or square cross-section. Alternative constructions may provide a variety of shapes, which may be identical to each other or different from each other. The first protrusion 152 may be shaped to prevent separation of the plunger rod from the stopper. The second protrusion 154 may be shaped to prevent air that has already been evacuated into the stopper cavity 166 from entering the chamber 118 through the porous portion 190, for example, as a force in the distal direction is applied to the plunger rod to expel the liquid from within the chamber 118.

Figure 11:
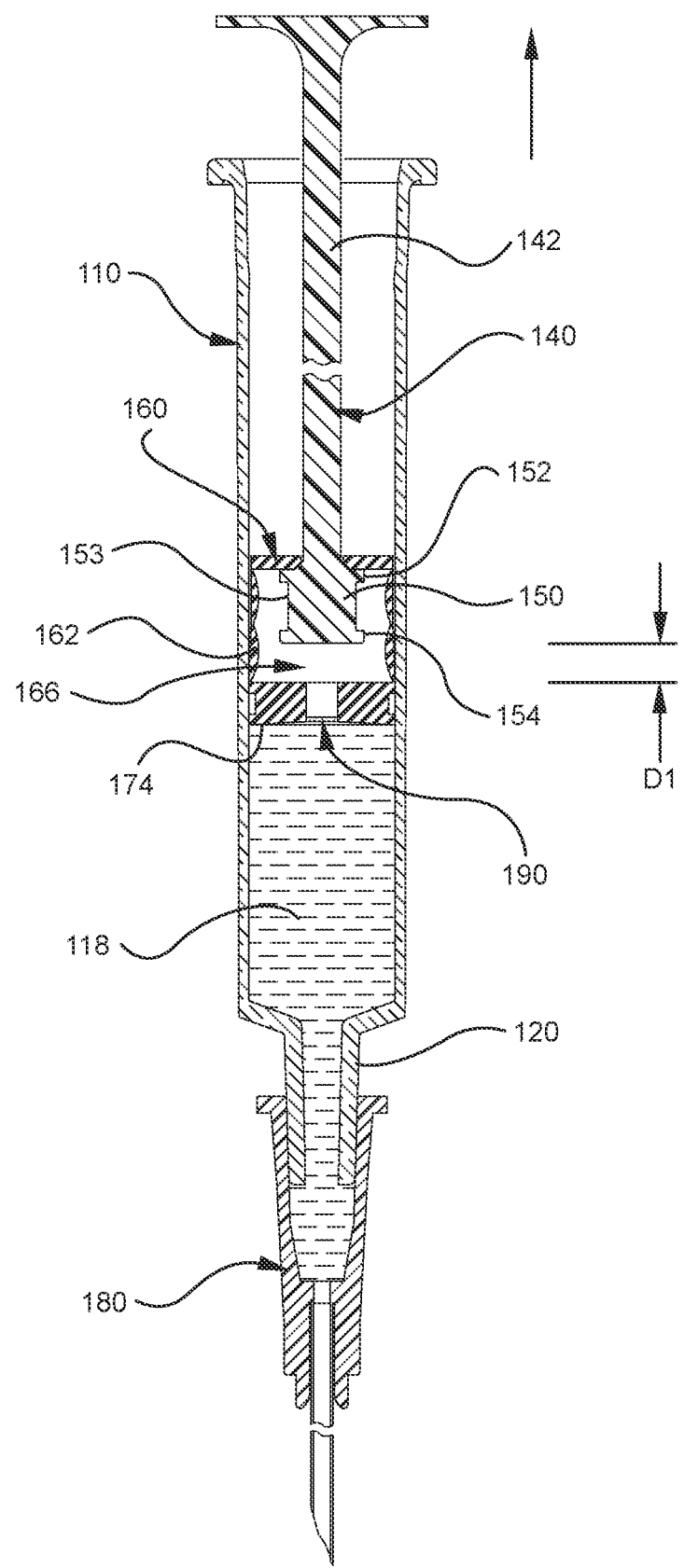
FIG. 11 illustrates the medical device shown in FIG. 10 after air is evacuated from the syringe barrel into the stopper cavity and as the continuous force is applied to the plunger rod in the proximal direction.

The boss member 153 and/or the stopper 160 have a length that permits the stopper-engaging portion 150 to move distally and proximally within the stopper cavity 166 of the stopper 160 a pre-selected axial distance D1 relative to the stopper 160, as shown more clearly in FIG. 11. In a specific embodiment, the boss member 153 has a length that permits such movement of the plunger rod 140 without separation of the plunger rod 140 from the stopper 160. In one or more embodiments, the movement of the plunger rod 140 for the length D1 relative to the stopper 160 permits the plunger rod 140 and the first protrusion 152 to exert enough force on the inside surface 164 of the stopper to facilitate the expansion of the expandable portion 162 of the stopper. The cross-sectional width and length of the boss member 153 may be sized to allow the stopper-engaging portion 150 to fit within the stopper cavity 166 of the stopper 160 when the stopper 160 is an unexpanded or compressed state.

The tapered neck portion 156 of the stopper-engaging portion 150 may be shaped to form a seal with the rim 179 of the stopper 160 at the aperture 178. As will be described more fully below, formation of a seal between the plunger rod 140 and the rim 179 at the aperture 178 of the stopper ensures a vacuum is created between the distal face 174 of the stopper 160 and the chamber 118 of the syringe barrel 110 or other container so that fluid may be aspirated into the chamber 118. In embodiments where the seal is releasable, the structure of the stopper-engaging portion 150 and/or plunger rod 140 prevents the seal from being released during aspiration but permits the release of the seal when the liquid is being expelled from the chamber 118 of the syringe barrel 110 so the air within the stopper cavity 166 may be vented.

In a specific embodiment, the tapered neck portion 156 of the stopper engaging-portion 150 may be shaped to form a releasable seal with the rim 179 at the aperture 178 of the stopper. As shown more clearly in FIG. 9A, the tapered neck portion 156 has a cross-sectional width that increases from the elongate body 142 of the plunger rod to the first protrusion 152. Alternatively, the cross-sectional width of the tapered neck portion 156 increases at the same angle as the angle of the undercut 173 of the stopper 160. In accordance with a specific embodiment, the tapered neck portion 156 is contoured so that at least one portion of the tapered neck portion 156 forms a fluid-tight engagement with the undercut 173 as the plunger rod 140 and stopper 160 move in the proximal direction. In one or more embodiments, the tapered neck portion 156 forms a seal with the rim 179 of the stopper 160 that can be formed and released as the plunger rod 140 moves distally and proximally relative to the stopper 160.

In use, as shown in FIGS. 8-13, the plunger rod 140 and stopper 160 are assembled as medical device 100 and are inserted into the open proximal end 119 of the syringe barrel 110. Before aspirating fluid into the chamber 118 of the syringe barrel 110 or other container, the distal face 174 of the stopper 160 is positioned adjacent to the distal wall 112 of the syringe barrel 110, so the air within the chamber 118 is minimized and is primarily present in the tip 120 of the syringe barrel 110 or other container. In one or more embodiments, the distal face 174 is flexed concavely to further minimize the air within the chamber 118 by applying a force to the plunger rod in the distal direction, prior to aspirating liquid into the chamber 118. In addition, the expandable portion 162 of the stopper 160 is configured to a compressed state (as also shown in FIGS. 3-5 and 8). Before use, the user may compress the stopper before assembly with the plunger rod 140 and the syringe barrel 110 and/or other container.

To fill the chamber 118 of the syringe barrel 110 or other container, the needle cannula 184 is inserted into a container, such as a vial 50, to draw the liquid from a vial into the chamber 118 of the syringe barrel 110, as shown in FIG. 9. Thereafter, a proximally directed force is applied to the plunger rod 140 so that the stopper-engaging portion 150 applies a proximally directed force to the inside surface 164 of the proximal wall 176 of the stopper. The application of this proximally directed force causes or allows the expandable portion 162 to expand to an expanded state, as demonstrated in FIGS. 8, 9 and 9A. The tapered neck portion 156 forms a seal with the rim 179 and undercut 173. The expansion of the expandable portion 162 creates a "spring back" motion that creates a vacuum within the stopper cavity 166 of the stopper 160, drawing air and liquid into the chamber 118. The porous portion 190 of the stopper permits air present within the chamber 118 and/or tip 120 to permeate therethrough into the stopper cavity 166 of the stopper. The vacuum within the stopper cavity 166 draws air and possibly liquid into the chamber 118 prior to the creation of a vacuum within the chamber 118 caused by the movement of the stopper 160 in the proximal direction. The expansion of the expandable portion 162 may draw some liquid into the needle cannula 184 and chamber 118 before the stopper 160 moves, however, the porous portion 190 prevents liquid from permeating through the porous portion 190 into the stopper cavity 166. Expansion of the expandable portion 162 shown in FIGS. 3-5 is shown in FIGS. 6 and 7, where the single inward bend or single pinched area is released and the length and/or cross-sectional width of the bendable wall 172 expands to expand the size or volume of the stopper cavity 166.

Figure 10:
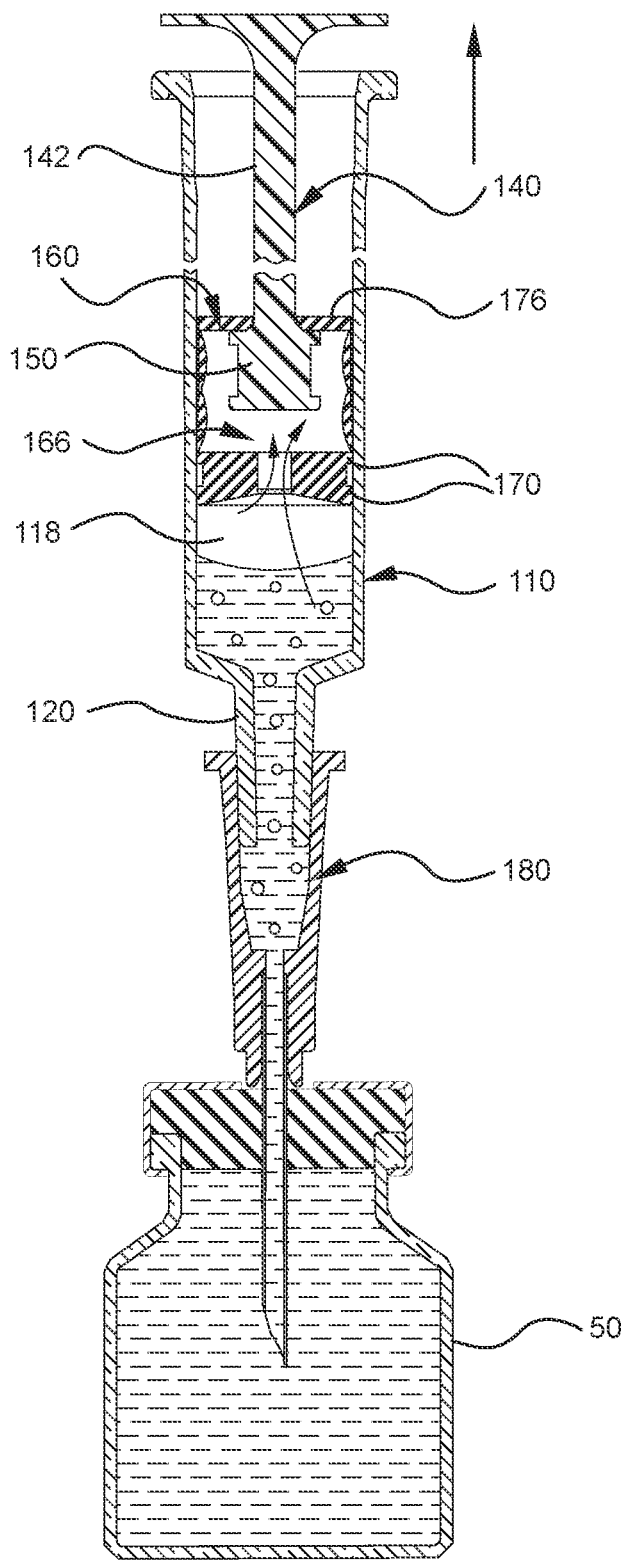
FIG. 10 shows the medical device shown in FIG. 9 drawing liquid from the vial into the syringe barrel upon application of a continuous force to the plunger rod in the proximal direction.

During use, the user may apply a continuous force on the plunger rod 140 and stopper 160 without having to wait for the air to be drawing into the stopper cavity 166 from the chamber 118. As shown in FIG. 10, the continued application of a proximally directed force to the plunger rod 140 during a normal aspiration step causes the plunger rod 140 and stopper 160 to move together in the proximal direction. The peripheral seal 170 of the stopper 160 forms a fluid-tight seal with the interior surface 116 of the syringe barrel 110 or other container and the tapered neck portion 156 continues to form a seal with the rim 179 and undercut 173. The movement of the plunger rod 140 and stopper 160 in the proximal direction creates a vacuum within the chamber 118. The air drawn into the chamber 118 rises above the liquid toward the stopper 160 and permeates through the porous portion 190 into the stopper cavity 166 of the stopper.

In some instances, as shown in FIGS. 9-11, the syringe barrel 110 will be positioned vertically so that the liquid aspirated into the chamber 118 forms a column of liquid and air trapped within the chamber 118 rises to the top of the liquid column. The air then permeates through the porous portion 190 into the stopper cavity 166 of the stopper 160. As this occurs, the liquid forms a column that approaches the porous portion 190 until the air is evacuated from the chamber 118 into the stopper cavity 166 and no air remains in the chamber 118, as shown in FIG. 11. As otherwise described herein, the porous portion 190 prevents the liquid from permeating through the porous portion into the stopper cavity 166. In one or more embodiments, the fluid-tight seal between the peripheral seal 170 and interior surface 116 of the syringe barrel and the application of a proximally directed force to the plunger rod 140 and stopper 160 causes the distal face 174 to flex concavely. As shown in FIG. 10, the concave shape of the distal face 174 during aspiration permits more air to permeate through the porous portion 190 before the liquid reaches the porous portion 190. After the desired amount of liquid is aspirated in to the chamber 118, the porous portion 190 prevents liquid from entering the stopper cavity 166 and the liquid may be expelled from the chamber 118 without taking any additional steps to remove air from the chamber 118.

To expel the liquid contained within chamber 118, a distally directed force is applied to the plunger rod 140, causing the plunger rod 140 to move the pre-selected axial distance D1, as shown in FIG. 11, in the distal direction relative to the stopper while the stopper 160 remains stationary, as shown in FIG. 12. Movement of the plunger rod 140 in the distal direction relative to the stopper 160 releases the proximally directed force that was applied to the inside surface 164 of the proximal wall 176 of the stopper by the plunger rod 140. The release of the proximally directed force on the inside surface 164 of the proximal wall 176 allows the expandable portion 162 of the stopper to collapses or compress into an unexpanded state. Thereafter, the plunger rod 140 and stopper 160 to move together in the distal direction. The peripheral seal 170 of the stopper 160 continues to form a fluid tight seal with the interior surface 116 of the syringe barrel 110. As the aspirated liquid is expelled, the expandable portion 162 of the stopper 160 remains collapsed or compressed in an unexpanded state.

In embodiments where the seal formed between the rim 179 at the aperture 178 of the stopper and tapered neck portion 156 of the plunger rod is releasable, the movement of the plunger rod 140 in the distal direction relative to the stopper 160, which is stationary, releases the seal and allows the air contained within the stopper cavity 166 to be released through the aperture 178. In a specific embodiment, the distal movement of the plunger rod 140 relative to the stopper 160 permits the perpendicular face 158 of the stopper engaging portion 150 to cover the porous portion 190 and block the conduit 175 and prevent the air contained within the stopper cavity 166 from escaping through the porous portion 190 toward the chamber 118. The position of the perpendicular face 158 over the porous portion 190 forces the air to escape through the aperture 178 or remain within the stopper cavity 166 of the stopper.

In an alternative embodiment, the plunger rod 140 may be locked in a fixed relationship with respect to the stopper after the initial distal movement of the plunger rod 140 relative to the stopper 160. For example, the distal end 161 of the stopper 160 may include a rim or other locking structure (not shown) for retaining the second protrusion 154 of the plunger rod 140. Thereafter, the plunger rod 140 and stopper 160 move together in the proximal and distal directions in a fixed relationship. In such embodiments, the expandable portion 162 of the stopper collapses or compresses to an unexpanded state as the plunger rod 140 and the stopper 160 move together in the proximal and distal directions. In one or more embodiments, the expandable portion 162 of the stopper 160 resists compression so that the air within the stopper cavity 166 does not escape through the porous portion 190 in the distal direction and remains within the stopper cavity 166.

As shown in FIGS. 12 and 13, the continued application of a distally directed force to the plunger rod 140 or continuous movement of the plunger rod 140 and stopper 160 in the distal direction causes the perpendicular face 158 of the stopper-engaging portion 150 to contact the inside surface 164 of the stopper 160 adjacent to the conduit 175 and causes the plunger rod 140 and stopper 160 to move in the distal direction together. In one or more embodiments that utilize a stopper 160 having a distal face 174 that flexes, the application of a continuous and distally directed force to the plunger rod 140 causes the distal face 174 to flex convexly as the distal face 174 contacts the distal wall 112 of the syringe barrel 110. In embodiments which utilize a stopper 160 having a convexly-shaped distal face 174, the distal face 174 conforms more closely to the distal wall 112 upon contact with the distal wall 112. In accordance with one or more embodiments, the convex shape of the distal face 174 forces more liquid out of the chamber 118, allowing more accurate dosing, as shown in FIG. 13.

A second aspect of the present invention pertains to a medical device 200 that utilizes a stopper assembly, including a stopper 260 and a stopper hub 250, wherein the stopper hub 250 utilizes a pump body 253. In one or more embodiments, the pump body 253 includes a bendable wall in the shape of a bellows or having corrugated or accordion-style walls. One or more embodiments according to the second aspect of the present invention are shown in FIGS. 14-25. As used herein, the term "bellows" as used herein is used to describe a structure possessed by what are traditionally referred to as bellows or accordion-style walls. The term "bellows" also includes the alterable structure achieved by repeated corrugations or bends extending around the circumference or perimeter of a body. The term "bellows" also includes other deformable containers or flexible or semi-flexible fluid enclosures or containers that may hold fluid and function as a pump, such as diaphragm devices, springs, and the like.

The medical device 200 shown in FIGS. 14-25 includes a plunger rod 240 attached to stopper hub 250 that is attached or integrally formed to a stopper 260. For illustration, the medical device 200 is shown in use with a container in the form a syringe barrel 210 with a needle cannula 284 attached thereto. As shown more clearly in FIG. 14, the syringe barrel 210 includes an open proximal end 219 and a distal end 211 and a distal wall 212. A sidewall 214 extends from the distal end 211 to the open proximal end 219 and includes an interior surface 216 that defines a chamber 218 for retaining or holding fluids, which may include liquid medication and/or other liquids. The distal end 211 may also include a tip 220 having an open passageway 222 therethrough in fluid communication with the chamber 218. As shown, the distal end 211 of the syringe barrel 210 includes an optional luer fitting 288. The open proximal end 219 of the syringe barrel 210 may include a flange 224. A needle cannula 284 including a lumen 286 or opening therethrough and may be attached to the tip 220 so that the lumen 286 is in fluid communication with the open passageway 222 and the chamber 218. In the embodiments shown in FIGS. 14-23, a needle cannula 284 is attached directly to the tip 220. Alternatively, a needle hub (not shown) may be used to attach a needle to the tip. The interior surface 216 of the syringe barrel 210 may have a smooth surface that is free of any protrusions or depressions. In use, the plunger rod 240, stopper hub 250 and stopper 260 are inserted into the open proximal end 229 of the syringe barrel 210.

Figure 14:
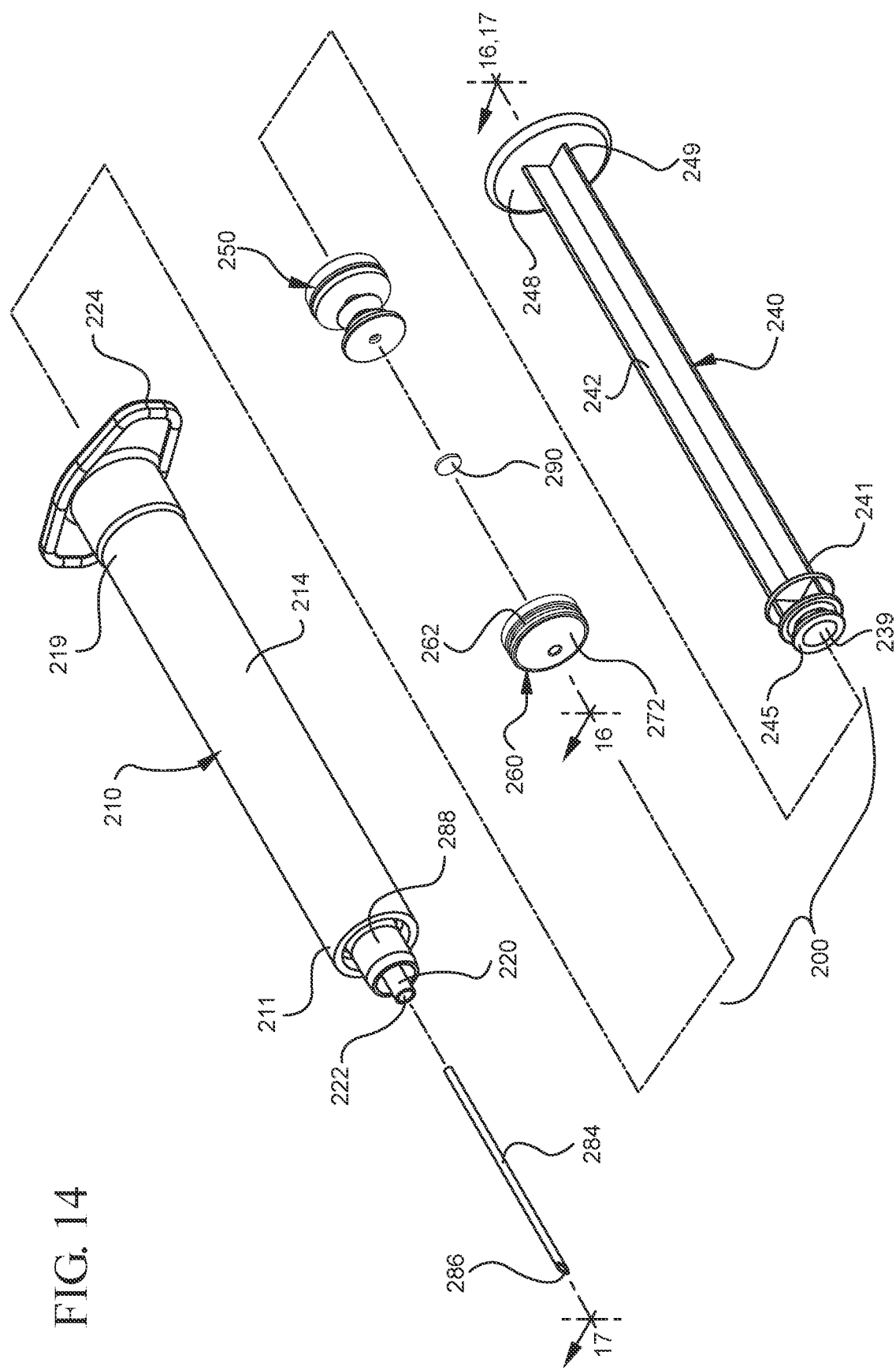
FIG. 14 illustrates a disassembled view of a syringe according to a second aspect of the present invention.
Figure 15:
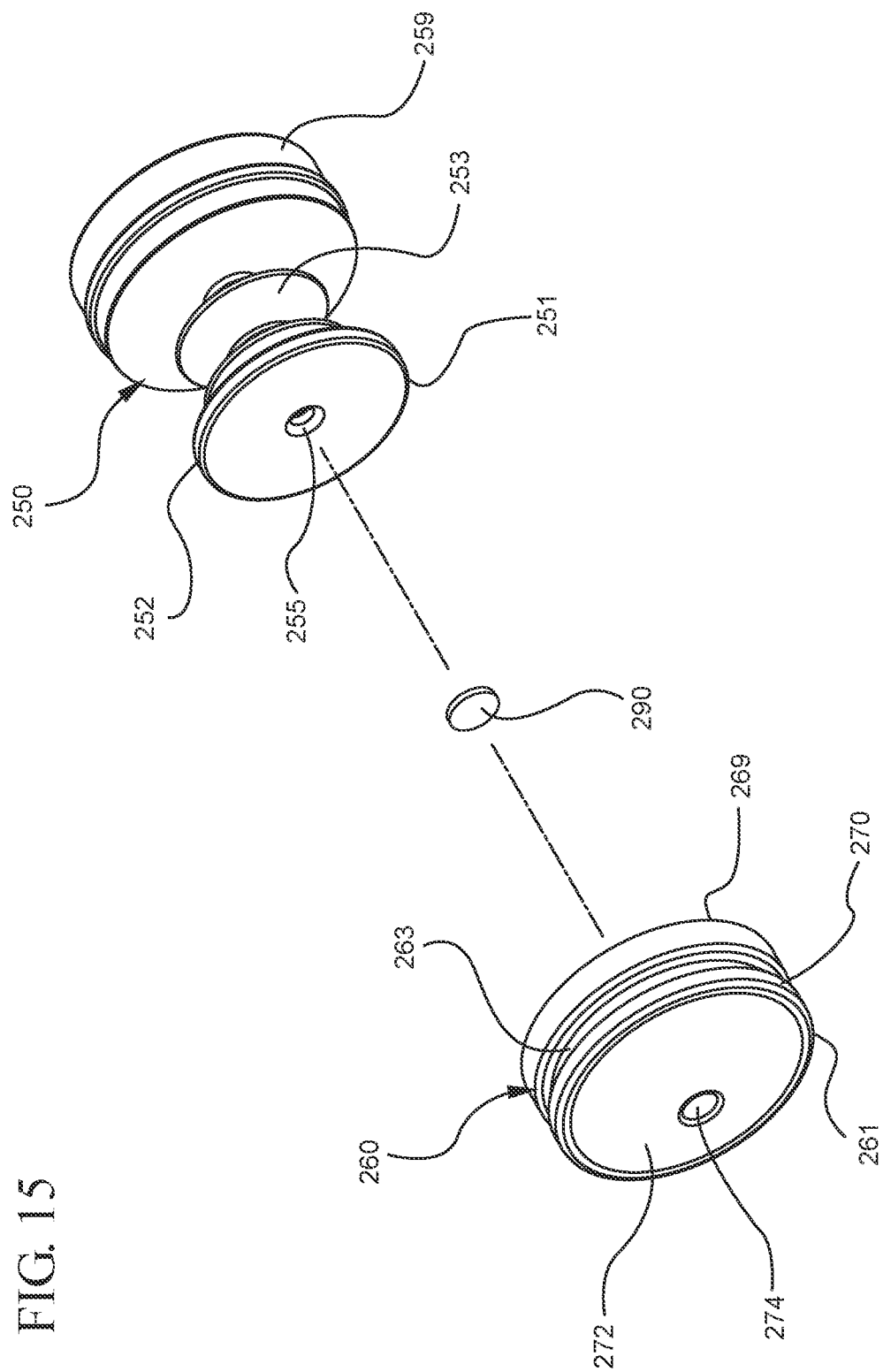
FIG. 15 illustrates an enlarged partial view of the stopper assembly shown in FIG. 14.
Figure 16:
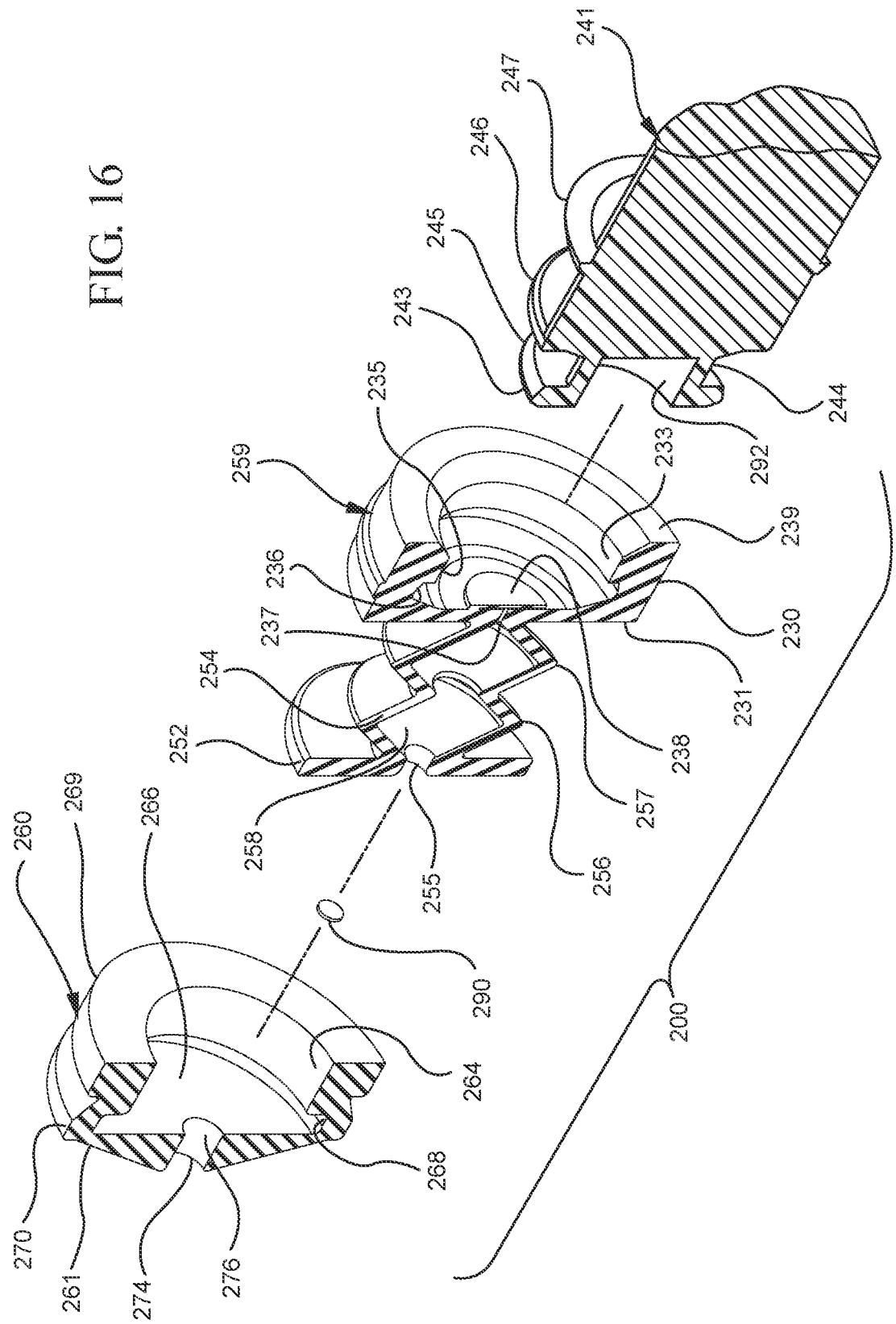
FIG. 16 shows a perspective cross-sectional view of the stopper assembly and a distal end of the plunger rod shown in FIG. 14 taken along line 16A-16A.

As more clearly shown in FIGS. 15 and 16, the stopper 260 includes a distal end 261 and an open proximal end 269. The stopper 260 includes body 262 extending from the distal end 261 to the open proximal end 269, an outside surface 263 and an inside surface 264 defining a stopper cavity 266. In one or more embodiments, the inside surface 264 of the body 262 may include a peripheral channel 268 forming a groove or ridge within the body for engagement with the stopper hub 250, as will be described in detail below and is shown more clearly in FIG. 16. As shown in FIGS. 14-22, the outside surface 263 of the body 262 includes a sealing portion 270. As shown, the sealing portion 270 is disposed on the outside surface 263 adjacent the distal end 261, however, it may also be formed at any location on the outside surface 263 along the length of the body 262. The stopper 260 may be formed from an elastomeric material, polymeric material or other suitable material known in the art. In one or more embodiments, the sealing portion 270 may includes one or more grooves (not shown) shaped to form a fluid-tight seal with the inside surface of a syringe barrel. In one or more embodiments, the sealing portion 270 may have a circular cross-section for forming a fluid-tight seal with a syringe barrel having an interior surface with a circular cross-section. The sealing portion 270 may be formed from a material suitable for forming a fluid-tight seal with the interior surface 216 of the syringe barrel and may include the same or different material utilized to form the stopper 260.

The distal end 261 of the stopper 260 includes a convex distal face 272 having an opening 274 therethrough in fluid communication with the stopper cavity 266. The distal end 261 of the stopper may also include a path 276 in fluid communication with the stopper cavity 266 and the opening 274. As shown in FIGS. 14-25, the distal face 272 may be shaped convexly so that it conforms more closely to the shape of the distal wall 212 of the syringe barrel 210 to expel as much liquid from the chamber 218 as possible. In one or more embodiments, the distal face 272 may be flexible (not shown) and may flex concavely and convexly.

A porous portion 290 is disposed in the path 276 and/or opening 274 and in fluid communication with the path 276, stopper cavity 266 and the opening 274. In one or more embodiments, the porous portion 290 is air permeable and liquid impermeable. In other words, the porous portion 290 forms a selective barrier that a liquid penetration pressure and an air penetration pressure that is less than the liquid penetration pressure.

In one or more embodiments, the porous portion 290 has a circular shape. Alternatively, the porous portion 290 may have a square and/or rectangular shape. In one or more embodiments, the porous portion 290 may be integrally formed or disposed on the distal face 272, adjacent to the opening 274. In a specific embodiment, the porous portion has a cross-sectional width that is smaller than the cross-sectional width of the distal face 272. The porous portion may also be integrally formed and/or disposed adjacent to the path 276 on the inside surface 264 of the stopper. In a specific embodiment, the porous portion 290 may have a cross-sectional with that is smaller than the cross-sectional width of the inside surface 264 of the stopper.

The porous portion 290 may be integrally formed on the distal face 272, with the peripheral edges of the distal face 272 and the sealing portion 270 remaining non-porous. Alternatively, the porous portion 290 is separated from the sealing portion 270 by the distal face 272.

The porous portion 290 may also be shaped to fit within the opening 274 and form a fluid-tight engagement with the opening 274. For example, the porous portion 290 may extend from the distal face 272 into the path 276. The porous portion 290 may have a periphery that is molded to a portion of the distal face 272. In one or more embodiments, the porous portion 290 may be attached to the distal face 272 of the stopper by mechanical means, for example, adhesives and/or molding. In a specific embodiment, the distal face 272 may include a pocket (not shown) for holding and securing the porous portion 290 adjacent to the distal face 272 and the opening 274.

The stopper hub 250 includes an open distal end 251 and an open proximal end 259. The stopper-engaging portion 252 includes an aperture 255 in fluid communication with the stopper cavity 266, path 276 and opening 274. The open distal end includes a stopper-engaging portion 252, which may be provided in the form of a disc extending radially outwardly, for attachment of the stopper hub 250 to the stopper 260. Specifically, as more clearly shown in FIG. 19, the stopper-engaging portion 252 extends radially outwardly to engage the peripheral channel 268 of the stopper 260. In one or more embodiments, the stopper-engaging portion 252 may be in the form of a tab (not shown), which corresponds to an opening or other corresponding structure on the inside surface 264 of the stopper. In a specific embodiment, the stopper-engaging portion 252 may have an opening and the inside surface 264 of the stopper may include a tab extending radially inwardly to engage with the opening of the stopper 260. Other means to engage the stopper hub 250 to the stopper 260 may also be utilized. Alternatively, the stopper 260 may be integrally formed on the distal end 251 of the stopper hub 250 and the stopper 260 and the stopper hub 250 may be provided as a single unit.

The stopper hub 250 includes a pump body 253 and a plunger engaging portion 230 for attaching the stopper assembly to a plunger rod, as will be described in more detail below. The pump body 253 includes a wall 254 defining a pump cavity 258 in fluid communication with the opening 274 and the stopper cavity 266. In use, the pump body 253 is utilized to create a vacuum within the stopper hub 250 and stopper 260 assembly by operating as a positive displacement pump to expand the pump cavity 258 when sealed. The pressure difference between the pump cavity 258 and the chamber 218 and stopper cavity 266 draws air and possibly liquid within the chamber 218 into the pump cavity 258. To expand the pump cavity, the wall 254 is provided in the shape of a bellows or having a plurality of corrugations that can fold into one another to collapse and expand the length of the wall 254. The pump cavity 258 has a volume that varies as the wall 254 expands and collapses.

The wall 254 may be configured to compress and remain compressed upon application of a force on the pump body 253 in the distal direction. The wall 254 may be configured expand and remain in an extended length when no force is being applied the bellows. In this regard, the wall 254 may include a spring-type insert (not shown) that maintains an extended length or expanded state and may require a force to be applied to it to reach a compressed state. The wall 254 may require a continuous force to be applied to it or compressing force to remain in a compressed state. In a more specific embodiment, the wall 254 is formed from an elastomeric material. The elastomeric material can be used to form the wall and may be modified so that the wall 254 possesses a spring constant that allows rapid expansion from a compressed state. The pump body 253 may resist compression after air enters the pump cavity 258.

Figure 17:
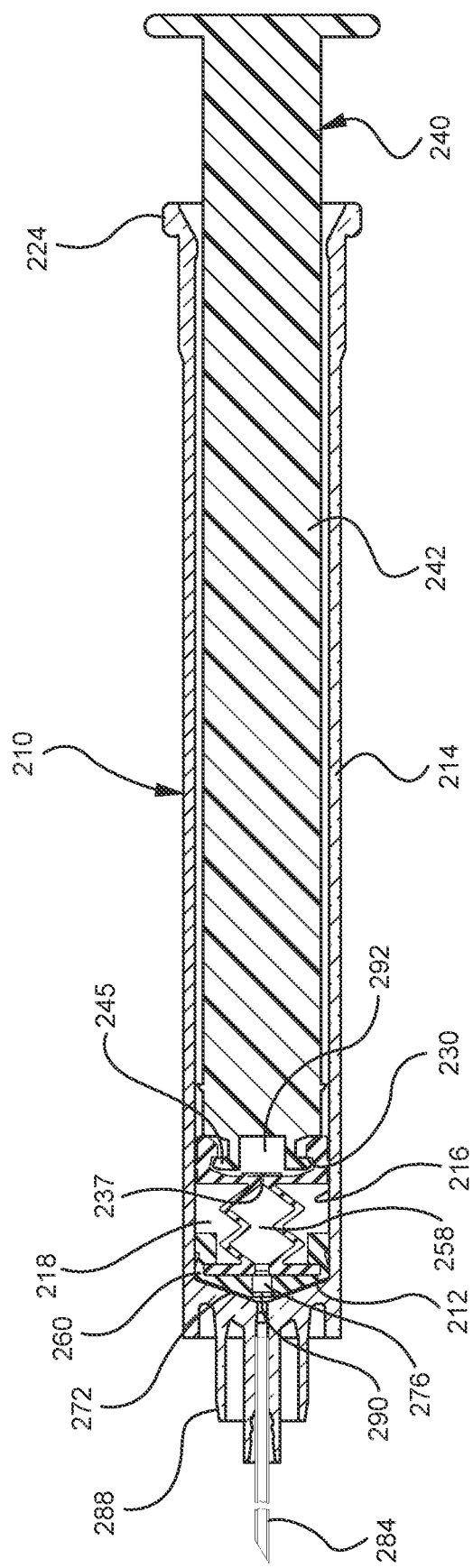
FIG. 17 shows a cross-sectional view of the assembled medical device illustrated in FIG. 14 taken along line 17-17.
Figure 18:
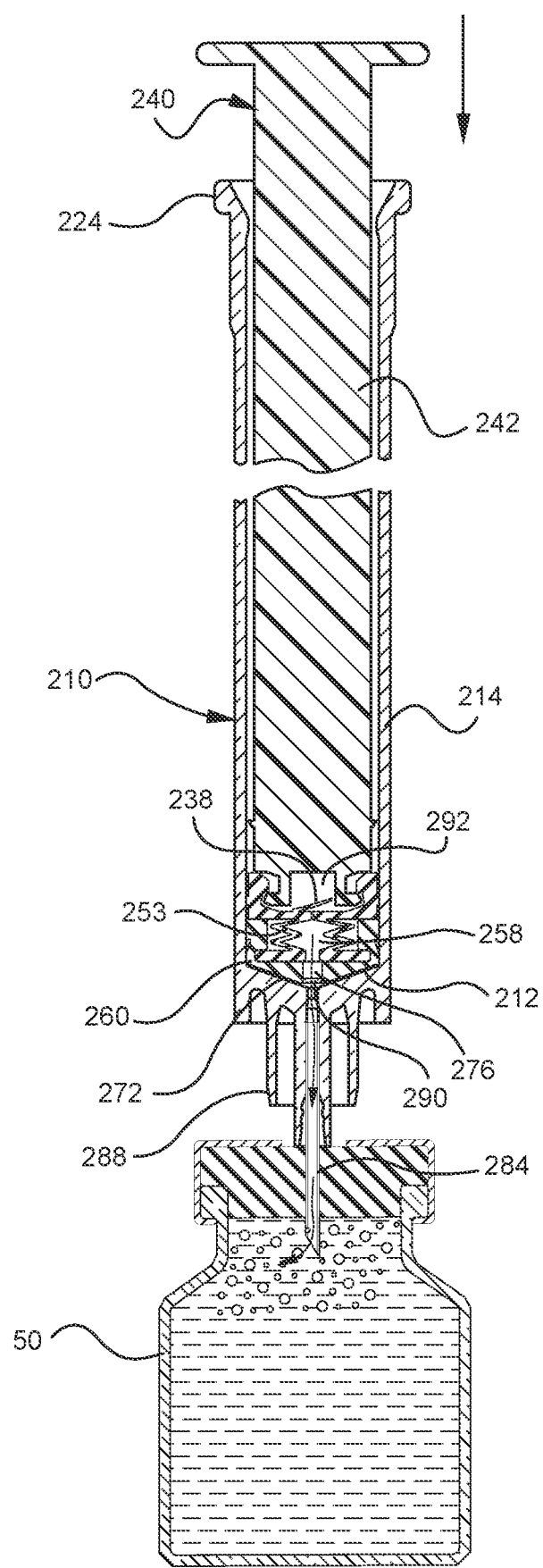
FIG. 18 shows a cross-sectional view of the assembled medical device shown in FIG. 17 upon application of an initial force in the distal direction on the plunger rod.
Figure 19:
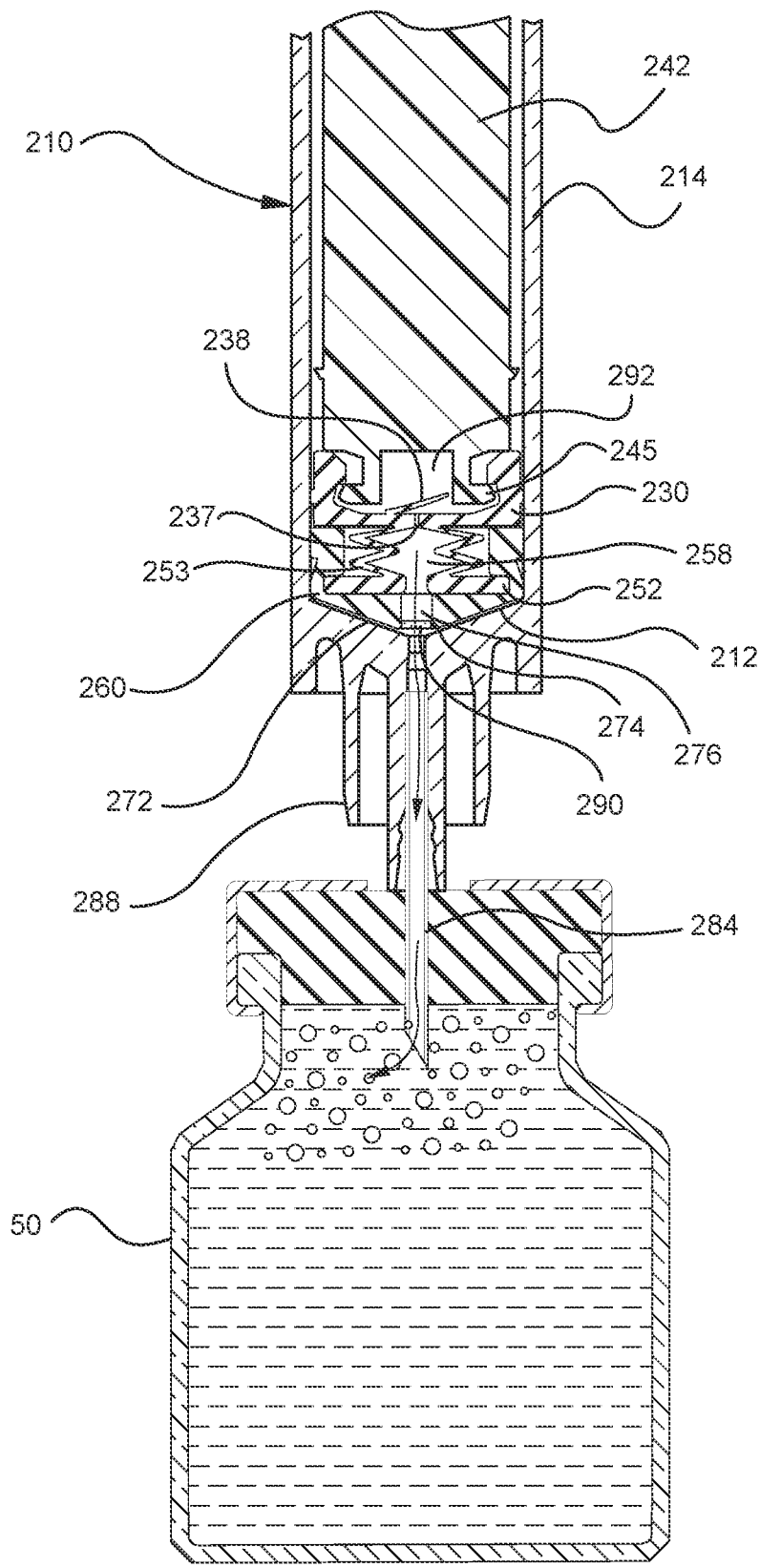
FIG. 19 shows an enlarged partial view of the distal end of the syringe shown in FIG. 18.
Figure 20:
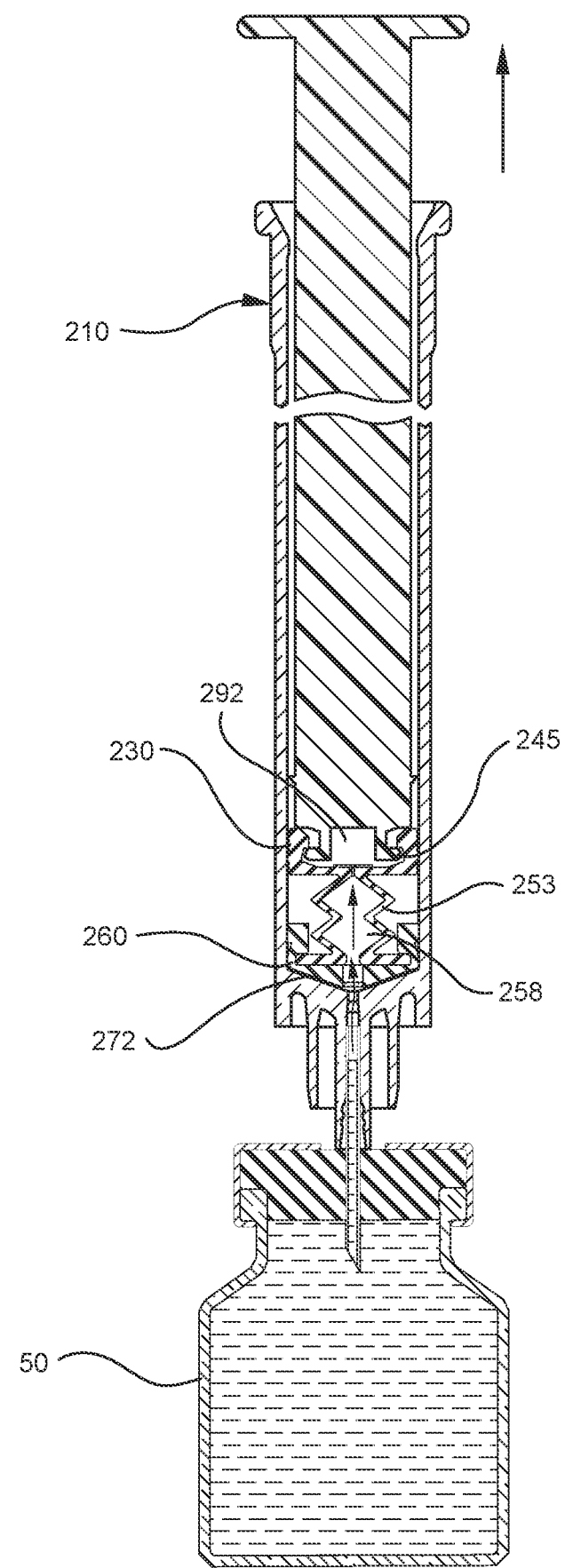
FIG. 20 illustrates a cross-sectional view of medical device shown in FIG. 19 positioned to draw liquid from a vial after application of an initial force to the plunger rod in the proximal direction.
Figure 21:
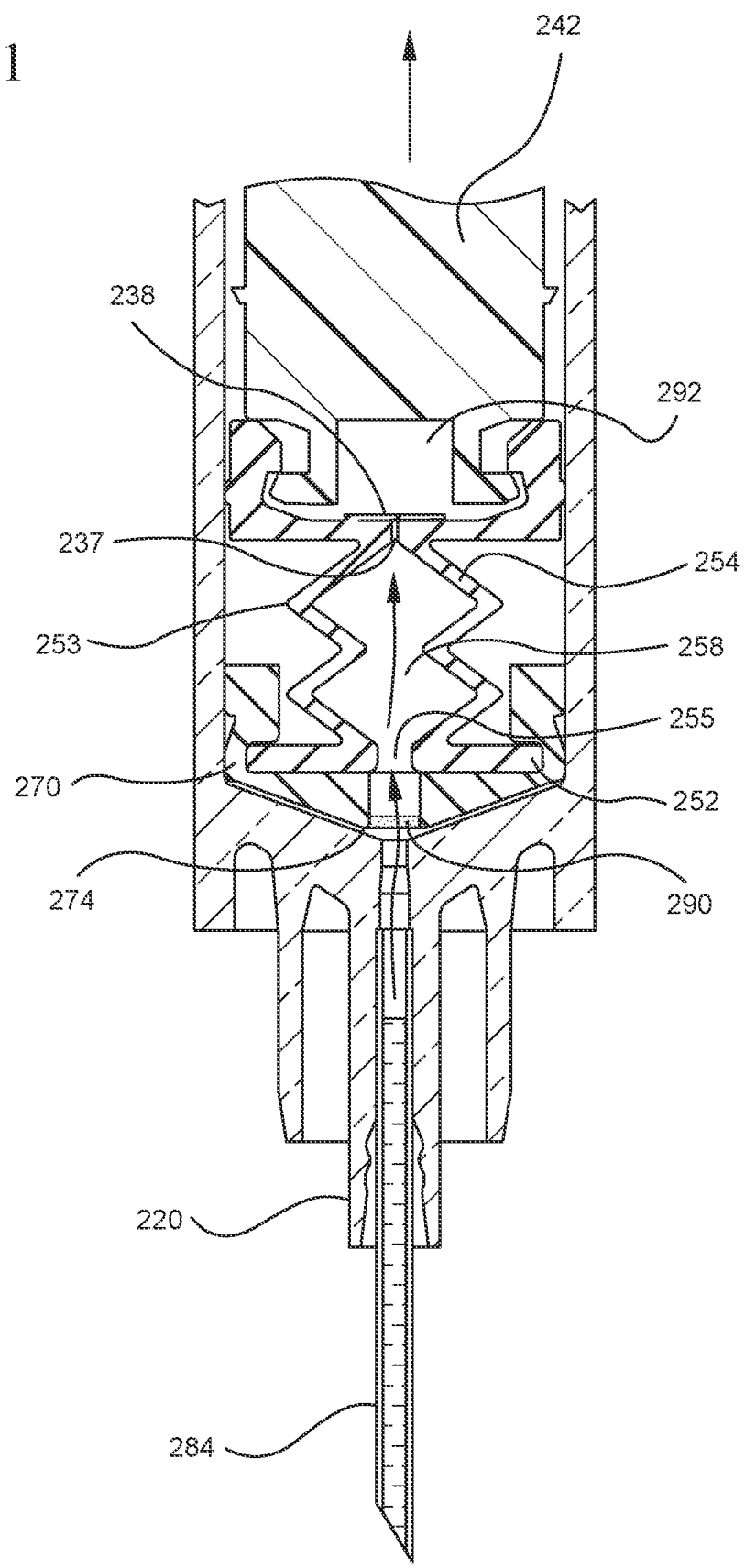
FIG. 21 is an enlarged partial view of the air being evacuated from the cavity of the stopper shown in FIG. 20.
Figure 22:
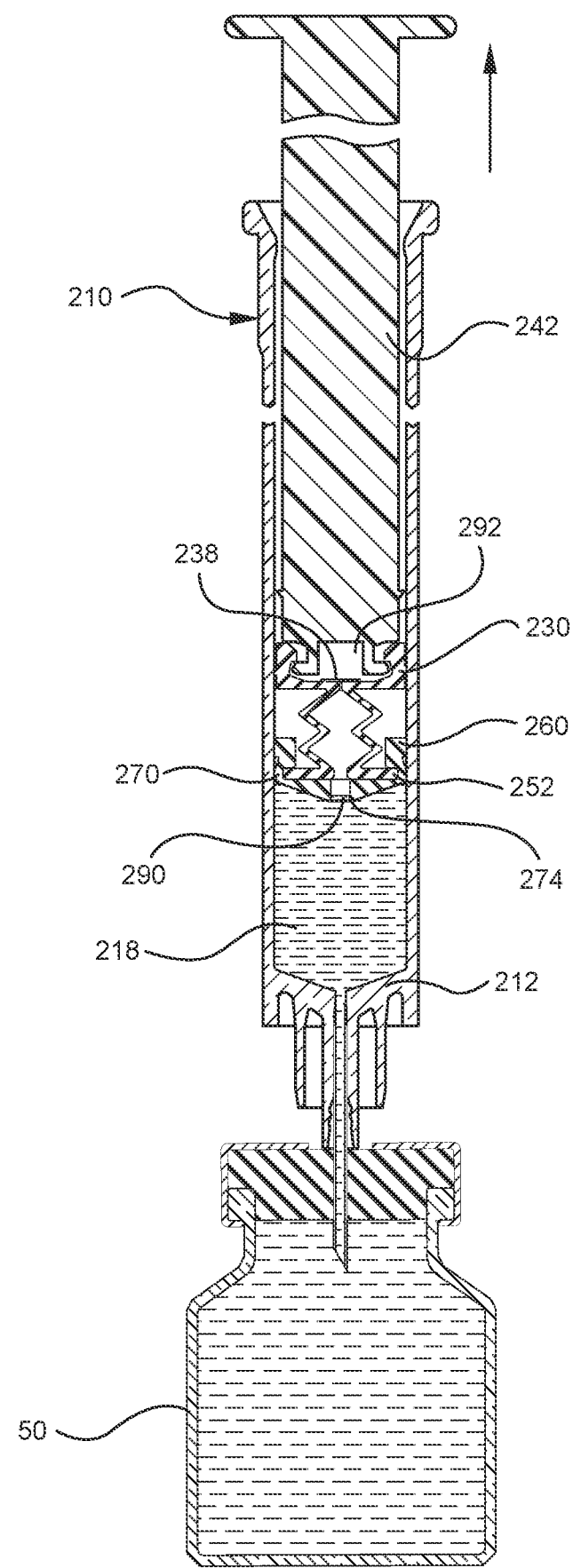
FIG. 22 shows a cross-sectional view of the medical device shown in FIG. 21 drawing liquid from the vial into the syringe barrel upon application of a continuous force to the plunger rod in the proximal direction.

In the embodiments shown in FIGS. 14-25, the wall 254 includes two bends 256, 257 that fold together to shorten or collapse the length of the wall 254 The wall 254 may include more than two bends or corrugations or, alternatively, include a single bend or corrugation. The volume of the pump cavity 258 expands and contracts as the length of the wall 254 increases and decreases. Changes in the length and/or cross-sectional width of the wall 254 cause the pump body 253 to compress to a compressed state and expand to an expanded state, as shown in FIGS. 19 and 20. The length and/or cross-sectional width of the wall 254 may decrease as an initial force is applied to the plunger rod 240 in the distal direction. This occurs, for example, when the plunger rod 240, the stopper hub 250 and the stopper 260 are assembled within the chamber 218 of a syringe barrel 210 and an initial force is applied to the plunger rod 240 in the distal direction to "bottom" or "park" the medical device 200 within the syringe barrel so the distal face 272 is adjacent the distal wall 212 of the syringe barrel. In one or more embodiments, the length and/or cross-sectional width of the wall 254 increases as the force applied to the plunger rod 240 in the distal direction is released. In a specific embodiment, the length and/or cross-sectional width of the wall 254 increases as an initial force is applied to the stopper 260 in the proximal direction, for example, during aspiration of a syringe barrel.

Alternatively, the wall 254 resists compression after expansion. In one or more embodiments, the wall 254 is molded or formed to have a geometry that creates a spring-like effect or reaction to the application of forces in the distal and/or proximal direction. In a specific embodiment, the wall 254 is initially in an expanded state and may require application of a force to be compressed. The wall 254 may be formed from an elastomeric material or other material that has a spring constant to expand and compress during normal operation of the medical device 200 and syringe barrel 210. Specifically, in one or more embodiments, the wall 254 has a spring constant that permits expansion in a rapid manner in a rapid manner so the user does not experience any significant tactile response to the expansion and/or is not required to take active steps to expand the stopper 260. In one or more embodiments, the spring constant of the wall 254 may be modified depending on the application and the viscosity of the liquid to be aspirated into the syringe barrel 210.

As shown in FIGS. 15-16, the wall 254 is compacted inwardly at the two bends 256, 257 to have a reduced length and/or cross-sectional width of the pump body 253, resulting in reducing the size or volume of the pump cavity 258. It will be understood the wall 254 may curve inwardly to reduce the length and/or cross-sectional width of the pump body 253. Alternatively, the pump body 253 may include a collapsible wall (now shown) having more than one telescoping segment that reduce and expand the length of the pump body 253.

The length and/or cross-sectional width of the pump body 253 of the stopper may be pre-determined for specific applications. In one or more embodiments, the length and/or cross-sectional width of the pump body 253 may be sized to draw in a pre-determined amount of air trapped within a syringe barrel. The length and/or cross-sectional width of the pump body 253 may be sized to draw in a pre-determined amount of air trapped within the tip of a syringe. In a more specific embodiment, the volume of the pump cavity 258 may be sized to hold a pre-determined amount of air trapped within a syringe barrel. In a specific embodiment, the volume of the pump cavity 258 may be sized to hold a pre-determined amount of air trapped within the tip of a syringe.

The stopper hub 250 includes a plunger-engaging portion 230 that includes an open distal end 231 and an open proximal end 239 and an inside surface 233 defining a socket 235 configured to frictionally engage the outside surface of the plunger rod 240, as will be described below. As shown in FIG. 16, the socket 235 includes a groove 236 disposed along the inside surface 233 forming a fitting for the distal end of the plunger rod. In one or more embodiments, a plurality of grooves may be disposed along the inside surface 233 for gripping the distal end of the plunger rod 240. In a specific embodiment, the plunger-engaging portion 230 includes one or more indentations (not shown) disposed along the inside surface 233 for receiving the distal end of the plunger rod 240, which may include a plurality of corresponding tabs (not shown) which form a frictional fit with the indentations. Alternatively, the inside surface 233 may have a textured surface or a coating (not shown) that creates or increases frictional interference with the distal end of the plunger rod 240. In another alternative configuration, the plunger rod 240 and stopper hub 250 may be integrally formed or permanently attached using methods know in the art.

The distal end 231 of the plunger-engaging portion includes an outlet 237 and a valve 238. The outlet 237 is in fluid communication with the socket 235. The valve 238 comprises a one-way valve configured to open to permit fluid communication between the pump cavity 258 and the outlet 237. The outlet 237, when sealed, facilitates the formation of a vacuum within the chamber 218 of the syringe. The valve 238 may be in form of any one-way valve or check valve that opens in one direction.

In one or more embodiments, the valve 238 provides a means for venting the air evacuated into the pump cavity 258. In a specific embodiment, the valve 238 provides a relief valve for the pump cavity 258. In one or more embodiments the distal end of the plunger-engaging portion does not include a valve 238 and the outlet 237 is in fluid communication with the pump cavity 258. In a specific embodiment, the distal end of the plunger rod 240 is enclosed and does not include an outlet 237 or a valve 238.

In one or more embodiments which incorporate a valve 238, the valve 238 closes during expansion of the wall 254 and seals the outlet 237 from the socket 235. During compression or when the wall 254 is collapsing, the valve 238 opens. In one or more embodiments, the valve 238 is in the form of a flap.

In use, a plunger rod 240 is attached to the proximal end 259 of the stopper hub. The plunger rod 240 shown more clearly in FIG. 14 includes a distal end 241, a proximal end 249, and an elongate body 242 extending from the distal end 241 and the proximal end 249. The plunger rod 240 may be made of a rigid plastic or other material that has a greater rigidity than the stopper 260. Examples of such materials include polypropylene, polyethylene, polycarbonate and combinations thereof. The elongate body 242 may be cylindrical. In one or more embodiments, the shape of the elongate body 242 may be rectangular or other shape. The proximal end 249 of the plunger rod 240 includes an optional thumbpress 248. The body 242 may include a cavity (not shown), which may be in fluid communication with the pump cavity 258.

The distal end 241 of the plunger rod includes a structure for engaging the stopper hub 250. As shown in FIGS. 14 and 16, the distal end 241 of the plunger rod includes such a structure for engaging the stopper hub 250 in the form of a distal portion 245, having a disc-shaped plug 243 disposed perpendicularly to the elongate body 242 of the plunger rod. In one or more embodiments, the disc-shaped plug 243 may include a beveled adjacent to the distal end 241 of the plunger rod. In a specific embodiment, the disc-shaped plug 243 includes one beveled edge disposed on the distal side of the plug 243 and one beveled edge on the proximal side of the plug 243. The beveled edge may be formed around the periphery of the disc-shaped plug 243. The distal end 241 of the plunger rod 240 may include an optional a neck portion 244 proximally adjacent to the disc-shaped plug 243 disposed between the disc-shaped plug 243 and the distal portion 245. The plunger rod 240 may also include two peripheral ribs 246, 247 disposed along the elongate body 242 and positioned proximally adjacent the neck portion 244. In one or more embodiments, the plunger rod 240 may not include a neck portion 244 and the disc-shaped plug 243 may be formed at the distal end of the plunger rod 240 adjacent to the elongate body 242. As shown in FIG. 16, the distal portion 245 includes a recess 292 allowing space for the valve 238 to open, as will be described below.

In use, as shown in FIG. 17, the plunger rod 240 including a recess, stopper hub 250 and stopper 260 are assembled as a medical device 200 and are inserted into the open proximal end 219 of the syringe barrel 210. Before aspirating fluid into the chamber 218 of the syringe barrel 210 or other container, the distal face 272 of the stopper 260 is positioned adjacent to the distal wall 212 of the syringe barrel 210, so that the air within the chamber 218 is minimized and is primarily present in the tip 220 of the syringe barrel 210 or other container.

In the assembled state, the stopper hub 250 and the plunger rod 240 form a unitary piece that moves together distally and proximally within the chamber. The wall 254 causes the stopper 260 to remain stationary with respect to movement of the plunger rod 240, as the length of the stopper hub 250 is elongated or expanded.

As shown in FIG. 17, the wall 254 is in an expanded state before use. To create a vacuum within the pump cavity 258, which causes the evacuation of air from the syringe, an initial distally directed force is applied to the plunger rod 240, as shown in FIGS. 18 and 19. The user may insert the needle cannula 284 into a vial and submerge it into the liquid applying the force to the plunger rod 240 in the distal direction to compress the wall 254. The compression of the wall 254, after inserting the needle cannula 284 into vial 50, causes air within the pump cavity 258 to escape through the needle cannula 284 and lumen 286 and also possibly through the open valve 238, which opens during compression of the wall 254, as shown in FIGS. 18 and 19.

Alternatively, the user may apply a force in the distal direction to the plunger rod 240 and compress the wall 254 prior to inserting the needle cannula 284 into the vial 50 (not shown). The user would continue to apply the distally directed force on the plunger rod 240 and then submerge the lumen 286 in the liquid contained within the vial. The compression of the wall 254 prior to inserting the needle cannula 284 into vial 50, causes air within the pump cavity 258 to escape through the lumen 286 and the open valve 238 and outlet 237, which opens during compression of the wall 254.

After submerging the lumen 286 into the liquid contained within the vial 50, the user releases the force applied to the plunger rod 240 in the distal direction. The spring constant and properties of the wall 254 cause the wall 254 to expand from the compressed state to an expanded state upon the release of the force applied on the plunger rod 240 in the distal direction. The release of the force applied to the plunger rod 240 also causes the stopper 260 to remain stationary and causes the plunger rod 240 to move proximally, as the length of the wall 254 expands. The expansion of the pump cavity 258 creates a vacuum within the pump cavity 258, which causes the valve 238 to close, as shown more clearly in FIGS. 20 and 21.

The expansion of the pump cavity 258 causes any air present within the needle cannula 284 and the syringe barrel 210 to be evacuated into the pump cavity 258, through the porous portion 290 of the stopper 260. In one or more embodiments, the expansion of the pump cavity 258 may cause some liquid to be drawn into the tip 220 and/or chamber 218 prior to the formation of a vacuum within the chamber 218 caused by movement of the stopper 260 in the proximal direction. The porous portion 290 prevents this liquid from entering the stopper cavity 266, as will be described below.

As shown in FIG. 23, to actively aspirate the desired amount of liquid into the syringe barrel 210, the user applies a proximally directed force on the plunger rod 240 or, more specifically, the thumbpress 248, which draws the liquid from the vial 50 into the needle cannula 284 and into the chamber 218. The valve 238 remains closed and the vacuum within the pump cavity 258 is maintained and continues to draw any air present in the chamber 218 into the pump cavity 258. In use, the movement of the plunger rod 240 relative to the stopper 260, when the wall 254 is expanded, and movement of the plunger rod 240, stopper hub 250 and stopper 260 together in the proximal direction occurs as part of a continuous aspiration stroke that is similar to an aspiration stroke using conventional syringes known in the art.

Figure 23A:
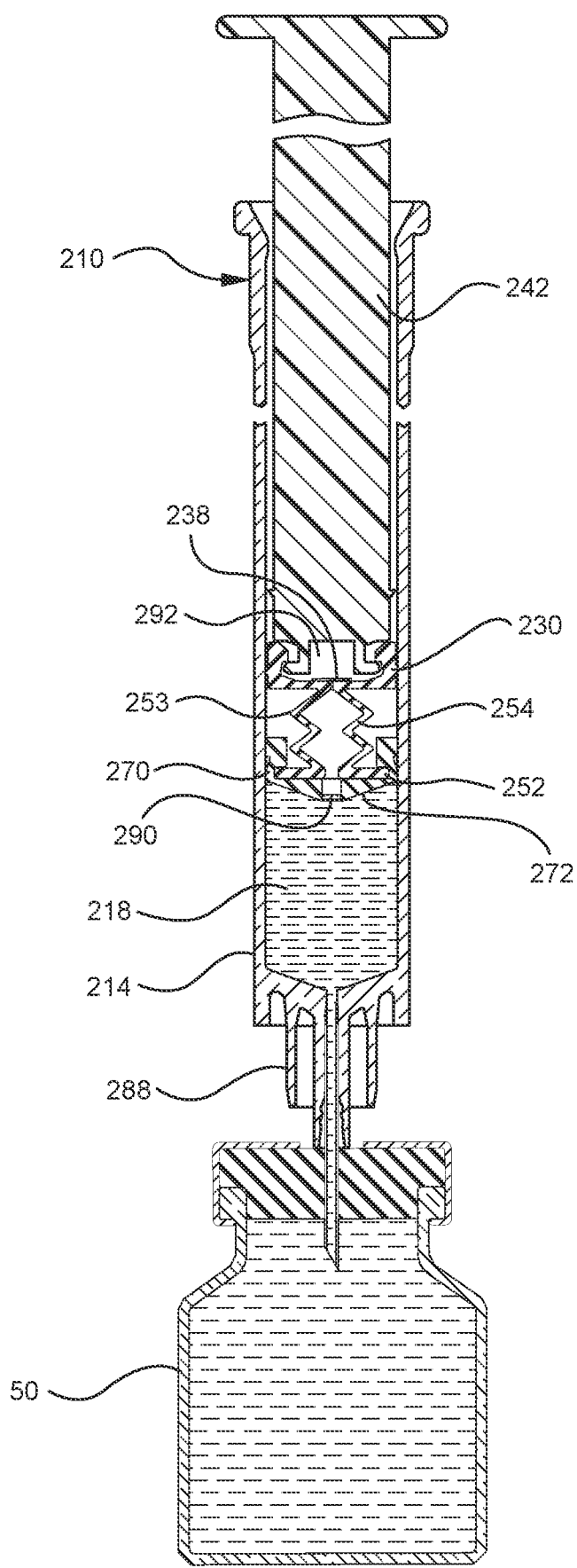
FIG. 23A illustrates a cross-sectional view of the medical device shown in FIG. 21A filled with liquid from the vial prior to the expulsion of the liquid from the syringe barrel upon application of a continuous force to the plunger rod in the distal direction.
Figure 23B:
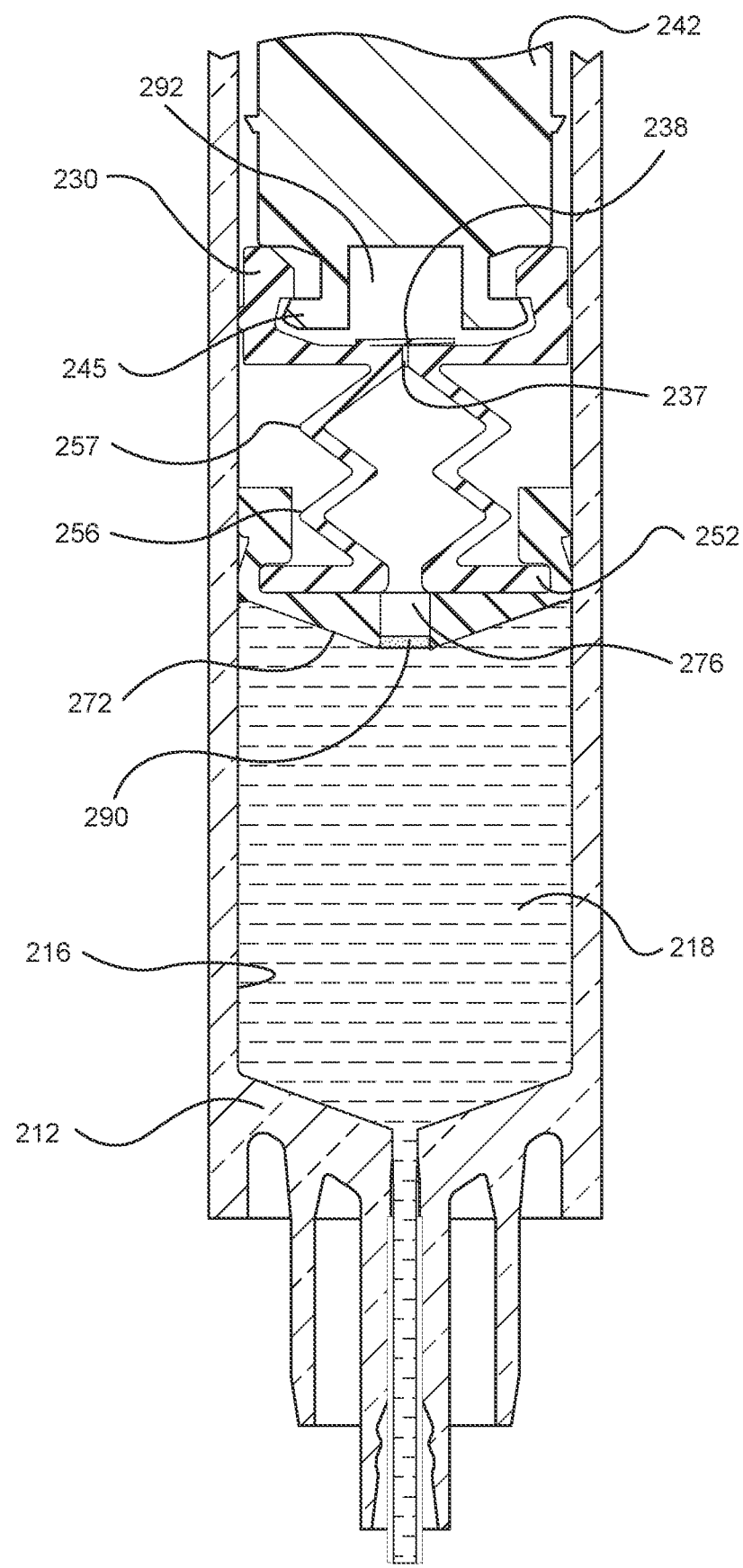
FIG. 23B illustrates an enlarged partial view of the medical device shown in FIG. 23A.

As shown in FIGS. 23A-B, as liquid fills the chamber 218, any remaining air rises to the top of the aspirated liquid or between the liquid and the distal face 272 of the stopper 260. This remaining air permeates through the porous portion 290 and the liquid is prevented from passing through the porous portion 290 into the stopper cavity 266. The porous portion may be formed from hydrophobic filter, a swellable polymer and combinations thereof, as described herein. When the porous portion includes a swellable polymer, the openings present in the swellable polymer close upon contact with the liquid. In embodiments which include a porous portion including a hydrophobic filter or membrane, the hydrophobic filter prevents liquid from permeating through the porous portion 290 and entering the stopper cavity 266. FIG. 23B illustrates a syringe barrel 210 filled with liquid and no air.

The valve 238 remains closed as the pressure within the pump cavity 258 remains lower than the pressure outside of the pump cavity 258. For example during aspiration, as the wall 254 of the pump body expands, the vacuum created within the pump cavity 258 draws the in valve 238 or forces the valve 238 closed. As the pressure within the pump cavity 258 equalizes or, as will be discussed, the user expels the liquid within the chamber 218, the valve 238 opens and vents the evacuated air from within the pump cavity 258.

Figure 24:
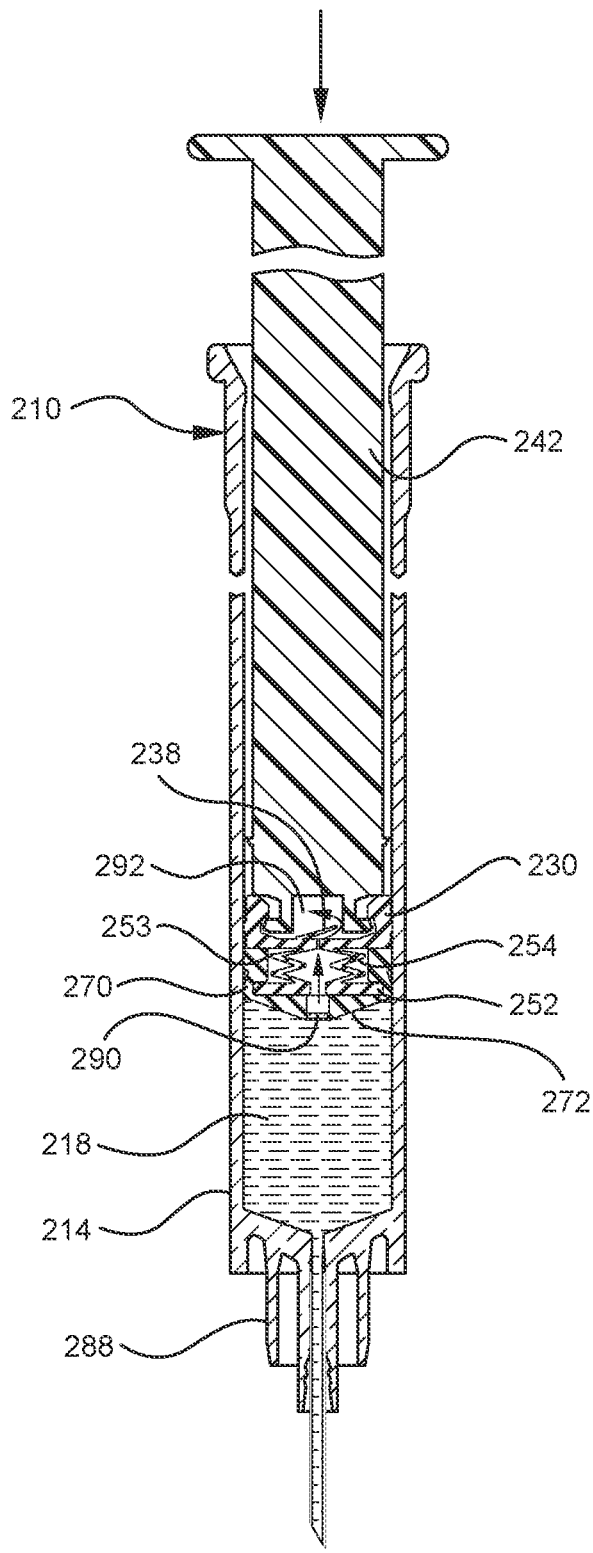
FIG. 24 illustrates a cross-sectional view of the medical device shown in FIG. 23 upon application of an initial force to the plunger rod in the distal direction.

To expel the fluid, a distally directed force is applied to the plunger rod 240 and the stopper hub 250 move with the stopper 260 in the distal direction. As shown in FIG. 24, the force applied to the plunger rod in the distal direction overcomes the resistance between the sealing portion 270 of the stopper 260 and the interior surface of the syringe barrel 210 and also the resistance of the wall 254 to collapsing. The compressed wall 254 causes the valve 238 to open and allows the air within the pump cavity 258 to escape through the outlet 237 instead of through the porous portion 290. The recess 292 of the plunger rod provides space for the valve 238 to open.

Figure 25:
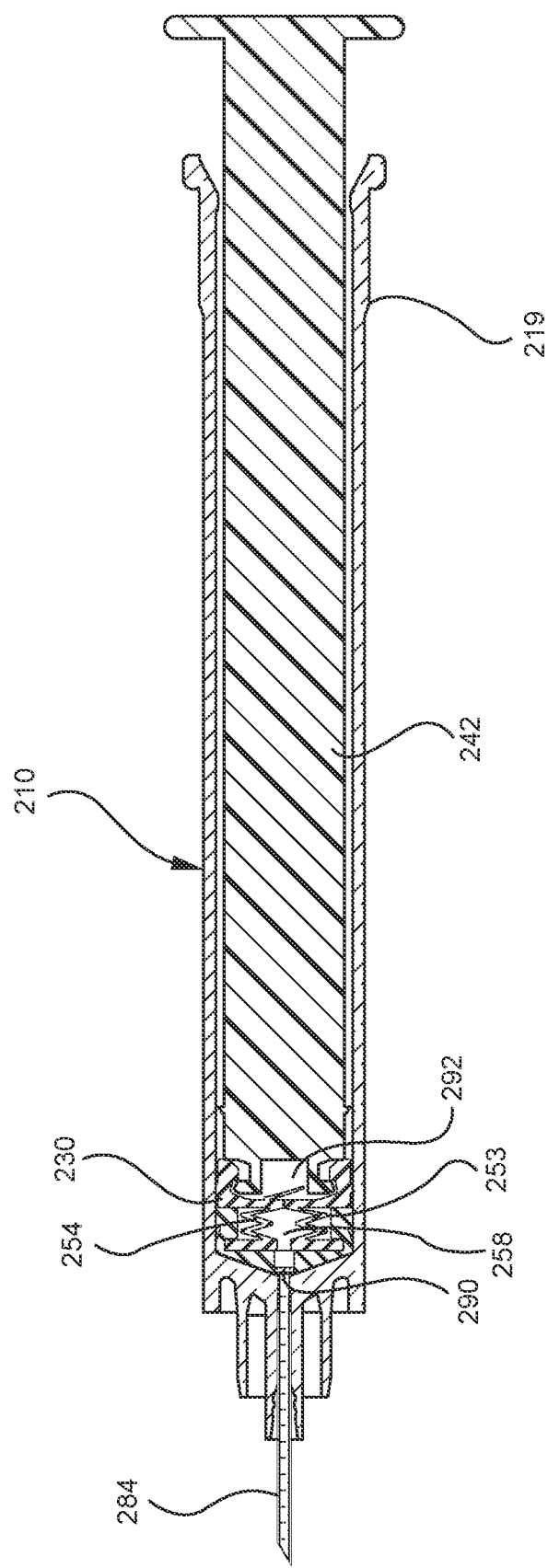
FIG. 25 shows a cross-sectional view of the medical device shown in FIG. 24 after expulsion of the liquid from the syringe barrel upon application of a continuous force to the plunger rod in the distal direction.

In embodiments which utilize a flexible distal face, the application of a continuous and distally directed force on the plunger rod 240 causes the distal face 272 to flex as the distal face 272 contacts the distal wall 212 of the syringe barrel. As shown in FIG. 25, in embodiments that utilize a stopper 260 having a convexly-shaped distal face 272, the distal face 272 conforms more closely to the distal wall 212 upon contact with the distal wall 212. The convex shape of the distal face 272 upon contact with the distal wall 212 expels even more liquid from the syringe barrel 210.

Figure 26:
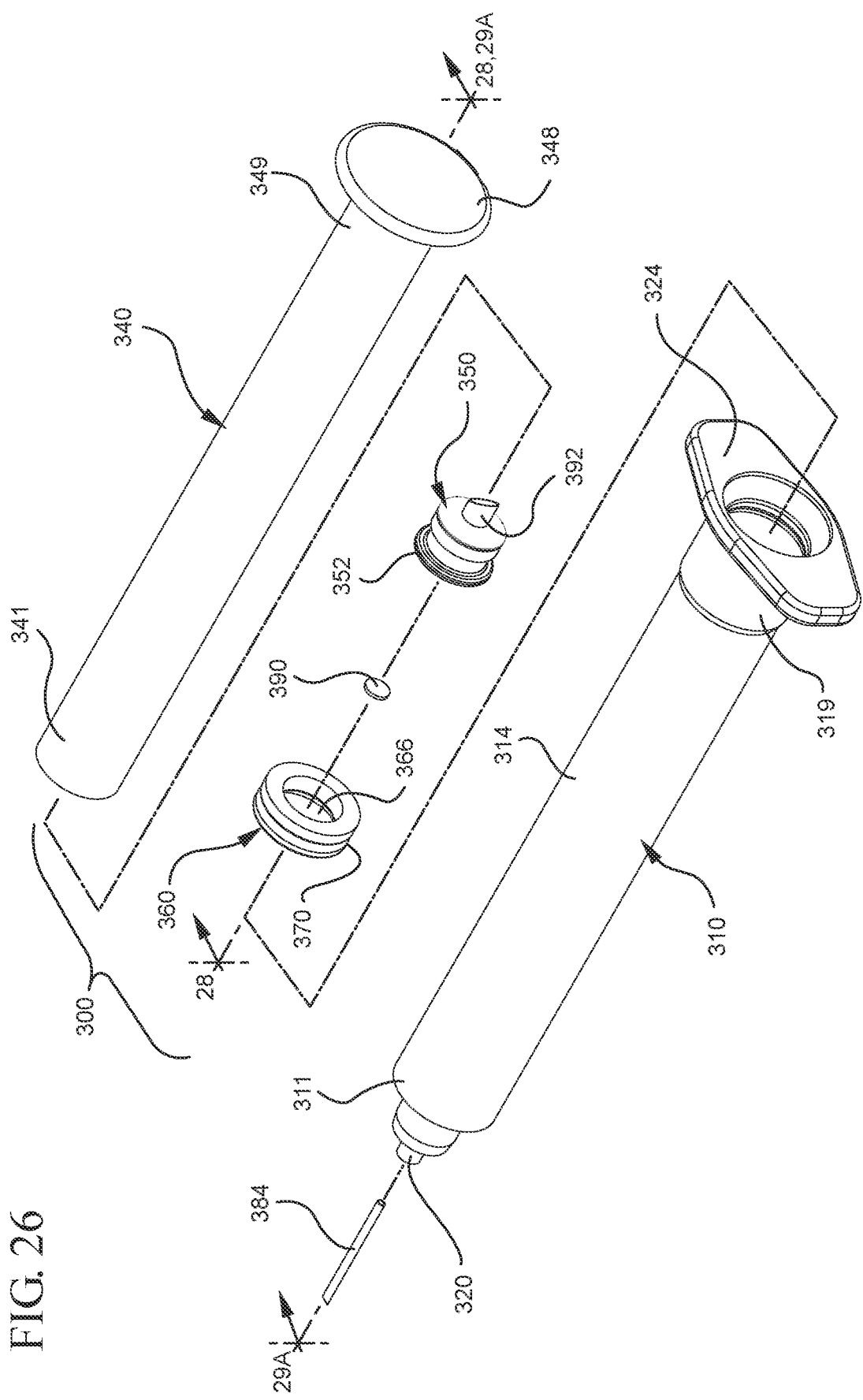
FIG. 26 illustrates a disassembled view of a syringe barrel and one or more embodiments of a medical device according to a third aspect of the present invention.

FIGS. 26-34 illustrate a medical device 300 according a third aspect of the invention. The medical device 300 includes a plunger rod 340 that may be attached to a stopper hub 350 and stopper 360 assembly. For illustration, the medical device 300 is shown in use with a container in the form a syringe barrel 310 with a needle cannula 384 attached thereto. As shown more clearly in FIGS. 26 and 29A, the syringe barrel 310 includes an open proximal end 319 and a distal end 311 and a distal wall 312. A sidewall 314 extends from the distal end 311 to the open proximal end 319 and includes an interior surface 316 that defines a chamber 318 for retaining or holding fluids, which may include liquid medication and/or other liquids. The distal end 311 may also include a tip 320 having an open passageway 322 therethrough in fluid communication with the chamber 318. A needle cannula 384 includes a lumen 386 or opening therethrough and may be attached to the tip 320 so that the lumen 386 is in fluid communication with the open passageway 322 and the chamber 318. In the embodiments shown in FIG. 26, a needle cannula 384 is attached to the tip 320. Alternatively, a needle hub (not shown) may be used to attach a needle to the tip. As shown in FIG. 26, the distal end 311 includes an option luer fitting 388 and the proximal end 319 includes an optional finger flange 324. The interior surface 316 of the syringe barrel 310 may have a smooth surface that is free of any protrusions or depressions. In use, the plunger rod 340, stopper hub 350 and stopper 360 are inserted into the open proximal end 319 of the syringe barrel 310.

Figure 27:
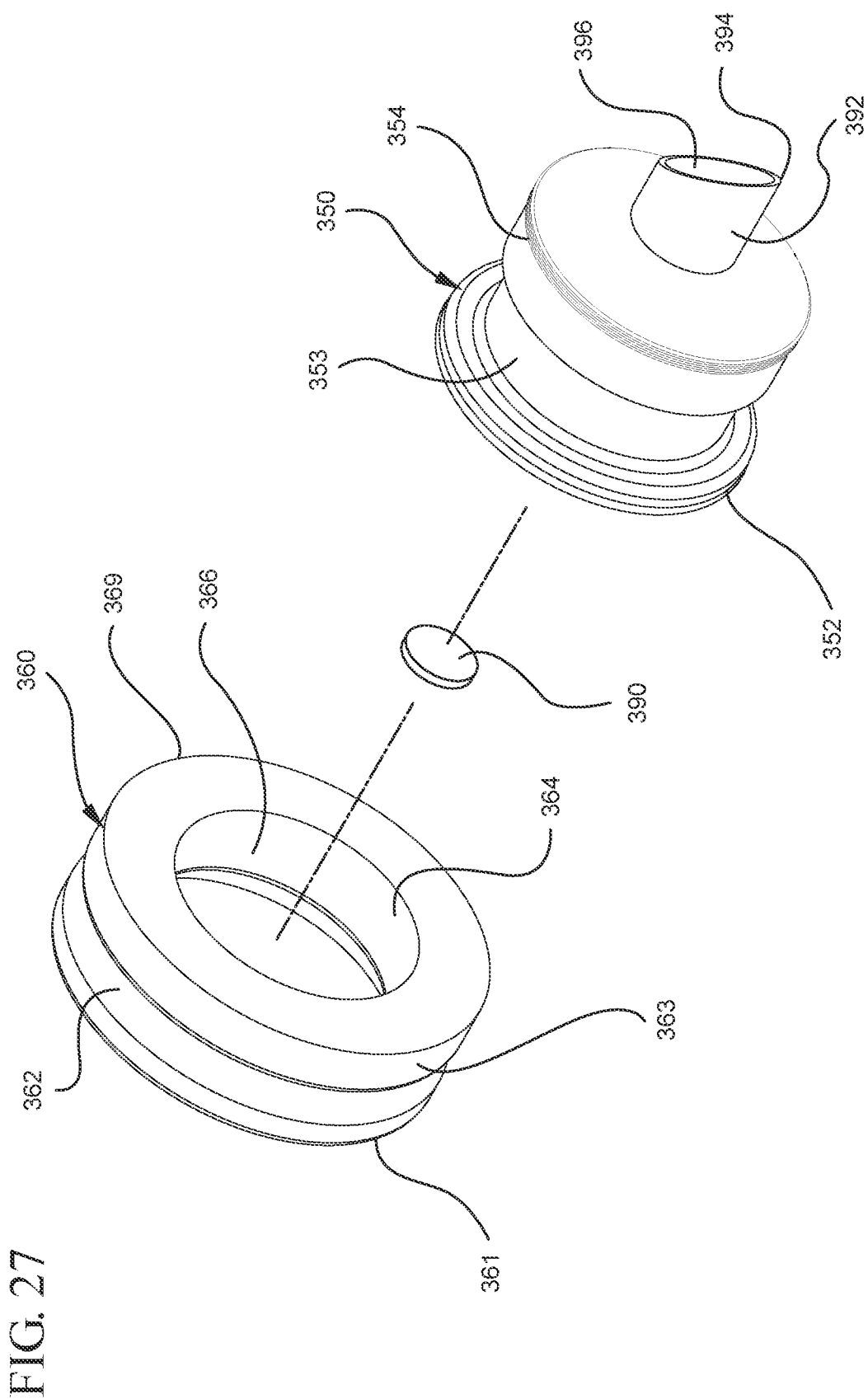
FIG. 27 illustrates an enlarged partial view of the stopper assembly shown in FIG. 26.
Figure 28:
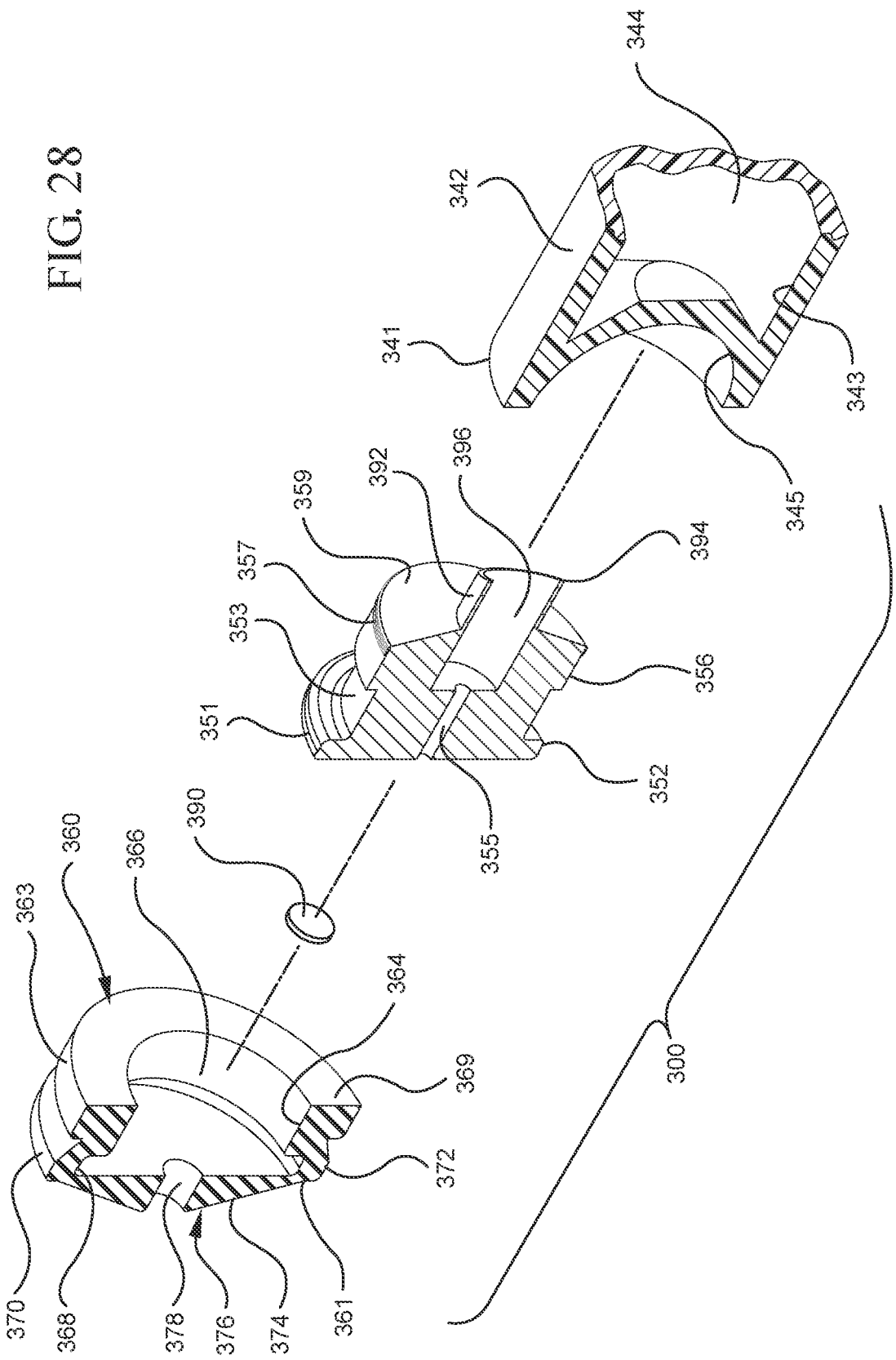
FIG. 28 illustrates a perspective cross-sectional view of the stopper assembly and the plunger rod shown in FIG. 26 taken along line 28-28.

As more clearly shown in FIGS. 27 and 28, the stopper 360 includes a distal end 361 and an open proximal end 369. The stopper 360 includes a stopper body 362 extending from the distal end 361 to the open proximal end 369 that includes an inside surface 364 defining a stopper cavity 366. In one or more embodiments, the inside surface 364 of the stopper body 362 may include a peripheral channel 368 forming a groove or ridge within the stopper body 362 for engagement with the stopper hub 350, as will be described in detail below. As shown in FIGS. 26-34, the stopper body 362 includes an outside surface 363 with a sealing portion 370. As shown, the sealing portion 370 is formed adjacent the distal end 361, however, the sealing portion 370 may also be formed along the entire length of the outside surface 363 or at other locations along the length of the outside surface. The stopper 360 may be formed from an elastomeric material, polymeric material or other suitable material. The sealing portion 370 includes at least one peripheral edge 372 shaped to form a fluid-tight seal with the inside surface of a syringe barrel. The sealing portion 370 and/or the peripheral edge 372 may be formed from a material suitable for forming a fluid-tight seal with the interior surface 316 of the syringe barrel, which may include the same or different material as the stopper 360. In one or more embodiments, the peripheral edge 372 may have a circular cross-section for forming a fluid-tight seal with a syringe barrel having an interior surface with a circular cross-section.

The distal end 361 of the stopper 360 includes a convex distal face 374 having an opening 376 therethrough in fluid communication with the stopper cavity 366. The distal end 361 of the stopper may also include a path 378 in fluid communication with the stopper cavity 366 and the opening 376. In one or more embodiments, the distal face 374 is flexible and flexes concavely and convexly, as will be described in greater detail below. The distal face 374 may also be shaped convexly so that it conforms more closely to the shape of the distal wall 312 of the syringe barrel 310 to expel as much liquid from the chamber 318 as possible.

A porous portion 390 is disposed in the path 378 and/or opening 376 and in fluid communication with the path 378, stopper cavity 366 and the opening 376. In one or more embodiments, the porous portion 390 is air permeable and liquid impermeable. In other words, the porous portion 390 forms a selective barrier that a liquid penetration pressure and an air penetration pressure that is less than the liquid penetration pressure.

The porous portion 390 may have a circular shape. Alternatively, the porous portion 390 may have a square and/or rectangular shape. In one or more embodiments, the porous portion 390 may be integrally formed or disposed on the distal face 374, adjacent to the opening 376. In a specific embodiment, the porous portion 390 has a cross-sectional width that is smaller than the cross-sectional width of the distal face 374. The porous portion 390 may also be integrally formed and/or disposed adjacent to the path 378 on the inside surface 364 of the stopper. The porous portion 390 may have a cross-sectional width that is smaller than the cross-sectional width of the inside surface 364 of the stopper. The thickness of the porous portion 390 may be adjusted so the porous portion extends along the length of the path 378.

The porous portion 390 may be integrally formed on the distal face 374, with the peripheral edges of the distal face 374 and the sealing portion 370 remaining non-porous. In a specific embodiment, the porous portion 390 is separated from the sealing portion 370 by the distal face 374.

The porous portion 390 may also be shaped to fit within the opening 376 and form a fluid-tight engagement with the opening 376. For example, the porous portion 390 may extend from the distal face 374 into the path 378. In one or more embodiments, the porous portion 390 may have a periphery that is molded to a portion of the distal face 374. In one or more embodiments, the porous portion 390 may be attached to the distal face 374 of the stopper by mechanical means, for example, adhesives and/or molding. In a specific embodiment, the distal face 374 may include a pocket (not shown) for securing the porous portion 390 adjacent to the distal face 374 and the opening 376.

The stopper hub 350 includes an open distal end 351 and an open proximal end 359. The open distal end 351 includes a stopper-engaging portion 352, which may include a disc extending radially outwardly, for attachment of the stopper hub 350 to the stopper 360. Specifically, as more clearly shown in FIGS. 29A and 29B, the stopper-engaging portion 352 extends radially outwardly to engage the peripheral channel 368 of the stopper 360. The stopper-engaging portion 352 may be in the form of a tab (not shown), which corresponds to an opening or other corresponding structure on the inside surface 364 of the stopper. In a specific embodiment, the stopper-engaging portion 352 may have an opening and the inside surface of the stopper may include a tab (not shown) extending radially inwardly to engage with the opening (not shown). Other means to engage the stopper hub 350 to the stopper 360 may also be utilized. Alternatively, the stopper 360 may be integrally formed on the distal end 351 of the stopper hub 350 or permanently attached to the distal end 351 of the stopper hub 350 using methods know in the art. The stopper hub may be formed from a rigid plastic or other material.

A boss 353 extends from the stopper-engaging portion 352 to a plunger-engaging portion 354 that is disposed adjacent to the open proximal end 359 of the stopper hub 350. A hollow spike 392 is attached to the open proximal end 359 and extends from the boss 353 in a proximal direction. The hollow spike 392 defines a space 396 in fluid communication with the conduit 355 and includes a piercing end 394. The hollow spike 392 may be formed from a rigid plastic, metal or other material suitable to pierce and penetrate the distal end 241 of the plunger rod 340 as will be described herein. The boss 353 includes a hollow interior in fluid communication with the open distal end 351 and the open proximal end 359. As shown in FIGS. 27 and 28, the boss 353 has a cylindrical shape with a conduit 355 that extends from the open distal end 351 to the hollow spike 392. The plunger-engaging portion 354 includes an exterior surface 356 configured to frictionally engage the inside surface of the plunger rod 340, as will be described below. As shown in FIG. 28, the plunger-engaging portion 354 includes an axial length and a plurality of grooves 357 disposed along its axial length. Alternatively, the plunger-engaging portion 354 may have a textured surface or a coating (not shown) that creates or increases frictional interference between the exterior surface 356 of the plunger-engaging portion 354 and the inside surface of the plunger rod 340. Alternatively, the plunger rod 340 may be attached in a slidable relationship with the plunger-engaging portion 354 of the stopper hub 350 such that the plunger rod 340 slides proximally and distally over the exterior surface 356 of the stopper hub 350.

During use, the plunger rod 340 is configured to be attached to the proximal end 359 of the stopper hub. The plunger rod shown more clearly in FIGS. 29A and 29B includes a distal end 341, a proximal end 349, and a hollow elongate body 342 extending from the distal end 341 and the proximal end 349. The plunger rod 340 may be made of a rigid plastic or other material that has sufficient rigidity to withstand movement in the proximal and distal direction within the syringe barrel 310. Examples of such materials include polypropylene, polyethylene, polycarbonate and combinations thereof. The elongate body 342 may be cylindrical. In one or more embodiments, the shape of the hollow elongate body 342 may be rectangular or other shape. The proximal end 349 of the plunger rod 340 includes an optional thumbpress 348.

The hollow elongate body 342 includes an inside surface 343 that defines a plunger rod cavity or a void space 344 having a vacuum. The distal end 341 of the plunger rod includes a pierceable wall 345 or septum that seals the vacuum within the void space 344 of the hollow elongate body 342. The vacuum within the elongate body 342 may be formed prior to formation of the pierceable wall 345 by means known in the art. The plunger rod 340 may include an interior plunger (not shown) disposed telescopically within the elongate body 342, as will be described herein with reference to embodiments according to the seventh aspect of the present invention. The interior plunger (not shown) may be partially withdrawn from the elongate body to create a vacuum within the elongate body 342.

As shown, the pierceable wall 345 is concavely shaped with respect to the distal end 341 of the plunger rod. The pierceable wall 345 accommodates the hollow spike 392 without allowing the hollow spike 392 to pierce the pierceable wall 345. In one or more embodiments, this configuration allows the plunger rod 340 to at least partially engage the stopper hub 350 without penetrating the pierceable wall 345. In one or more embodiments, the pierceable wall 345 is formed across the open distal end 341, forming a perpendicular surface to the hollow elongate body 342. The pierceable wall 345 is adhered to the distal end 341 of the plunger rod at the inside surface 343 of the elongate body 342. The pierceable wall 345 may be formed from an elastomeric material and may have a uniform thickness that extends across the cross-sectional width of the void space 344. In a specific embodiment, the thickness of the pierceable wall 345 may be modified to facilitate or to resist accidental piercing of the pierceable wall 345. For example, the thickness of the pierceable wall 345 may be decreased at the point at which the piercing end 394 pierces the pierceable wall 345 to facilitate penetration of the hollow spike 392. Alternatively, the thickness of the pierceable wall 345 may be increased at the point at which the piercing end 394 pierces the pierceable wall 345 to prevent accidental penetration of the pierceable wall 345.

Figure 29A:
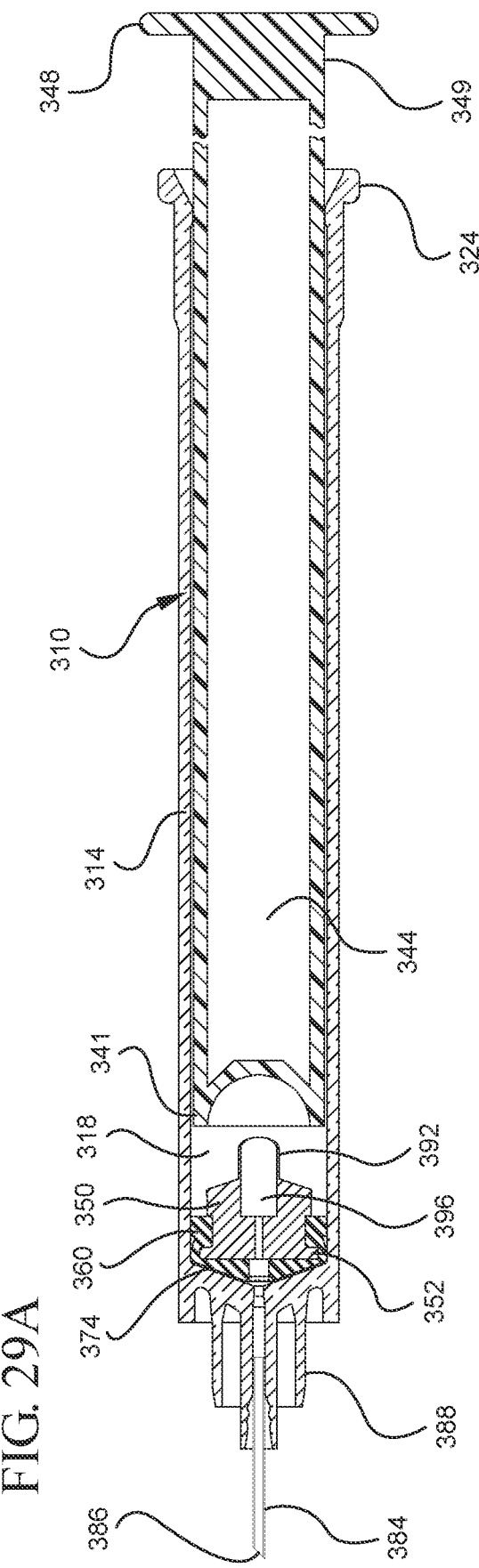
FIG. 29A illustrates a cross-sectional view of the assembled medical device illustrated in FIG. 26 taken along line 29A-29A.
Figure 29B:
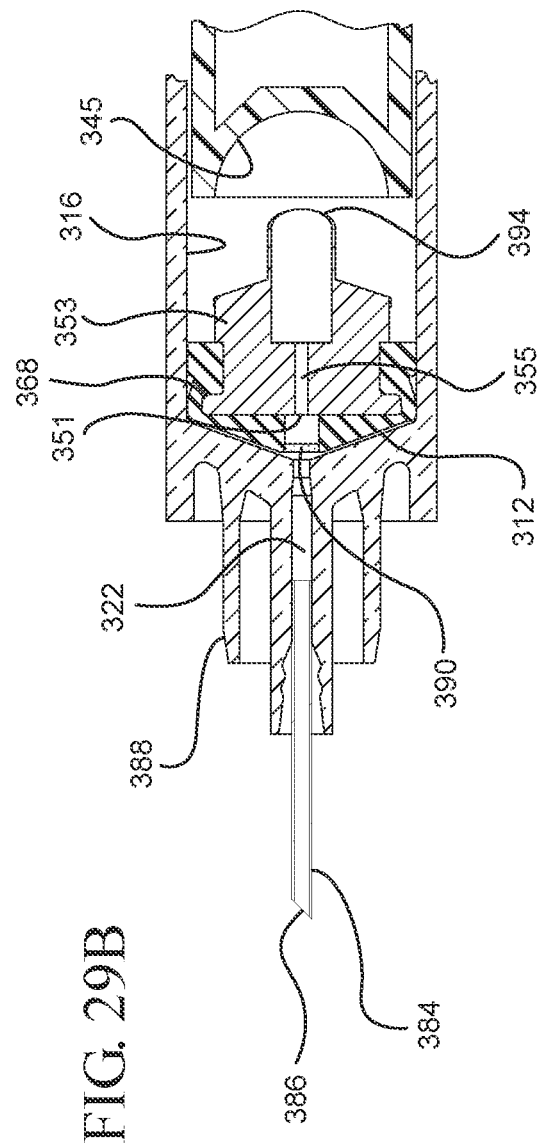
FIG. 29B illustrates an enlarged partial view of the medical device illustrated in FIG. 29A.

In use, as shown in FIGS. 29A and 29B, the plunger rod 340, stopper hub 350 and stopper 360 are inserted into the open proximal end 329 of the syringe barrel 310. Before aspirating fluid into the chamber 318 of the syringe barrel 310 or other container, the distal face 374 of the stopper 360 is positioned adjacent to the distal wall 312 of the syringe barrel 310, so that the air within the chamber 318 is minimized and is primarily present in the tip 320 of the syringe barrel 310 or other container.

In the assembled state, the stopper 360 and stopper hub 350 are fully assembled with the stopper-engaging portion 352 engaged with the peripheral channel 368 of the stopper 360. The stopper hub 350 and the plunger rod 340 are engaged in a first position. In the first position, the plunger rod 340 and, specifically, the pierceable wall 345 are positioned so that the piercing end 394 of the hollow spike 392 does not penetrate completely through the pierceable wall 345 and the vacuum within the elongate body 342 remains intact. The plunger rod 340 is disposed within the chamber 318 of the syringe barrel 310 so the pierceable wall 345 is positioned at a distance from the hollow spike 392 as shown in FIGS. 29A and 29B. In a specific embodiment, the pierceable wall 345 may be positioned adjacent to the piercing end 394 of the hollow spike 392 and the pierceable wall 345 and vacuum within the void space 344 remains intact. In a more specific embodiment, the piercing end 394 may partially penetrate the pierceable wall 345, while leaving the vacuum within the void space 344 intact. In these positions, the plunger-engaging portion 354 and the distal end 341 of the plunger rod may be engaged, partially engaged or disengaged. Engagement of the stopper hub 350 and the plunger rod 340 in the first position may be facilitated by the length of the plunger-engaging portion 354. The length of the plunger-engaging portion 354 or the position and shape of the pierceable wall 345 may allow full and/or partial engagement of the stopper hub 350 and the plunger rod 340 without penetration of the hollow spike 392 through the pierceable wall 345.

Figure 30:
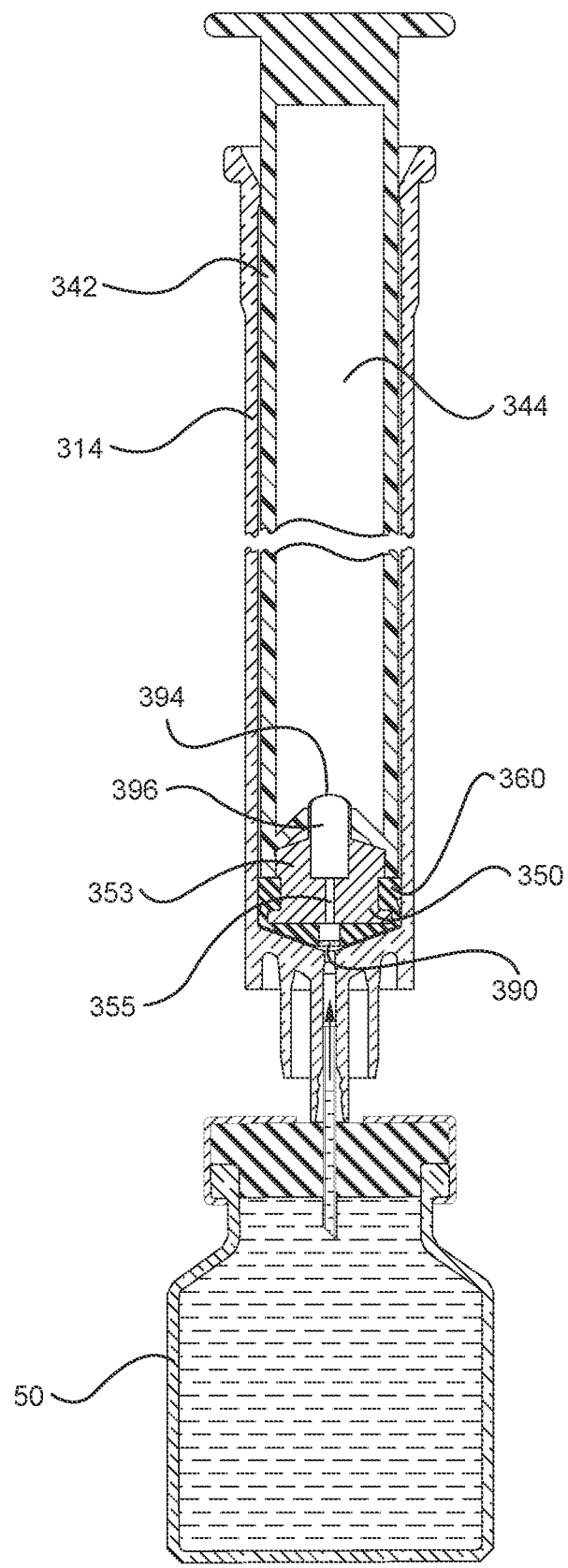
FIG. 30 illustrates a cross-sectional view of the medical device shown in FIG. 29A positioned to draw liquid from a vial after application of an initial force to the plunger rod in the distal direction.
Figure 31:
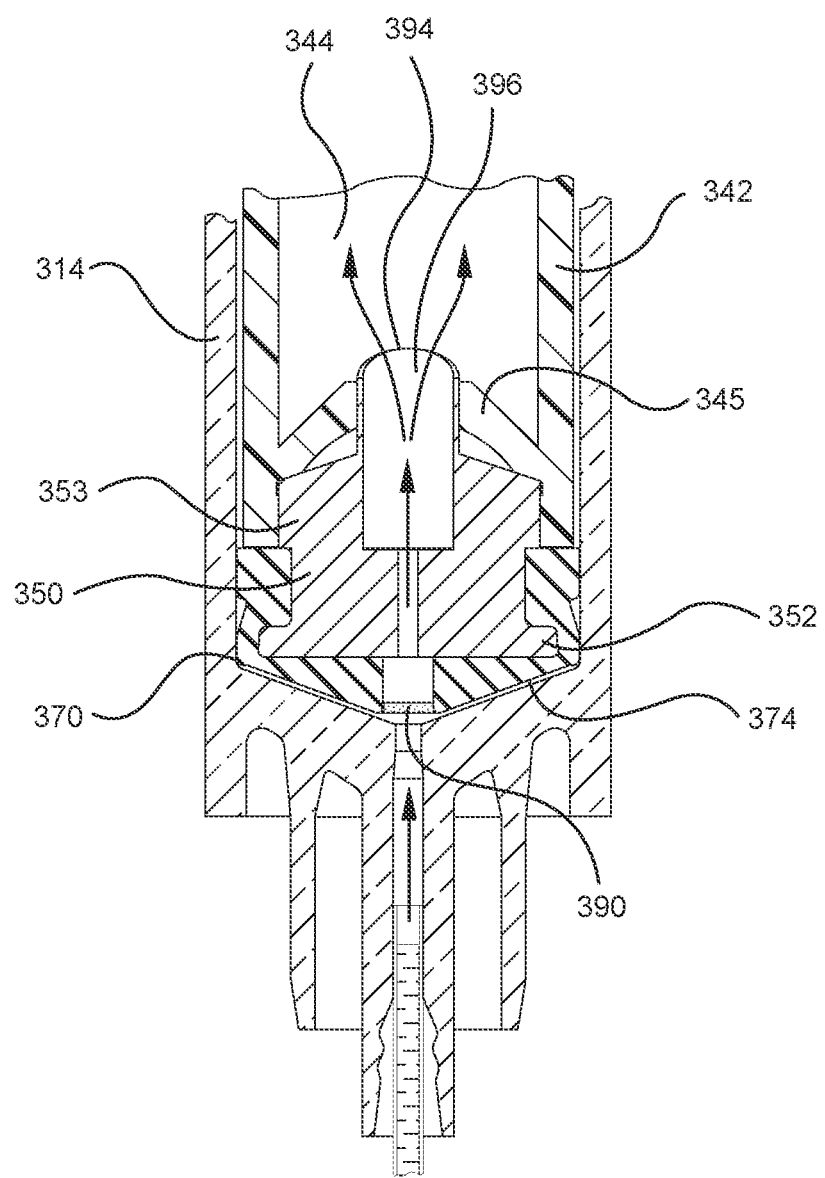
FIG. 31 illustrates an enlarged partial view of the stopper, plunger rod and syringe barrel shown in FIG. 30.

As shown in FIGS. 30 and 31, to fill the chamber 318 of the chamber 318 of the syringe barrel 310 or other container, the needle cannula 384 is inserted into a container, such as a vial 50, to draw the fluid within the container into the syringe barrel 310. Thereafter, an initial force in the distal direction is applied to the plunger rod 340 to engage the stopper hub 350 and plunger rod 340 from the first position to a second position. In the second position, the piercing end 394 of the hollow spike 392 fully penetrates the pierceable wall 345 and releases the vacuum contained within the void space 344 of the plunger rod.

When configured in the second position, the plunger-engaging portion 354 engages the distal end 341 of the plunger rod to form a fluid-tight seal and fluid communication between the void space 344, conduit 355 and stopper cavity 366. The vacuum is released to the conduit 355 and stopper cavity 366 and draws air into the tip 320 and/or chamber 318 of the syringe barrel without any movement of the stopper 360, as shown in FIGS. 30 and 31. Liquid may also be drawn into the tip 320 and/or chamber 318 however, the porous portion 390 prevents the liquid from entering the stopper cavity 366, as described above. As described herein, the porous portion 390 may include a hydrophobic filter, a swellable polymer or a combination thereof. For example, when the porous portion 390 utilizes a swellable polymer, the openings present in the swellable polymer close upon contact with the liquid. In embodiments utilize a porous portion 390 including a hydrophobic filter or membrane, the hydrophobic filter prevents liquid from permeating through the porous portion 390.

Figure 32:
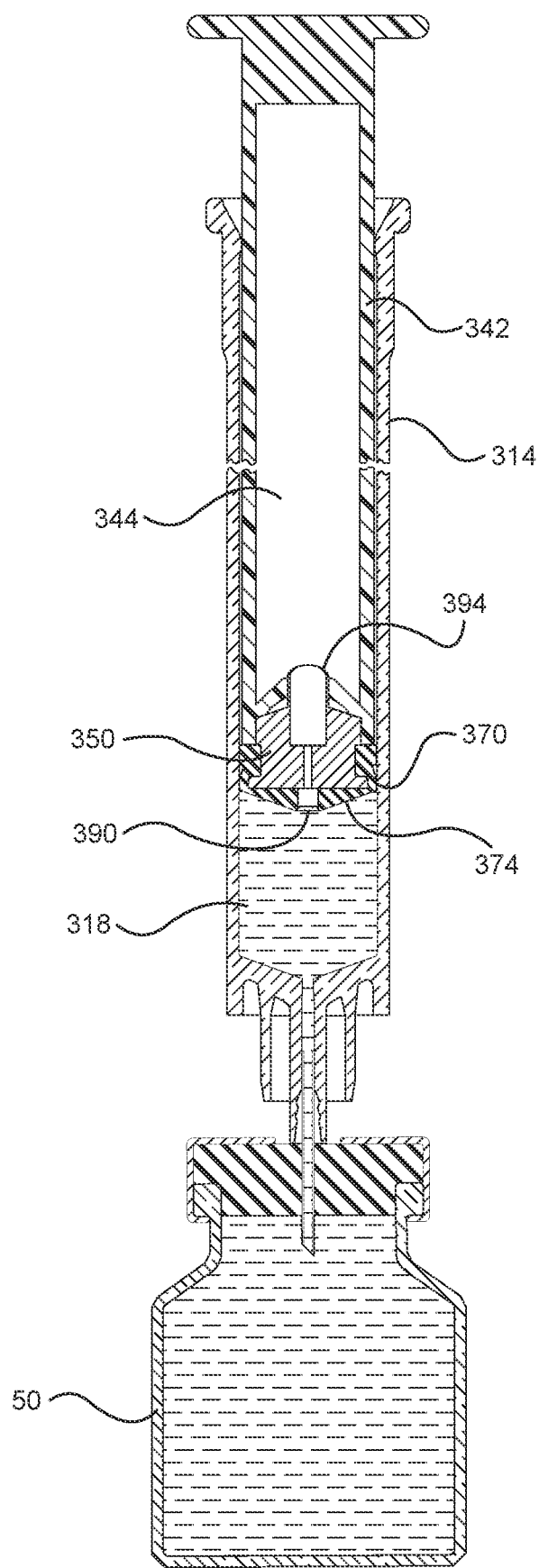
FIG. 32 shows a cross-sectional view of the medical device shown in FIG. 31 drawing liquid from the vial into the syringe barrel upon application of a continuous force to the plunger rod in the proximal direction.
Figure 33:
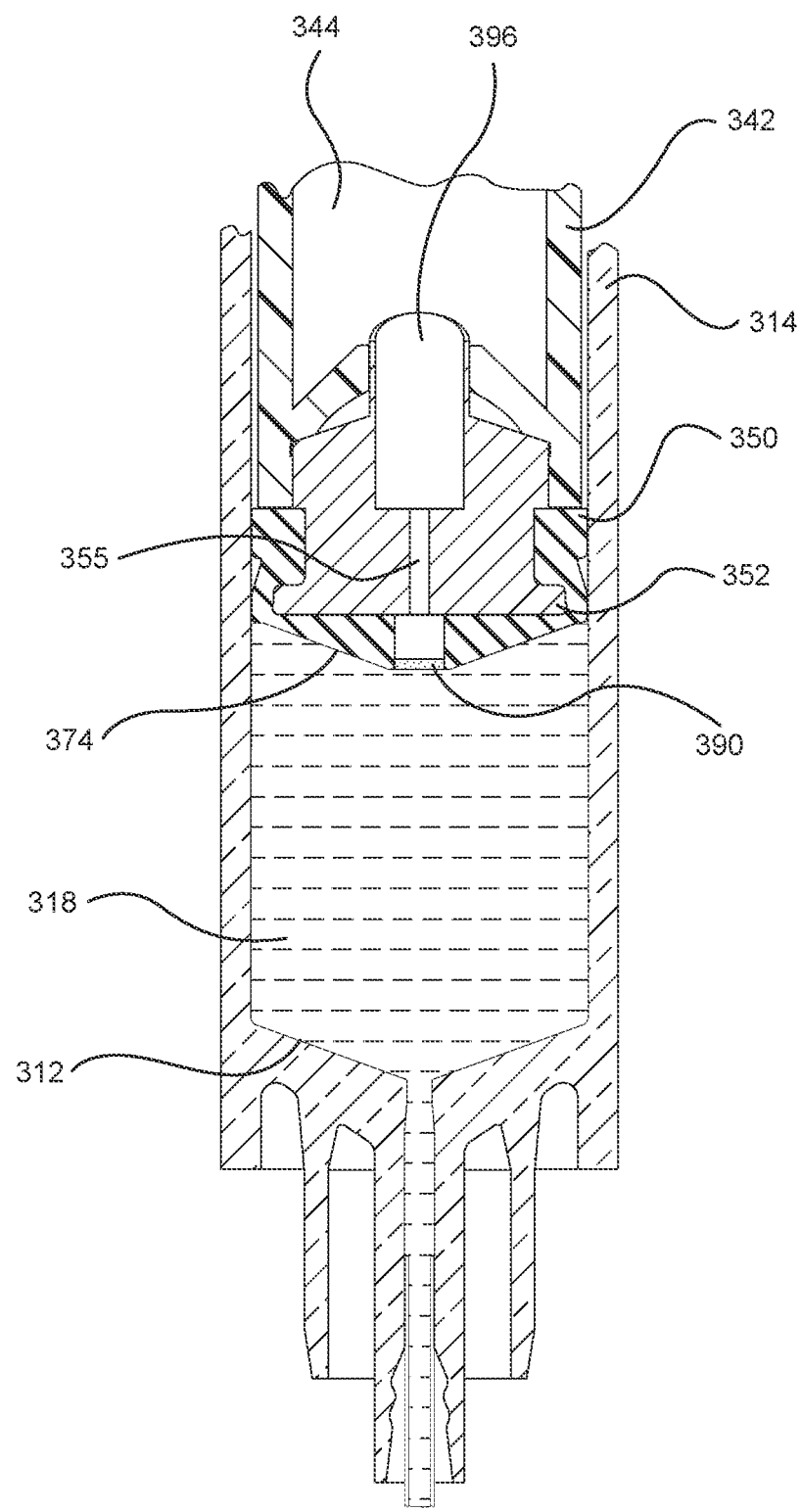
FIG. 33 illustrates an enlarged partial view of the air being evacuated from the cavity of the stopper shown in FIG. 32.
Figure 34:
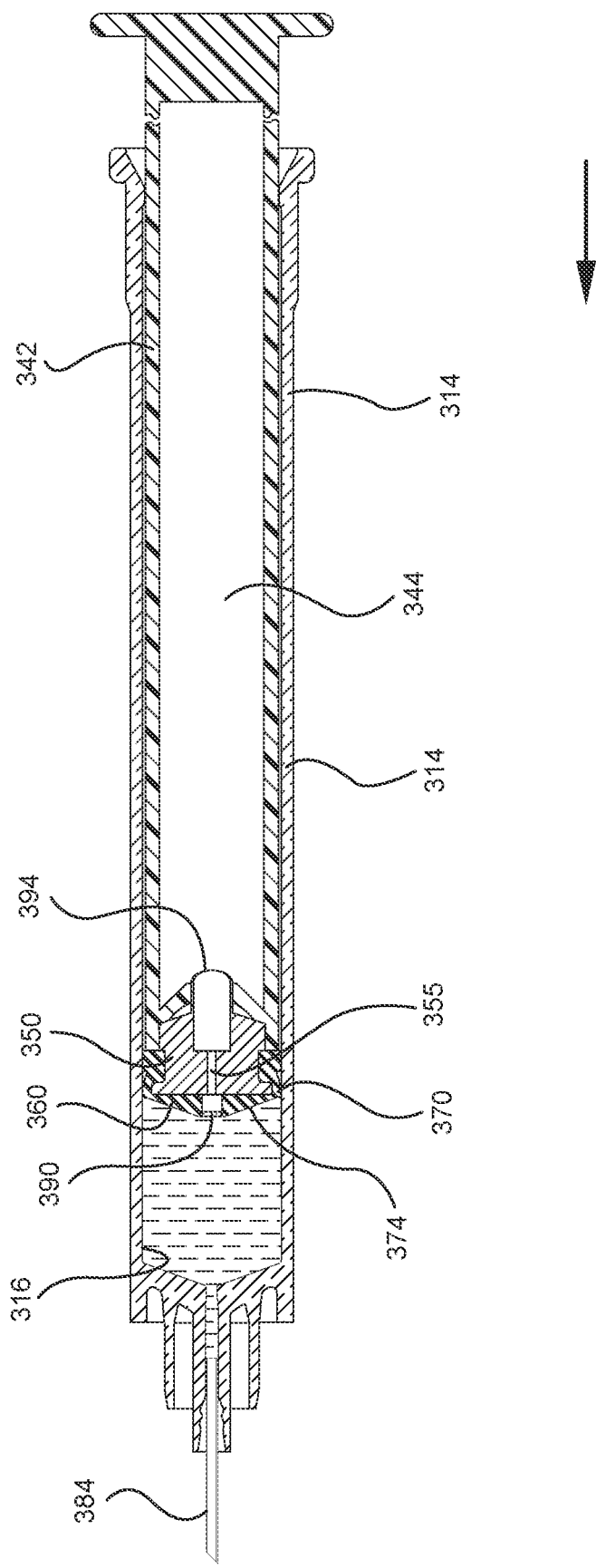
FIG. 34 illustrates a cross-sectional view of the medical device shown in FIG. 32 filled with liquid from the vial prior to the expulsion of the liquid from the syringe barrel upon application of a continuous force to the plunger rod in the distal direction.
Figure 35:
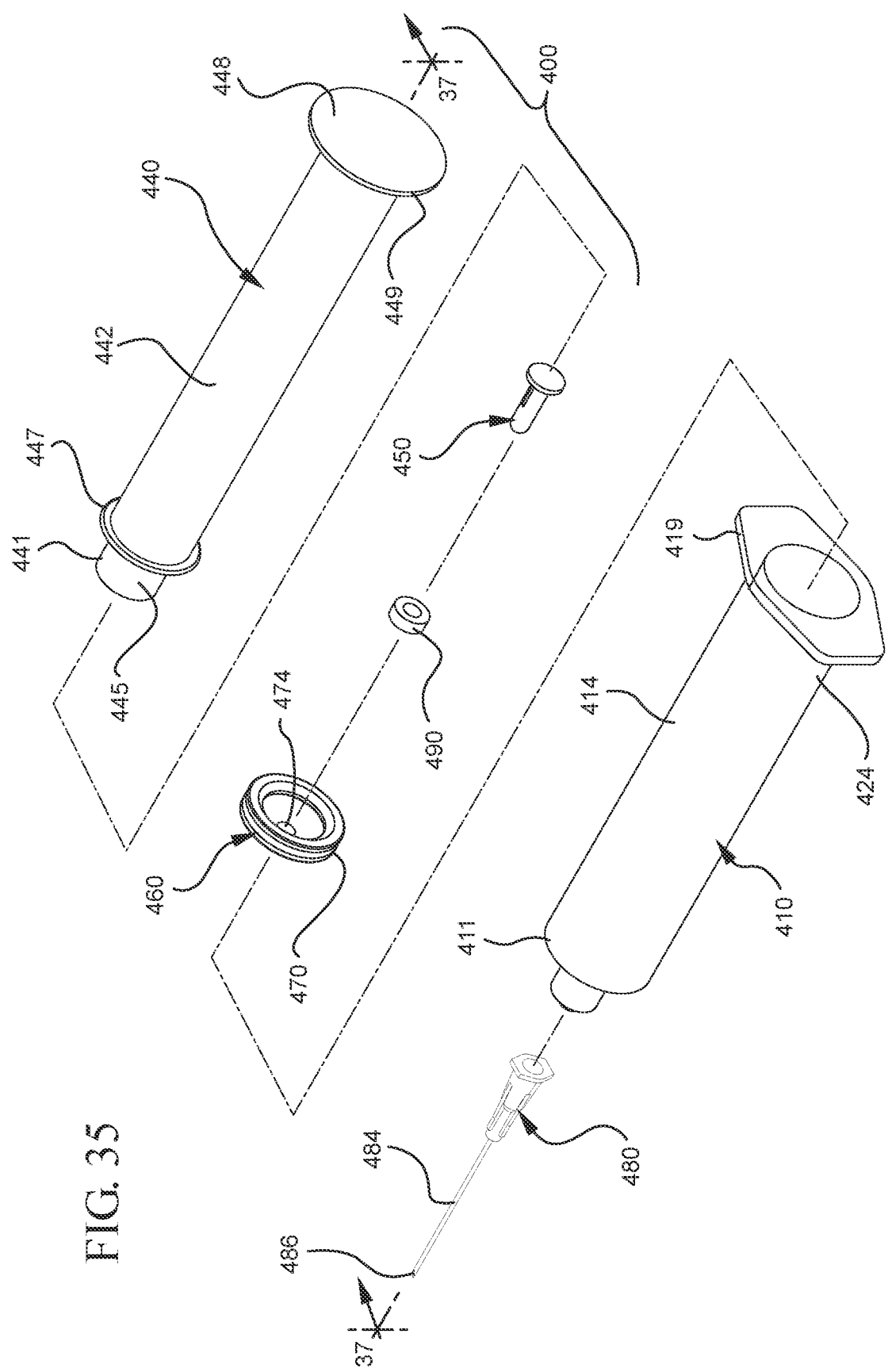
FIG. 35 illustrates a disassembled view of a syringe barrel, needle hub and one or more embodiments of a medical device according to a fourth aspect of the present invention.

As the user aspirates the liquid from the vial 50 into the chamber 318 of the syringe barrel 310 by applying a proximally directed force on the plunger rod 340 or, more specifically, the thumbpress 348, any air trapped within the chamber 318 rises to the top of the aspirated liquid or between the liquid and the stopper 360, as shown in FIGS. 32-33. The air continues to be drawn into the stopper 360 and stopper hub 350 and, in one or more embodiments, into the hollow spike 392, which delivers the air into the void space 344 of the plunger rod, as shown more clearly in FIGS. 32 and 33. As shown in FIG. 34, the desired amount of liquid may be filled into the syringe barrel, without the presence of air.

To expel the fluid, the stopper hub 350 and plunger rod 340 remained engaged in the second position and move together in the distal direction, with the stopper 360, as a user applies a force on the plunger rod 340 or thumbpress 348 in the distal direction. In one or more embodiments that utilize a stopper 360 having a distal face 374 that flexes, the application of a continuous and distally directed force on the plunger rod 340 causes the distal face 374 to flex convexly as the distal face 174 contacts the distal wall 312 of the syringe barrel 310. In embodiments which utilize a stopper 360 having a convexly-shaped distal face 374, the distal face 374 conforms more closely to the distal wall 312 upon contact with the distal wall 312. The convex shape of the distal face 374 upon contact with the distal wall 312 expels even more liquid from the syringe barrel 310.

FIGS. 35-45 illustrate a medical device 400 according to a fourth aspect of the invention. The medical device 400 includes a plunger rod 440 with a first stopper 447, a second stopper assembly 460 including an porous portion 490 and plug 450 to aspirate a liquid into a container, for example a syringe barrel 410 and expel the aspirated liquid. This configuration may be utilized as a traditional dose syringe, where the user aspirates and expel a desired amount of liquid in a single use, as shown in FIG. 37-41, and/or as a "fixed-dose" syringe, where a user may aspirate and expel a fixed amount of liquid in a single use, as shown in FIGS. 42-45.

The medical device 400 includes a first stopper 447 disposed on a plunger rod 440 and a second stopper assembly 460 is attachable to the plunger rod. For illustration, the medical device 400 is shown in use with a container in the form of a syringe barrel 410 with needle cannula 484 attached thereto. The syringe barrel 410 includes an open proximal end 419 and a distal end 411 and a distal wall 412. A sidewall 414 extends from the distal end 411 to the open proximal end 419 and includes an interior surface 416 that defines a chamber 418 for retaining or holding fluids, which may include liquid medication and/or other liquids. The distal end 411 may also include a tip 420 having an open passageway 422 therethrough in fluid communication with the chamber 418. The needle cannula 484 is attached to the barrel 410 using a needle hub 480, which is attached to an optional luer fitting 488. The needle cannula 484 includes a lumen 486 or opening therethrough in fluid communication with the open passageway 422 and the chamber 418. Alternatively, the needle cannula 484 may be pre-attached directly to the tip 420, using methods known in the art. The proximal end 419 of the syringe barrel 410 includes an optional flange 424. The interior surface 416 of the syringe barrel 410 may have a smooth surface that is free of any protrusions or depressions. In use, second stopper assembly 460 is attached to a stopper-engaging portion 445 of the plunger rod 440, and the assembled plunger rod and second stopper assembly 460 are inserted into the open proximal end 419 of the syringe barrel 410.

Figure 36:
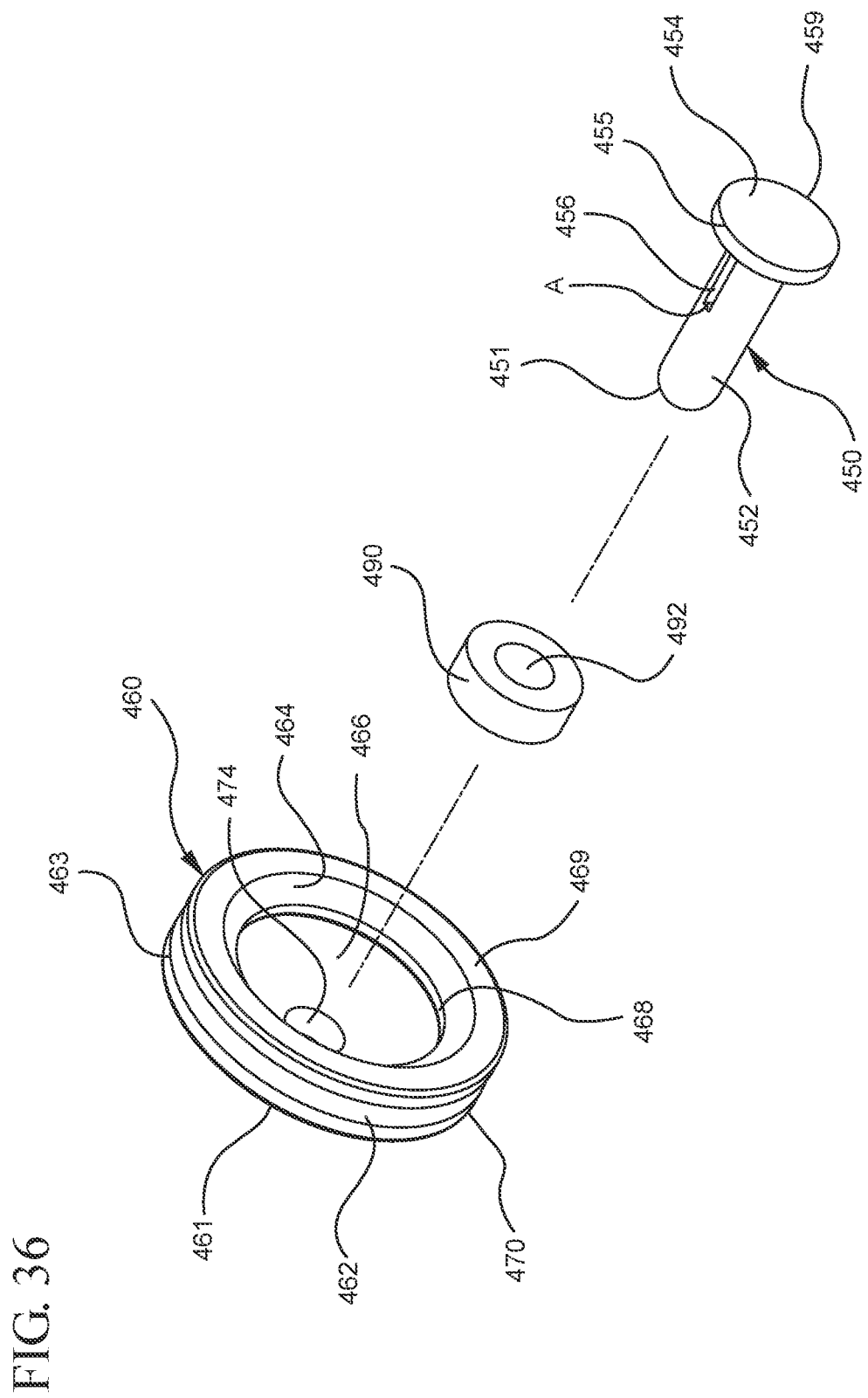
FIG. 36 illustrates an enlarged partial view of the stopper assembly shown in FIG. 35.

As more clearly shown in FIG. 36, the second stopper assembly 460 includes a distal end 461, an open proximal end 469 and a stopper body 462 extending from the open distal end 461 to the open proximal end 469 that includes an inside surface 464 defining a cavity 466. In one or more embodiments, the inside surface 464 of the stopper body 462 may include an attachment structure 468 for connecting the stopper body 462 of the second stopper assembly 460 to the plunger rod 440. For example, the attachment structure 468 may include a depression or groove formed on the inside surface 464 of the stopper body 462 for engagement with a corresponding structure of the plunger rod 440. In one or more embodiments, the attachment structure 468 may include a plurality of grooves (not shown) formed to grip the stopper-engaging portion 445 of the plunger rod when the stopper-engaging portion 445 is inserted into the open proximal end 469 and into the cavity 466. Alternatively, the inside surface 464 is free of any structure and relies on a material, coating or texture to create or enhance the frictional interference between the inside surface 464 and the plunger rod 440. For example, As shown in FIG. 36, the stopper body 462 and/or inside surface 464, is formed from an elastomeric material, polymeric material or other known materials, which may facilitate frictional engagement between the inside surface 464 of the stopper body 462 and the plunger rod 440.

The stopper body 462 includes an outside surface 463 including a sealing portion 470. The sealing portion 470 is formed adjacent the distal end 461. The sealing portion 470 may include one or more peripheral edges (not shown) that are shaped to form a fluid-tight seal with the interior surface 416 of a syringe barrel. In one or more embodiments, the sealing portion 470 may have a circular cross-section for forming a fluid-tight seal with a syringe barrel having an interior surface with a circular cross-section. The distal end 461 of the stopper body 462 includes a convex distal face 472 having an opening 474 therethrough in fluid communication with the cavity 466. In one or more embodiments, the distal face 472 may be flexible and can flex concavely and convexly. The sealing portion 470 may be formed from a material suitable for forming a fluid-tight seal with the interior surface 416 of the syringe barrel, which may include the same or different material utilized to form the stopper body 462.

The second stopper assembly 460 includes a plug 450 that is disposed within the cavity 466 of the stopper and extends partially through the opening 474 of the stopper body 462. As shown more clearly in FIGS. 36-37, the plug 450 includes a distal end 451 and a proximal end 459, and an elongate core 452 extending from the distal end 451 to the proximal end 459. The plug 450 includes a head 454 at the proximal end 459 of the elongate core 452. The length, shape and/or cross-sectional width of the elongate core 452 permit the plug 450 to extend partially through the opening 474 and permits movement of the plug 450 distally and proximally through the opening 474. The length, shape and/or cross-sectional width of the head 454 prevent the plug 450 from fully extending through the opening 474. In one or more embodiments, the elongate core 452 has a cross-sectional width that permits some liquid to enter the opening 474 to contact a porous portion 490 disposed between the head 454 and the opening 474. As shown, the head 454 is in the form of a flat disc having a cross-sectional width larger than the cross-sectional width of the opening. Alternatively, the head 454 may have a square or rectangular shape to prevent the head from extending through openings 474 having a circular shape.

The elongate core 452 includes a channel 456 extending from below the head 454 and along a portion of the length of the elongate core 452. More specifically, the channel 456 extends from below the head 454 to a point A along the length of the elongate core 452, wherein point A is located between the distal end 451 of the elongate core 452 and the head 454. In one or more embodiments, A is disposed at a midpoint along the length of the elongate core 452. Alternatively, the elongate core 452 includes a tapered end at the distal end 451 of the plug 450 and the point A is proximally adjacent to the tapered end distally adjacent to the opening 474 to permit fluid communication between the chamber 418 and the stopper cavity 466.

Figure 37:
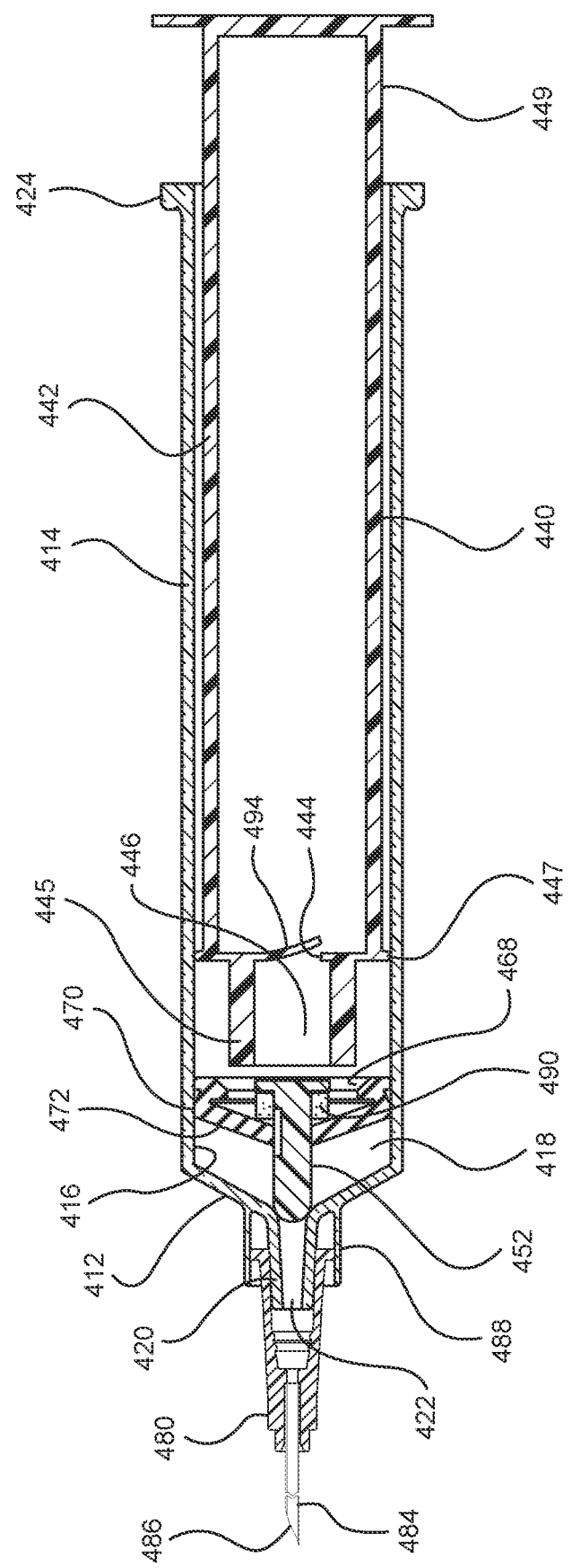
FIG. 37 illustrates a cross-sectional view of the assembled medical device illustrated in FIG. 35.

A porous portion 490 is disposed within the cavity 466 of the stopper body 462 between at least a portion of the plug 450 and the inside surface 464 of the stopper. The porous portion 490 is formed from a swellable polymer, as described herein. The porous portion 490 remains in an unexpanded state and porous to air before contact with a liquid. Upon contact with a liquid, the porous portion 490 expands and becomes impervious to air or liquid. Specifically, in one or more embodiments, the swellable polymer includes one or more openings that remain open to air flow but are closed due to the swellable polymer swelling upon contact with a liquid, thereby preventing liquid from permeating through the porous portion 490. In one or more embodiments, the porous portion 490 is disposed to form a buffer between the head 454 and the inside surface 464 of the stopper body 462. In use, upon contact with a liquid, the expansion of the porous portion 490 moves the head 454 and the plug 450 in the proximal direction, with respect to the opening 474 and inside surface 464 of the stopper. The presence of the porous portion 490 between at least a portion of the plug 450 and the inside surface 464 of the stopper, as shown in FIG. 37, blocks distal movement of the plug 450 relative to the opening 474 by forming a barrier between the head 454 and the inside surface 464 of the stopper body 462. As shown in FIG. 34, the porous portion 490 may be cylindrically shape with a hollow interior 492. The elongate core 452 of the plug 450 extends through the hollow interior 492. The length, shape and/or cross-sectional width of the porous portion 490 may be modified to any length, shape and/or cross-sectional width which permits the porous portion 490 to form a barrier between the head 454 and the inside surface 464 of the stopper and that is positioned to contact the liquid within the chamber 418. In a specific embodiment, the porous portion 490 may be in the shape of a torus, a cylindrical shape or any other shape surrounding the channel 456 and the elongate core 452. Alternatively, the porous portion 490 may be integrally formed on the elongate core 452. In one or more embodiments, the position and shape of the porous portion 490 may extend into the channel 456 that is disposed along a portion of the length of the plug 450.

The expansion of the swellable polymer functions to move the plug 450 proximally, by exerting a force in the proximal direction to the head 454. When in an unexpanded state, the porous portion 490 is disposed between the head 454 and the inside surface 464 of the stopper body 462 such that the channel 456 of the plug partially extends distally through the opening 474, permitting fluid communication between the chamber 418 and the cavity 466. When in an expanded state, the porous portion is disposed between the head 454 and the inside surface 464 of the stopper body 462 such that the channel 456 does not extend through the opening 474 and remains proximally adjacent to the opening 474. When the porous portion 490 is in the expanded state, the position of the channel 456 prevents fluid communication between the chamber 418 and the cavity 466. In one or more embodiments, the elongate core 452 forms a fluid-tight seal with the opening 474 when the channel 456 is disposed proximally adjacent to the opening 474.

The plunger rod 440 may be attached to the second stopper assembly 460. The plunger rod 440 shown more clearly in FIG. 35 includes a distal end 441, a proximal end 449, and an elongate body 442 extending from the distal end 441 and the proximal end 449 having a space 443. The space 443 is shown to extend along the length of the elongate body 442, however, it may be of any size or dimension to provide a vent for the air evacuated from the needle hub 480, tip 420 and chamber 418 between the second stopper assembly 460 and distal wall 412 of the syringe barrel.

The distal end 441 of the plunger rod shown in FIGS. 35-45 includes an outlet 444 and a valve 494 that provide a vent for the air evacuated from the syringe barrel 410 during use. The vent may be provided using alternative structures, for example, the first stopper 447 may have the shape and structure to provide a resilient barrier to fluid flow between the chamber 418 between the second stopper assembly 460 and the plunger rod 440 and the exterior of the syringe barrel 410 and the medical device 400. For example, the first stopper 447 may provide a fluid-tight seal with the interior surface 416 of the syringe barrel 410 during movement of the plunger rod 440 in the proximal direction but releases the fluid-tight seal with the interior surface 416 of the syringe barrel 410 during movement of the plunger rod 440 in the distal direction.

The outlet 444 and valve 494 permit fluid communication with the void 443. The outlet 444, when sealed, facilitates the formation of a vacuum within the chamber 418 of the syringe barrel 410 between the second stopper assembly 460 and the plunger rod 440. The valve 494 may be in form of any one-way valve or check valve that opens in one direction.

In one or more embodiments, the valve 494 provides a means for venting the air evacuated into the chamber 418 of the syringe barrel 410 between the second stopper assembly 460 and the plunger rod 440. In a specific embodiment, the valve 494 provides a relief valve for the vacuum created within the chamber 418, between the second stopper assembly 460 and the plunger rod 440, as will be explained in more detail below. In one or more embodiments the distal end 441 of the plunger rod 440 does not include a valve 494 or an outlet 444. The air evacuated into the chamber 418 remains within the space of the chamber 418 between the second stopper assembly 460 and the plunger rod 440.

In one or more embodiments which incorporate a valve 494 and an outlet 444, the valve 494 closes during creation of the vacuum within the chamber 418 between the second stopper assembly 460 and the plunger rod 440 and seals the outlet 237. During when the plunger rod 440 is attached to the second stopper assembly 460, the valve 494 opens to permit the air contained within the chamber between the plunger rod 440 and the second stopper assembly 460 escapes through the outlet 444. In one or more embodiments, the valve 494 is in the form of a flap.

The plunger rod 440 may be made of a rigid plastic or other material that has sufficient rigidity to withstand movement in the proximal and distal direction within the syringe barrel 410. Examples of suitable materials include polypropylene, polyethylene, polycarbonate and combinations thereof. The elongate body 442 may be cylindrical. In one or more embodiments, the shape of the elongate body 442 may be rectangular or other shape. The proximal end 449 of the plunger rod 440 includes an optional thumbpress 448.

The distal end 441 of the plunger rod includes the stopper-engaging portion 445, mentioned above, for attaching the second stopper assembly 460 to the distal end 441 of the plunger rod. In one or more embodiments, the first stopper 447 is disposed between the stopper-engaging portion 445 and the elongate body 442, however, it may be disposed at other locations on the plug 450. As shown, the first stopper is in the form of a disc formed around the elongate body 442, however, it may be attached as a separate component. The first stopper 447 may be formed from a material suitable for forming a fluid-tight seal with the interior surface 416 of the syringe barrel, which may include the same or different material utilized to form the stopper body 462 and/or the sealing portion 470. Exemplary materials include elastomeric materials, polymeric materials or other materials known in the art.

As shown in FIGS. 35-44, the stopper-engaging portion 445 is shaped to fit within the cavity 466 of the stopper body 462. In one or more embodiments, the stopper engaging portion 445 may includes a separate attachment structure. In a specific embodiment, the plunger rod 440 and second stopper assembly 460 may be attached after the plug 450 and porous portion 490 are disposed within the cavity 466, as will be discussed below. As shown more clearly in FIG. 36, the stopper-engaging portion 445 includes a void 446 in fluid communication with the cavity 466 of the stopper body 462, the channel 456 and the opening 474 of the stopper body. In one or more embodiments, the void 446 accommodates movement of the plug 450 in the proximal direction after expansion of the porous portion 490.

When utilizing medical device 400 in a traditional method, the plunger rod 440 and second stopper assembly 460 are inserted into the open proximal end 419 of the syringe barrel 410 but remain unattached. FIG. 37 illustrates the medical device 400 assembled and positioned for use as a traditional dose syringe. In FIG. 37, the medical device 400 is inserted into the syringe barrel 410 with the distal face 472 of the second stopper assembly 460 adjacent to the distal wall 412 of the syringe barrel and the plunger rod 440 is positioned at a short distance from the proximal end 269 of the second stopper assembly 460. The channel 456 is positioned so it extends through the opening 474 and is, at least partially, distally adjacent the opening 474 of the stopper body 462.

The unattached plunger rod 440 and the second stopper assembly 460 configuration permits the formation of a vacuum within the chamber 418 between the second stopper assembly 460 and the plunger rod 440 by utilizing the first stopper 447 to form a fluid-tight seal with the interior surface 416 of the syringe barrel 410 and moving the plunger rod 440 in the proximal direction relative to the separated and stationary second stopper assembly 460, which utilizes the sealing portion 470 to form a fluid-tight seal with the interior surface 416 of the syringe barrel.

FIGS. 37-40 illustrate a plunger rod 440 and second stopper assembly 460 assembled within the chamber 418 prior to aspiration.

The second stopper assembly 460 and plunger rod 440 may be assembled in the syringe barrel such that a vacuum may be created between the second stopper assembly 460 and the plunger rod 440. This configuration may be utilized when using the medical device 400 with a syringe barrel as a traditional dose syringe or fixed-dose syringe. FIGS. 37-41 specifically illustrate the use of the medical device 400 with a syringe barrel as a traditional dose syringe. The vacuum formed between the plunger rod 440 and the second stopper assembly 460 drives the air through the channel 465 and into the cavity 466.

Figure 38:
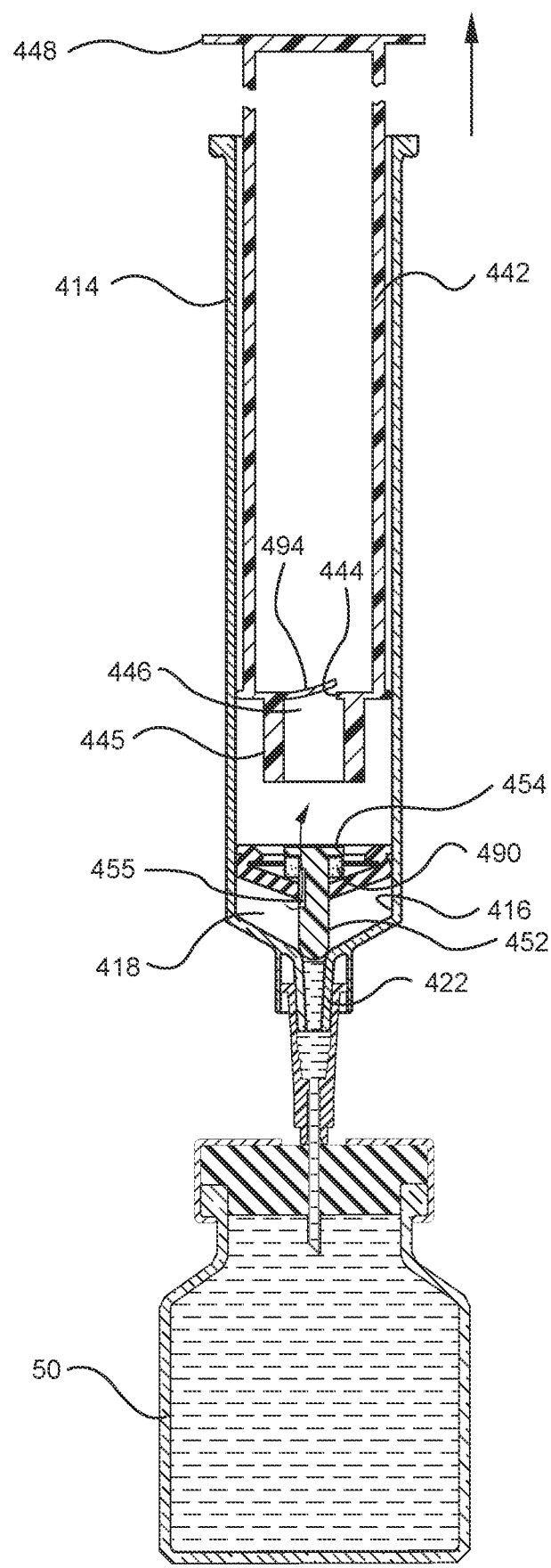
FIG. 38 illustrates a cross-sectional view of the medical device shown in FIG. 37 upon application of an initial force to the plunger rod in the proximal direction.

As shown in FIG. 37, the second stopper assembly 460 may be disposed within the syringe barrel 410 such that the distal face 472 contacts the distal wall 412 or is positioned as close as possible to the distal wall 412. The plunger rod 440 is also disposed within the syringe barrel 410 and remains unattached to the second stopper assembly 460. In this configuration, the user may insert the needle cannula 484 into a vial 50 and apply an initial force on the plunger rod 440 in the proximal direction to cause the plunger rod 440 to move in the proximal direction, while the second stopper assembly 460 remains stationary, as shown in FIG. 38. The first stopper 447 on the plunger rod 440 forms a fluid tight seal with the inside surface 416 of the syringe barrel 410 and movement of the first stopper 447 in the proximal direction causes a vacuum to form between the second stopper assembly 460 and the plunger rod 440. The vacuum draws the valve 494 closed and prevents fluid communication between the chamber 418 and the space 443 of the plunger rod through the outlet 444.

As shown in FIG. 38, the air trapped within the needle hub 480 and the syringe barrel 410 is drawn into the chamber 418 by the vacuum within the chamber 418 between the second stopper assembly 460 and the plunger rod 440. The vacuum also draws air into the channel 456, through the opening 474 of the stopper body 462 and into the stopper-engaging portion 445 of the plunger rod 440. The vacuum may also draw some liquid into the chamber 418 before movement of the second stopper assembly 460, however, once the liquid contacts the porous portion 490, the porous portion 490 expands and exerts a force on the head 454 in the proximal direction. This exertion of force causes the plug 450 to move proximally through the opening 474 into the cavity 466. Movement of the plug 450 causes the channel 456 to be positioned proximally adjacent to the opening 474, permitting the elongate core 452 of the plug 450 to seal the opening 474 of the second stopper or stopper assembly 460, thereby cutting off or blocking any escape path for the liquid through the channel 465. In this position, the elongate core 452 forms a fluid-tight engagement with the opening 474 of the stopper body, preventing any liquid from entering the opening 474 and the cavity 466 of the stopper body.

Figure 39:
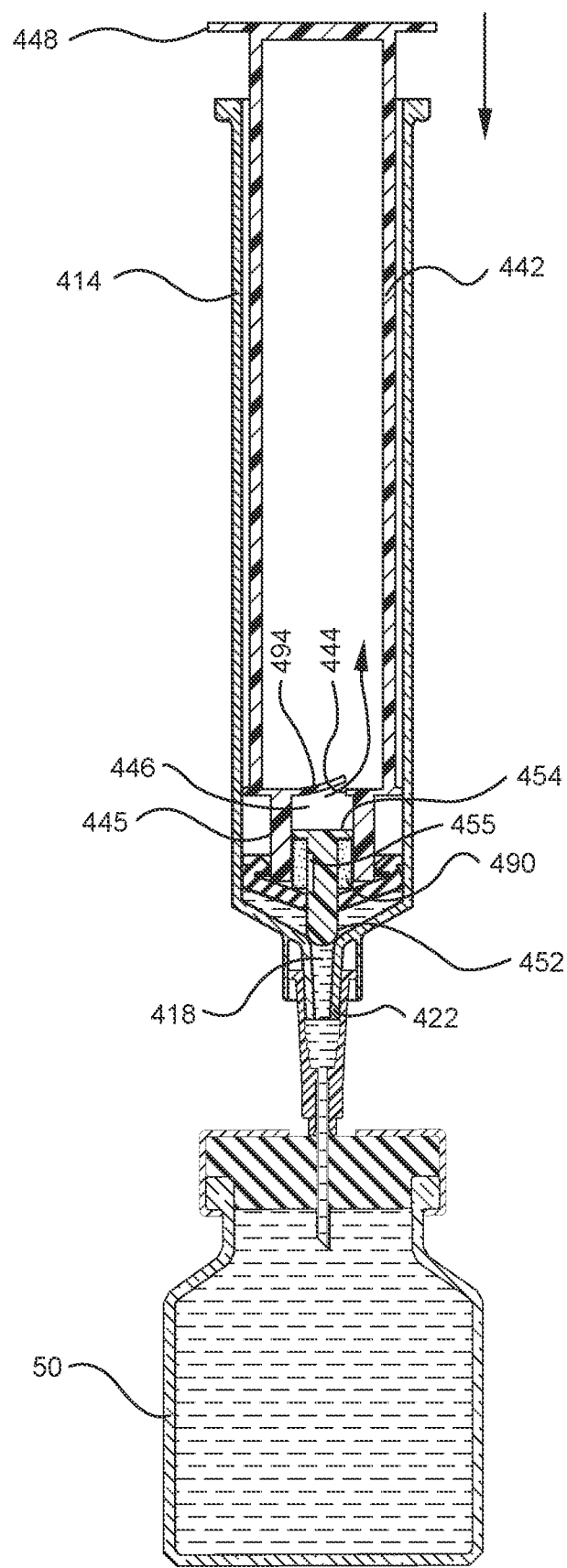
FIG. 39 illustrates the medical device shown in FIG. 38 upon application of a force to the plunger rod in the distal direction to attach the plunger rod and stopper.
Figure 40:
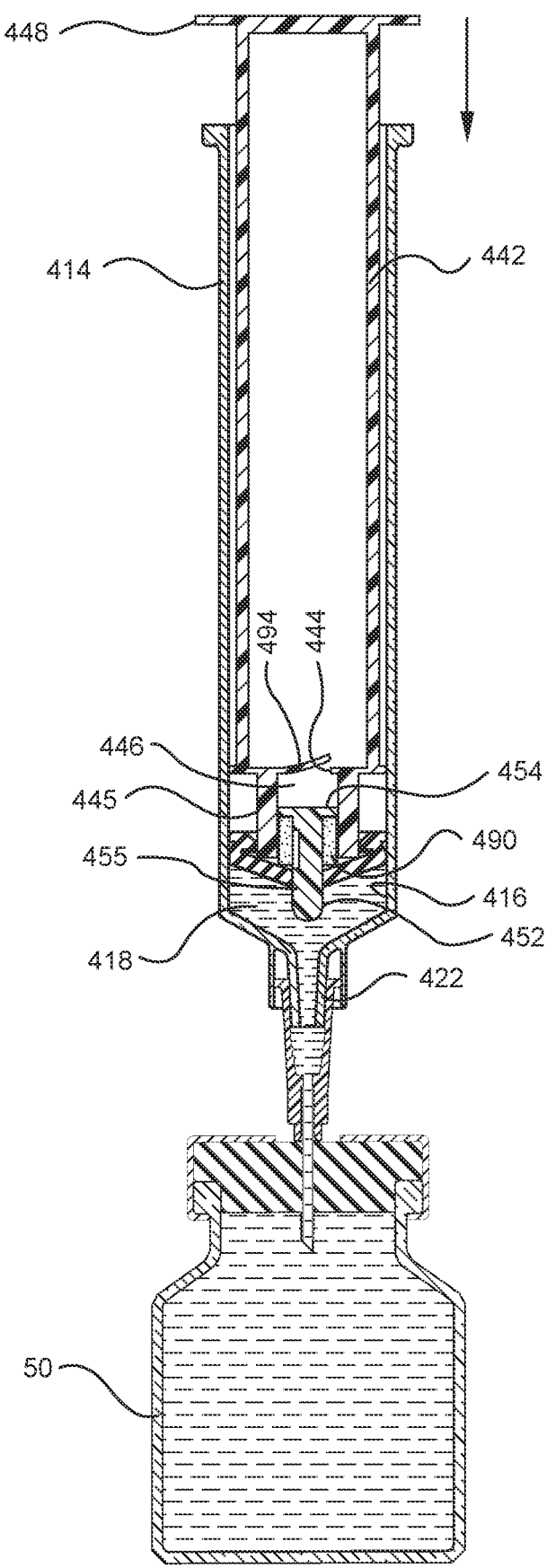
FIG. 40 illustrates the medical device shown in FIG. 39 drawing a desired amount of liquid from a vial into the syringe upon application of a force in the proximal direction to the attached plunger rod and stopper.
Figure 41:
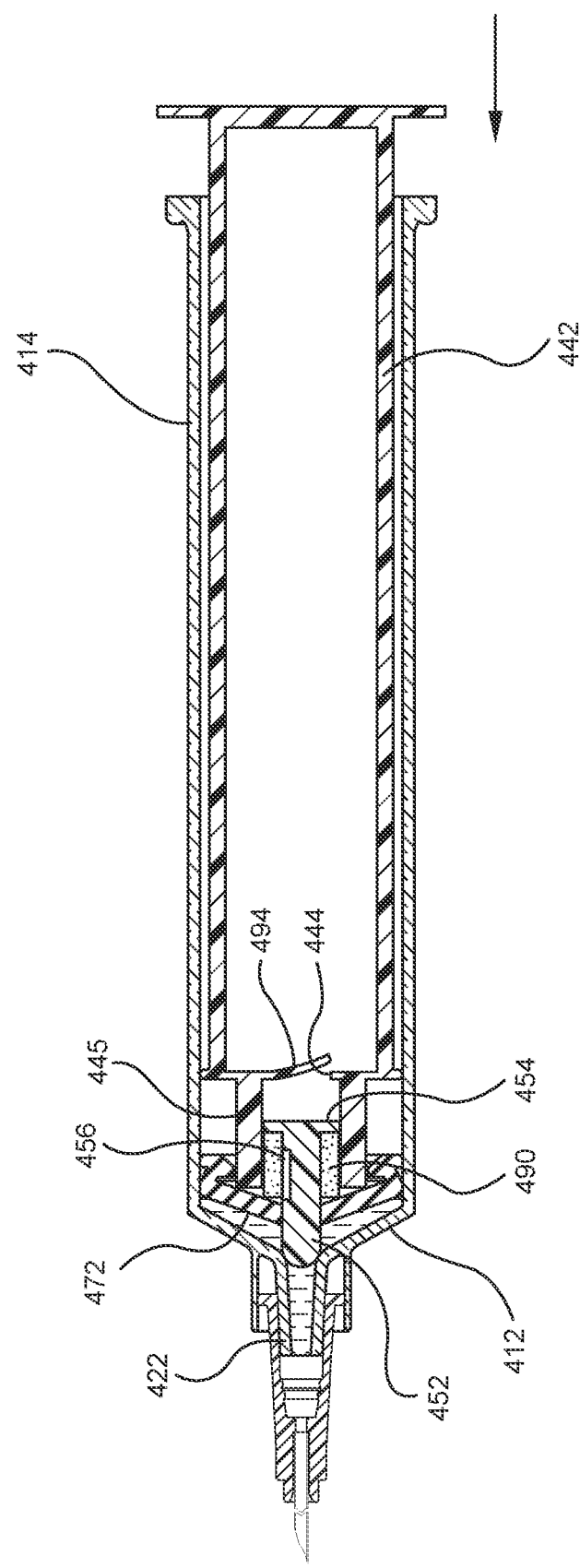
FIG. 41 illustrates the medical device shown in FIG. 40 after expulsion of the liquid from the syringe barrel upon application of a continuous force to the plunger rod in the distal direction

The user may aspirate a desired amount of liquid into the chamber 418 by attaching the plunger rod 440 to the second stopper assembly 460 and moving the second stopper assembly 460 in the proximal direction. The plunger rod 440 is attached to the second stopper assembly 460 upon application of a force on the plunger rod 440 in the distal direction so the stopper-engaging portion 445 engages the attachment structure 468 of the second stopper assembly 460, as shown in FIG. 39. Movement of the plunger rod 440 in the distal direction causes the valve 494 to open and vents the air contained within the chamber 418 between the second stopper assembly 460 and the plunger rod into the space 443 of the plunger rod. After attachment of the plunger rod 440 and the second stopper assembly 460, the user may apply a force on the assembled plunger rod 440 and second stopper assembly 460 in the proximal direction, as shown in FIG. 40. To expel the aspirated liquid, a force may be applied to the attached plunger rod 440 and second stopper assembly 460 in the distal direction until the desired amount of liquid is expelled from the chamber 418.

Figure 42:
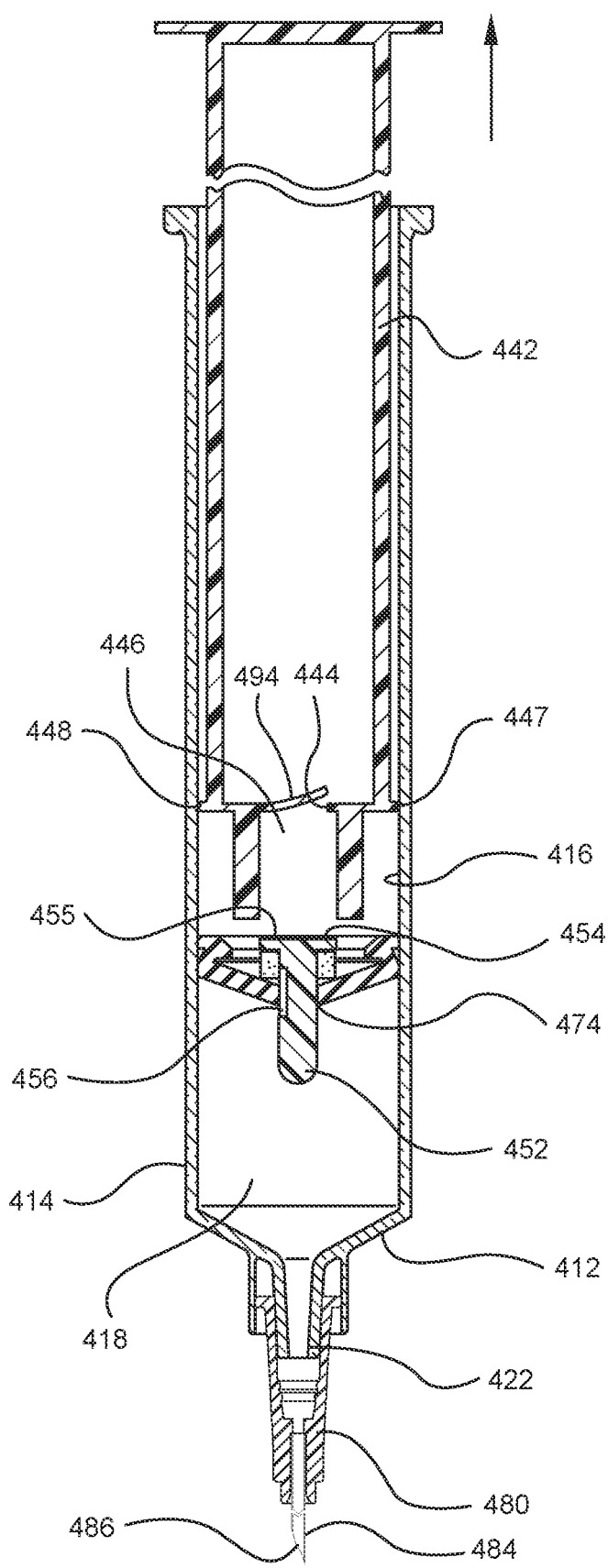
FIG. 42 shows a cross-sectional view of the medical device illustrated in FIG. 35 assembled in a fixed-dose configuration.
Figure 43:
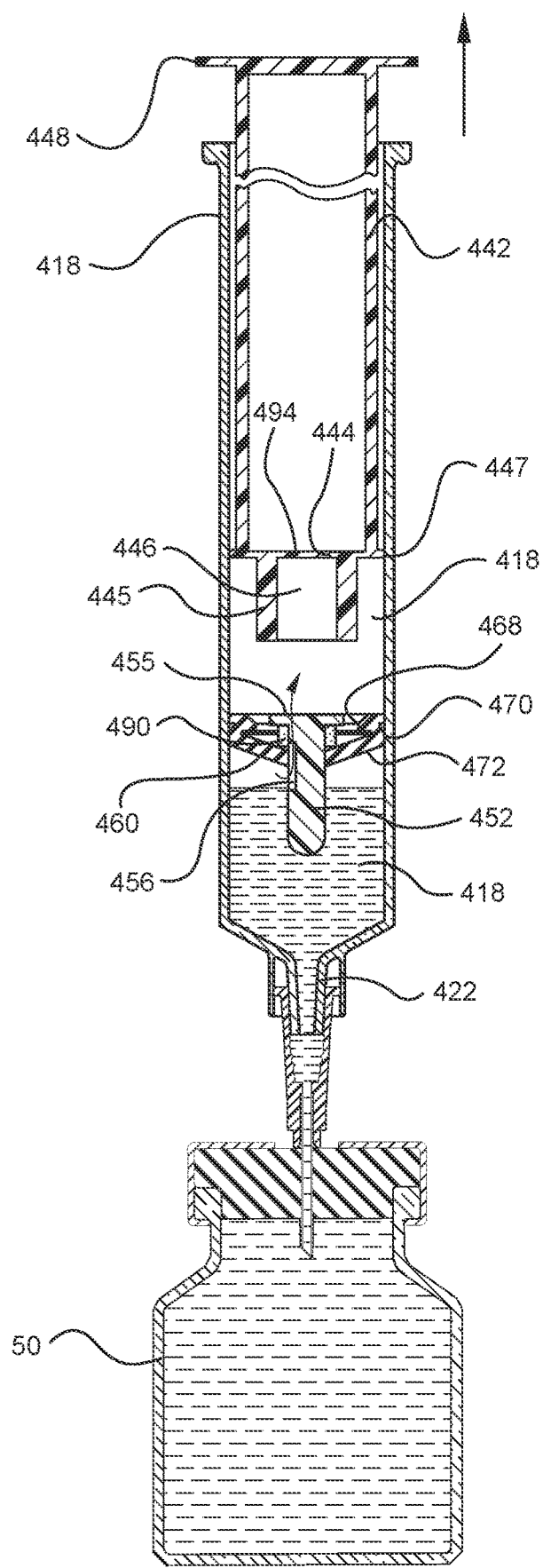
FIG. 43 illustrates a cross-sectional view of the medical device shown in FIG. 42 drawing liquid from a vial into the syringe barrel after application of a continuous force to the plunger rod in the proximal direction.

FIG. 42 illustrates the medical device 400 positioned for use as a fixed dose syringe. In FIG. 42, the medical device 400 is inserted into the syringe barrel 410 with the distal face 472 of the second stopper assembly 460 positioned at a pre-determined distance from the distal wall 412 of the syringe barrel. The plunger rod 440 is unattached to the second stopper assembly 460 and the position of the stopper assembly 460 at a distance from the distal wall 412 permits aspiration of a pre-selected amount of liquid into the chamber 418 of the syringe barrel. As shown in FIG. 43, to fill the chamber 418 of the syringe barrel 410 or other container, the needle cannula 484 is inserted into a container, such as a vial 50, to draw the fluid within the container into the syringe barrel 410. Thereafter, the user applies a continuous force in the proximal direction to the plunger rod 440 or, more specifically, the thumbpress 448, to aspirate the desired amount of liquid from the vial 50 into the syringe barrel 410. As shown in FIG. 43, the plunger rod 440 is movable in the proximal and distal direction, independently of the second stopper assembly 460, which remains stationary. The first stopper 447 forms a fluid-tight seal with the syringe barrel and the movement of the plunger rod 440 in the proximal direction forms a vacuum within the chamber 418. The vacuum draws the valve 494 closed and prevents fluid communication between the chamber 418 and the space 443 of the plunger rod 440 through the outlet 444.

The vacuum causes the air within the needle cannula 484 to be drawn into the chamber 418. The air is evacuated into the second stopper assembly 460 through the opening 474 and the channel 456 of the plug 450. The openings in the porous portion 490 remain open and permit air flow into the stopper cavity 466. The vacuum also draws liquid into the chamber 418. Any remaining air trapped within the needle hub 480 and the syringe barrel 410 rises to the top of the aspirated liquid or between the liquid and the distal face 472 of the stopper body 462.

Figure 44:
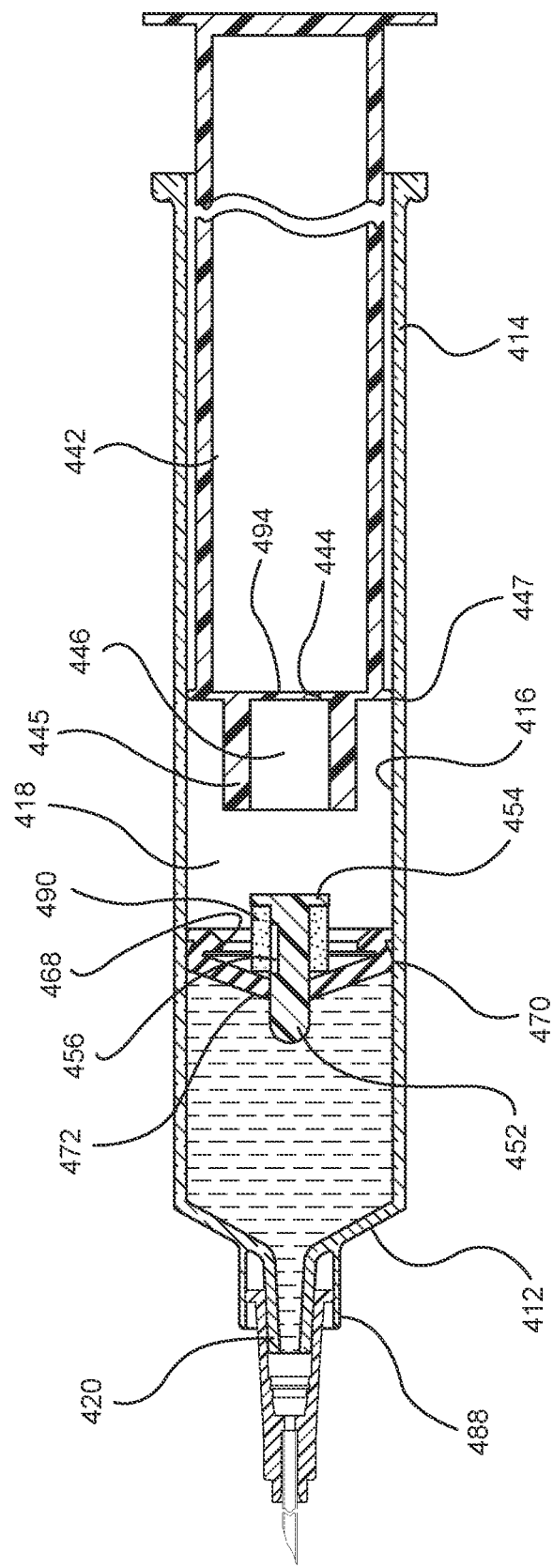
FIG. 44 illustrates a cross-sectional view of the medical device shown in FIG. 43 filled with liquid from the vial.
Figure 45:
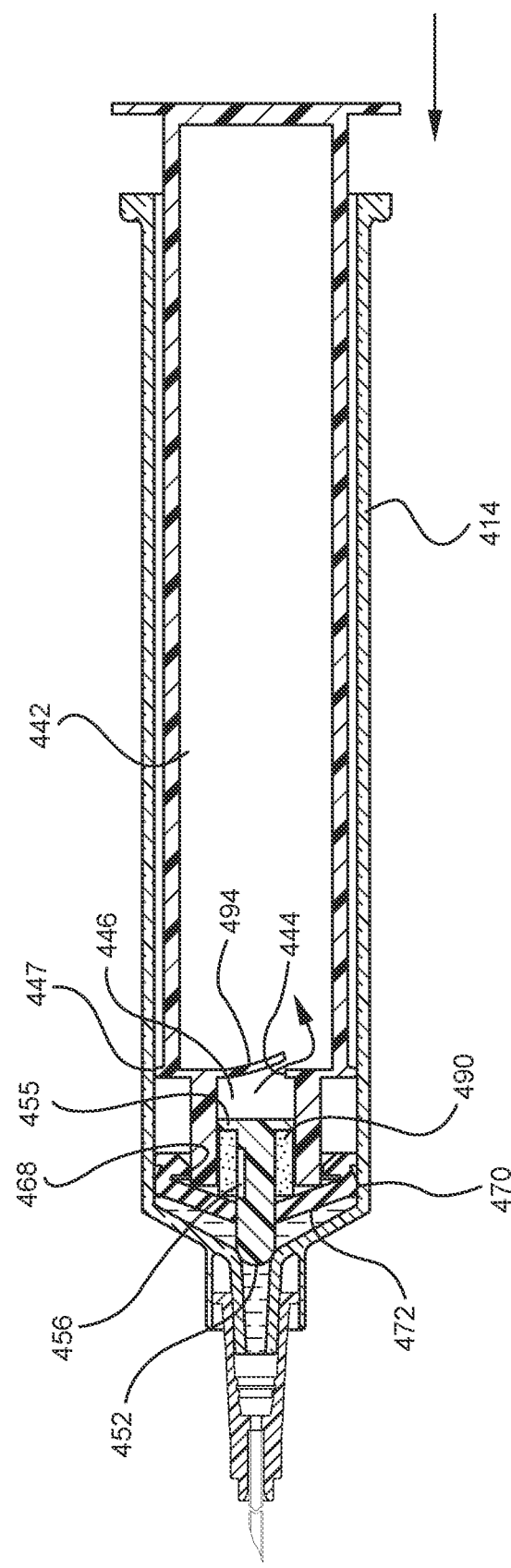
FIG. 45 illustrates a cross-sectional view of the medical device shown in FIG. 44 after expulsion of the liquid from the syringe barrel upon application of a continuous force to the plunger rod in the distal direction.

As shown in FIG. 44, once the air contained within the syringe barrel 410 escapes through the channel 456 and the aspirated liquid reaches the plug 450, the aspirated liquid also begins to enter the channel 456. Once the liquid contacts the porous portion 490, the porous portion 490 expands and exerts a force on the head 454 in the proximal direction. The openings in the swellable polymer of the porous portion 490 close due to swelling of the swellable polymer, forming a physical barrier to liquid flow. The exertion of force causes the plug 450 to move proximally through the opening 474 into the cavity 466. Movement of the plug 450 causes the channel 456 to be positioned proximally adjacent to the opening 474 and the elongate core 452 of the plug 450 forms a fluid-tight seal with the opening 474, thereby cutting off or blocking any escape path for the liquid through the channel 465. In this position, as more clearly shown in FIG. 40, the elongate core 452 forms a fluid-tight engagement with the opening 474 of the stopper body, preventing any liquid from entering the opening 474 and the cavity 466 of the stopper body.

To expel the liquid aspirated into the syringe barrel 410 in the fixed-dose configuration shown in FIGS. 42-45, the user may apply a distally directed force on the plunger rod 440 or thumbpress 448 to cause the plunger rod 440 to move in the distal direction. As the plunger rod 440 moves in the distal direction, the stopper-engaging portion 445 engages the inside surface 464 of the stopper body 462. During movement of the plunger rod 440 in the distal direction, the valve 494 opens to permit fluid communication between the chamber 418 and the space 443 of the plunger rod through the outlet 444.

Continuous application of a distally directed force causes the plunger rod 440 and second stopper assembly 460 move together in the distal direction toward the distal wall 412 of the syringe barrel 410. The porous portion 490 remains expanded and prevents movement of the plug 450 in the distal direction, maintaining the position of the channel 456 proximally adjacent the opening 474. This continuous force is applied to the plunger rod 440 until the distal face 472 contacts the distal wall 412 and the liquid is expelled or until the desired amount of liquid is expelled.

FIGS. 46-55 illustrate a medical device 500 according to a fifth aspect of the invention. In one or more embodiments, the medical device 500 includes a plunger rod 540 attached to a stopper hub 550 and a stopper assembly 560 including an actuated duct assembly 530 for aspirating liquid into a container and expelling the aspirated liquid.

For illustration, the medical device 500 is shown in use with a container in the form a syringe barrel 510. As shown more clearly in FIGS. 46-55, the syringe barrel 510 includes an open proximal end 519, a distal end 511 and a distal wall 512. A sidewall 514 extends from the distal end 511 to the open proximal end 519 and includes an interior surface 516 that defines a chamber 518 for retaining or holding fluids, which may include liquid medication and/or other liquids. The distal end 511 may also include a tip 520 having an open passageway 522 therethrough in fluid communication with the chamber 518. A needle cannula 584 is attached to the tip 520 and includes a lumen 586 or opening therethrough in fluid communication with the open passageway 522 and the chamber 518. In the embodiments shown in FIG. 47, the needle cannula 584 is attached directly to the tip 220 using methods known in the art. Alternatively, a needle hub (not shown) may be used to attach the needle cannula 584 to the tip 520. The proximal end 519 of the syringe barrel 510 may include optional flanges 524. The interior surface 516 of the syringe barrel 510 may have a smooth surface that is free of any protrusions or depressions. In use, the plunger rod 540, stopper hub 550 and stopper assembly 560 are inserted into the open proximal end 519 of the syringe barrel 510.

Figure 46:
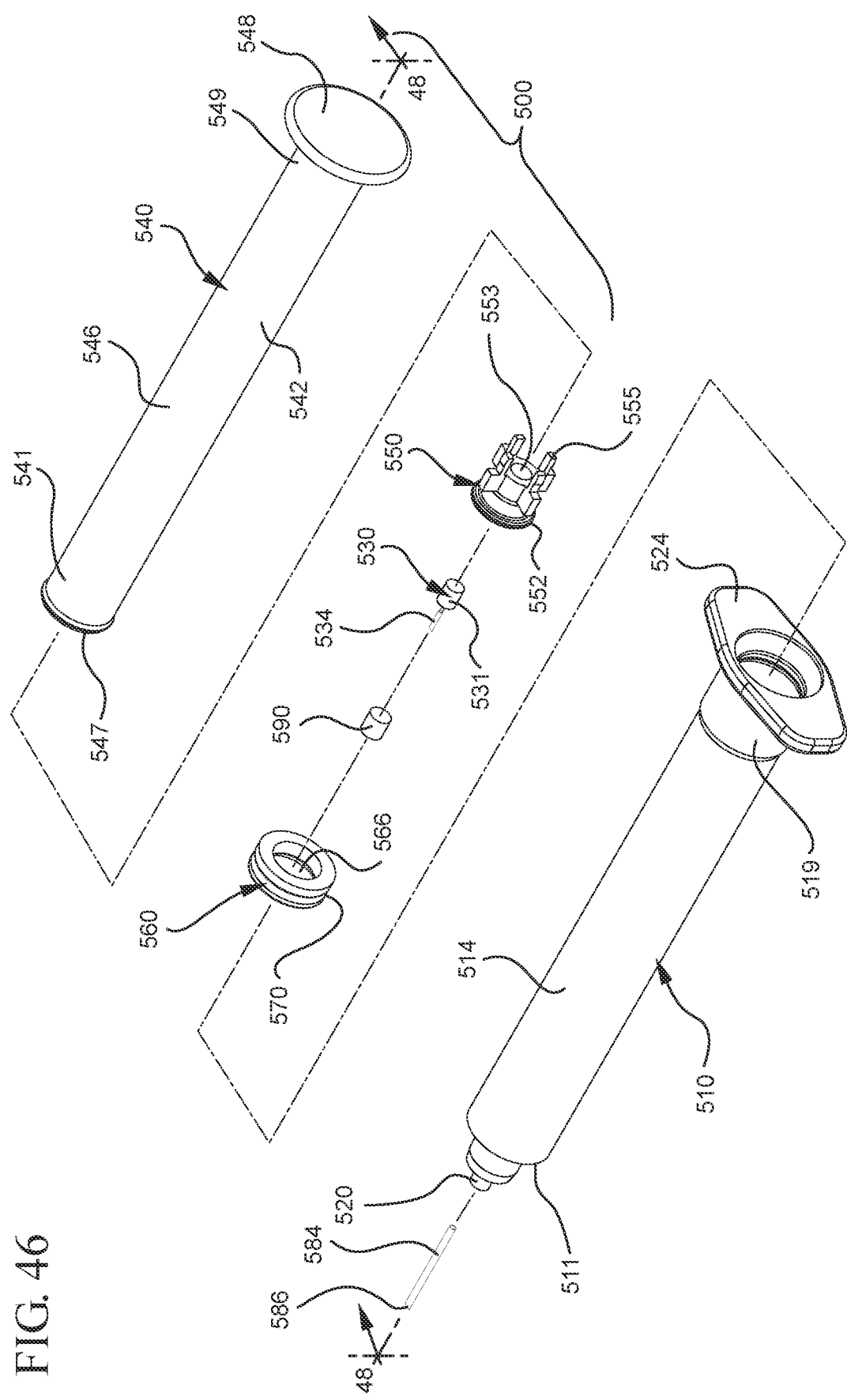
FIG. 46 shows a disassembled view of a syringe barrel and one or more embodiments of a medical device according to a fifth aspect of the present invention.
Figure 47:
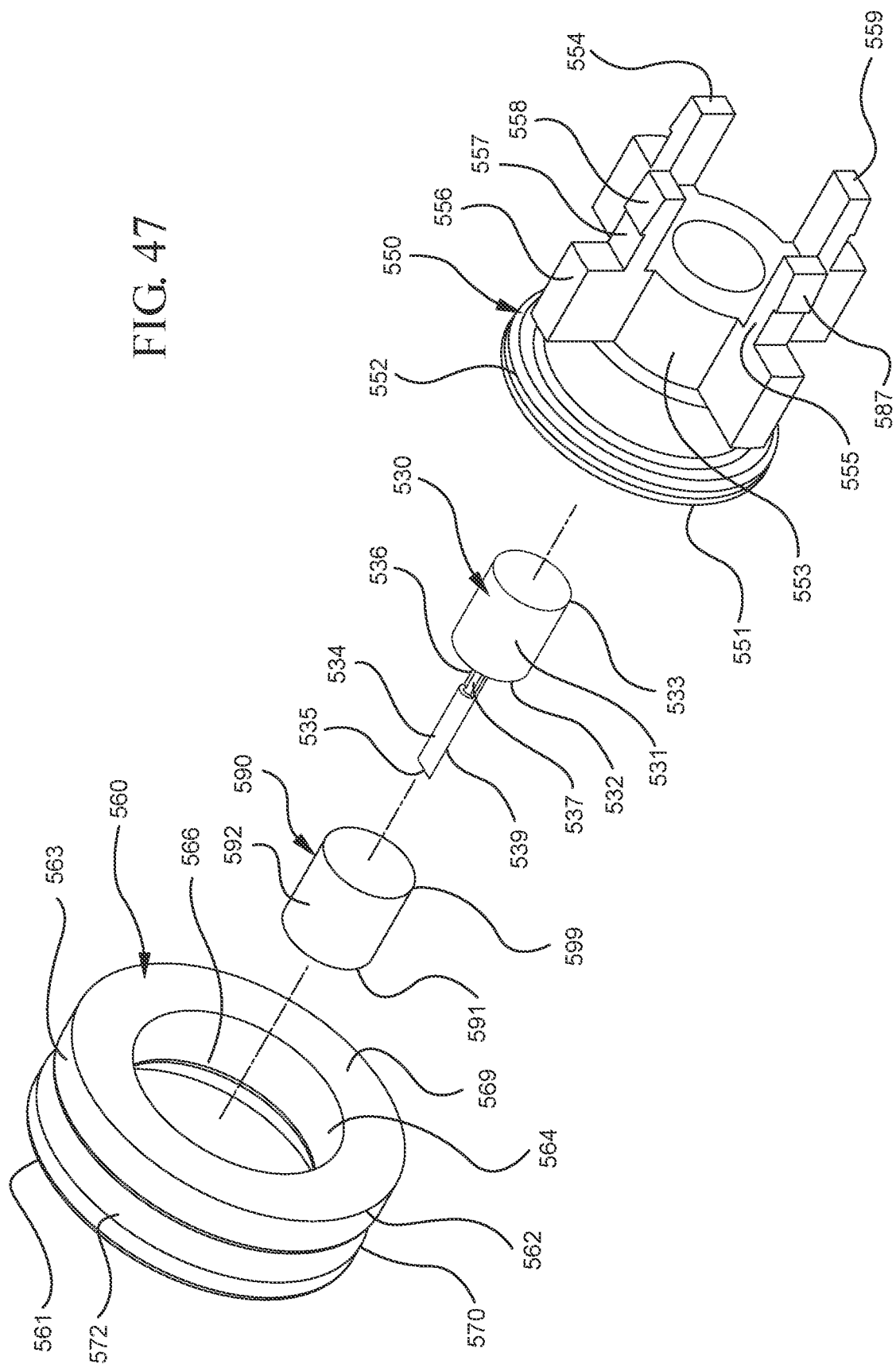
FIG. 47 illustrates an enlarged partial view of the stopper assembly shown in FIG. 46.

As more clearly shown in FIG. 47, the stopper assembly 560 includes a distal end 561, an open proximal end 569 and a stopper body 562 extending from the distal end 561 to the open proximal end 569. The stopper body 562 includes an outside surface 563 and an inside surface 564 defining a stopper cavity 566. In one or more embodiments, the inside surface 564 of the stopper body 562 may include a peripheral channel 568 forming a groove or ridge within the body for engagement with the stopper hub 550, as will be described in detail below. The stopper body 562 also includes a sealing portion 570 formed on the outside surface 563 for forming a fluid-tight seal with a syringe barrel having an interior surface with a circular cross-section. As shown in FIG. 46, the sealing portion 570 is formed adjacent the distal end 561, however, it may also be formed at other locations along the length of the outside surface 563 of the body 562. The sealing portion 570 includes at least one peripheral edge 572 shaped to form a fluid-tight seal with the inside surface of a syringe barrel. In one or more embodiments, the peripheral edge 572 may have a circular cross-section for forming a fluid-tight seal with a syringe barrel having an interior surface with a circular cross-section.

The stopper assembly 560 may be formed from an elastomeric material, polymeric material or other material known in the art. In one or more embodiments, the sealing portion 570 and/or the peripheral edge 572 may be made from a material suitable for forming a fluid-tight seal with the interior surface 516 of the syringe barrel 510 and may include the same or different material than the remaining components of the stopper assembly 560.

Figure 49:
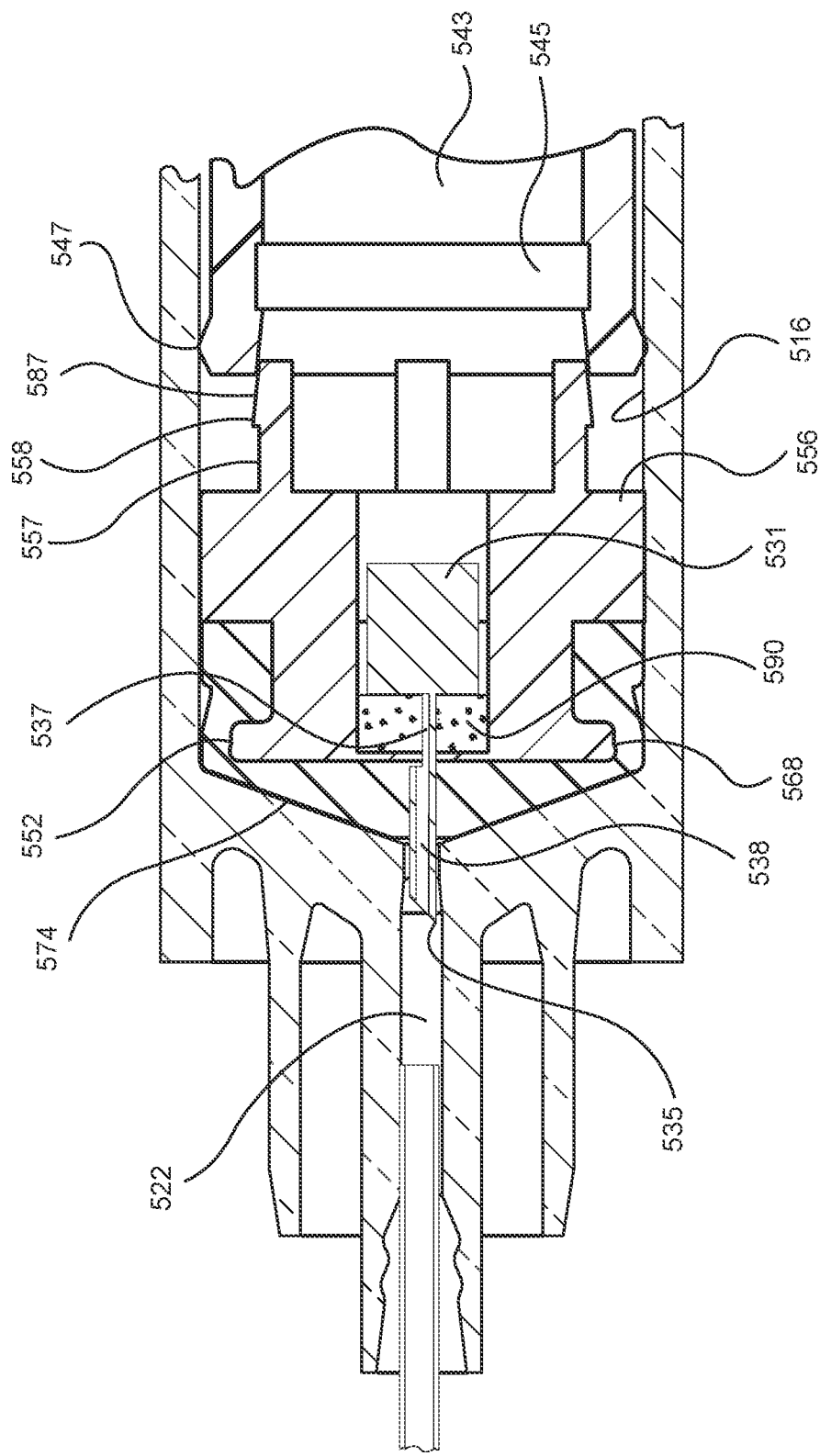
FIG. 49 illustrates an enlarged partial view of the medical device shown in FIG. 48.

As more clearly shown in FIG. 49, the distal end 561 of the stopper assembly 560 includes a distal face 574. In one or more embodiments, the distal face 574 is pierceable, as will be described in more detail below. Alternatively, the distal face 574 includes an opening in fluid communication with the stopper cavity 566. The distal face 574 may have a convex shape or be flexible to flex to a convex shape which conforms to the distal wall 512 of the syringe barrel 510. In one or more embodiments, the distal face 574 may also be shaped convexly so that it conforms more closely to the shape of the distal wall 512 of the syringe barrel 510 to expel as much liquid from the chamber 518 as possible. The distal face 574 may be formed from a material that reforms a fluid tight seal after being pierced. For example, the distal face 574 may be formed from a material that permits the distal face 574 to function as a septum.

The stopper assembly 560 includes an actuated duct assembly 530 that is disposed within the stopper cavity 566 and may be positioned to extend partially through the distal face 574 of the stopper body 562. The actuated duct assembly 530 includes a base 531 having a distal end 532 and a proximal end 533. The distal end 532 of the base 531 includes a duct member 534 attached thereto that extends in the distal direction from the distal end 532 of the base 531. In one or more embodiments, the duct member 534 has a structure for piercing the distal face 574 of the stopper to form an opening and extends through the opening. Alternatively, the duct member 534 extends through a pre-formed opening in the distal face 574.

The length, shape and/or cross-sectional width of the base 531 prevent the actuator duct assembly 530 and, specifically, the base 531, from extending completely through the distal face 574. As shown, the base 531 has a circular cross-section having a cross-sectional width larger than the cross-sectional width of the opening created in the distal face 574 by the duct member 534 or an opening preformed in the distal face. Alternatively, the base 531 may have a square or rectangular cross-section to prevent the actuator duct assembly 530 from extending through a circular opening created in the distal face 574 by the duct member 534 or a circular opening preformed in the distal face 574. The base 531 shown in FIG. 47 has a cylindrical shape or any other shape to facilitate movement of the base 531 in the proximal direction. For example, the base 531 may be shaped to fit within the stopper hub 550 and the hollow member 553 of the stopper hub 550. In one or more embodiments, the base 531 may have other shapes, for example, the base 531 may be shaped to include a flat disc (not shown) that is attached to the duct member 534.

The duct member 534 includes a closed proximal end 536 attached to the distal end 532 of the base 531, an open distal end 535 and a tubular wall 539 defining a channel 538 that extends from the closed proximal end 536 to the open distal end 535. The tubular wall 539 includes an open lateral opening 537 adjacent to the closed proximal end 536 in fluid communication with the open distal end 535. When the medical device 500 is assembled, the lateral opening 537 permits fluid communication between the open distal end 535 and the stopper cavity 566. As shown in FIG. 47, the lateral opening 537 extends partially along the length of the duct member 534 from the distal end of the tubular wall 539 such that the channel 538 is enclosed adjacent to the open distal end 535 and partially enclosed adjacent to the lateral opening 537. As shown more clearly in FIG. 47, the lateral opening 537 may be in the form of a notch or cut out in the tubular wall 539.

The open distal end 535 of the duct member 534 shown in FIG. 47 includes a beveled edge, however, a straight edge may also be utilized. The edge of the open distal end 535 is utilized to pierce through the distal face 574, allowing the tubular wall 539 to extend through the opening formed in the distal face 574. The open distal end 535 also permits fluid communication between the chamber 518 and the channel 538 of the duct member 534. The length, shape and/or cross-sectional width of the duct member 534 permit the actuated duct assembly 530 to extend through the open distal end 551 of the stopper hub 550 and partially through the opening formed in the distal face 574 of the stopper body 562. The length, shape and/or cross-sectional width of the duct member 534 also permit movement of the actuator duct assembly 530 and, more specifically, the base 531 in the distal and proximal directions relative to the distal face 574.

The actuated duct assembly 530 also includes a porous portion 590 having a distal end 591, a proximal end 599 and a core 592 extending from the distal end 591 to the proximal end 599. The porous portion 590 is formed from a swellable polymer, as described above. The porous portion 590 remains in an unexpanded state and porous to air before contacting a liquid. Upon contact with a liquid, the porous portion 590 expands and becomes impervious to air and/or liquid. Specifically, in one or more embodiments, the swellable polymer includes one or more openings that remain open to air flow prior to contact with a liquid but are closed due to the swellable polymer swelling upon contact with a liquid, thereby preventing liquid from permeating through the porous portion 590. In one or more embodiments, the porous portion 590 is disposed within the stopper cavity 566, adjacent to the duct member 534. In one or more embodiments, the porous portion 590 is disposed to form a buffer or barrier between the base 531 and the inside surface 564 of the stopper body 562. The presence of the porous portion 590 between at least ha portion of the base 531 and the inside surface 564 of the stopper, as shown in FIG. 49, blocks distal movement of the base 531 relative to the distal face 574 by forming a barrier between the base 531 and the inside surface 564 of the stopper body 562. In use, upon contact with a liquid, the expansion of the porous portion 590 moves the base 531 and duct member 534 in the proximal direction, with respect to the inside surface 564 of the stopper.

The length, shape and/or cross-sectional width of the porous portion 590 may be modified to any length, shape and/or cross-sectional width which permits the porous portion 490 to form a barrier between the base 531 and the inside surface 564 of the stopper and that is positioned to contact the liquid within the chamber 518. In a specific embodiment, the porous portion 590 may be in the shape of a torus or may have a cylindrical shape or any other shape to surround the lateral opening 537 and prevent liquid from flowing between the lateral opening 537 and the stopper cavity 566. Alternatively, the porous portion 590 may be integrally formed on the duct member 534. In one or more embodiments, the position and shape of the porous portion 590 may extend into the lateral opening 537 that is disposed along a portion of the length of the duct member 534.

Figure 48:
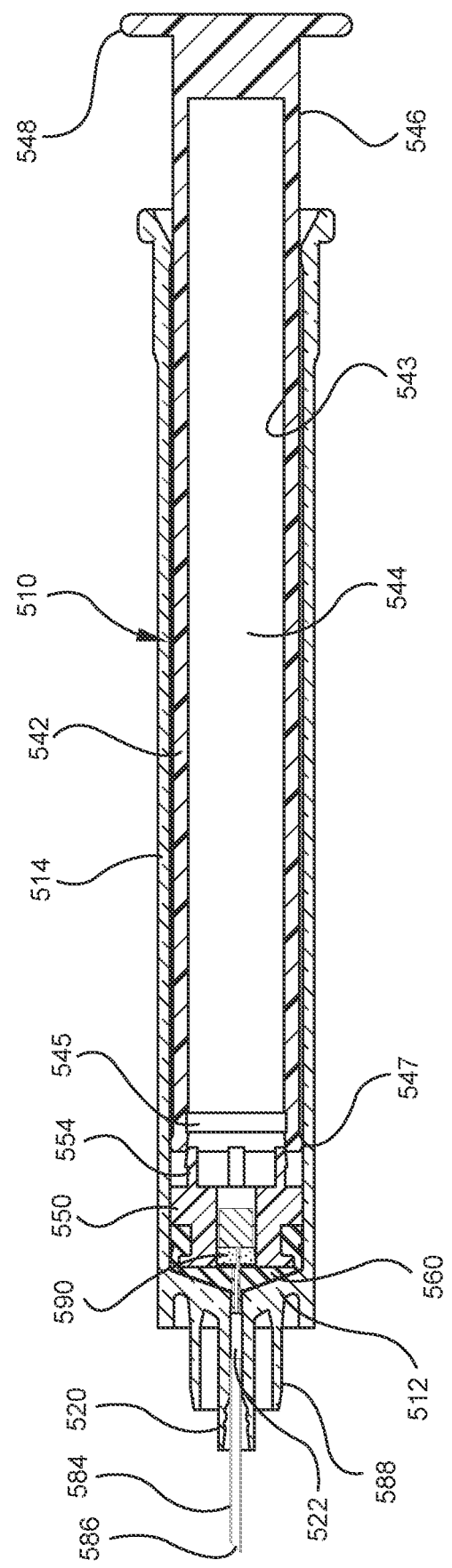
FIG. 48 illustrates a cross-sectional view of the assembled medical device illustrated in FIG. 47 assembled with a syringe barrel taken along line 48-48.

As shown in FIG. 49, the duct member 534 and the porous portion 590 are engaged such that the duct member 534 extends through the core 592 of the porous portion 590. As shown, the open distal end 535 of the duct member extends through the core 592 and past the distal end 591 of the porous portion 590. According to one or more embodiments, the duct member 534 is engaged with the porous portion 590 by using the open distal end 535 of the duct member 534 to pierce the core 592 at the proximal end 599 and through to the distal end 591 of the core 592 so the open distal end 535 extends past the distal end 591 of the core, as shown in FIG. 48. In one or more embodiments, the core 592 forms a fluid-tight seal with the duct member 534 after swelling or activation but and permits fluid communication between the chamber 518 and the stopper cavity 566 before swelling or activation. In one or more alternative embodiments, the porous portion 590 includes an inlet (not shown) at the proximal end 599 and an outlet (not shown) at the distal end 591 that define a path (not shown) through the porous portion 590. In such embodiments, the duct member 534 is inserted through the inlet and extends past the outlet. The path may have a size and length, shape and/or cross-sectional width to form a fluid-tight seal with the tubular wall 539 of the duct member 534.

The actuator duct assembly 530 is positioned with respect to the porous portion 590 such that the expansion of the swellable polymer functions to move the base 531 in the proximal direction, by exerting a force on the distal end 532 of the base 531 in the proximal direction. When in an unexpanded state, the porous portion 590 is disposed between the distal end 532 of the base 531 and the inside surface 564 of the stopper body 562 such that the duct member 434 partially extends distally through the distal face 574. In the unexpanded state, as shown in FIGS. 48-49, the open distal end 535 of the duct member 534 extends distally past the distal face 574. The lateral opening 537 remains disposed proximally adjacent to the distal face 574. In one or more embodiments, the lateral opening 537 may be partially or completely surrounded by the porous portion 590. In the event the lateral opening 537 is partially or completely surrounded by the porous portion 590, expansion of the porous portion may close or seal the lateral opening 537 upon contact with a liquid and prevent fluid communication between the lateral opening 537 and the open distal end. The expansion of the porous portion 590 causes the base 531, duct member 534 and, consequently, the open distal end 535 to move proximally relative to the distal face 574. The movement of the duct member 534 causes the open distal end 535 of the duct member 534 to be enclosed within the stopper cavity 566 and disposed proximally adjacent the distal face 574. The distal face 574 reforms a fluid-tight seal to prevent communication between the stopper cavity 566 and the chamber 518. The positioning of the open distal end 535 proximally adjacent the distal face 574 and enclosed within the stopper cavity 566 prevents fluid communication between the stopper cavity and chamber 518. In one or more embodiments, the movement of the duct member 534 may also cause the lateral opening 537 to be completely surrounded by the porous portion 590, which is rendered impervious to air and liquid upon contact with a liquid. In such embodiments, fluid communication between the stopper cavity 566 and chamber 518 is further prevented by the seal formed around the lateral opening 537.

As shown in FIGS. 46-48, the stopper hub 550 is attached to the proximal end 569 of the stopper body. The stopper hub 550 includes an open distal end 551 and an open proximal end 559. The open distal end 551 of the stopper hub 550 provides a support on which the base 531 of the actuated duct assembly 530 rests. The duct member 534 extends through the open distal end 551.

The stopper hub 550 also includes a stopper-engaging portion 552, which may include a disc extending radially outwardly, for attachment of the stopper hub 550 to the stopper assembly 560. Specifically, as more clearly shown in FIG. 48, the stopper-engaging portion 552 is disposed at the distal end 551 of the stopper hub 550 and extends radially outwardly to engage the peripheral channel 568 of the stopper assembly 560. In one or more embodiments, the stopper-engaging portion 552 may be in the form of a tab (not shown), which corresponds to an opening or other corresponding structure on the inside surface 564 of the stopper. In a specific embodiment, the stopper-engaging portion 552 may have an opening (not shown) and the inside surface of the stopper may include a tab (not shown) extending radially inwardly to engage with the opening (not shown). Other means to engage the stopper hub 550 to the stopper assembly 560 may also be utilized. Alternatively, the stopper assembly 560 may be integrally formed on the distal end 551 of the stopper hub 550. The stopper hub may be formed from a rigid plastic or other material.

A hollow member 553 extends from the stopper-engaging portion 552 to a plunger-engaging portion 554, disposed adjacent to the proximal end 559 of the stopper hub 550. As shown, the plunger-engaging portion 554 is formed on the outside surface of the hollow member 553. In one or more alternative embodiments, the plunger-engaging portion 554 may be formed on the inside surface of the hollow member 553. As shown in FIG. 47, the plunger-engaging portion 554 includes a plurality of projecting fingers 555 extending from the hollow member 553 toward the proximal end 559. In one or more embodiments, the plurality of projecting fingers 555 are configured to frictionally engage the inside surface of the plunger rod, as will be described below. As shown in FIG. 47, one or more of the projecting finger 555 may include a support member 556 formed along the outside surface of the hollow member 553. The support members 556 extend radially outwardly from the outside surface of the hollow member 553. As shown in FIG. 47, the support members 556 have a rectangular cross-section, however, the support members 556 may have other shapes. The projecting fingers 555 extend in the proximal direction from the support members 556. As shown in FIG. 47, the projecting fingers 555 include a notched portion 557 forming a hooked portion 558 facing radially outwardly. The hooked portion 558 may include a tapered surface 587 that facilitates movement of the plunger rod 540 in the distal direction relative to the stopper hub 550 to facilitate engagement of the plunger rod 540 and the stopper hub 550. When assembled to a plunger rod, the hooked portions 558 engage with a corresponding structure formed on the plunger rod 540 as will be described in additional detail below. Alternatively, the plunger-engaging portion 554 may be formed on the outside surface of the hollow member 553 and may include a wall (not shown) having a groove (not shown) formed on the wall for engagement with a corresponding structure on the plunger rod. In one or more embodiments, the plunger-engaging portion 554 may include a wall (not shown) having a textured surface or a coating that creates or increases frictional interference between the exterior surface of the plunger-engaging portion 554 and the inside surface of the plunger rod. The plunger rod 540 and the stopper hub may also be attached using other means known in the art.

The plunger rod shown more clearly in FIGS. 46 and 48 includes an open distal end 541, a proximal end 549, and a hollow elongate body 542 extending from the distal end 541 and the proximal end 549. The hollow elongate body 542 includes an inside surface 543 that defines a void space 544 and an outside surface 546 including a sealing edge 547. The sealing edge 547 forms fluid-tight seal with the interior surface 516 of the syringe barrel 510 and may be formed from an elastomeric material, polymeric material or other known material suitable for forming a fluid-tight seal with the interior surface 516 of the syringe barrel. The plunger rod 540 may be made of a rigid plastic or other material that has sufficient rigidity to withstand movement in the proximal and distal direction within the syringe barrel 510. Examples of such materials include polypropylene, polyethylene, polycarbonate and combinations thereof. The elongate body 542 may be cylindrical. In one or more embodiments, the shape of the elongate body 542 may be rectangular or other shape. The proximal end 549 of the plunger rod 540 includes an optional thumbpress 548.

The inside surface 543 of the plunger rod 540 includes an engaging means for engaging the plunger-engaging portion 554 of the stopper hub 550. As shown in FIG. 48, the engaging means includes a peripheral groove 545 disposed adjacent to the open distal end for engaging the hooked portion 558 of the projecting fingers 555.

In use, the stopper hub 550 is engaged to the stopper assembly 560 and disposed within the chamber 518 of the syringe barrel 510. The plunger rod 540 is inserted into the syringe barrel 510 and remains unattached to the plunger-engaging portion 554 of the stopper hub 550. During use, the plunger rod 540 may be engaged to the stopper hub 550, as shown in FIGS. 48-55. Before aspirating fluid into the chamber 518 of the syringe barrel 510 or other container, the distal face 574 of the stopper assembly 560 is positioned adjacent to the distal wall 528 of the syringe barrel 510, so that the air within the chamber 518 is minimized and is primarily present in the tip 520 of the syringe barrel 510 or other container. The open distal end 535 pierces the distal face 574 or, alternatively, extends through a preformed opening in the distal face 574 to permit fluid communication between the chamber 518 and the stopper cavity 566. In one or more embodiments, the distal face 574 forms a fluid tight seal with the tubular wall 539 of the duct member 534. The plunger rod 540 is positioned unattached to the plunger-engaging portion 554 of the stopper hub 550 in a first position, as shown more clearly in FIG. 49. In the first position, the plunger rod 540 is not engaged with the stopper hub 550 and is moveable in the proximal and distal directions within the chamber 518, independently of the stopper assembly 560 and/or stopper hub 550. In one or more embodiments, the open distal end 541 of the plunger rod is positioned adjacent to the tapered surface 587 of the hooked portion 558 of the projecting fingers 555 but not engaged with the notched portion 557 of the plunger-engaging portion 554.

Figure 50:
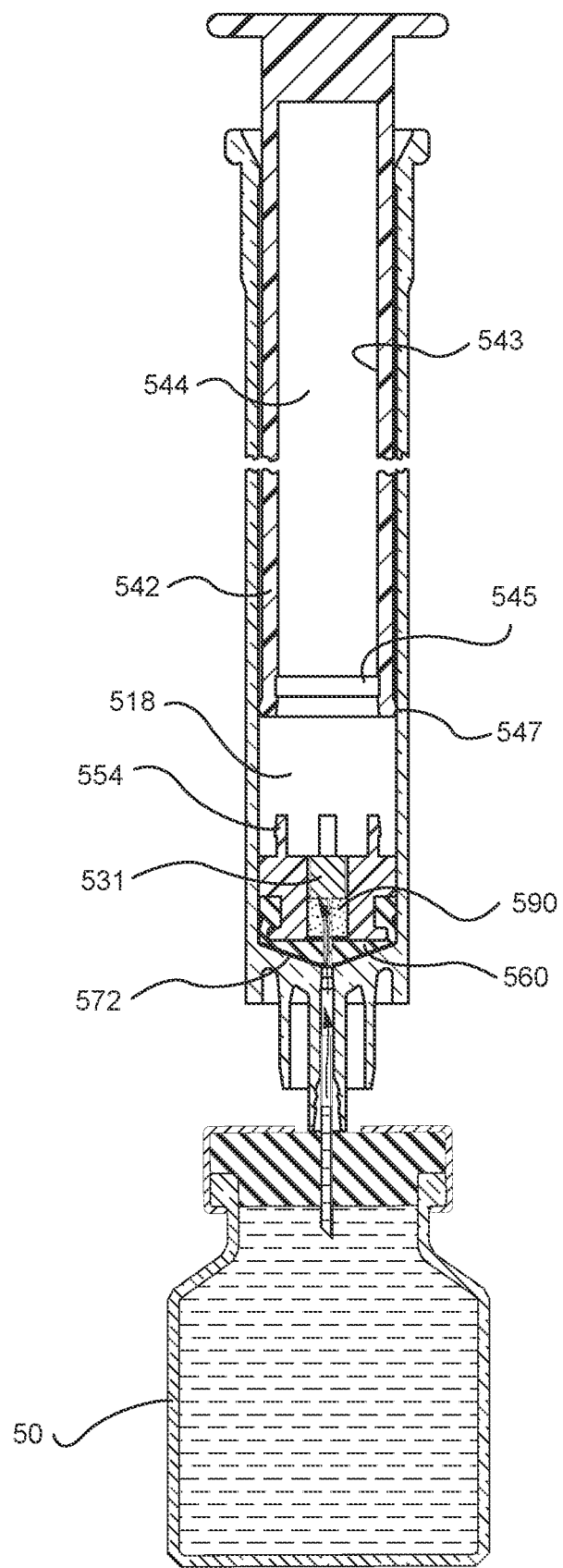
FIG. 50 illustrates the medical device shown in FIG. 48 drawing liquid from a vial into the syringe barrel and upon application of an initial force to the plunger rod in the proximal direction.
Figure 51:
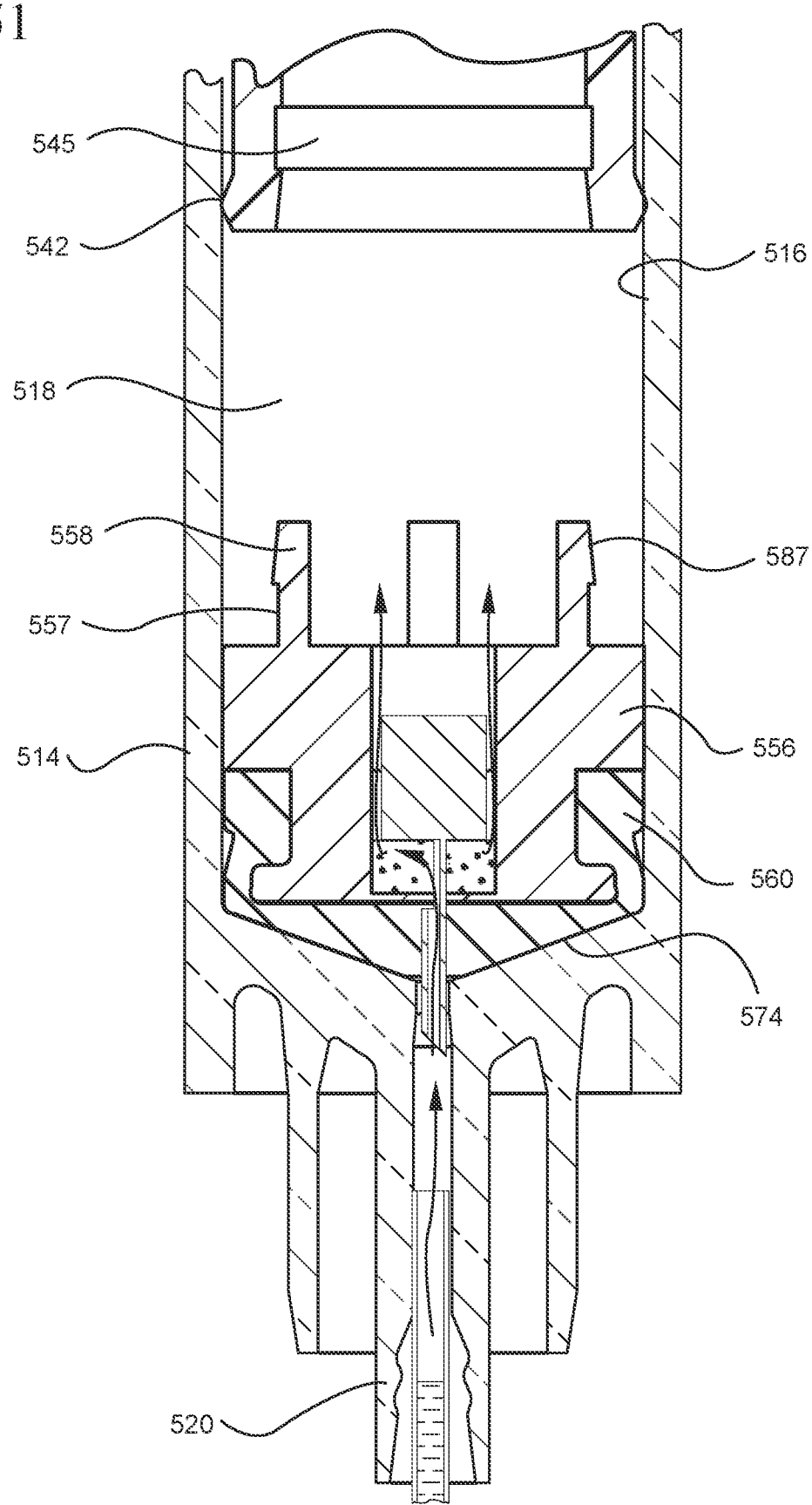
FIG. 51 illustrates an enlarged partial view of the medical device shown in FIG. 50.
Figure 52:
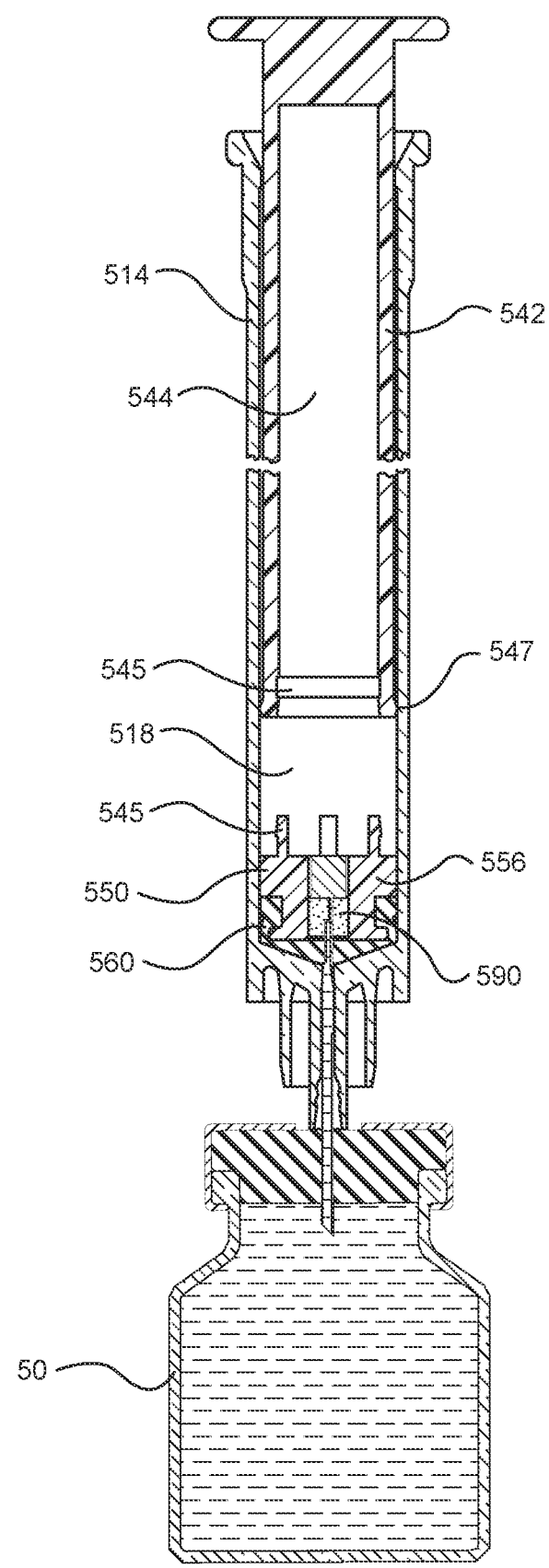
FIG. 52 illustrates the medical device shown in FIG. 50 after application of the initial force to the plunger rod in the proximal direction.
Figure 53:
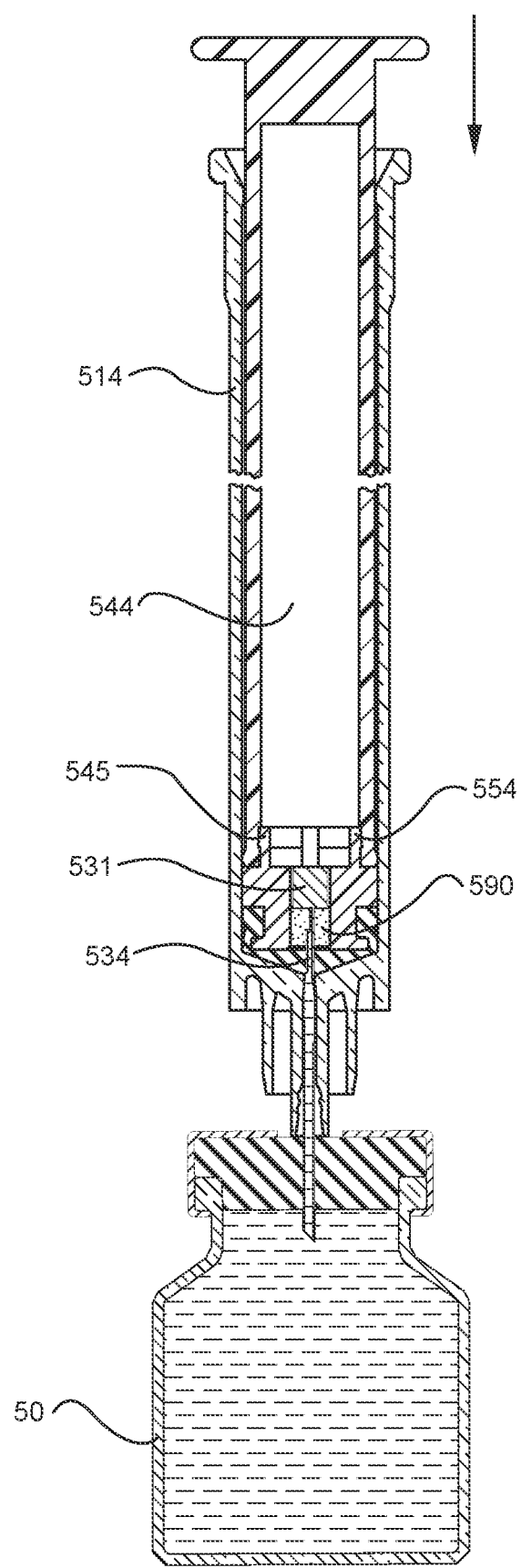
FIG. 53 illustrates the medical device shown in FIG. 52 after application of a force on the plunger rod in the distal direction.

As shown in FIG. 50, to fill the chamber 518 of the syringe barrel 510 or other container, the needle cannula 584 is inserted into a container, such as a vial 50, to draw the fluid within the container into the syringe barrel 510. A force in the proximal direction is applied to the plunger rod 540 while the plunger rod 540 is positioned in the first position. The sealing edge 547 forms a fluid-tight seal with the interior surface 516 of the syringe barrel as the plunger rod is pulled or moved in the proximal direction. The movement of the plunger rod 540 also creates a vacuum within the chamber 518 between the stopper hub 550 and the plunger rod 540. The vacuum causes a pressure differential between area within the tip 520 and chamber 518 between tip 520 and the distal face 574 of the stopper body 562 and the area within the chamber 518 between inside surface 564 of the stopper body 562 and the inside surface 543 of the plunger rod 540. The pressure differential facilitates evacuation of air trapped within the needle cannula 584, tip 520 and chamber 518 through the open distal end 535 and lateral opening 537 of the duct member 534. In one or more embodiments, the air is evacuated through the porous portion 590, which remains porous to air because liquid has not yet entered the duct member 534. The air escapes through the porous portion 590 through the hollow member 553 of the stopper hub 550 and into the chamber formed between the stopper hub 550 and the plunger rod 540. The evacuation of air from the syringe barrel 510 and tip 520 is shown more clearly in FIGS. 50-51.

As air begins to escape through the duct member 534, the vacuum within the chamber 518 between the inside surface 564 of the stopper assembly 560 and the inside surface 543 of the plunger rod may also draw liquid into the chamber 518 of the syringe barrel 510. As the liquid enters the duct member 534 and flows through the lateral opening 537, it comes in contact with the porous portion 590. Upon contact with the liquid, the swellable polymer of the porous portion 590 begins to expand and the openings in the porous portion 590 begin to close. The expansion of the porous portion 590 causes a force in the proximal direction to be applied to the distal end 532 of the base 531. This force causes the base 531 to move in the proximal direction, relative to the distal face 574 of the stopper body 562. This movement also causes the open distal end 535 of the duct member 534 to move in the proximal direction so it is proximally adjacent to the distal face 574. The distal face 574 of the stopper reforms a fluid tight seal, preventing fluid communication between the chamber 518 and the stopper cavity 566. In one or more embodiments, the porous portion may also seal or close the lateral opening 537 to further prevents fluid communication between the chamber 518 and stopper cavity 566.

Figure 54:
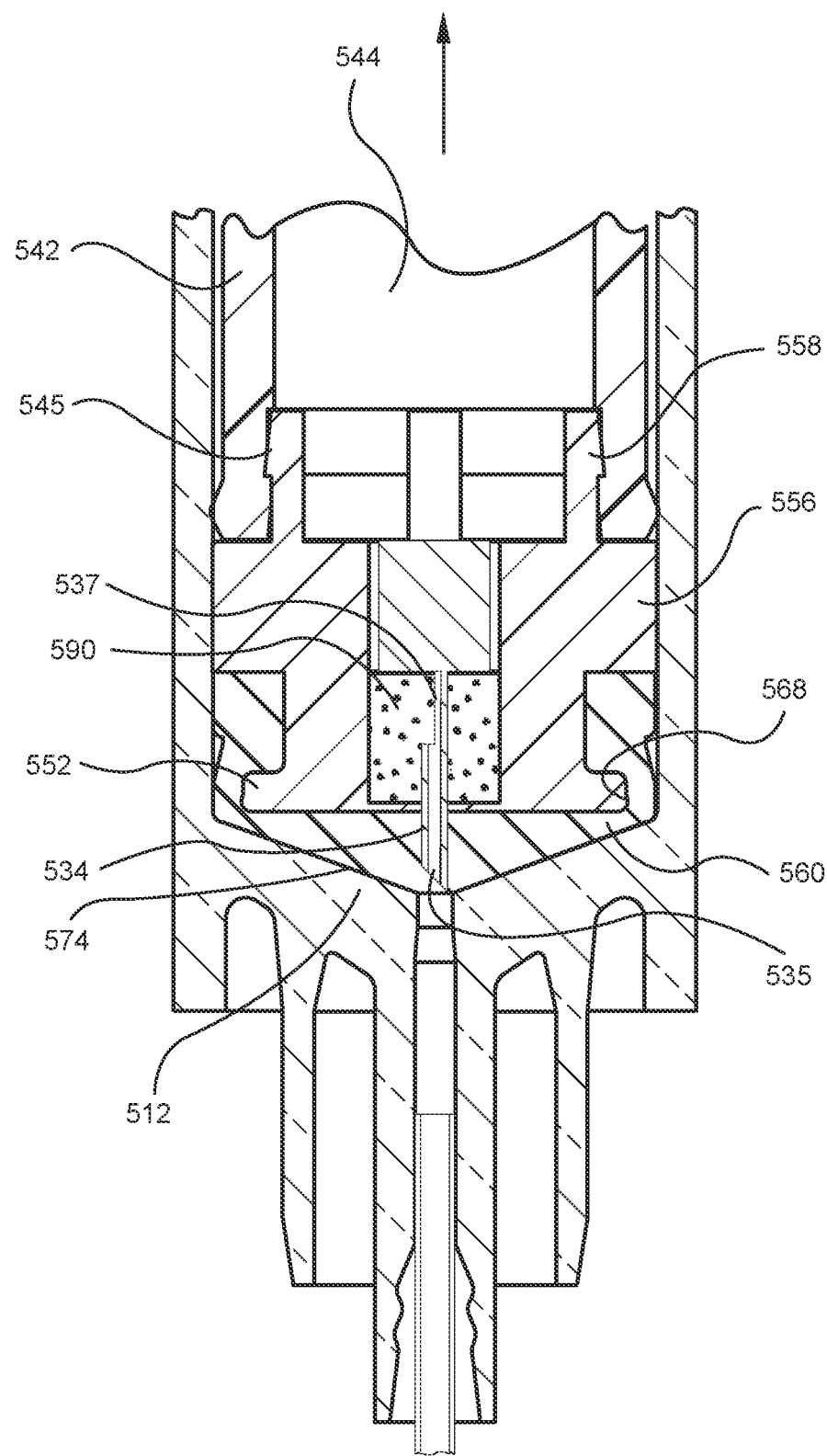
FIG. 54 shows an enlarged partial view of the medical device shown in FIG. 53.

Thereafter, a force in the distal direction is applied to the plunger rod to engage the stopper hub 550 and plunger rod 540 from the first position to a second position to aspirate a desired amount of liquid into the chamber 518. In the second position, the projecting hooked portion 558 of the projecting finger 555 engages the peripheral groove 545 of the plunger rod, as shown in FIG. 54. When engaged, the plunger rod 540, stopper hub 550 and the stopper assembly 560 are moveable in the proximal and distal direction within the chamber 518 of the syringe barrel 510, as a unit.

Figure 55:
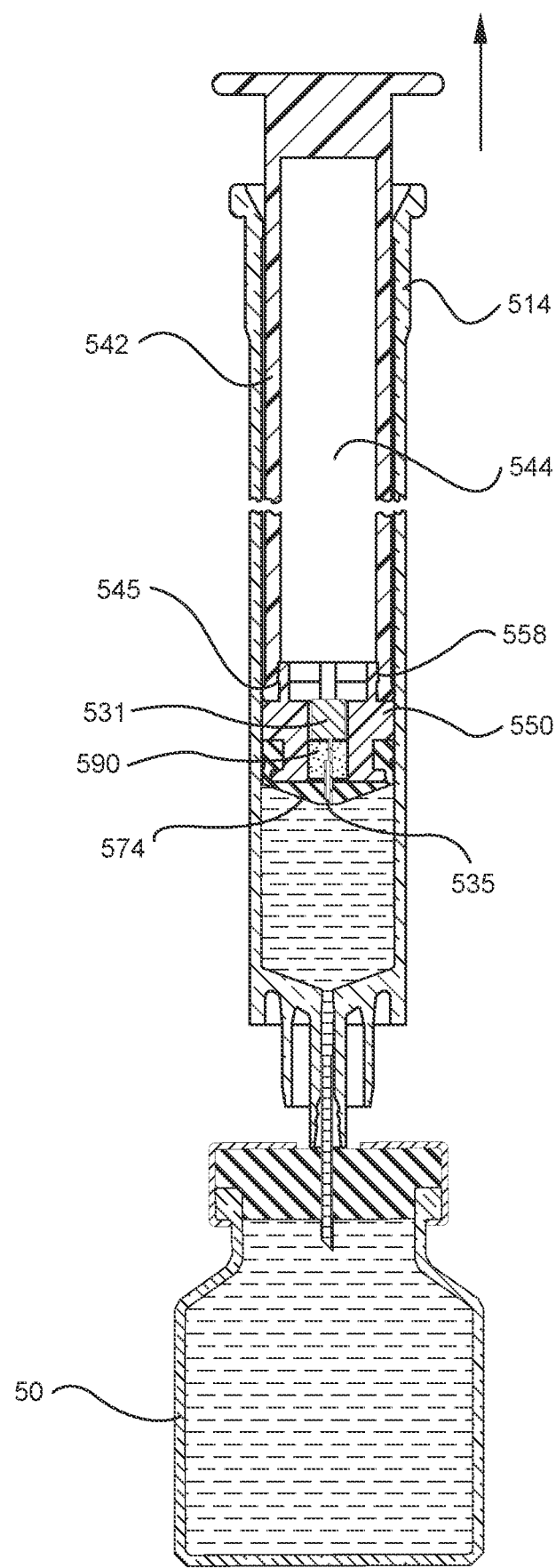
FIG. 55 illustrates the medical device shown in FIG. 53 filled with liquid from the vial.
Figure 56:
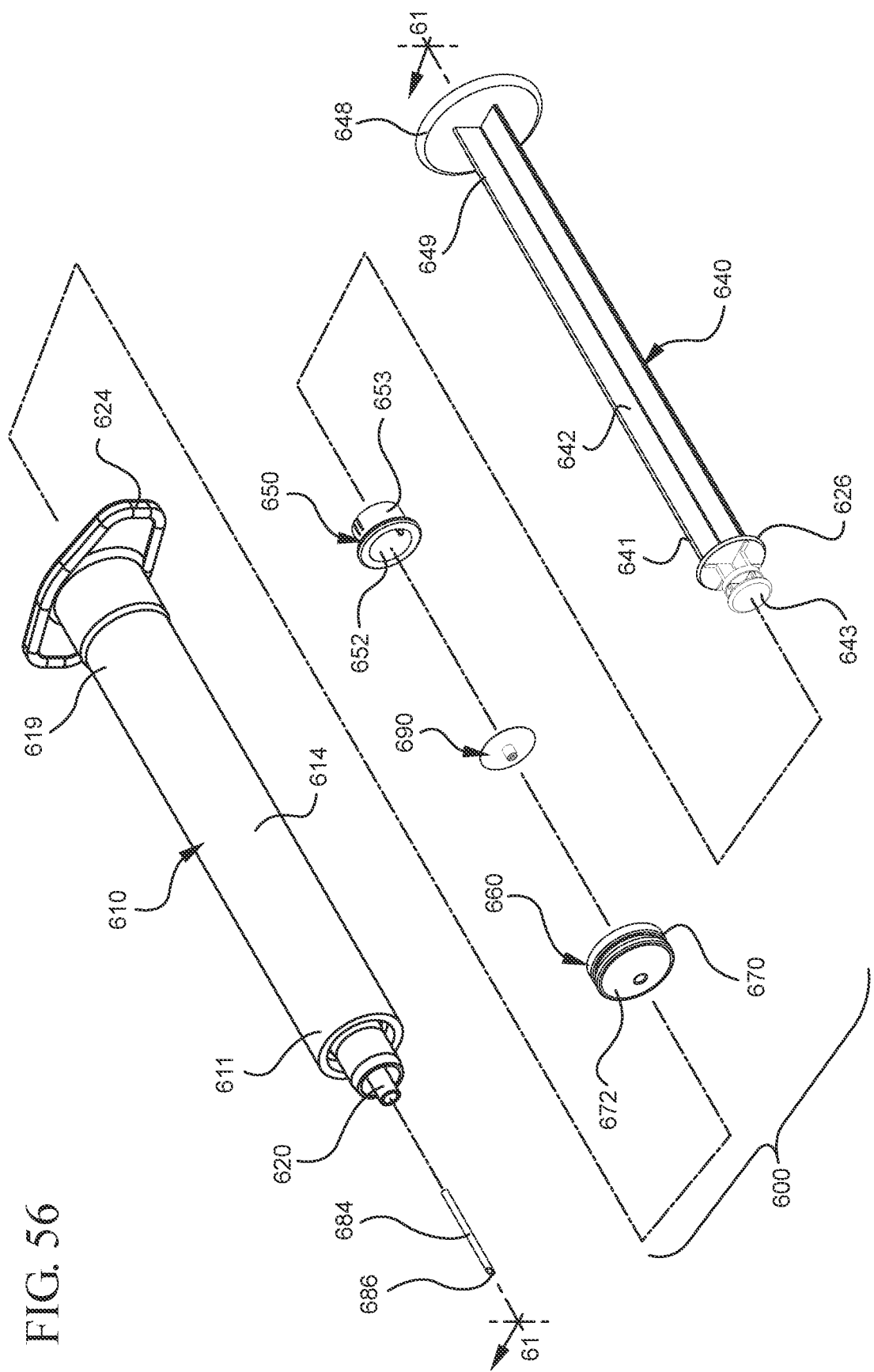
FIG. 56 illustrates a disassembled view of a syringe barrel and one or more embodiments of a medical device according to a sixth aspect of the present invention.

As the user aspirates the liquid from the vial 50 into the syringe barrel 510 by applying a proximally directed force on the plunger rod 540 or, more specifically, the thumbpress 548, the stopper assembly 560, stopper hub 550 and plunger rod 540 move in the proximal direction together and the liquid is filled into the chamber 518 of the syringe barrel, as shown more clearly in FIG. 55. The position of the open distal end 535 within the stopper cavity 566 590 prevents liquid from entering the stopper cavity 566. As shown in FIG. 55, the desired amount of liquid may be filled into the syringe barrel, without the presence of air.

To expel the fluid, the stopper assembly 560, stopper hub 550 and plunger rod 540 remained engaged in the second position and move together in the distal direction, as a user applies a force on the plunger rod 540 or thumbpress 548 in the distal direction. In one or more embodiments that utilize a stopper assembly 560 having a distal face 574 that is flexible, the application of a continuous and distally directed force on the plunger rod 540 causes the distal face 574 to flex convexly as the distal face contacts the distal wall 512 of the syringe barrel 510. In embodiments which utilize a stopper assembly 560 having a convexly-shaped distal face 354, the distal face 574 conforms more closely to the distal wall 512 upon contact with the distal wall 512. The convex shape of the distal face 574 upon contact with the distal wall 512 expels even more liquid from the syringe barrel 510.

A medical device 600 according to a sixth aspect of the present invention is shown in FIGS. 56-67. One or more embodiments of the medical device 600 includes a plunger rod 640, a stopper 660 and a stopper hub 650, wherein a distal end 641 of the plunger rod 640 and stopper hub 650 are slidably engaged to allow the user to create a vacuum between the stopper hub 650 and plunger rod 640. For illustration, the medical device 600 is shown in use with a container in the form a syringe barrel 610. The syringe barrel 610 includes an open proximal end 619, a distal end 611 and a distal wall 612. As more clearly shown in FIGS. 61-62, a sidewall 614 extends from the distal end 611 to the open proximal end 619 and includes an interior surface 616 that defines a chamber 618 for retaining or holding fluids, which may include liquid medication and/or other liquids. The distal end 611 also includes a tip 620 having an open passageway 622 therethrough in fluid communication with the chamber 618. The open proximal end 519 of the syringe barrel 510 may include optional flanges 624. A needle cannula 684 is attached to the tip 620 and includes a lumen 686 or opening therethrough in fluid communication with the open passageway 622 and the chamber 618. In the embodiments shown in FIGS. 56-67, the needle cannula 684 is attached directly to the tip 620 using methods known in the art. Alternatively, a needle hub (not shown) may be used to attach a needle to the tip 620. The interior surface 616 of the syringe barrel 610 may have a smooth surface that is free of any protrusions or depressions. In use, the plunger rod 640, stopper hub 650 and stopper 660 are inserted into the open proximal end 629 of the syringe barrel 610.

Figure 57:
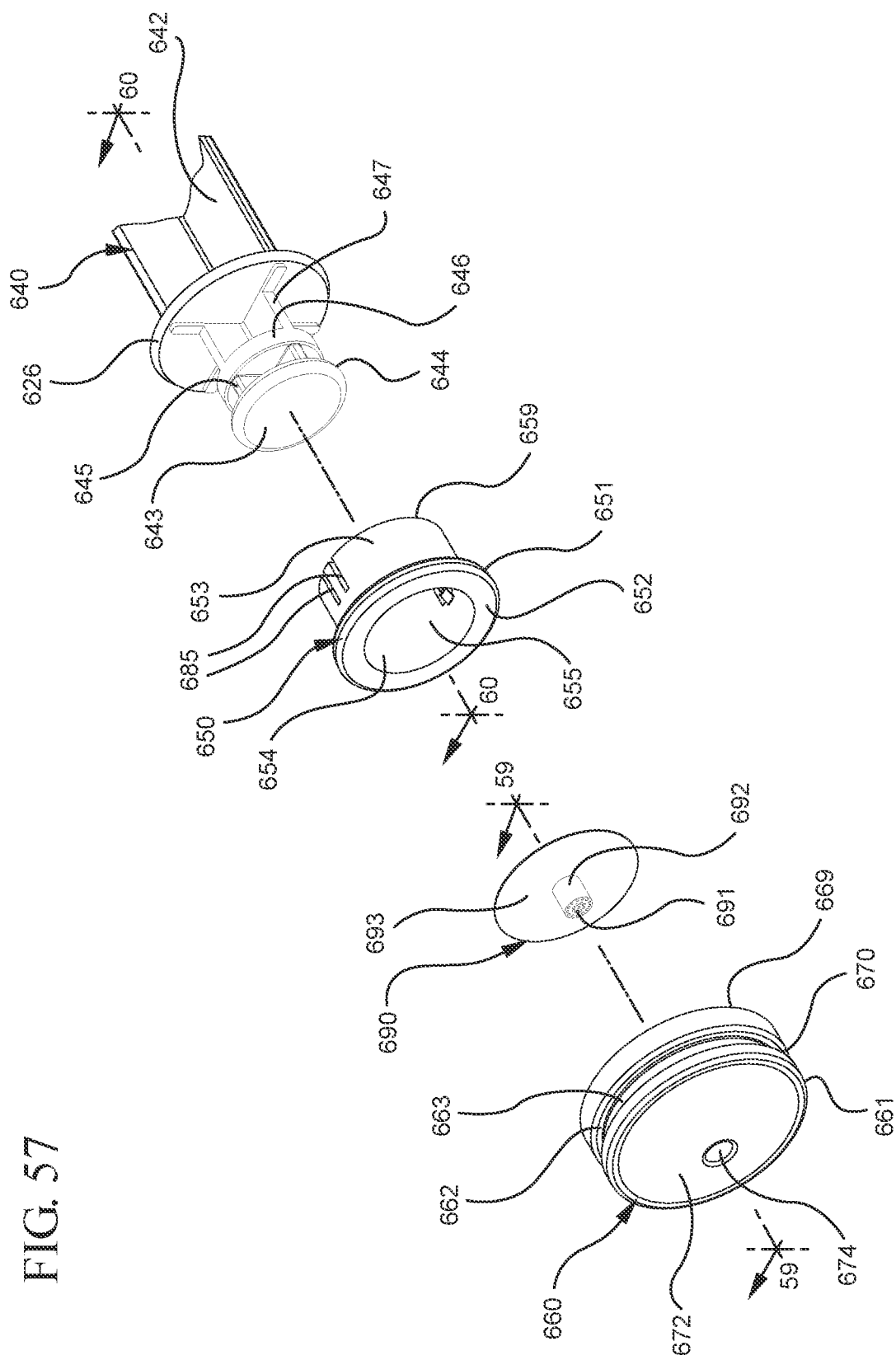
FIG. 57 illustrates an enlarged partial view of the stopper, stopper hub and enlarged partial view of the plunger rod shown in FIG. 56.
Figure 59:
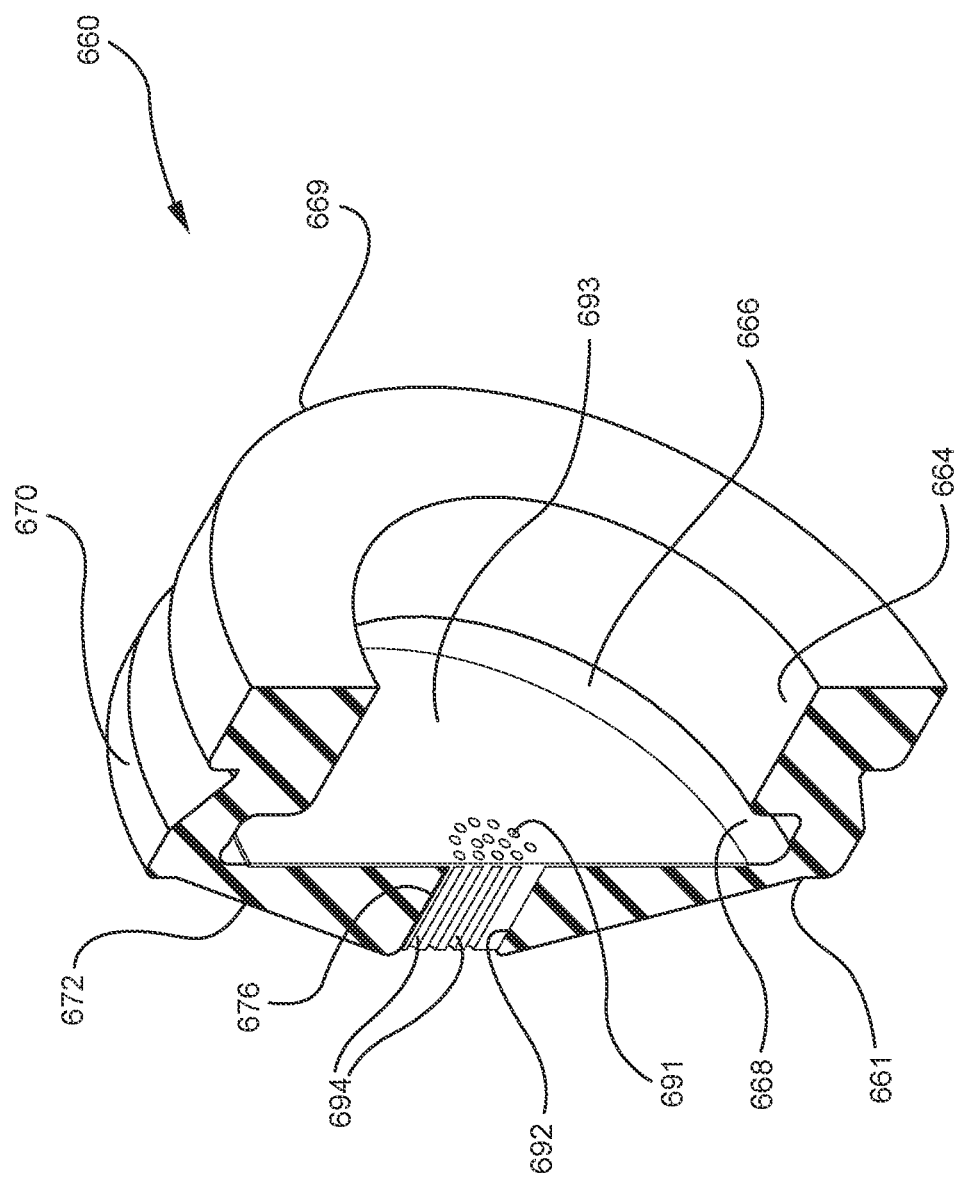
FIG. 59 illustrates a perspective cross-sectional view of the filter and the stopper shown in FIG. 57 in an assembled state taken along line 59-59.

As more clearly shown in FIGS. 57 and 59, the stopper 660 includes a distal end 661 and an open proximal end 669 and a body 662 extending from the distal end 661 to the open proximal end 669. The body 662 includes an outside surface 663 and an inside surface 664 defining a stopper cavity 666. In one or more embodiments, the inside surface 664 of the body 662 may include a peripheral channel 668 forming a groove or ridge, within the body 662 for engagement with the stopper hub 650, as will be described in detail below and is shown more clearly in FIG. 61. As shown in FIGS. 57 and 59, the body 662 includes a sealing portion 670 for forming a fluid-tight seal with the interior surface 616 of a syringe barrel. As shown, the sealing portion 670 is disposed on the outside surface 663 adjacent the distal end 661. In one or more embodiments, the sealing portion 670 may includes one or more grooves (not shown) shaped to form a fluid-tight seal with the interior surface 616 of a syringe barrel. In one or more embodiments, the sealing portion 670 may have a circular cross-section for forming a fluid-tight seal with a syringe barrel having an interior surface with a circular cross-section. The stopper 660 may be formed from an elastomeric material, polymeric material or other material known in the art. In one or more embodiments, the sealing portion 670 may be formed from a material suitable for forming a fluid-tight seal with the interior surface 616 of the syringe barrel 610, which may include the same or different material utilized to form the remaining components of the stopper 660.

The distal end 661 of the stopper 660 includes a distal face 672 having an opening 674 therethrough in fluid communication with the stopper cavity 666. The distal end 661 also includes a path 676 extending from the opening 674 to the stopper cavity 666 allowing fluid communication from the opening 674 to the open proximal end 669. The distal face 672 may have a convex shape or be flexible to flex to a convex shape which conforms to the distal wall 612 of the syringe barrel 610. In one or more embodiments, the distal face 672 may also be shaped convexly so that it conforms more closely to the shape of the distal wall 612 of the syringe barrel 610 to expel as much liquid from the chamber 618 as possible.

As shown in FIGS. 57-59, a filter 690 is disposed in the stopper cavity 666 adjacent to the distal face 672. As shown, the filter 690 has a shape and size to cover the opening 674, the path 676 and surrounding portions of the inside surface 664 of the body 662 of the stopper. In one or more embodiments, the filter 690 is shaped to cover the opening 674 and the path 676, but not any portions of the inside surface 664 surrounding the opening 674 or path 676.

Figure 58A:
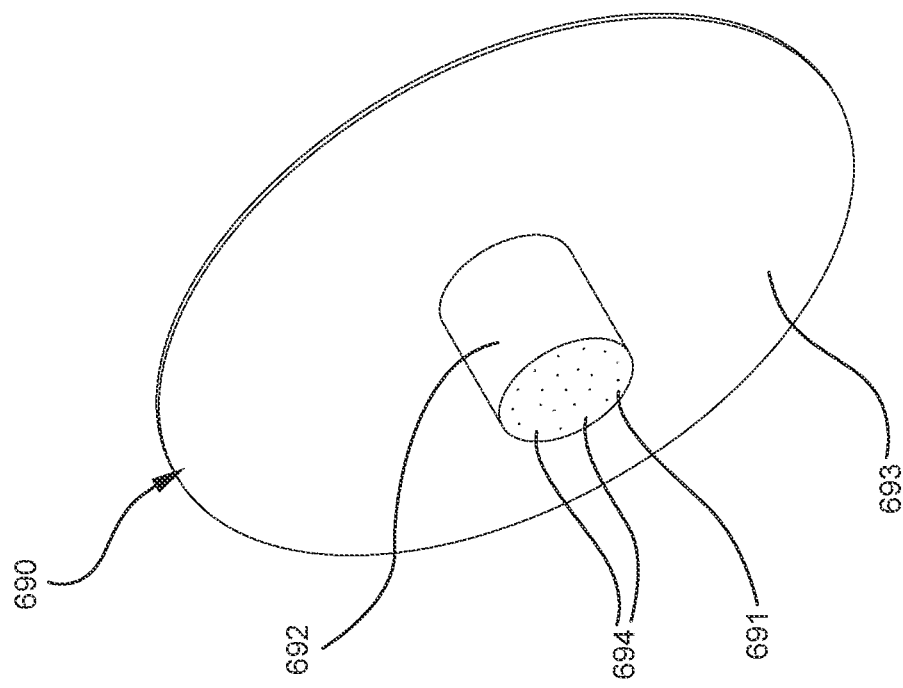
FIG. 58A shows a perspective view of the filter shown in FIG. 57 prior to contact with a liquid.
Figure 58B:
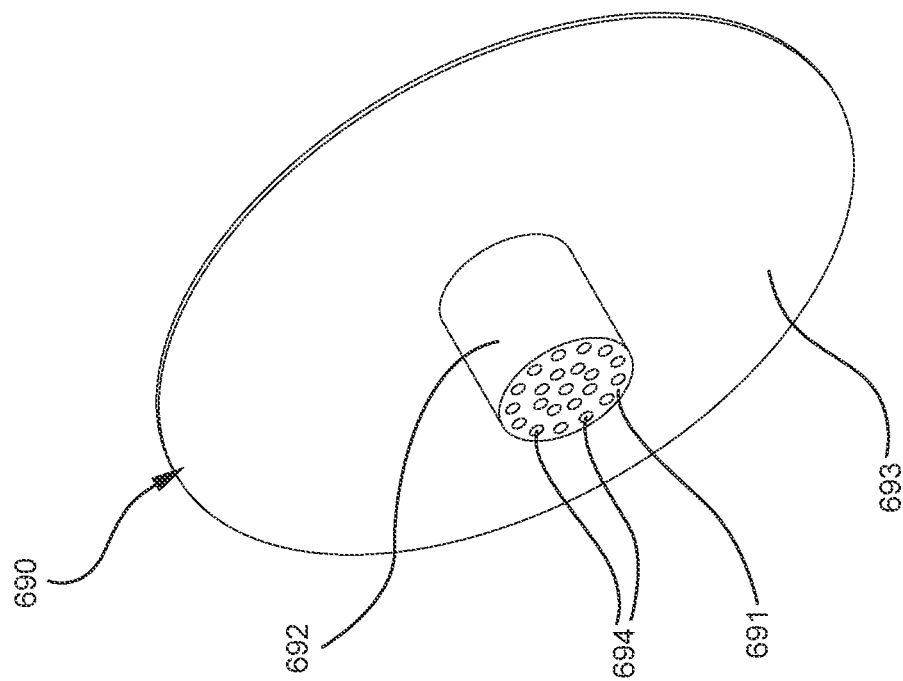
FIG. 58B shows a perspective view of the filter shown in FIG. 57 after contact with a liquid.

As shown in FIGS. 58A and 58B, the filter 690 includes a porous portion 691 formed from a hydrophobic filter, swellable polymer or combinations thereof. The porous portion 691 as shown in FIG. 57 has a cross-sectional width to permit the porous portion 691 to cover or be disposed within the opening 674. A barrier wall 692 surrounds the porous portion 691 and extends in the proximal direction, perpendicularly to the porous portion 691. As shown, the filter 690 includes a shield portion 693 disposed around the barrier wall 692 and extending radially outwardly from the barrier wall 692. In one or more embodiments, the barrier wall 692 may have a length long enough to permit the porous portion 691 to be positioned within the opening 674 and the shield portion 693 to be disposed adjacent to the inside surface 664 of the stopper 660 at the distal face 672, as shown in FIG. 59. In one or more embodiments, the barrier and shield may be solid or may be porous. In embodiments where the barrier and/or shield are porous, the barrier and/or shield may be formed from a hydrophobic filter, a swellable polymer or combinations thereof.

The filter 690 may be a separate component that is inserted and attached within the path 676, adjacent the opening 674. In one or more embodiments, the filter 690 may include only the porous portion 691 and no barrier wall 692 or shield portion 693. In a specific embodiment, the filter 690 may include the porous portion 691 and the barrier wall 692 but no shield portion 693. In an even more specific embodiment, the filter 690 may include the porous portion 691 and the shield portion 693 but no barrier wall 692. In one or more embodiments, the filter 690 may be integrally formed on the distal face 672, with the peripheral edges of the distal face 672 and the sealing portion 670 of the stopper 660 remaining non-porous. As shown FIG. 58A and FIG. 58B, the porous portion 691 is formed from a swellable polymer, as described above. The porous portion 691 may include a plurality of apertures 694 or holes that allow fluid communication of air through the openings. In one or more embodiments, the swellable polymer expands upon contact with a liquid and causes the plurality of to close. Accordingly, in such embodiments, air contained within the syringe barrel is permitted to escape through the plurality of apertures 694 prior to contact between the swellable polymer and liquid. Upon contact with a liquid, the plurality of apertures 694 of the swellable polymer close and no fluid is permitted to enter the plurality of apertures 694 or escape from the chamber 618.

Alternatively, the porous portion 691 may be provided as a separate component and may be disposed in the path 676 and/or opening 674 and in fluid communication with the path 676, stopper cavity 666 and the opening 674. In one or more embodiments, the porous portion 691 has a circular shape. Alternatively, the porous portion 691 may have a square and/or rectangular shape. The porous portion 691 may be integrally formed or disposed on the distal face 672, adjacent to the opening 674. In a specific embodiment, the porous portion has a cross-sectional width that is smaller than the cross-sectional width of the distal face 672. The porous portion may also be integrally formed and/or disposed adjacent to the path 676 on the inside surface 664 of the stopper. The porous portion 691 may have a cross-sectional with that is smaller than the cross-sectional width of the inside surface 664 of the stopper.

The porous portion 691 may be integrally formed on the distal face 672, with the peripheral edges of the distal face 672 and the sealing portion 670 remaining non-porous. In a specific embodiment, the porous portion 691 is separated from the sealing portion 670 by the distal face 672.

The porous portion 691 may also be shaped to fit within the opening 674 and form a fluid-tight engagement with the opening 674. For example, the porous portion 691 may extend from the distal face 672 into the path 676. In one or more embodiments, the porous portion 691 may have a periphery that is molded to a portion of the distal face 672. In one or more embodiments, the porous portion 691 may be attached to the distal face 672 of the stopper 660 by mechanical means, for example, adhesives and/or molding. In a specific embodiment, the distal face 672 may include a pocket (not shown) for securing the porous portion 691 adjacent to the distal face 672 and the opening 674.

The stopper hub 650 includes an open distal end 651 and an open proximal end 659. The open distal end 651 includes a stopper-engaging portion 652, which may include a disc extending radially outwardly, for attachment of the stopper hub 650 to the stopper 660. Specifically, as more clearly shown in FIG. 61, the stopper-engaging portion 652 extends radially outwardly to engage the peripheral channel 668 of the stopper 660. In one or more embodiments, the stopper-engaging portion 652 may be in the form of a tab (not shown), which corresponds to an opening (not shown) or other corresponding structure on the inside surface 664 of the stopper. In a specific embodiment, the stopper-engaging portion 652 may have an opening (not shown) and the inside surface of the stopper may include a tab (not shown) extending radially inwardly to engage with the opening (not shown). Other means to engage the stopper hub 650 to the stopper 660 may also be utilized. In one or more alternative embodiments, the stopper 660 may be integrally formed on the distal end 651 of the stopper hub 650.

The stopper hub 650 includes a peripheral wall 653 extending from the open distal end 651 to the open proximal end 659. The peripheral wall 653 includes an inside surface 654 defining a hub cavity 655 in fluid communication with the opening 674 and the stopper cavity 666. The hub cavity 655 has a volume that varies as position of the plunger rod 640 with respect to the stopper hub 650 changes, as will be discussed below in greater detail.

In one or more embodiments, the peripheral wall 653 includes a plunger-engaging portion 656 for attaching the stopper hub 650 to the plunger rod 640 in a slidable relationship or to allow the plunger rod 640 to move proximally and distally relative to the stopper hub 650. The slidable relationship between the plunger rod 640 and stopper hub 650 forms a vacuum within the hub cavity 655. The plunger-engaging portion 656 may include a structure formed on the peripheral wall 653 that prevents separation of the plunger rod 640 and stopper hub 650. As shown in FIGS. 56-67, the inside surface 654 of the peripheral wall 653 has a length, shape and/or cross-sectional width that forms a fluid tight seal with the distal end 641 of the plunger rod 640. The plunger-engaging portion 656 may include a textured surface or coating disposed on the inside surface 654 of the stopper hub 650 to increase the frictional interference between the plunger rod 640 and the inside surface 654 to prevent disengagement. Other examples of such structures include depression (not shown) formed along the inside surface of the peripheral wall 653 for engaging a corresponding protrusion (not shown) on the plunger rod 640, wherein the depression is sized to allow proximal and distal movement of the plunger rod 640 relative to the stopper hub 650 but prevent separation of the plunger rod 640 from the stopper hub 650.

Figure 60:
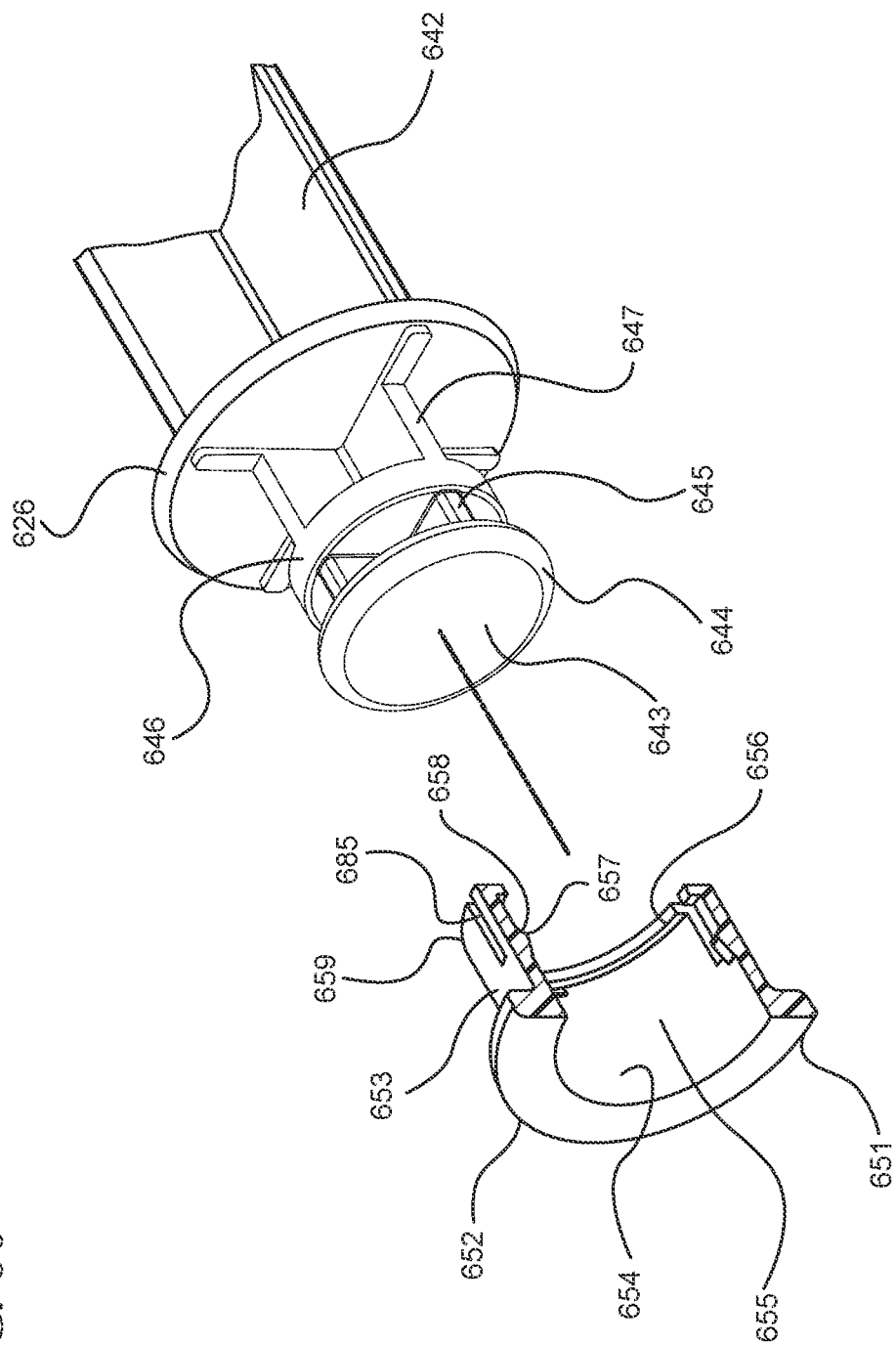
FIG. 60 shows a perspective cross-sectional view of the stopper hub shown in FIG. 57 taken along line 60-60 and an enlarged partial view of the plunger rod shown in FIG. 56.

In one embodiment, the plunger-engaging portion 656 includes means for prevent movement of the plunger rod 640 in a distal direction relative to the stopper hub 650, after an initial movement of the plunger rod 640 in the proximal direction relative to the stopper hub 650. In other words, the plunger-engaging portion 656 includes means for maintaining a vacuum within the hub cavity 655 formed from movement of the plunger rod 640 in the proximal direction relative to the stopper hub 650. As shown in FIG. 60, the means for maintaining a vacuum may include a ridge 657 formed on the inside surface 654. As shown, the ridge 657 engages the distal end 641 of the plunger rod 640, as will be discussed below in more detail and includes a stop face disposed between the ridge 657 and the open proximal end 659 of the stopper hub 650. The stop face 658 forms a barrier to block movement of the plunger rod 640 in the distal direction, once it has moved in the proximal direction past the stop face 658, as will also be discussed in more detail below. The plunger-engaging portion 656 also includes a means for preventing disengagement of the plunger rod 640 and the stopper hub 650. In the embodiment shown, the plunger-engaging portion 656 is shown in the form of a raised ridge formed on the periphery of the inside surface 654 of the stopper hub 650 adjacent to the open proximal end 659. The raised ridge may be formed at interrupted intervals along the periphery of the inside surface 654 of the stopper hub adjacent to the open proximal end 659. In one or more embodiments, the inside surface 654 of the peripheral wall 653 may include one or more tabs (not shown) adjacent the open proximal end 659 to prevent disengagement of the plunger rod 640 during movement in the proximal direction relative to the stopper hub 650. Alternatively, the frictional engagement between the inside surface 654 of the stopper hub 650 and the distal end 641 of the plunger rod 640 prevents separation of the plunger rod 640 and the stopper hub 650.

In the embodiment shown, the peripheral wall 653 includes at least one vent 685 disposed along its length. The at least one vent 685 is in fluid communication with the exterior of the syringe barrel 610 and plunger rod 640. As shown more clearly in FIGS. 61 and 64, the plunger rod 640 does not form a fluid-tight seal with the interior surface 616 of the syringe barrel 610, thereby permitting fluid communication between the at least one vent 685, the hub cavity 655 and the exterior of the syringe barrel 610. In one or more embodiments, the at least one vent 685 is a formed adjacent the open proximal end 659 of the stopper hub 650 and permit fluid communication after the distal end 641 of the plunger rod 640 moves in the proximal direction past the vent 685. As shown in FIG. 60, the least one vent 685 is formed on the peripheral wall 653 in the form of two openings adjacent to the open proximal end 659 of the stopper hub 650. In one or more alternative embodiments (not shown), the peripheral wall 653 may be free of any vents or openings.

The length of the peripheral wall 653 may be modified to have a length and/or cross-sectional width to provide enough volume within the hub cavity 655 to evacuate all of the air present in the chamber 618, tip 620 and/or needle cannula 682. In embodiments which do not incorporate at least one vent in the peripheral wall 653, the length of the peripheral wall 653 may be modified to provide enough volume within the hub cavity 655 to maintain all of the air evacuated from the chamber 618, tip 620 and/or needle cannula 682.

As mentioned above, the slidable engagement of the stopper hub 650 and the plunger rod 640 permits the volume of the hub cavity 655 to expand and contract as the plunger rod 640 moves in a proximal direction and a distal direction relative to the stopper hub 650. The expansion of the hub cavity 655 during movement of the plunger rod 640 in a proximal direction relative to the stopper hub 650 creates a vacuum within the hub cavity 655.

In use, the distal end 641 of the plunger rod 640 is attached to the plunger-engaging portion 656 at the proximal end 659 of the stopper hub 650. The plunger rod 640 shown more clearly in FIGS. 56-57 also includes a proximal end 649 and an elongate body 642 extending from the distal end 641 and the proximal end 649. The proximal end 649 of the plunger rod 640 may include an optional thumbpress 648. The plunger rod 640 may be made of a plastic or other material that has sufficient rigidity to withstand movement within the syringe barrel 610 in the proximal and distal direction. Examples of such materials include polypropylene, polyethylene, polycarbonate and combinations thereof. The elongate body 642 may be cylindrical. In one or more embodiments, the shape of the elongate body 642 may be rectangular or other shape.

The distal end 641 of the plunger rod includes a means for engaging the stopper hub 650. As shown in FIG. 60, the means for engaging the stopper hub 650 includes a disc member 643 disposed perpendicularly to the elongate body 642 of the plunger rod. The disc member 643 extends radially and, in one or more embodiments, may include a beveled edge 644 adjacent to the distal end 641 of the plunger rod. In a specific embodiment, the disc member 643 includes one beveled edge disposed on the distal side of the disc member and one beveled edge on the opposite side of the disc member 643. The beveled edge may be formed around the periphery of the disc member 643. As shown, the disc member 643 has a cross-sectional width equal that permits the disc member 643 to form a fluid-tight seal with the peripheral wall 653 and cooperates with the stop face 658 of the ridge 657 as means for preventing distal movement of the plunger rod 640 with respect to the stopper hub 650. The plunger rod 640 includes a first strut member 645 proximally adjacent to the disc member 643 disposed between the disc member 643 and a first support 646. As shown in FIG. 60, the first strut member 645 may be formed from two perpendicular beams, wherein at least one beam includes at least one beveled edge on one or both ends of the beam. The first support 646 may be attached directly to the elongate body 642 of the plunger rod 640 or may further include a secondary strut member 647 and a second support 626 attached to the elongate body 642, as shown in FIG. 60. The secondary strut member 647 may be formed from two perpendicular beams having elongated support legs 628 for attachment to the second support 626, which is disposed distally adjacent to the elongate body 642. The second support 626 may have a cross-sectional width greater than the cross-sectional width of the peripheral wall 653 of the stopper hub 650.

Figure 61:
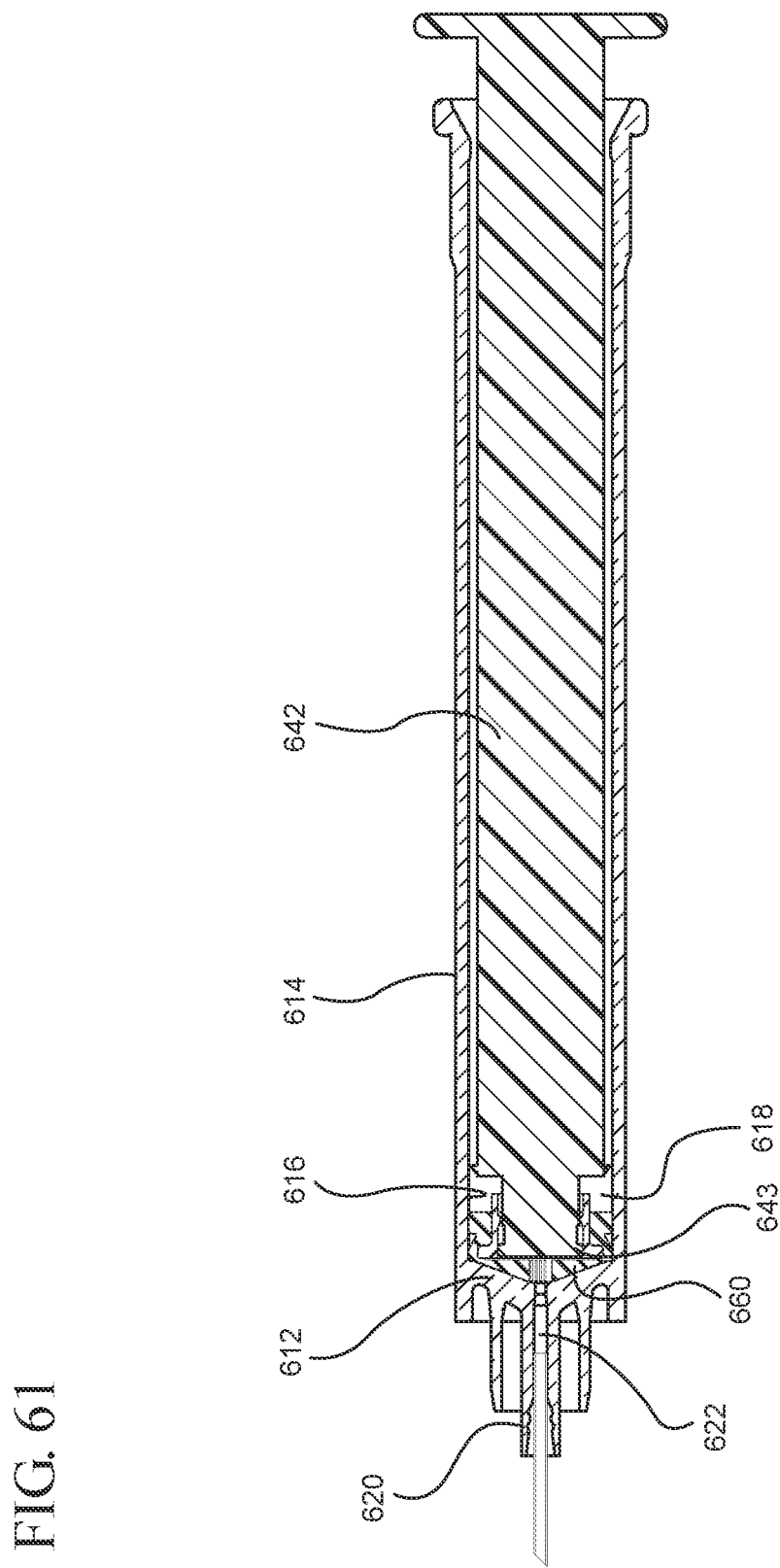
FIG. 61 illustrates a cross-sectional view of the assembled medical device illustrated in FIG. 56 taken along line 61-61.
Figure 62:
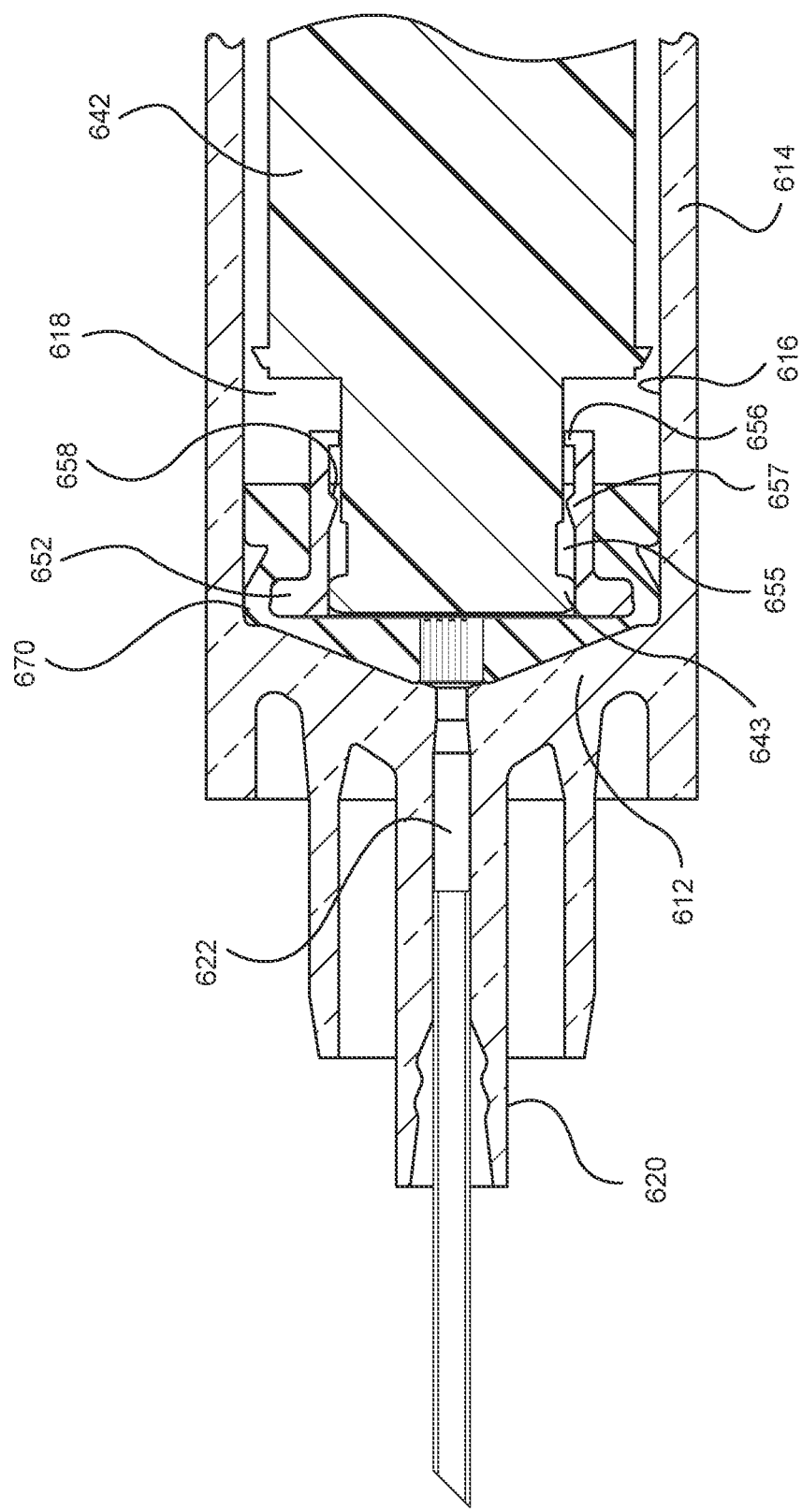
FIG. 62 illustrates an enlarged partial view of the medical device shown in FIG. 61.

In use, as shown in FIG. 61, the plunger rod 640, stopper hub 650 and stopper 660 are assembled as a medical device 600 and are inserted into the open proximal end 619 of the syringe barrel 610. The disc member 643 of the plunger rod 640 is positioned adjacent to the open distal end 651 of the stopper hub 650 and distally adjacent to the stop face 658 of the ridge 657, as shown in FIGS. 61 and 62. Before aspirating fluid into the chamber 618 of the syringe barrel 610 or other container, the distal face 672 of the stopper 660 is positioned adjacent to the distal wall 612 of the syringe barrel 610, so that the air within the chamber 618 is minimized and is primarily present in the tip 620 of the syringe barrel 610 or other container.

In the assembled state, the stopper 660 and stopper hub 650 form a unitary piece that moves together in the distal and proximal directions within the chamber 618. The plunger rod 640 and stopper hub 605 are engaged in a slidable relationship where the plunger rod 640 may move in the proximal and distal direction relative to the stopper hub 650. This relative movement occurs as the stopper hub 650 and stopper 660 to remain stationary with respect to movement of the plunger rod 640.

Figure 63:
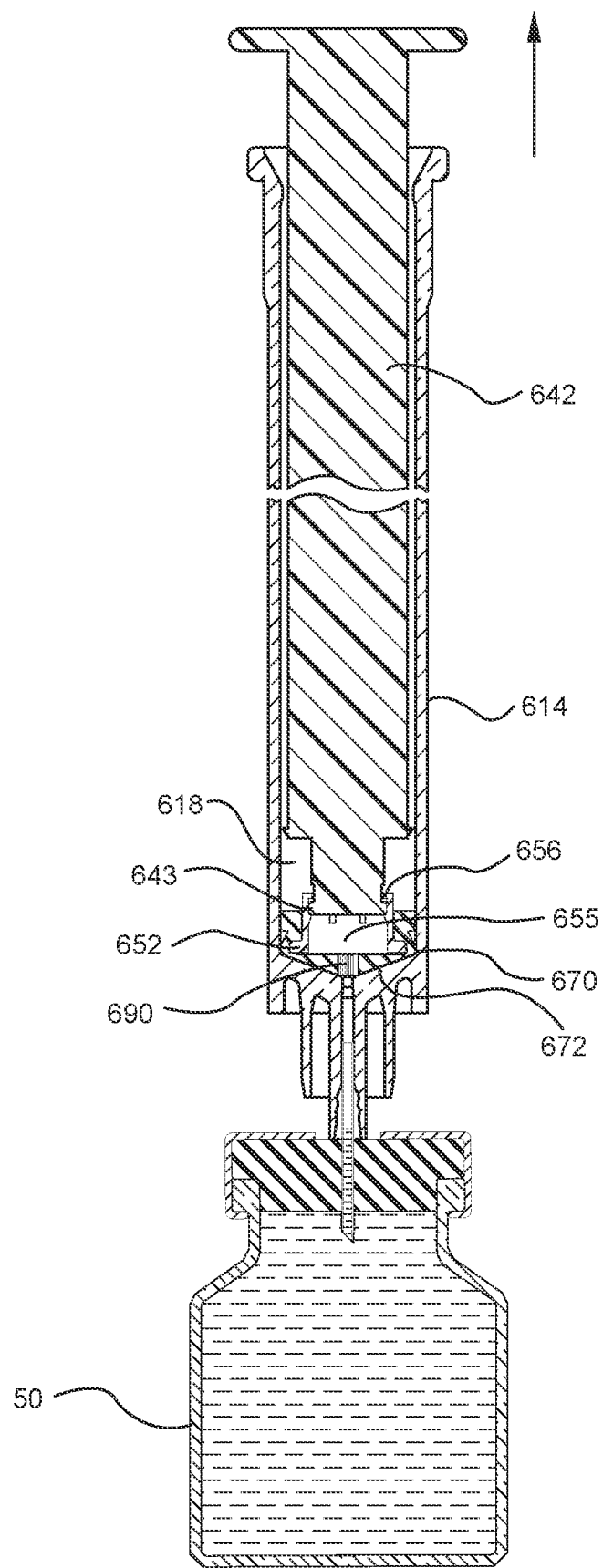
FIG. 63 illustrates the medical device shown in FIG. 61 drawing liquid from a vial into the syringe barrel after application of the initial force to the plunger rod in the proximal direction.
Figure 64:
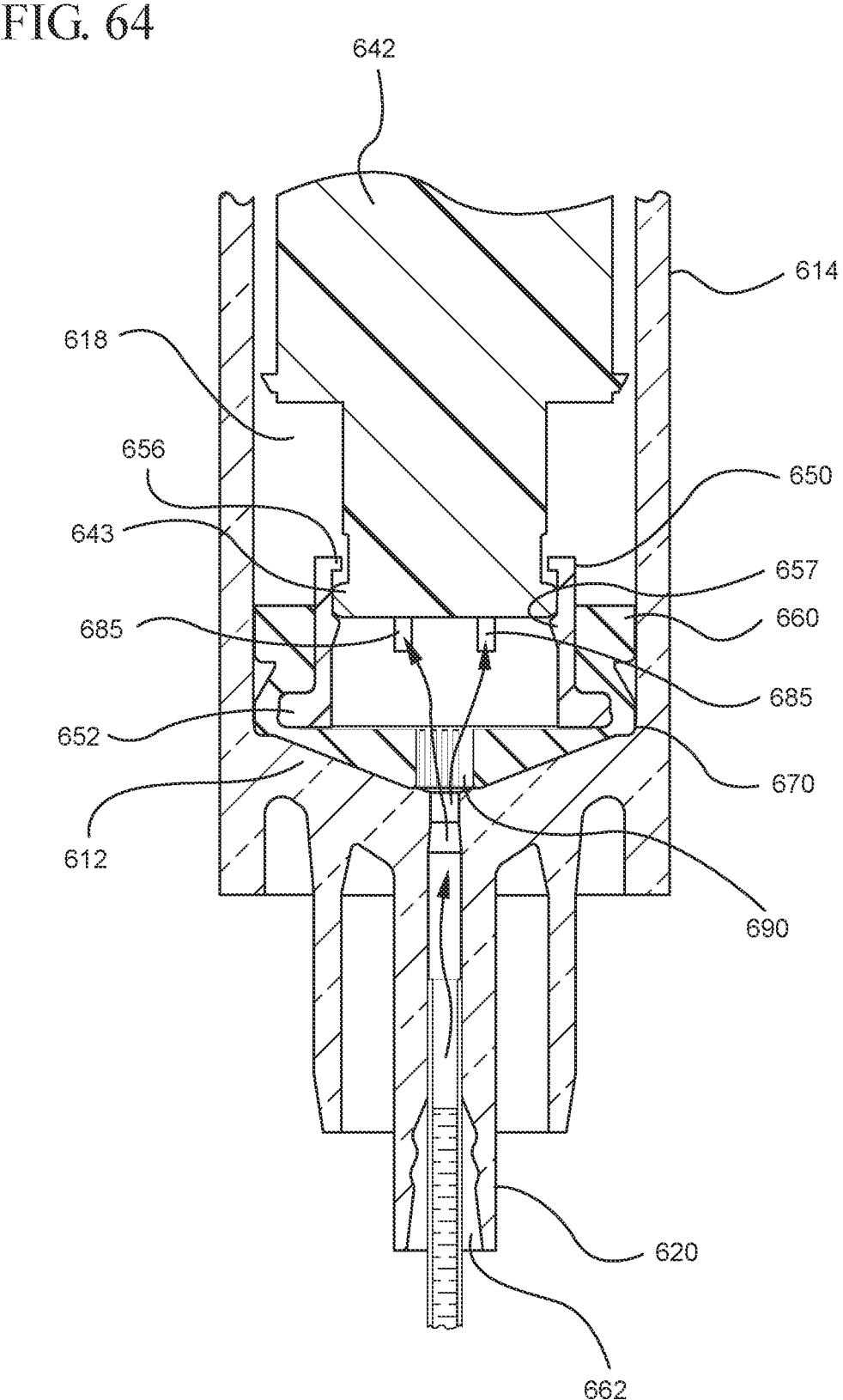
FIG. 64 illustrates an enlarged partial view of the medical device and syringe shown in FIG. 63.

As shown in FIGS. 61-62, the hub cavity 655 is in an unexpanded state before use. To aspirate liquid into the chamber 618, the user may position the syringe barrel 610 or other container and needle assembly 680 over a vial 50 and insert the needle cannula 684 into the vial before applying the initial proximal force to the plunger rod 640, as shown in FIG. 63. To create a vacuum within the hub cavity 655, which causes the evacuation of air from the syringe, an initial proximally directed force is applied to the plunger rod 640, as shown in FIGS. 63-64. The expansion of the hub cavity 655 creates a vacuum within the hub cavity 655 that draws the air contained in the tip 620 and chamber 618 of the syringe barrel 610 into the hub cavity 655 through the opening 674 of the stopper 660 and the plurality of apertures 694 disposed on the porous portion 691 of the filter 690. In one or more embodiments, the evacuated air may escape from the syringe barrel 610 through the at least one vent 685 formed on the peripheral wall 653 to the exterior of the syringe barrel. In embodiments which do not utilize any vents in the peripheral wall 653, the air remains within the hub cavity 655 and does not enter the chamber 618 of the syringe barrel 610.

Figure 65:
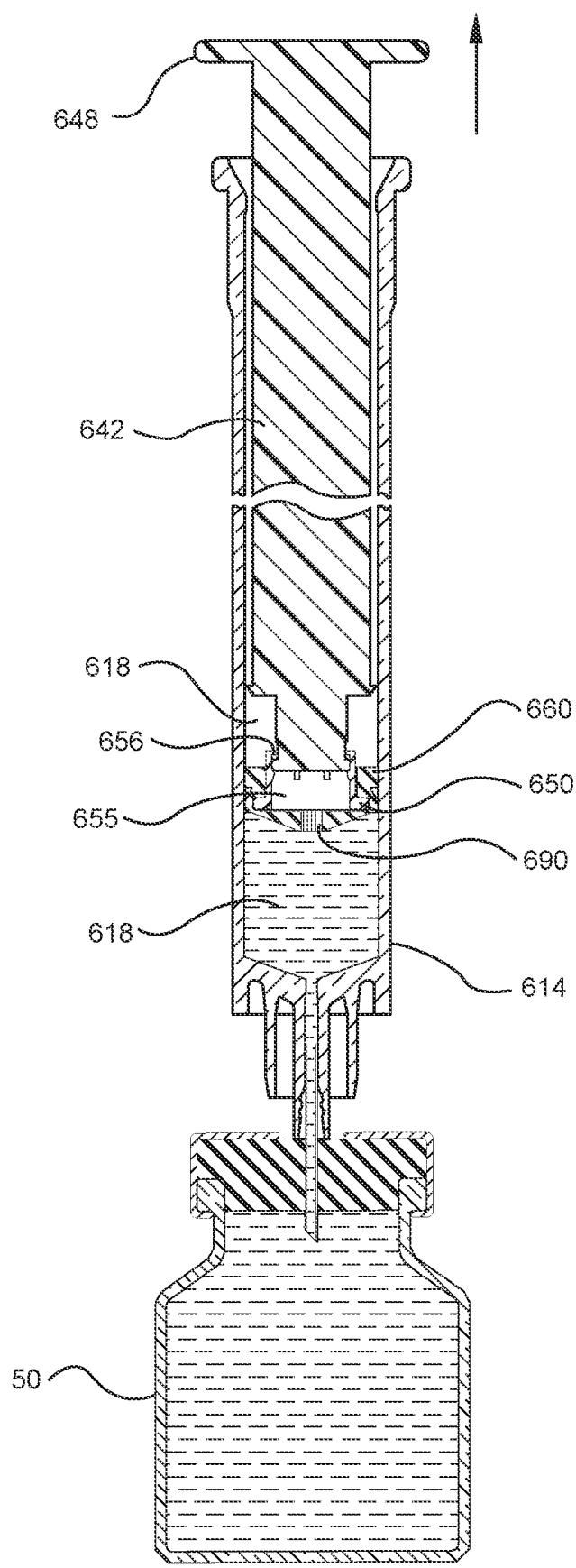
FIG. 65 shows the medical device shown in FIG. 63 filled with liquid from the vial.

As the air is evacuated from the chamber 618 into the hub cavity 655, some liquid may also be drawn into the chamber 618 of the syringe barrel 610 by the vacuum within the hub cavity 655 or by application of a continuous proximal force on the plunger rod 640, which causes the and attached stopper 660 and stopper hub 650 to move with the plunger rod 640 in the proximal direction, as shown in FIG. 65. Once the liquid contacts the filter 690 and, more specifically, the porous portion 691, the swellable polymer begins to expand and swell, thereby closing the plurality of apertures 694 that allow air to be evacuated from the chamber 618 to the hub cavity 655. When closed, the plurality of apertures 694 prevents the aspirated liquid from entering the hub cavity 655. As the force is applied to the plunger rod 640 in the proximal direction, the plunger-engaging portion 656 prevents the plunger rod 640 from separating from the stopper hub 650.

Figure 66:
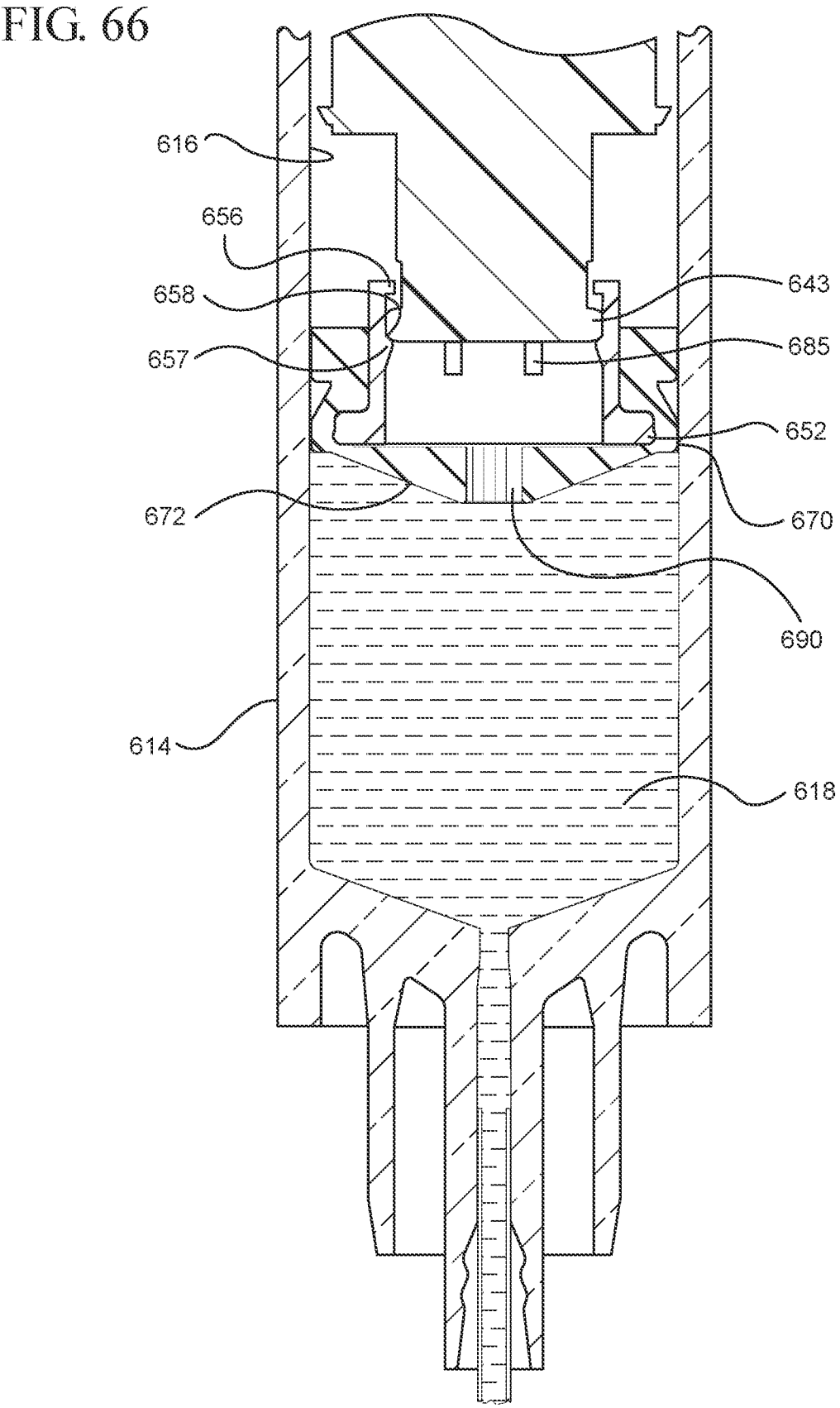
FIG. 66 shows an enlarged partial view of the medical device shown in FIG. 65.
Figure 67:
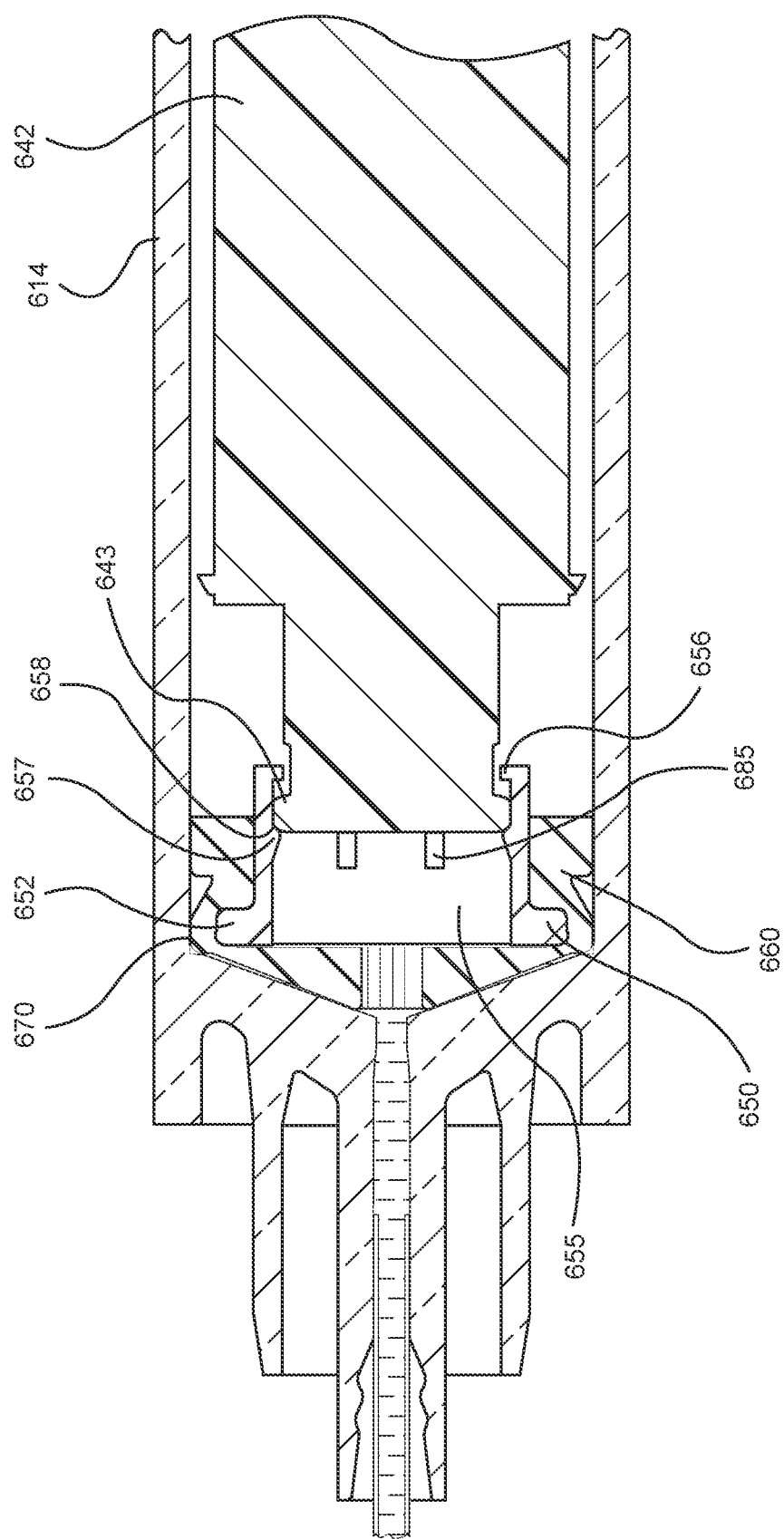
FIG. 67 illustrates the medical device shown in FIG. 65 after application of a continuous force on the plunger rod in the distal direction to expel the fluid contained within the syringe barrel.

To expel the fluid, a force in the distal direction is applied to the plunger rod 640 and the plunger rod 640, stopper hub 650 and stopper 660 move together in the distal direction. As shown in FIG. 66, the stop face 658 prevents movement of the plunger rod 640 in the distal direction relative to the stopper hub 650, and maintains the expanded volume of the hub cavity 655. In embodiments which utilize a flexible distal face 672, the application of a continuous and distally directed force on the plunger rod 640 causes the distal face 672 to flex convexly as the distal face 672 contacts the distal wall 612 of the syringe barrel 610. In embodiments which utilize a stopper 660 having a convexly-shaped distal face 672, the distal face 672 conforms more closely to the distal wall 612 upon contact with the distal wall 612. The convex shape of the distal face 672 upon contact with the distal wall 612 expels even more liquid from the syringe barrel 610.

A medical device 700 according to a seventh aspect of the present invention is shown in FIGS. 68-76. The medical device 700 includes a two-piece plunger rod assembly with a first plunger rod piece 730 and a second plunger rod piece 750 or a slidable portion that are slidably engaged to be positioned from a compressed state 797 to an extended state 795. The change in position of the first plunger rod piece 730 and the second plunger rod piece 750 from the compressed state 797 to an extended state 795 creates a vacuum within the plunger rod assembly to evacuate air from a container. The first plunger rod piece 730 includes a sealing edge 745 and a body 732, which may be tubular in shape, extending proximally from the sealing edge 745 defining a plunger rod cavity 734 and the second plunger rod piece 750 is inserted within the body 732. The second plunger rod piece 750 is disposed within the plunger cavity 734 and includes a sealing portion 765 for forming a fluid-tight seal with an inside surface 733 of the body 732.

For illustration, the medical device 700 is shown in use with a container in the form a syringe barrel 710. It will be understood that other types of containers may be utilized with the medical device 700. As shown more clearly in FIGS. 68-69, the syringe barrel 710 includes an open proximal end 719 and a distal end 711 and a distal wall 712. A sidewall 714 extends from the distal end 711 to the open proximal end 719 and includes an interior surface 716 that defines a chamber 718 for retaining or holding fluids, which may include liquid medication and/or other liquids. The distal end 711 may also include a tip 720 having an open passageway 722 therethrough in fluid communication with the chamber 718. The open proximal end of the barrel may include optional flanges 724. A needle cannula 784 is attached to the tip 720 and includes a lumen 786 or opening therethrough in fluid communication with the open passageway 722 and the chamber 718. As shown, the needle cannula 784 is attached directly to the tip 720 without the use of a needle hub, using methods known in the art. In one or more embodiments, the needle cannula 784 may be attached to the tip using a needle hub (not shown). The interior surface 716 of the syringe barrel 710 may have a smooth surface that is free of any protrusions or depressions. In use, the second plunger rod piece 750 is inserted into the body 732 of the first plunger rod piece 730, forming the medical device 700, which is then inserted into the open proximal end 719 of the syringe barrel 710.

Figure 69:
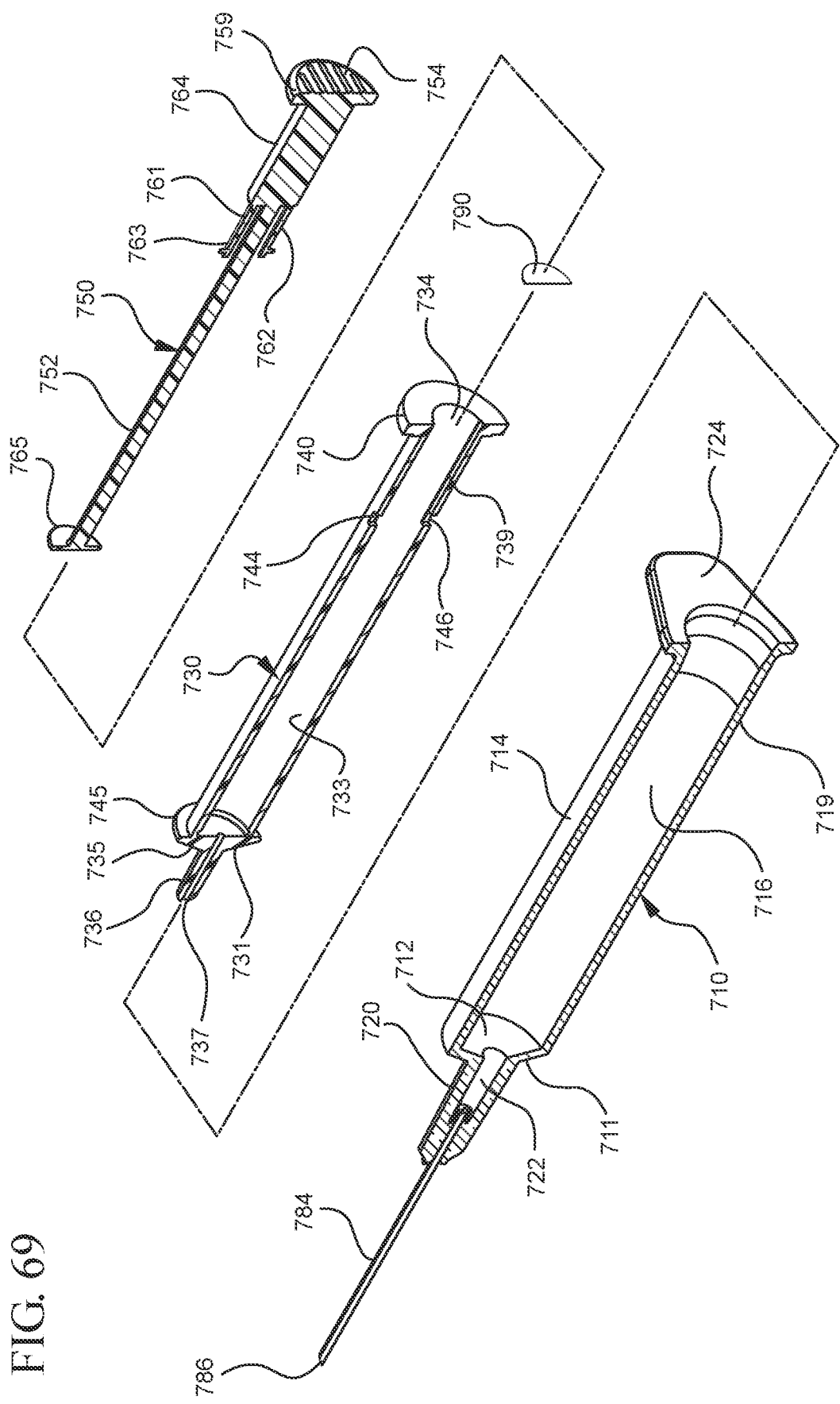
FIG. 69 illustrates cross-sectional view of medical device shown in FIG. 68 taken along line 69-69.

As more clearly shown in FIG. 69, the first plunger rod piece 730 includes a distal end 731, an open proximal end 739, with the body 732 extending from the distal end 731 to the open proximal end 739. The distal end 731 includes an opening in fluid communication with the plunger rod cavity 734. In the embodiment shown, the distal end 731 includes a distal face 735 and an extension 736 extending in the distal direction from the distal face. The extension 736 defines a path 738 extending from the opening 737 to the inside surface 733 of the body 732. The opening 737 and the path 738 are in fluid communication with the plunger rod cavity 734. The distal face 735 may have a convex shape or be flexible to flex to a convex shape which conforms to the distal wall 712 of the syringe barrel 710. In one or more embodiments, the distal face 735 may also be shaped convexly so that it conforms more closely to the shape of the distal wall 712 of the syringe barrel 710 to expel as much liquid from the chamber 718 as possible.

The body 732 may be made of a rigid plastic or other material. Examples of such materials include polypropylene, polyethylene, polycarbonate and combinations thereof. The body 732 may be cylindrical. In one or more embodiments, the shape of the body 732 may be rectangular or other shape.

Figure 71:
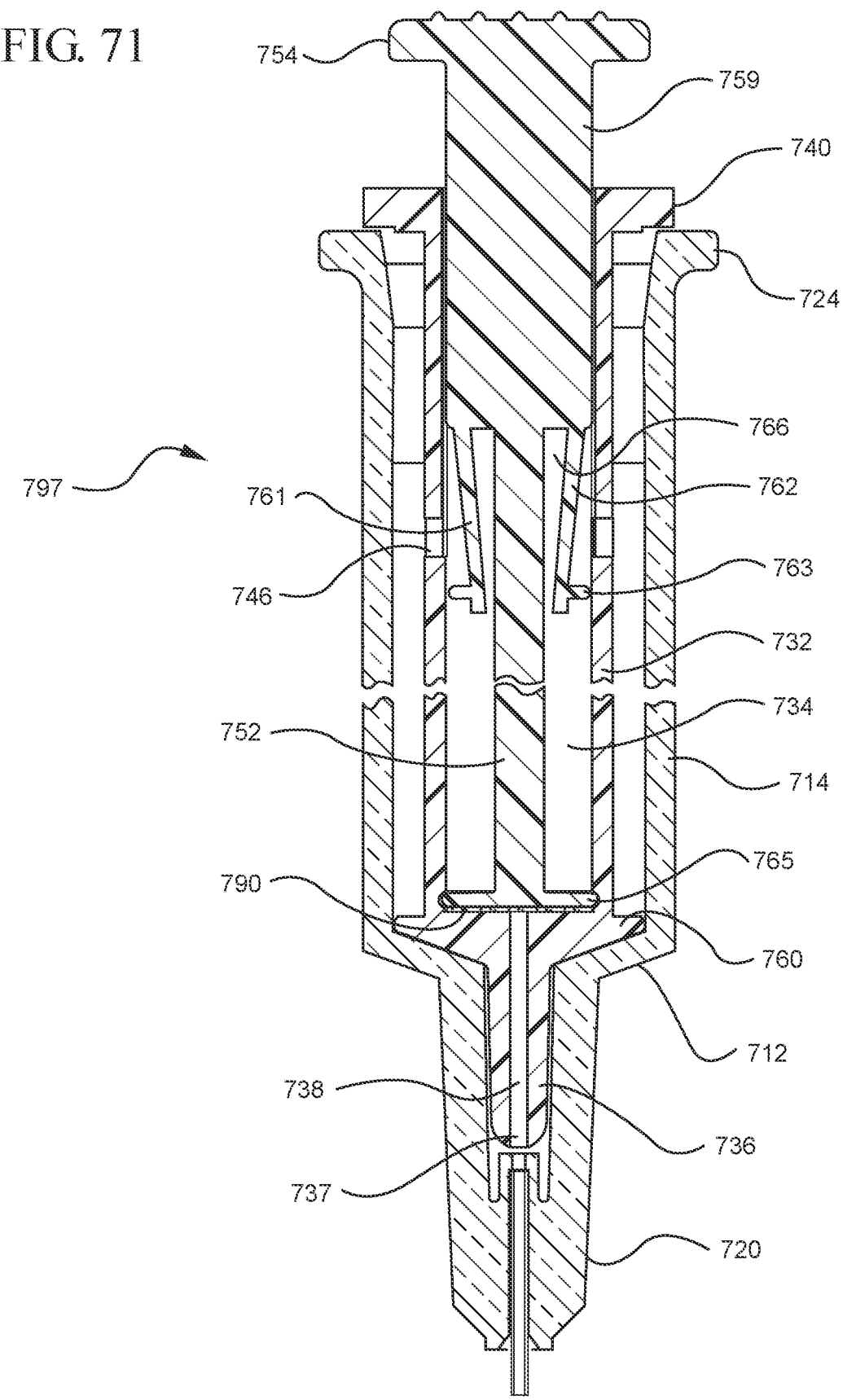
FIG. 71 illustrates an enlarged partial view of the medical device shown in FIG. 70.

A portion of the inside surface 733 the body 732 adjacent to the distal face 735 at the distal end 731 of the first plunger rod piece 730 may be shaped to include an enlarged cross-sectional width portion 743 having an enlarged cross-sectional width for accommodating the sealing portion 765 of the second plunger rod piece 750. The second sealing portion 765 fits within the enlarged cross-sectional width portion 743 of the first plunger rod piece 730 as shown in FIG. 71, when the first plunger rod piece 730 and second plunger rod piece 750 are assembled in the compressed state 797.

As shown in FIG. 69, the body 732 includes a retainer 744 disposed at a point along the length of the body 732. As shown in FIGS. 68-76, the retainer 744 includes at least one opening 746 disposed at a distance from the open proximal end 739 of the first plunger rod piece 730. When assembled with the second plunger rod piece 750, the at least one opening 746 engages a corresponding structure on the second plunger rod piece 750, to assemble the medical device 700 in an extended state 795, as shown more clearly in 71-75 and as will be described in additional detail below. In one or more embodiments, the retainer 744 may be formed on the inside surface 733 of the body 732 as a groove (not shown) or notch (not shown) for engaging a corresponding structure on the second plunger rod piece 750. As shown in FIGS. 68-76, the retainer 744 provides visual indication of assembly of the medical device 700 in the extended state 795. The retainer 744 and/or the corresponding structure on the second plunger rod piece 750 may have a shape that provides audible indication of assembly of the medical device 700 in the extended state 795.

The distal end 731 also includes a sealing edge 745 extending radially outwardly and forming a fluid-tight seal with the interior surface 716 of the syringe barrel 710. As shown in FIGS. 68-76, the sealing edge 745 is formed on the distal end 731 of the body 732 adjacent to the distal face 735 and includes a plunger rod cavity 734 in fluid communication with the void. The sealing edge 745 may be formed along the outer periphery of the distal face 735. Alternatively, the sealing edge 745 may be a separate piece and may attach to the distal end 731 of the body 732 or, in a specific embodiment, to the peripheral edge of the distal face 735. The sealing edge 745 may be formed form the same material as the body 732. In a more specific configuration, the sealing edge 745 is formed from an elastomeric material, polymeric material or other known material suitable for forming a fluid-tight seal with the interior surface 716 of the syringe barrel 710. As shown in FIG. 69, the sealing edge 745 may extend distally and form the extension 736 of the body 732 and/or the distal face 735 of the first plunger rod piece 730. In one or more embodiment, the distal end 731 may be free of an extension 736 and may terminate at the distal face 735.

The distal end 731 of the body includes a porous portion 790. The porous portion 790 as shown in FIG. 69 may be a separate component that is inserted and disposed within the plunger rod cavity 734 and positioned adjacent the distal face 735 and the path 738. In one or more embodiments, the porous portion 790 is integrally formed on the distal face 735 and may cover the opening 737 such that the extension 736 is disposed distally adjacent to the porous portion 790 and remains non-porous. The porous portion 790 may also be disposed proximally adjacent the opening 737 and within the path 738. In one or more embodiments, the porous portion 790 is integrally formed on the distal face 735, with the peripheral edges of the distal face 735 and the sealing edge 745 remaining non-porous. In a specific embodiment, the porous portion 790 is separated from the sealing edge 745 by the distal face 735. In one or more embodiments, the porous portion 790 is formed from a hydrophobic filter and/or a swellable polymer, as described herein. As otherwise described herein, the porous portion 790 is air permeable and liquid impermeable to permit air to flow from the container or syringe barrel 710 into plunger rod cavity 734 of the body.

Figure 68:
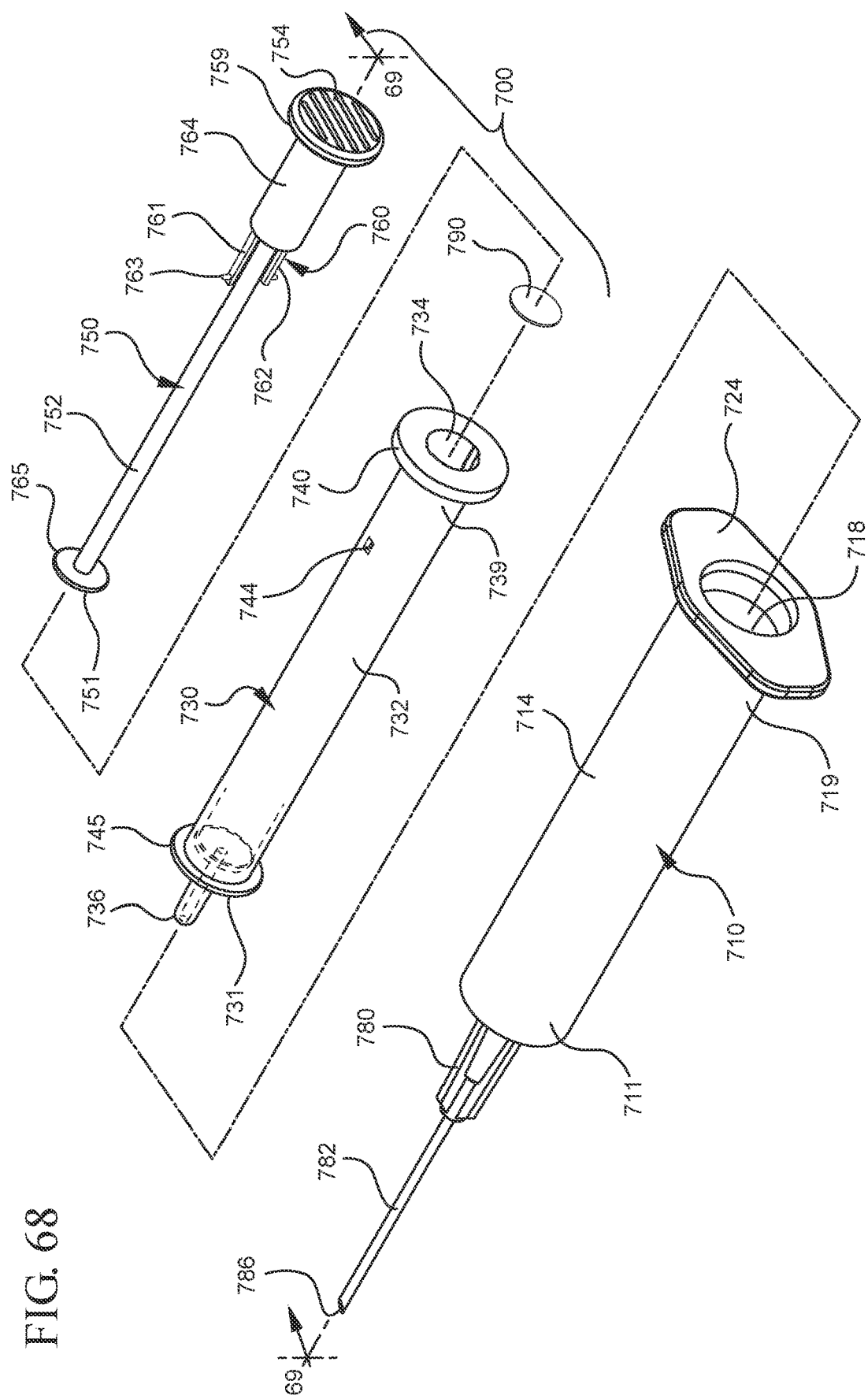
FIG. 68 illustrates a disassembled view of a syringe barrel and one or more embodiments of a medical device according to a seventh aspect of the present invention.

As shown in FIGS. 68-69, the porous portion 790 has a circular shape. Alternatively, the porous portion 790 may have a square and/or rectangular shape. In a specific embodiment, the porous portion 790 has a cross-sectional width that is equal to or larger than the cross-sectional width of the opening 737. In a more specific embodiment, the porous portion 790 has a cross-sectional with that is equal to or smaller than the cross-sectional width of the inside surface 733 of the body 732. In an even more specific embodiment, the porous portion 790 has a cross-sectional width between the cross-sectional width of the opening 737 and the cross-sectional width of the inside surface 733 of the body 732.

The second plunger rod piece 750 includes a distal end 751 and a proximal end 759 and a body or elongate stem 752 extending from the distal end 751 to the proximal end 759. The elongate stem 752 may be made of a rigid plastic or other material. Examples of such materials include polypropylene, polyethylene, polycarbonate and combinations thereof.

The distal end 751 includes a sealing portion 765 that forms a fluid-tight seal with the inside surface 733 of the body 732. The second plunger rod piece 750 is disposed within the plunger rod cavity 734 of the body 732 and is moveable in the proximal and distal direction within the plunger rod cavity 734 of the body 732. The sealing portion 765 may be integrally formed on the elongate stem 752 or may be a separate piece that is attached to the distal end 751 of the second plunger rod piece 750. The sealing portion 765 may also be disposed at other locations along the elongate stem 752 between the distal end 751 and the engagement portion 760, which will be described below, and is shown in the embodiments of FIGS. 68-69 as extending radially outwardly from the elongate stem 752 and having a disc-shape. The shape of the sealing portion 765 may be modified to form a fluid-tight seal with a body 732 having non-cylindrical shapes. The sealing portion 765 may be formed from the same material as the elongate stem 752 or may be formed from a different material. In one or more embodiments, the sealing portion 765 may be formed from an elastomeric material, polymeric material or other suitable material for forming a fluid-tight seal with the interior surface 716 of the syringe barrel 710.

The proximal end 759 of the second plunger rod piece includes a thumbpress 754. The thumbpress 754 has a cross-sectional width that is larger than the cross-sectional width defined by the inside surface 733 of the body 732 adjacent to its proximal end 739. In one or more embodiments, the thumbpress 754 is shaped and/or sized to abut the extension 740, and is prevented from entering the plunger rod cavity 734 of the body 732.

The second plunger rod piece 750 includes an engagement portion 760 adjacent to the proximal end 769. The engagement portion 760 has a structure to engage the retainer 744 of the body 732 of the first plunger rod piece 730 so the medical device 700 may be assembled in the extended state 795. The engagement portion 760 shown in FIG. 68-69 is in the form of two distally extending arms 761, 762. One or both of the arms 761, 762 may include a radially outwardly extending protrusion 763. In one or more embodiments, the engagement portion 760 may include only a single arm.

As shown, the arms 761, 762 extend in the distal direction from a support 764 disposed adjacent to the thumbpress 754. The arms 761, 762 are positioned in a parallel configuration and form a channel 757 with the elongate stem 752. As shown more clearly in FIG. 71, the arms 761, 762 and are radially inwardly flexible and flex into the channel 766 toward the elongate stem 752 upon application of an inwardly-directed radial force. The support 764 is shown in FIGS. 68-69 as integrally formed on the elongate stem 752, adjacent the proximal end 759 and extending partially along the length of the elongate stem 752. As shown in FIGS. 68-76, the support 764 enlarges the cross-sectional width of the elongate stem 752. The length of the support 764 and/or the length of the arms 761, 762 may be adjusted to adjust the length of the plunger rod assembly configured or arranged in the extended state 795. The engagement portion 760 may have an alternate structure that permits the engagement with the retainer 744 of the body 732 of the first plunger rod piece 730. For example, the elongate stem 752 may include one or more depressible protrusions (not shown) that may be depressed by the inside surface 733 of the body 732 to allow movement of the second plunger rod piece 750 in the proximal and distal directions within the plunger rod cavity 734 of the body 732. When aligned with the retainer 744 of the body 732, the force applied the one or more depressible protrusions (not shown) by the inside surface 733 of the body 732 is released so the protrusions 763 are no longer depressed and engage the retainer 744.

When the distal end 751 of the second plunger rod piece 750 is positioned immediately adjacent to the distal face 735 of the first plunger rod piece 730, the engaging portion 760 and the retainer 744 remain unengaged and the medical device 700 is assembled in the compressed state 797, as shown in FIG. 68. The second plunger rod piece 750 is moveable in the proximal and distal directions within the plunger rod cavity 734 of the first plunger rod piece 730 for the distance D1 without engagement between the engagement portion 760 or without the engagement of the opening 746 of the retainer 744 and the protrusion 763 disposed on one or both arms 761, 762. Movement of the second plunger rod piece 750 in the proximal direction relative to the first plunger rod piece 730 for a distance greater than D1 causes engagement of the engagement portion 760 of the second plunger rod piece 750 and the retainer 744 of the first plunger rod piece 730. This proximal movement of the second plunger rod piece 750 relative to the first plunger rod piece 730 also creates a vacuum within the plunger rod cavity 734 of the body as the volume of the plunger rod cavity 734 increases and the sealing portion 765 forms a fluid-tight seal with the inside surface 733 of the first plunger rod piece 730, as shown in FIGS. 72-76. The vacuum within the plunger rod cavity 734 is maintained once formed due to the protrusion 763 extending through the retainer 744 and locking the first plunger rod piece 730 and the second plunger rod piece 750 in the extended state 795. When engaged in the extended state 795, the first plunger rod piece 730 and the second plunger rod piece 750 are moveable as a unitary structure in the proximal and distal directions within the chamber 718 of the syringe barrel 710.

Figure 70:
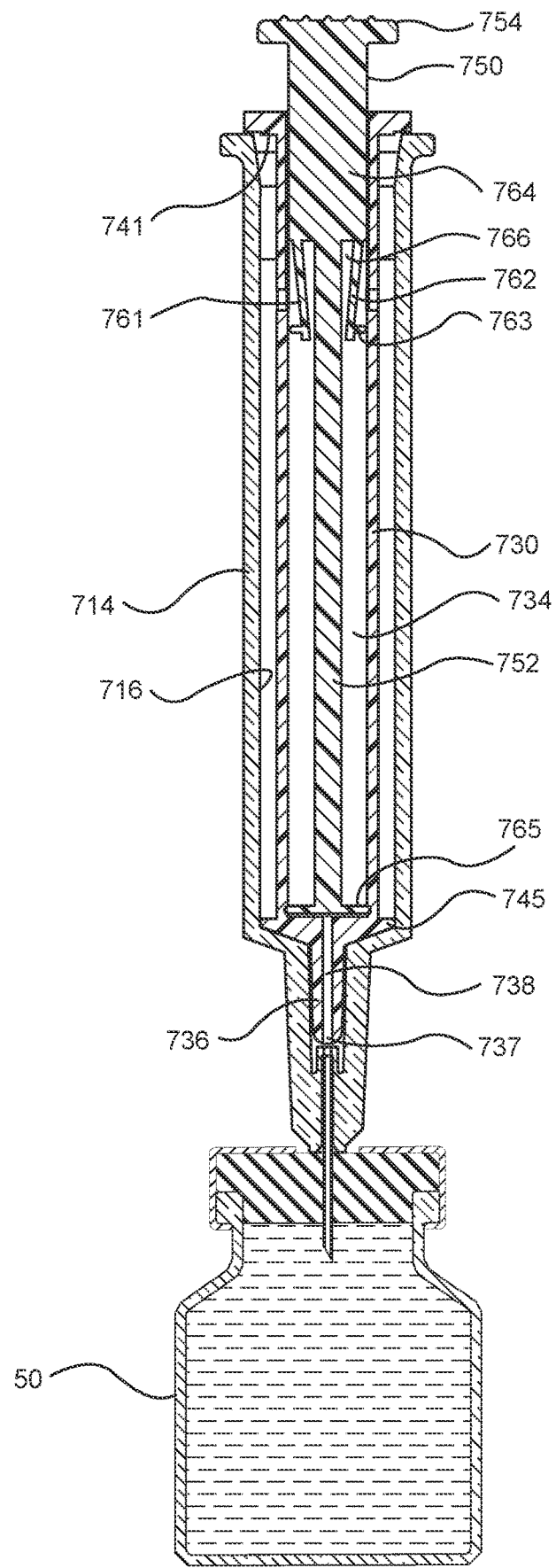
FIG. 70 shows a view of the medical device illustrated in FIG. 68 assembled and positioned to draw liquid from a vial into the syringe barrel.

Prior to use, the medical device 700 is disposed within the chamber 718 of the syringe barrel 710 in a compressed state 797, as shown in FIGS. 70-71. The distal face 735 is disposed adjacent to the distal wall 712 of the syringe barrel 710 so the air within the chamber 718 is minimized and is primarily present in the tip 720 of the syringe barrel 710 or other container. As shown in FIGS. 70-71, the extension 736 of the body 732 is disposed within the passageway 722 of the tip 720 at the distal end 711 of the syringe barrel to further minimize the amount of air within the syringe barrel 710. To aspirate liquid into the chamber 718 of the syringe barrel 710, the user may position the syringe barrel 710 or other container and the needle cannula 784 over a vial 50 and insert the needle cannula 784 into the vial 50, as shown in FIG. 70.

Figure 72:
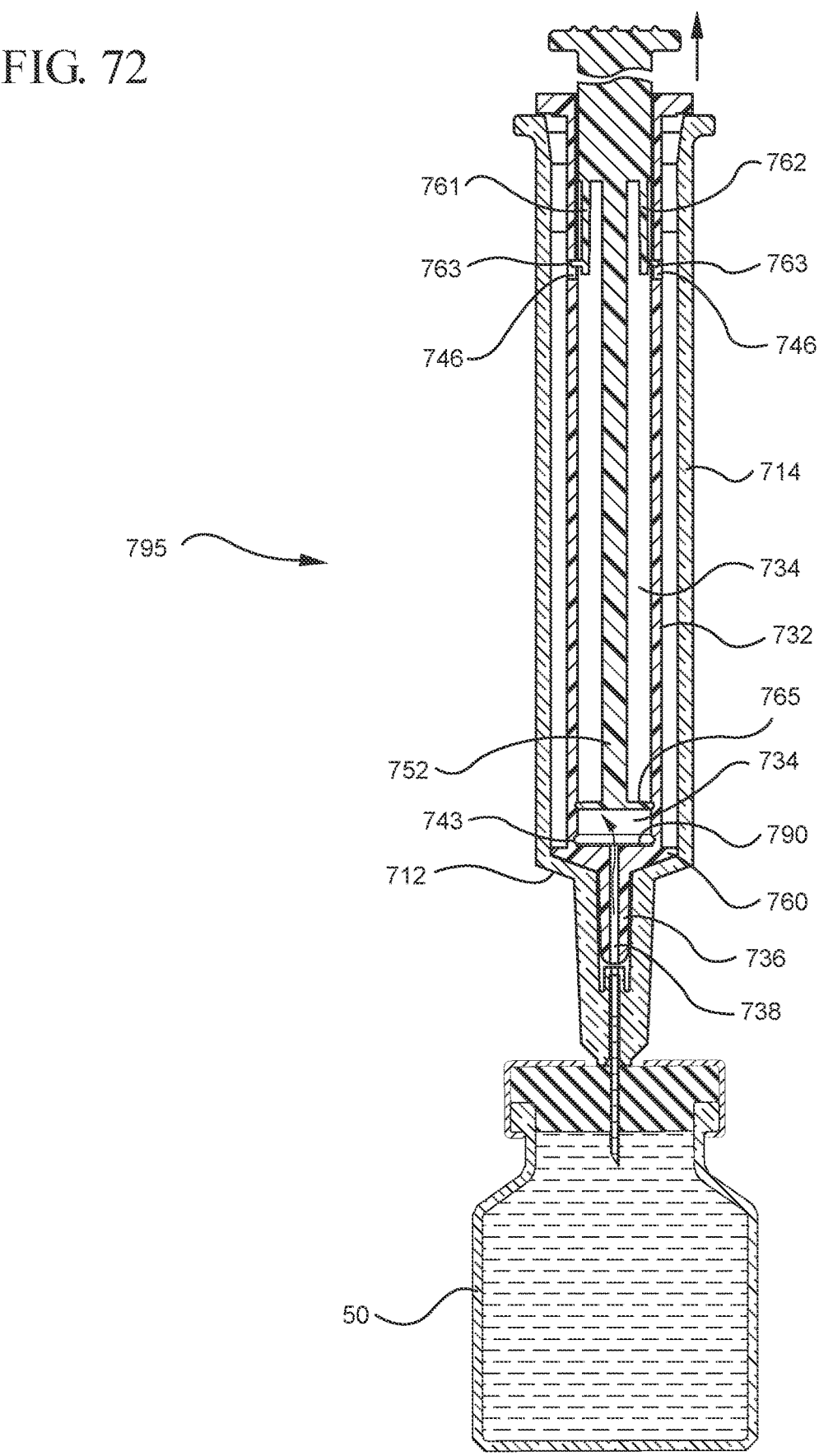
FIG. 72 illustrates the medical device shown in FIG. 70 with the medical device assembled in an extended state.
Figure 73:
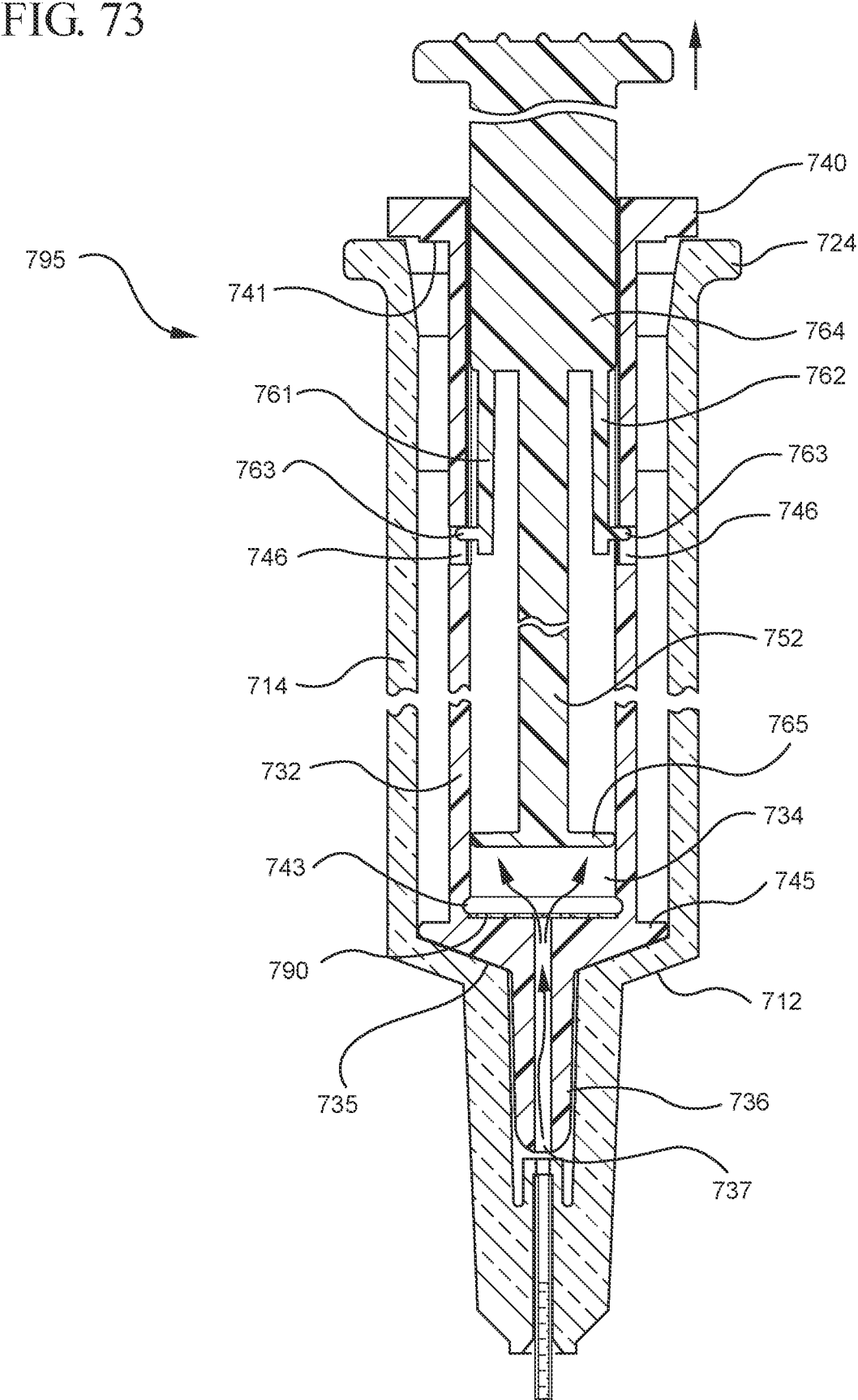
FIG. 73 shows an enlarged partial view of the medical device shown in FIG. 72.

As shown in FIGS. 72-73, to evacuate the air from the syringe barrel 710, the user applies an initial force in the proximal direction to the second plunger rod piece 750 while the first plunger rod piece 730 remains stationary. The second plunger rod piece 750 moves in the proximal direction for the distance of D1 or until the protrusion 763 engages the retainer 744 of the body 732 and the first plunger rod piece 730 and the second plunger rod piece 750 are assembled in the extended state 795. This movement of the second plunger rod piece 750 relative to the first plunger rod piece 730 creates a vacuum within the plunger rod cavity 734, which draws air and/or liquid from the vial 50, through the needle cannula 784 and tip 720 and into the chamber 718 of the syringe barrel 710. The air contained in the tip 720, needle cannula 784 and chamber 718 of the syringe barrel 710 is drawn into the plunger rod cavity 734 of the body 732 through the opening 737, path 738 and porous portion 790.

Figure 74:
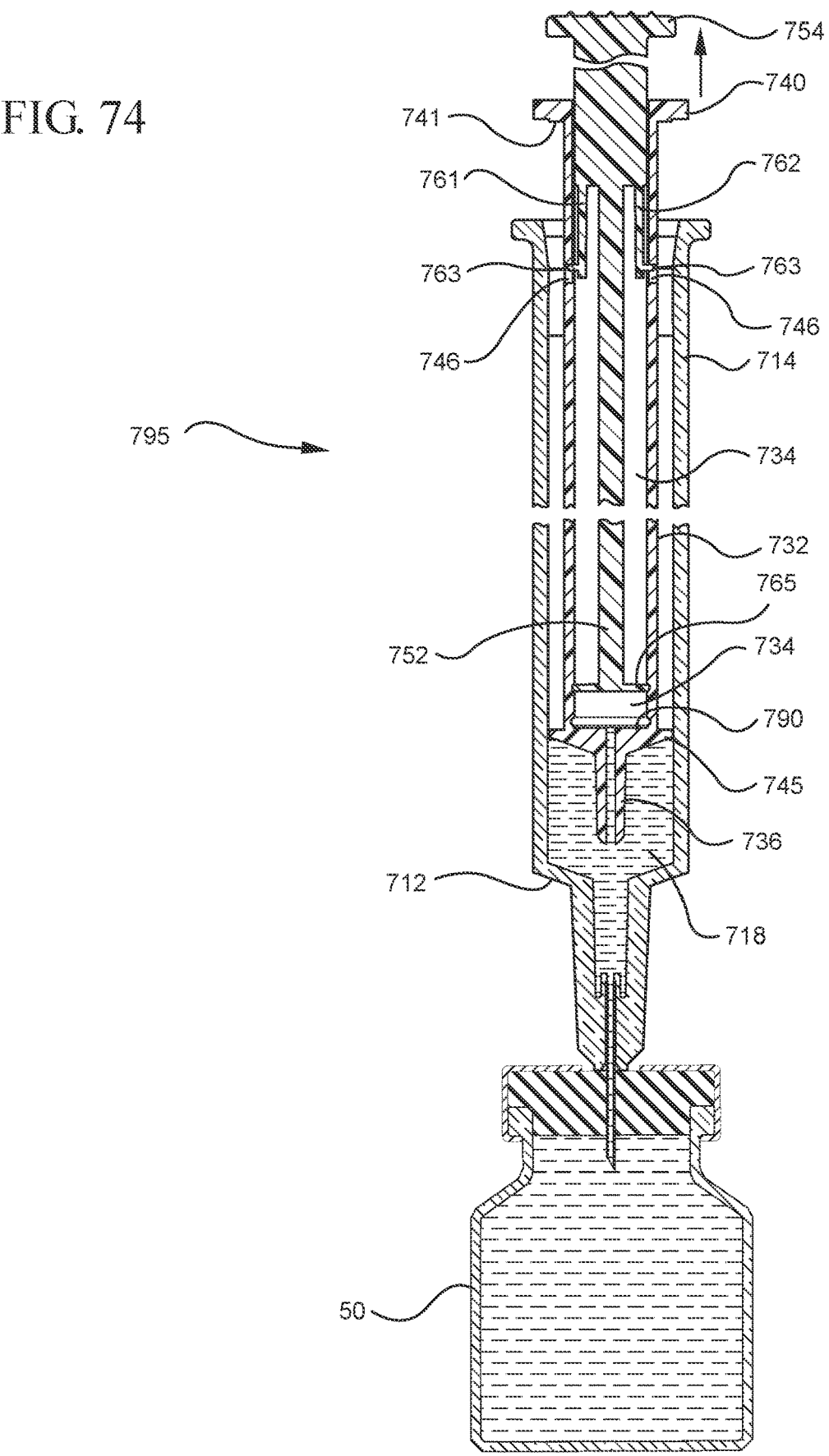
FIG. 74 the medical device shown in FIG. 72 filled with liquid from the vial.
Figure 75:
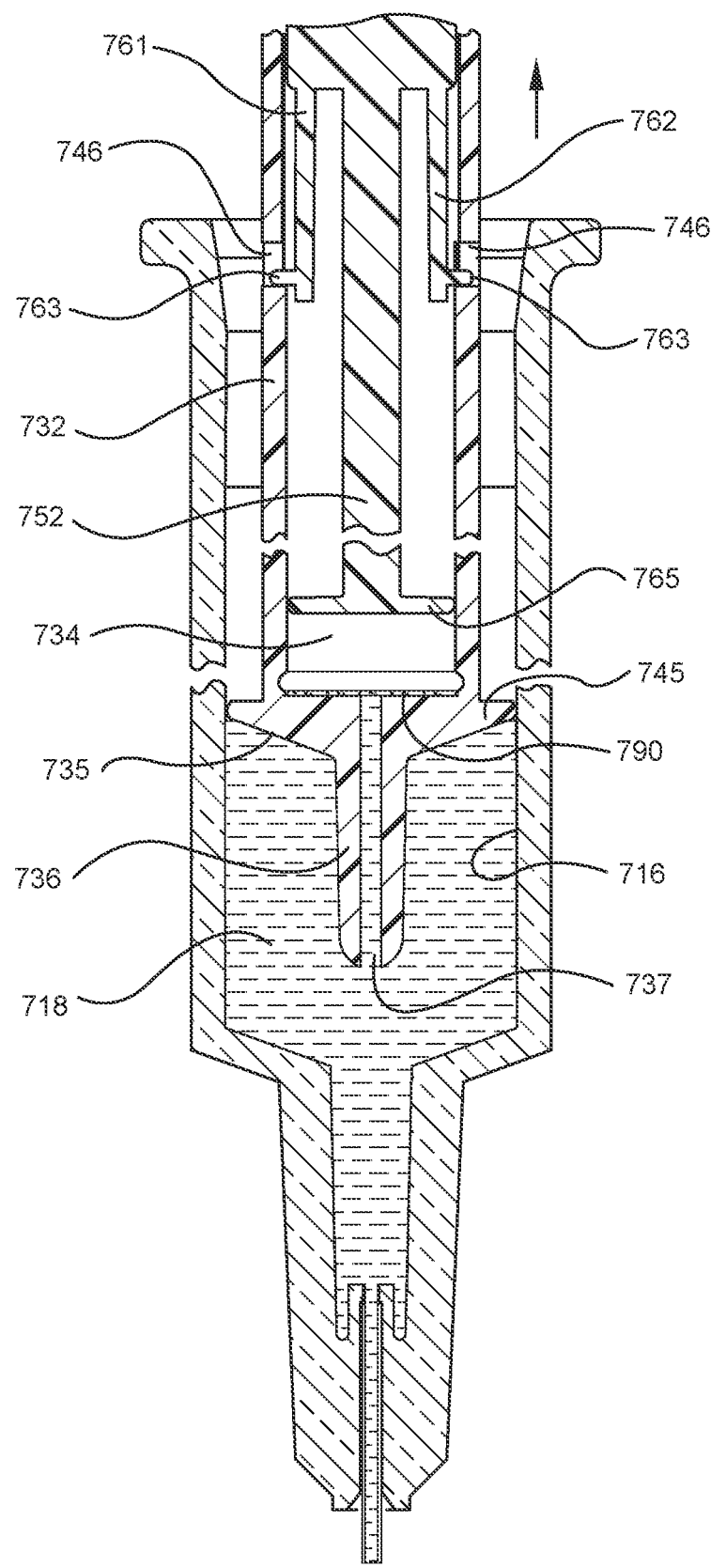
FIG. 75 shows an enlarged partial view of the medical device shown in FIG. 74.

As the air is evacuated into the plunger rod cavity 734, some liquid may be drawn into the chamber 718 of the syringe barrel 710 by the vacuum within the plunger rod cavity 734 of the body and/or by an application of a force on the plunger rod assembly in the proximal direction, which causes the first plunger rod piece 730 and second plunger rod piece 750 to move in the proximal direction together, while assembled in the extended state 795. The engagement of the retainer 744 and engagement portion 760 prevents the second plunger rod piece 750 from moving independently in the proximal or distal directions relative to the first plunger rod piece 730. In addition, the porous portion 790 prevents the aspirated liquid from permeating through the porous portion 790 into the plunger rod cavity 734 of the body 732, as shown in FIGS. 74-75.

As discussed above, the porous portion 790 may include a hydrophobic filter or a swellable polymer as described herein. In embodiments where the porous portion 790 includes a hydrophobic filter, the hydrophobic filter resists liquid from wicking through the filter at a reasonable pressure gradient. In embodiments which utilize a swellable polymer in the porous portion 790, the swellable polymer begins to expand and swell, closing any openings that permitted air to permeate through the porous portion 790 from the chamber 718 into the plunger rod cavity 734 of the body.

Figure 76:
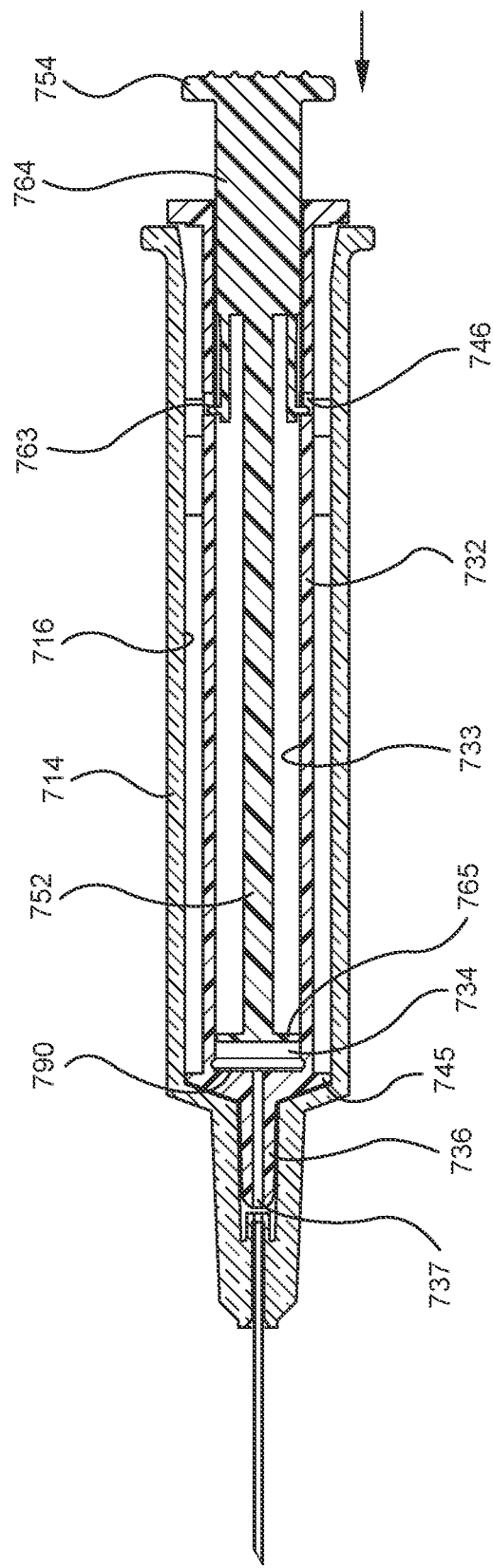
FIG. 76 illustrates the medical device shown in FIG. 74 after application of a continuous force on the medical device in the distal direction to expel the fluid contained within the syringe barrel.

To expel the fluid, a distally directed force is applied to the medical device 700, while it remains assembled in the extended state 795, to move the medical device 700 in the distal direction. As shown in FIG. 76, the engagement of the retainer 744 and the protrusion 763 prevents movement of the second plunger rod piece 750 in the distal direction relative to the first plunger rod piece 730, regardless of whether the user applies pressure to the thumbpress 754 of the second plunger rod piece 750 or the extension 740 of the first plunger rod piece 730. The volume of the plunger rod cavity 734 remains the expanded or enlarged after the initial proximal movement of the second plunger rod piece 750 relative to the first plunger rod piece 730 as the desired amount of liquid is expelled from the chamber 718 of the syringe barrel 710.

In one or more embodiments that utilize a first plunger rod piece 730 having a distal face 735 that flexes, the application of a continuous and distally directed force on the first plunger rod piece 730 and the second plunger rod piece 750 causes the distal face 735 to flex convexly as the distal face 735 contacts the distal wall 712 of the syringe barrel 710. In embodiments which utilize a first plunger rod piece 730 having a convexly-shaped distal face 735, the distal face 735 conforms more closely to the distal wall 712 upon contact with the distal wall 712. Upon contact with the distal wall 712, the convex shape of the distal face 735 expels even more liquid from the syringe barrel 710.

FIGS. 77-85 illustrate a medical device 800 according to an eighth aspect of the present invention. The medical device 800 includes a plunger rod and stopper assembly having a pre-formed vacuum and a needle supported on a container to pierce the vacuum to evacuate air from the container. In one or more embodiments, the medical device 800 may be utilized with a container, for example, a syringe barrel 810. As shown more clearly in FIG. 84, the syringe barrel 810 includes an open proximal end 819, a distal end 811 and a distal wall 812. A sidewall 814 extends from the distal end 811 to the open proximal end 819 and includes an interior surface 816 that defines a chamber 818 for retaining or holding fluids, which may include liquid medication and/or other liquids. The distal end 811 may also include a tip 820 having an open passageway 822 therethrough in fluid communication with the chamber 818. As shown, the distal end 811 of the syringe barrel 810 includes an optional luer fitting 826 and the open proximal end 819 of the barrel may include a flange 824. The needle 880 is shown attached directly to the tip 820, however, in one or more embodiments, a needle hub (not shown) may be utilized to attach the needle 880 to the tip 820. The interior surface 816 of the syringe barrel 810 may have a smooth surface that is free of any protrusions or depressions. In use, the plunger rod 840 and stopper 860 are inserted into the open proximal end 819 of the syringe barrel 810 a needle 880 is attached to the tip 820 in fluid communication with the chamber 818.

Figure 77:
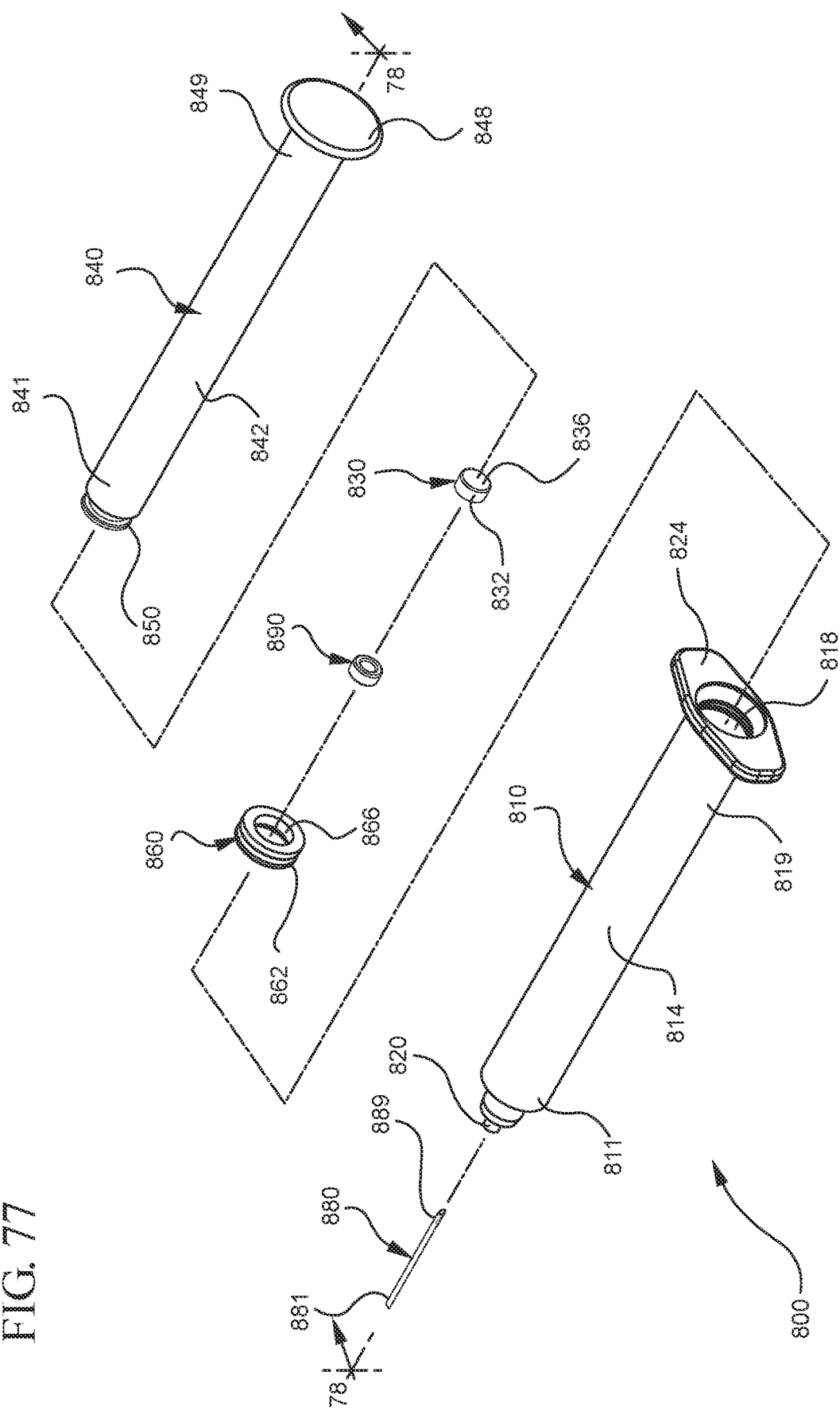
FIG. 77 illustrates a disassembled view of a syringe barrel and one or more embodiments of a medical device according to a eighth aspect of the present invention.
Figure 78:
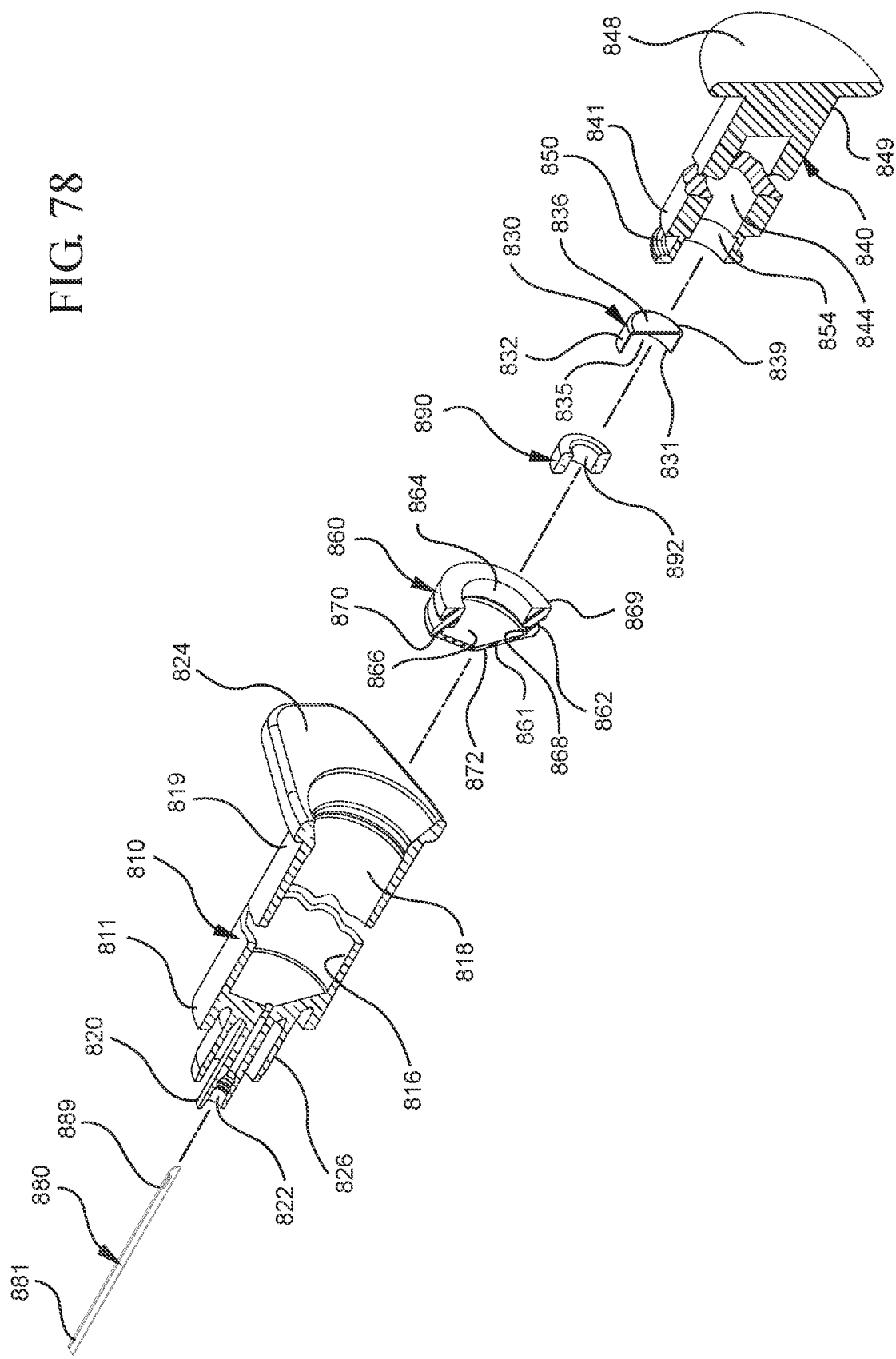
FIG. 78 illustrates a cross-sectional view of the syringe barrel and medical device shown in FIG. 77 taken along line 77-77.
Figure 79:
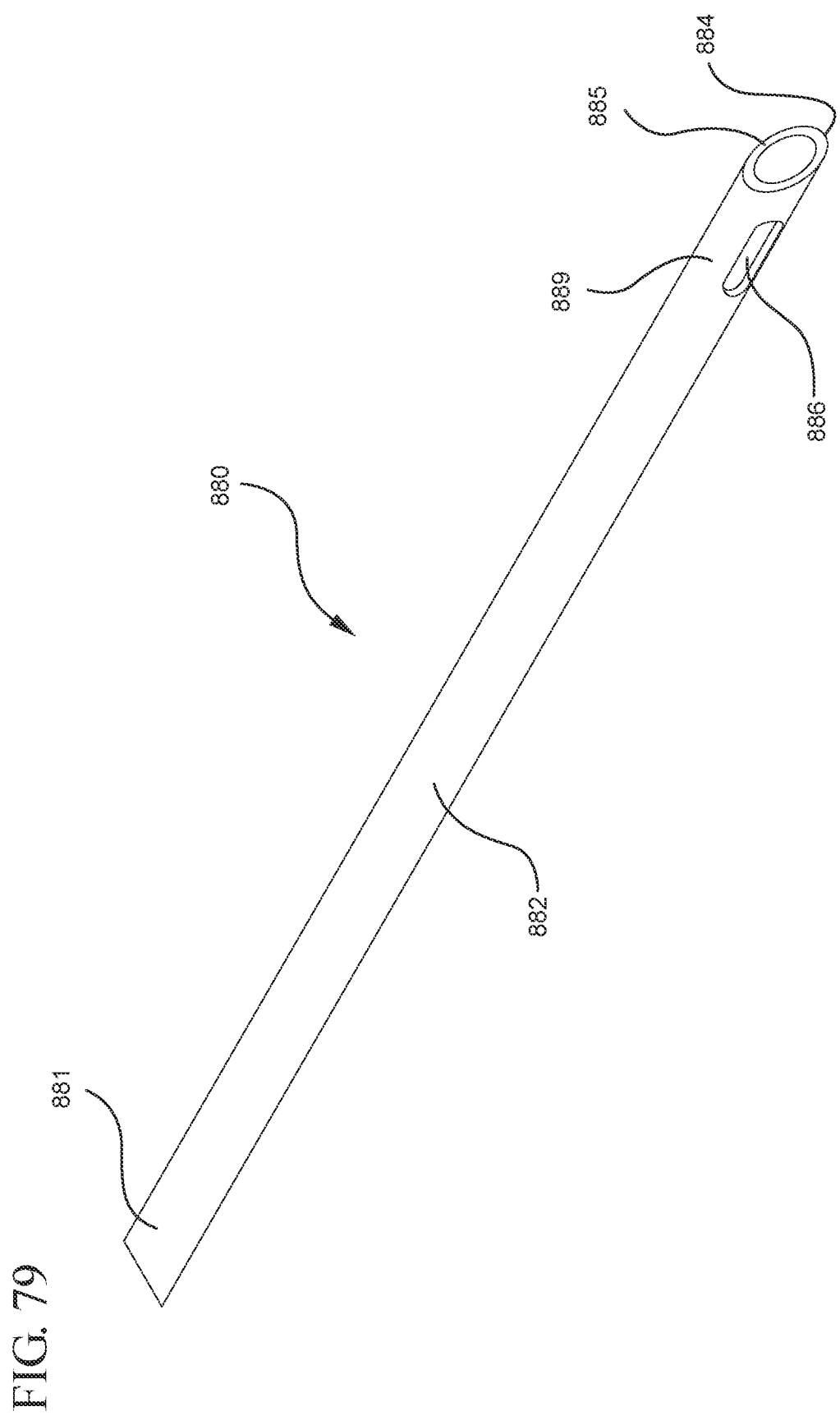
FIG. 79 shows a perspective view of the needle shown in FIG. 78.

As more clearly shown in FIGS. 77-78, the stopper 860 includes a distal end 861, an open proximal end 869 and a body 862 extending from the distal end 861 to the open proximal end 869. The body 862 includes an inside surface 864 defining a cavity 866. In one or more embodiments, the inside surface 864 of the body 862 may include a peripheral groove 868 forming a channel or ridge within the body 862 for engagement with the plunger rod 840, as will be described in detail below. As shown in FIGS. 77-85, the body 862 includes an outside surface 863 including a sealing portion 870. As shown, the sealing portion 870 is disposed adjacent the distal end 861 for forming a fluid-tight seal with the inside surface 816 of a syringe barrel 810. The stopper 860 may be formed from an elastomeric material, polymeric material or other material known in the art. The sealing portion 870 may have a circular cross-section for forming a fluid-tight seal with a syringe barrel 810 having an inside surface 816 with a circular cross-section. The shape of the sealing portion 870 may be modified to form a fluid-tight seal with syringe barrels having different cross-sectional shapes. The sealing portion 870 may be formed from any material suitable for forming a fluid-tight seal with the interior surface 816 of the syringe barrel 810, which may be the same or different material utilized to form the stopper 860.

The distal end 861 of the stopper 860 includes a pierceable distal face 872 or pierceable septum that forms a pierceable seal with the stopper cavity 866 and seals a vacuum formed within the plunger rod 840 when the open proximal end 869 of the stopper 860 is attached to the plunger rod 840. The vacuum within the plunger rod 840 may be formed prior to attachment of the stopper 860 and plunger rod 840 using means known in the art. For example, the plunger rod 840 may include an open distal end in fluid communication with the cavity 866 and an interior plunger (not shown) disposed telescopically within the plunger rod 840 and forming a fluid tight seal with the inside surface of the plunger rod 840. The interior plunger (not shown) may be partially withdrawn from the plunger rod 840 to create a vacuum within the plunger rod 840 and the cavity 866, as described with reference to the embodiments according to the seventh aspect of the present invention. Alternatively, the vacuum may be preformed within the plunger rod 840, during assembly with the stopper 860. The pierceable distal face 872 may have a convex shape or be flexible to flex to a convex shape which conforms to the distal wall 812 of the syringe barrel 810. In one or more embodiments, the distal face 872 may also be shaped convexly so that it conforms more closely to the shape of the distal wall 812 of the syringe barrel 810 to expel as much liquid from the chamber 818 as possible. The pierceable distal face 872 may be formed from an elastomeric material and may have a uniform thickness or a varying thickness. In one or more specific embodiments, the thickness of the pierceable distal face 872 may be varied to facilitate piercing by the needle 880.

As discussed above, the plunger rod 840 is attached to the open proximal end 869 of the stopper. The plunger rod 840 shown more clearly in FIGS. 77 and 80 includes an open distal end 841, a proximal end 849, and a hollow body 842 extending from the open distal end 841 and the proximal end 849. The hollow body 842 includes an interior surface 843 that defines a void 844. As discussed above, in one or more embodiments, the void 844 of the plunger rod 840 includes a vacuum. The vacuum may also be present within the stopper cavity 866 when the plunger rod 840 is assembled with the stopper 860. In one or more alternative embodiments, the open distal end 841 of the plunger rod may be covered and sealed by a pierceable wall (not shown) that is air and liquid impermeable to maintain the vacuum within the void 844 prior to release by the needle 880, as will be described in more detail below. The plunger rod 840 may be made of a rigid plastic or other material that has a greater rigidity than the stopper 860. Examples of such materials include polypropylene, polyethylene, polycarbonate and combinations thereof. The hollow body 842 may be cylindrical. In one or more embodiments, the shape of the hollow body 842 may be rectangular or other shape. The proximal end 849 of the plunger rod 840 includes an optional thumbpress 848.

The open distal end 841 of the plunger rod includes stopper-engaging portion 850 having a distal end 851 and a proximal end 859. The stopper-engaging portion 850 includes a sidewall support 852 extending from the proximal end 859 to the distal end 851 of the stopper-engaging portion 850. As shown in FIG. 78, a disc 853 extends radially outwardly from the distal end 851 of the sidewall support 852. Specifically, as more clearly shown in FIG. 78, the disc 853 extends radially outwardly to engage the peripheral groove 868 of the stopper 860. The stopper-engaging portion 850 may include a tab (not shown), which corresponds to an opening or other corresponding structure on the inside surface 864 of the stopper. In a specific embodiment, the stopper-engaging portion 850 may have an opening (not shown) and the inside surface 864 of the stopper 860 may include a tab (not shown) extending radially inwardly to engage with the opening (not shown) of the stopper 860. Other means to engage the plunger rod 840 to the stopper 860 may also be utilized. Alternatively, the stopper 860 may be integrally formed on the distal end 841 of the plunger rod 840.

A first porous portion 830 is disposed within the sidewall support 852. As shown, the sidewall support 852 defines a hollow interior 854 having a cross-sectional width greater than the cross-sectional width defined by the interior surface 843 of the plunger rod. The hollow body 842 of the plunger rod forms a ledge 855 for supporting the first porous portion 830 within the hollow interior 854 of the sidewall support 852. The first porous portion 830 shown in FIG. 78 includes an open distal end 831 and a proximal end 839 permitting fluid communication between the hollow interior 854 and the cavity 866 of the stopper 860. In the embodiment shown in FIGS. 77-85, the first porous portion 830 includes an outside wall 832 extending from the distal end 831 to the proximal end 839, a bottom support 836 at the proximal end 839. The first porous portion 830 may be formed from hydrophobic filter, a swellable polymer and combinations thereof, as described herein. When the first porous portion 830 includes a swellable polymer, the openings present in the swellable polymer close upon contact with the liquid. In embodiments which include a first porous portion 830 formed from a hydrophobic filter or membrane, the hydrophobic filter prevents liquid from permeating through the first porous portion 830 and entering the plunger rod 840. As shown, the bottom support 836 forms a liquid impermeable barrier between the cavity 866 of the stopper 860 and the void 844 of the plunger rod 840.

In the embodiment shown, the first porous portion 830 is shaped to support a second porous portion 890. In one or more embodiments, the medical device 800 includes only a first porous portion 830 and no second porous portion 890. In one or more alternative embodiments, the medical device 800 includes only a second porous portion 890 and no first porous portion 830. In a more specific embodiment, the first porous portion 830 may be replaced by a pierceable wall (not shown) to seal the vacuum within the void 844 of the plunger rod.

In the embodiment shown in FIGS. 77-85, the outside wall 832 and bottom support 836 form a space 835 in fluid communication with the stopper cavity 866 and forms a partial enclosure for the second porous portion 890, which is also in fluid communication with the cavity 866.

The second porous portion 890 disposed within the space 835 of the first porous portion 830 is air permeable and liquid impermeable. In one or more embodiments, the second porous portion 890 may include a hydrophobic filter or a swellable polymer as described herein. Alternatively, the second porous portion 890 may be composed of a plurality of hydrophobic papers.

The second porous portion 890 may be shaped to fit within the space 835. As shown, the second porous portion 890 is shown as a ring-shaped member having a hollow interior 892. In one or more embodiments, the second porous portion 890 may be disc-shaped or other shape to occupy the space 835. In one or more embodiments, the second porous portion 890 has a circular shape having an opening. In one or more embodiments, the second porous portion 890 is integrally formed within the space 835, bottom support 836 and outside wall 832 of the first porous portion 830. Alternatively, the second porous portion 890 may be disposed along the inside surface 864 of the stopper 860 at the distal face or across the open distal end 841 of the plunger rod.

Figure 81:
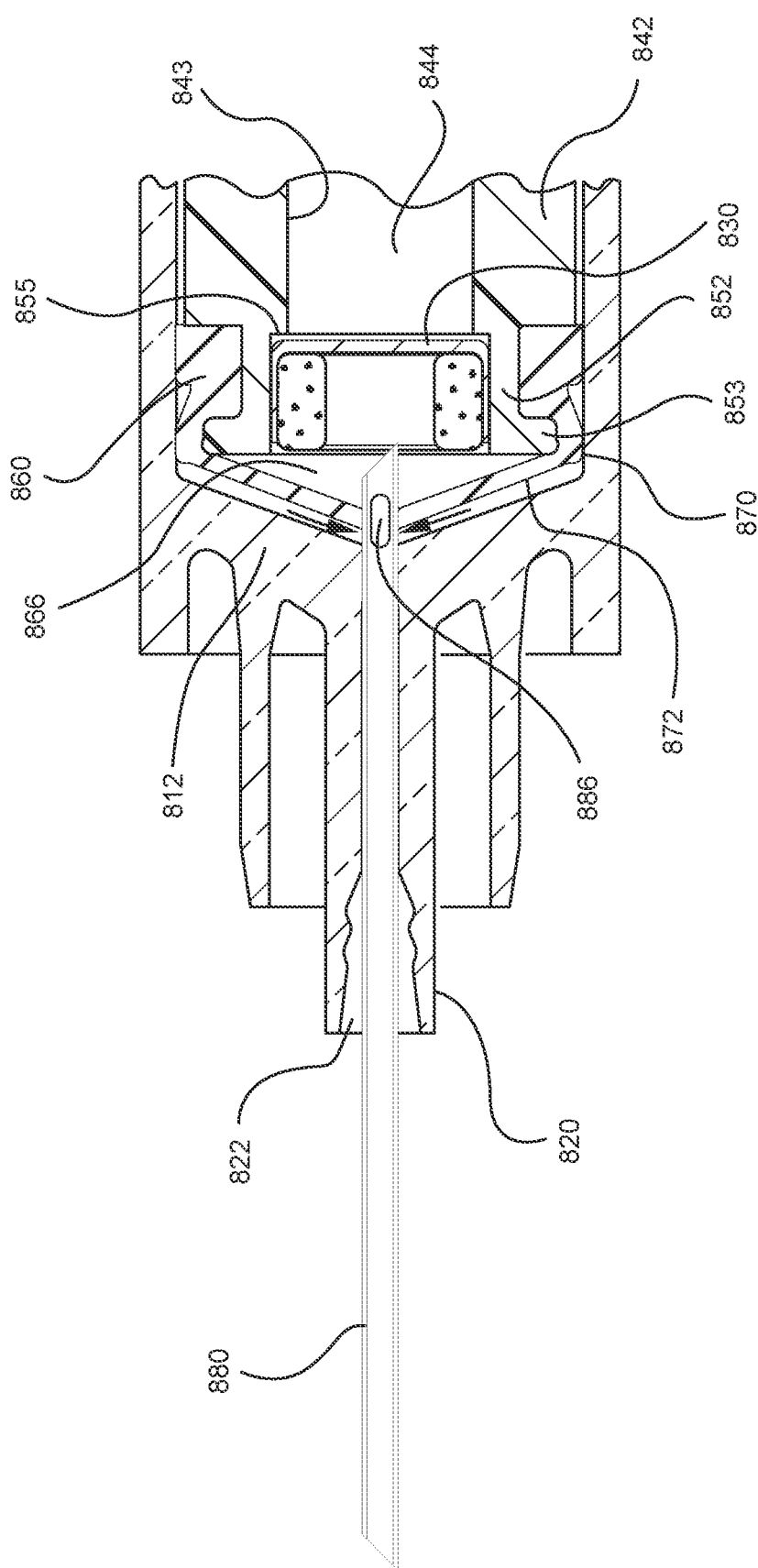
FIG. 81 illustrates an enlarged partial view of the medical device shown in FIG. 80.

The needle 880 is attached to the tip 820 of the syringe barrel 810 and extends partially into the chamber 818 of the syringe barrel. As more clearly shown in FIG. 79, the needle 880 includes an open distal end 881, an open proximal end 889 and a cannula 882 extending from the distal end 881 to the proximal end 889. The open proximal end 889 includes a beveled edge 885 forming a piercing point 884 for piercing the distal face 872 of the stopper. In one or more embodiments, the open distal end 881 may optionally include a beveled and/or blunt edge. The cannula 882 includes a vent 886 disposed adjacent to the open proximal end 889 of the needle. As shown in FIG. 81, the vent 886 is completely enclosed and may be in the shape of a circular opening.

Figure 80:
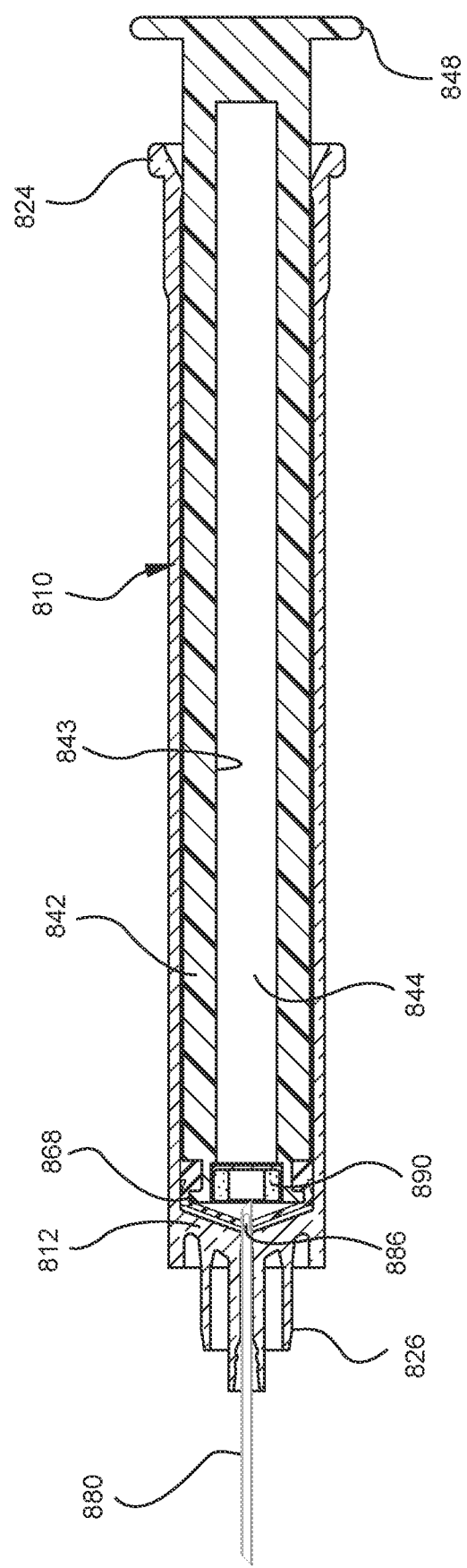
FIG. 80 illustrates a view of the medical device illustrated in FIG. 77 assembled.

In use, as shown in FIG. 80, the plunger rod 840 and stopper 860 are assembled as a medical device 800 and are inserted into the open proximal end 819 of the syringe barrel 810. Before aspirating fluid into the chamber 818 of the syringe barrel 810, the stopper 860 and plunger rod 840 are positioned so that the vacuum within the plunger rod 840 is maintained, while minimizing the air within the syringe barrel 810. In one or more embodiments, the vacuum is present within the plunger rod 840 and stopper 860 assembly and the pierceable distal face 872 is disposed at a minimal distance from the piercing point 884 to maintain the vacuum within the plunger rod 840 and stopper 860 assembly. In one or more embodiments, the pierceable distal face 872 may be positioned adjacent to the piercing point 884 of the needle 880. In a more specific embodiment, the piercing point 884 may partially penetrate the pierceable distal face 872, while the pierceable distal face 872 remains intact. In embodiments which utilize a plunger rod 840 including a pierceable wall (not shown) that covers the open distal end 841 of the plunger rod to seal the vacuum within the void 844, the needle 880 may be disposed such that it extends farther into the chamber 818 and into the stopper cavity 866 to a position that a minimal distance from the pierceable wall (not shown) so the vacuum within the void 844 is maintained.

Figure 82:
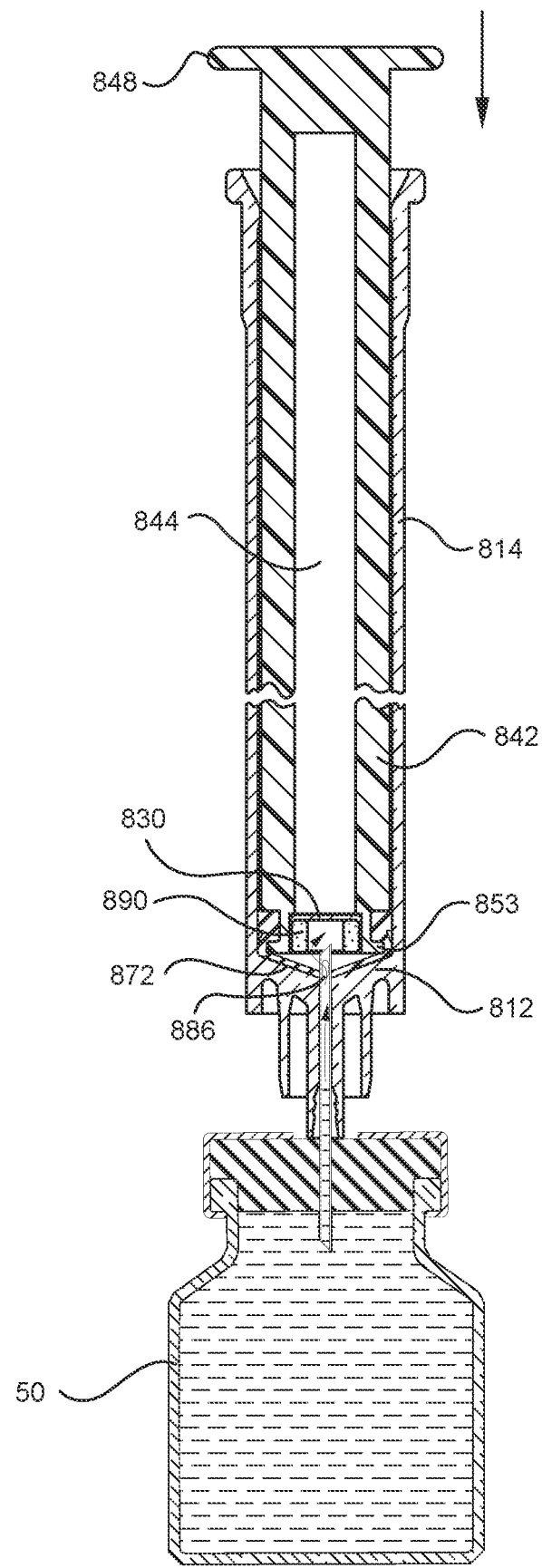
FIG. 82 illustrates the medical device shown in FIG. 81 drawing liquid from a vial into the syringe barrel after application of the initial force to the plunger rod in the distal direction.
Figure 83:
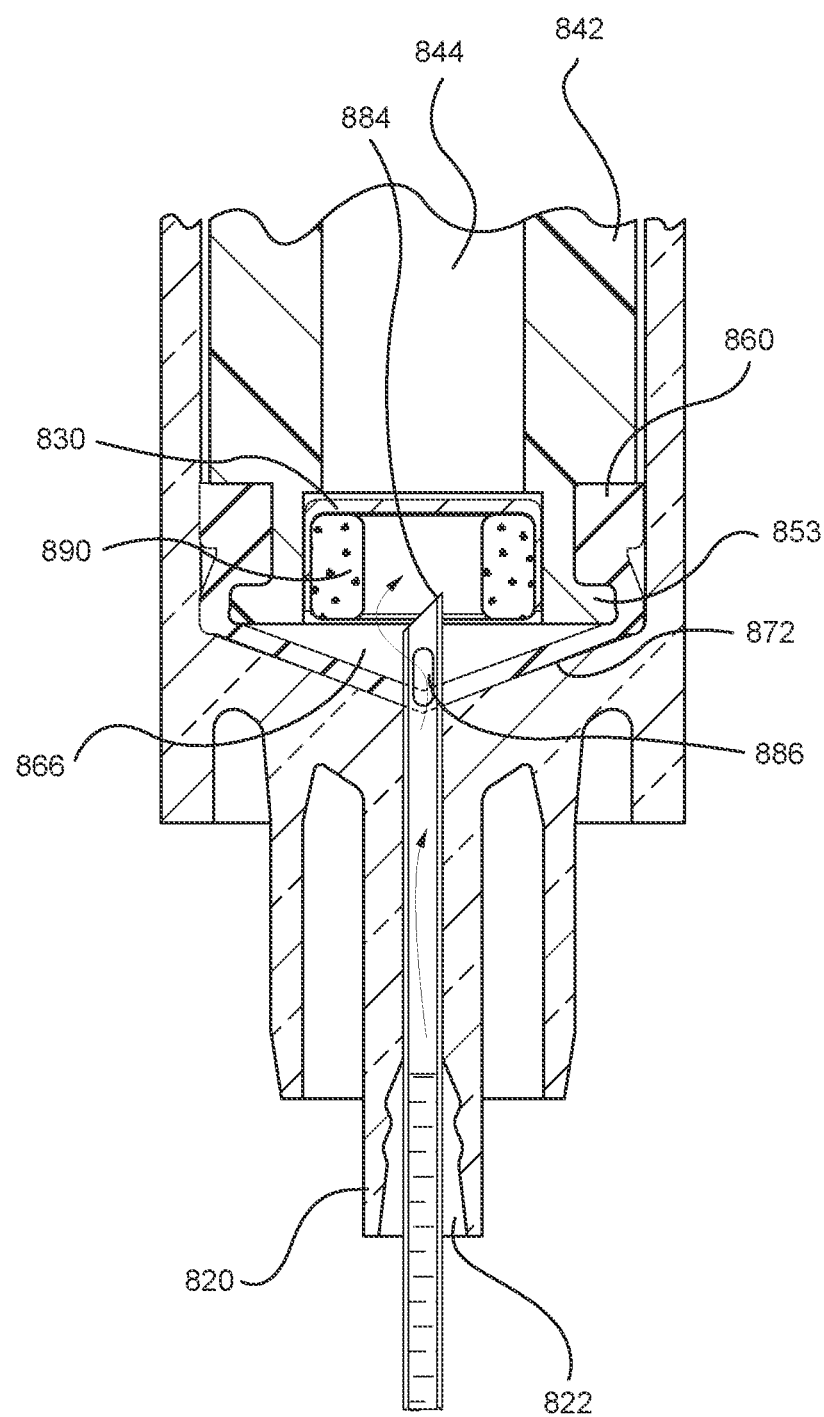
FIG. 83 shows an enlarged partial view of the medical device and syringe shown in FIG. 82.

As shown in FIGS. 81 and 82, to fill the chamber 818 of the syringe barrel 810, the distal end 881 of the needle 880 is inserted into a container, such as a vial 50. In the embodiment shown in FIGS. 81-82, after the needle 880 is inserted into the vial, the air is trapped between the liquid within the needle 880 and the pierceable distal face of the stopper. There is also air present in the chamber 818 between the stopper 860 and the distal wall 812 of the syringe barrel 810. Thereafter, an initial force in the distal direction is applied to the plunger rod 840 so the piercing point 884 pierces and penetrates through the pierceable distal face 872 to release the vacuum contained within the cavity 866 of the stopper 860 and the void 844 of the plunger rod 840. In embodiments that utilize a pierceable wall (not shown) to maintain a vacuum within the void 844 of the plunger rod, the piercing point 884 pierces the pierceable wall (not shown) to release the vacuum.

As the vacuum is released by the piercing point, the vacuum draws air from the chamber 818 and the needle 880 into the cannula 882 into the cavity 866 of the stopper. As the air is evacuated into the cavity 866, some liquid may be drawn into the cavity 866 of the stopper 860 by the vacuum within the plunger rod 840. The first porous portion 830 and/or the second porous portion 890 of the stopper 860 prevent liquid from entering the void 844 of the plunger rod 840. For example, in embodiments which utilize a first porous portion 830 and/or second porous portion 890 that includes a swellable polymer, the openings present in the swellable polymer close upon contact with the liquid. In embodiments which utilize a first porous portion 830 and/or second porous portion 890 including a hydrophobic filter or membrane, the hydrophobic filter prevents liquid from permeating through the porous portion.

As shown in FIG. 84, the desired amount of liquid may be filled into the syringe barrel 810, without the presence of air.

During aspiration, the needle 880 remains stationary and the user continues to apply a force on the thumbpress 848 in the proximal direction and the plunger rod 840 and stopper 860 move in the proximal direction. The hole or opening created in the pierceable distal face 872 by the piercing point 884 of the needle 880 reseals, providing a fluid tight seal or barrier to the liquid between the cavity 866 and the chamber 818. In other words, the pierceable distal face 872 forms a seal between the chamber 818 and the cavity 866 of the stopper 860 after the stopper 860 and plunger rod 840 move in the proximal direction away from the piercing point 884.

Figure 85:
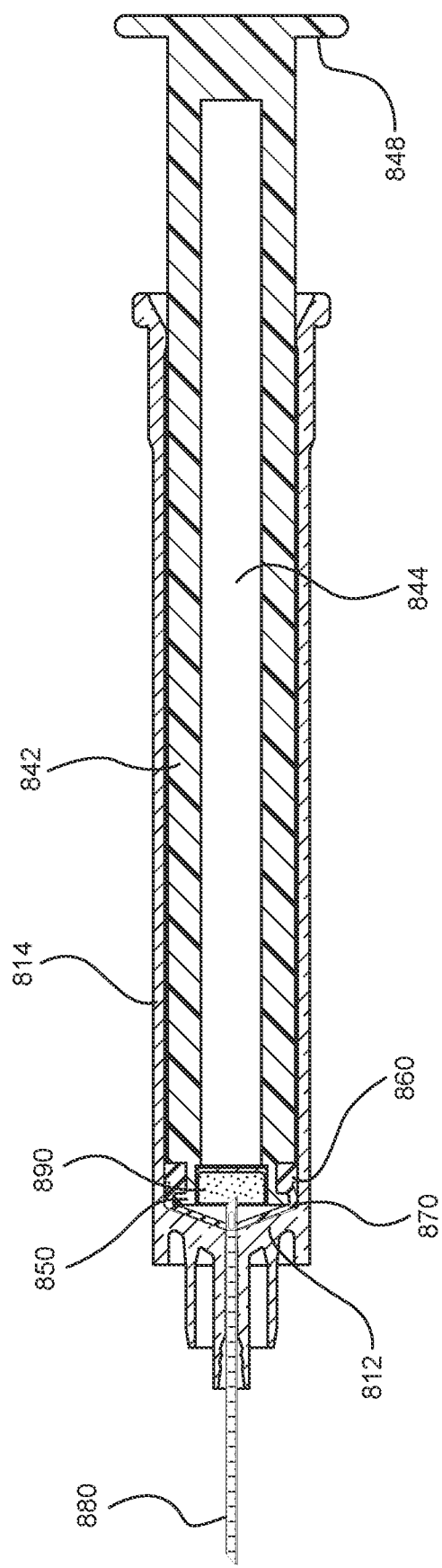
FIG. 85 illustrates the medical device shown in FIG. 84 after application of a continuous force on the plunger rod in the distal direction to expel the fluid contained within the syringe barrel.

To expel the fluid, the user applies a force on the plunger rod 840 or thumbpress 848 in the distal direction, causing the stopper 860 and plunger rod to move in the distal direction as shown in FIG. 85. In one or more embodiments that utilize a stopper 860 having a distal face 872 that flexes, the application of a continuous and distally directed force on the plunger rod 840 causes the distal face 872 to flex convexly as the distal face 872 contacts the distal wall 812 of the syringe barrel 810. In embodiments which utilize a stopper 860 having a convexly-shaped distal face 872, the distal face 872 conforms more closely to the distal wall 812 upon contact with the distal wall 812. The convex shape of the distal face 872 upon contact with the distal wall 812 expels even more liquid from the syringe barrel 810.

A ninth aspect of the present invention pertains to a method of aspirating a container using the various embodiments of medical devices described in this application. For illustration purposes, reference will be made to FIGS. 1-85. In one embodiment, the method for aspirating a syringe barrel or other container includes providing a needle cannula including a lumen or opening on the tip of the syringe barrel, inserting a plunger rod assembly having a sealing means within the syringe barrel and providing a vacuum within the plunger assembly. In one or more embodiments, the vacuum is provided by providing a plunger rod assembly with an expanding cavity. The method may include positioning the stopper immediately adjacent the distal wall of the syringe barrel to isolate an air source in the open passageway of the tip, submerging the opening or lumen of the needle cannula in a liquid, and drawing air and liquid into the syringe barrel and evacuating the air or air source from the liquid within the syringe barrel. The vacuum may be provided within the plunger rod assembly before or after submerging the opening of the needle cannula in a liquid. In one or more embodiments, the method may include applying a force in the distal direction to the plunger rod to cause distal face to flex convexly to minimize the air present in the chamber. In one or more embodiments, the method includes drawing the liquid into the syringe barrel by applying a continuous force to the plunger rod in the proximal direction so that the plunger rod and stopper move in the proximal direction together. The method of aspirating may also include the step of venting the air from the syringe barrel.

In one variant, separating air from the liquid includes forming a vacuum within the stopper and providing a distal face on the stopper, an opening in fluid communication with a cavity in the stopper and an air permeable and liquid impermeable filter between the opening and the cavity. In one or more embodiments, forming a vacuum includes expanding the volume of the stopper and/or plunger rod. The formation of a vacuum within the stopper draws air and liquid into the cavity. The filter permits air to enter the cavity and prevents liquid from entering the cavity.

Separating air from the liquid may include providing a pre-formed vacuum within the plunger rod, providing a distal face on the stopper, an opening in fluid communication with a cavity in the stopper and an air permeable and liquid impermeable filter between the opening and the cavity and providing a release means to release the vacuum in the plunger rod. In a specific embodiment, the method includes providing a release means on the stopper that pierces a pierceable barrier on the plunger rod. The release of the vacuum and attachment of the stopper and plunger rod draws air and liquid into the cavity of the stopper. The filter permits air to enter the cavity and prevents liquid from entering the cavity.

Alternatively, separating air from the liquid includes providing a pre-formed vacuum within the stopper, providing a pierceable distal face on the stopper and an air permeable and liquid impermeable filter within the stopper and/or plunger assembly and a release means attached to the container to pierce the pierceable distal face and to release the vacuum. The release of the vacuum draws air and liquid into the cavity of the stopper. The filter permits air to enter the cavity and prevents liquid from entering the cavity. Separating the air from the liquid may include forming a vacuum within the chamber between the plunger rod and the stopper. In a specific embodiment, forming a vacuum within the chamber between the plunger rod and the stopper includes providing a sealing means on the plunger rod for forming a fluid tight seal with the syringe barrel and a distal face on the stopper, an opening in fluid communication with a cavity in the stopper including an air permeable and liquid impermeable filter between the opening and the cavity, providing a sealing means on the stopper for forming a fluid tight seal with the syringe barrel and applying an force to the plunger rod in the proximal direction to expand the distance between the stopper and the plunger rod. The formation of a vacuum within the stopper draws air and liquid into the cavity. The filter permits air to enter the cavity and prevents liquid from entering the cavity.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical device comprising:
   a syringe barrel including a side wall having an inside surface defining a chamber for retaining fluid, an open proximal end and a distal end including a distal wall with a tip extending distally therefrom having an open passageway in fluid communication with said chamber;

a plunger rod having a proximal end, a distal end including a stopper-engaging portion, and a hollow elongate body extending from the proximal end to the distal end, the plunger rod disposed within the chamber and moveable in the proximal and distal directions within the chamber, wherein the hollow elongate body has an inside surface defining a void space containing a vacuum and the stopper-engaging portion includes a first porous portion disposed within the stopper-engaging portion which is air permeable and liquid impermeable;

a second porous portion which is air permeable and liquid impermeable and is disposed in a space formed by a bottom support and an outside wall of the first porous portion;

a stopper attached to the distal end of the plunger rod, the stopper having a distal end including a pierceable distal face or a pierceable septum, an open proximal end, and a body extending from the distal end to the open proximal end including an inside surface defining a cavity, wherein the pierceable distal face or the pierceable septum seals the vacuum within the void space of the hollow elongate body when the open proximal end of the stopper is attached to the plunger rod and the pierceable distal face or the pierceable septum reseals after piercing, and a needle attached to the tip of the syringe extending partially into the chamber, the needle having an open distal end, an open proximal end, and a vent adjacent to the open proximal end, the open proximal end having a beveled edge for piercing the pierceable distal face or the pierceable septum of the stopper.

2. The medical device according to claim 1, wherein the inside surface of the body includes a peripheral groove forming a channel or ridge for engagement with the plunger rod.

3. The medical device according to claim 2, wherein the stopper-engaging portion of the plunger rod includes a sidewall support extending from a proximal end to a distal end of the stopper-engaging portion and a disc extending radially outwardly from a distal end of the sidewall support to engage the peripheral groove.

4. The medical device according to claim 1, wherein the first and second porous portions are formed from a hydrophobic filter, a swellable polymer or combinations thereof.

5. A method for filling a syringe barrel with liquid and evacuating air from the syringe barrel, comprising:

providing a medical device according to claim 1, wherein the pierceable distal face or the pierceable septum of the stopper is disposed within the chamber at a minimum distance from the beveled edge at the open proximal end of the needle such that the beveled edge at the open proximal end of the needle only partially penetrates the pierceable distal face or the pierceable septum and such that the vacuum contained in the hollow elongate body is maintained;

submerging the needle in a liquid;

applying an initial distal force to the plunger rod in the distal direction so that the beveled edge at the open proximal end of the needle penetrates the pierceable distal face or the pierceable septum of the stopper to create an opening in the pierceable distal face or the pierceable septum and release the vacuum contained within the void space of the plunger rod, thereby drawing air from the chamber into the stopper and a stopper hub, and delivering the air into the void space of the plunger rod, and applying a proximally directed force on the plunger rod to aspirate the liquid into the chamber, thereby removing the beveled edge of the needle from the opening in the pierceable distal face or the pierceable septum of the stopper and causing the opening to reseal.

* * * * *